(12) United States Patent
Hawkins et al.

(10) Patent No.: US 7,459,444 B2
(45) Date of Patent: Dec. 2, 2008

(54) INHIBITORS OF CHYMASE

(75) Inventors: Michael J. Hawkins, Ambler, PA (US); Michael N. Greco, Lansdale, PA (US); Eugene Powell, Pipersville, PA (US); Lawrence de Garavilla, Downingtown, PA (US); Bruce E. Maryanoff, Forest Grove, PA (US)

(73) Assignee: Janssen Pharmaceutica N.V. (BE)

( * ) Notice: Subject to any disclaimer, the term of this patent is extended or adjusted under 35 U.S.C. 154(b) by 127 days.

(21) Appl. No.: 11/037,938

(22) Filed: Jan. 18, 2005

(65) Prior Publication Data
US 2005/0176769 A1 Aug. 11, 2005

Related U.S. Application Data

(60) Provisional application No. 60/538,663, filed on Jan. 23, 2004.

(51) Int. Cl.
*A61K 31/66* (2006.01)
*C07F 9/28* (2006.01)
*C07F 9/38* (2006.01)
*C07F 9/40* (2006.01)

(52) U.S. Cl. .............. 514/75; 514/95; 514/79; 514/80; 514/81; 514/89; 514/96; 548/414; 546/23; 558/169

(58) Field of Classification Search ............ 514/96
See application file for complete search history.

(56) References Cited

U.S. PATENT DOCUMENTS 5,508,273 A 4/1996 Beers et al.
6,852,734 B2 2/2005 Yamamoto et al.

FOREIGN PATENT DOCUMENTS

EP 0 661 260 A1 7/1995
GR 1399089 5/1971

OTHER PUBLICATIONS

Aoyama, Yasunori et al "Synthesis and Structure-Activity Relationships of a New Class of 1-Oxacephem-Based Human Chymase Inhibitors" Bioorganic & Medicinal Chemistry Letters 10 (2000) pp. 2397-2401 XP-002336087.
Bertrand, Jay A. et al "Inhibition of Trypsin and Thrombin by Amino(4-amidinophenyl)methanephosphonate Diphenyl Ester Derivatives: X-Ray Structures and Molecular Models" Biochemistry 35 (1996) pp. 3147-3155 XP-002336085.
Fukami, H. et al "Chymase: Its Pathophysiological Roles and Inhibitors" Current Pharmaceutical Design 4 (1998) pp. 439-453 XP-000885575.
Greco, Michael N. et al "Nonpeptide Inhibitors of Cathepsin G. Optimization of a Novel β-Ketophosphonic Acid Lead by Structure-Based Drug Design" J. Am. Chem. Soc. 124 (2002) pp. 3810-3811 XP002336084.
Lachkova, Victoria et al "Interaction Between Phenylmethanephosphonic Acid Diethyl Ester and Isothiocyanates" Phosphorus, Sulfur and Silicon 48 (1990) pp. 227-233 XP009050625.
Oleksyszyn, J et al "Irreversible Inhibition of Serine Proteases by Peptide Derivatives of (α-Aminoalkyl) phosphonate Diphenyl Esters" 30 (1991) pp. 485-493 XP002336086.
Tempest, P et al "MCC/S$_N$Ar Methodology, Part 1: Novel Access to a Range of Heterocyclic Cores" 42 (2001) pp. 4963-4968 XP002336083.
PCT International Search report PCT/US2005/001659 dated Aug. 3, 2005.
Schwender, Charles et al, "1-Naphthylmethyl Phosphonic Acid Derivatives as Osteoclastic Acid Phospatase Inhibitors," Bioorganic and Medicinal Chemistry Letters, 1995, pp. 1801-1806, vol. 5, No. 16, Elsevier Science, Ltd., Great Britain.
De Lombaert et al., "Non-Peptide Inhibitors of Neutral Endopeptidase 24.11 2. Design and Pharmacology of Orally Active Phosphonate Prodrugs," Bioorganic & Medicinal Chemistry Letters, 1995, pp. 151-154, vol. 5, No. 2, Elsevier Science Ltd., Great Britain.
De Lombaert et al., "N-Phosphonomethyl Dipeptides and Their Phosphonate Prodrugs, a New Generation of Neutral Endopeptidase (NEP, EC 3.4.24.11) Inhibitors," J. Med Chem, 1994, pp. 498-511, vol. 37, American Chemical Society.
Okamoto et al., "Chymase Inhibitor, BCEAB, Suppressed Peritoneal Adhesion Formation in Hamster," Journal Of Surgical Research, 2002, pp. 219-222, vol. 107, Elsevier Science (USA).
Yoa et al., "Association between the Expression of Mast Cell Chymase and Intraperitoneal Adhesion Formation in Mice," Journal Of Surgical Research, 2000, pp. 40-44, vol. 92, Academic Press.
Lucas et al., "Formation of Abdominal Adhesions is Inhibited by Antibodies to Transforming Growth Factor-β1," Journal Of Surgical Research, 1996, pp. 135-138, vol. 65, Academic Press.
Gotis-Graham et al., "Mast Cell Responses in Rheumatoid Synovium: Association of the MC sub TC subset with Matrix Turnover and Clinical Progession," 1997, pp. 479-489, vol. 40 (3), American College of Rheumatology.

(Continued)

Primary Examiner—Yvonne Eyler
Assistant Examiner—Yevgeny Valenrod

(57) ABSTRACT

The present invention is directed to a compound of formula (I),

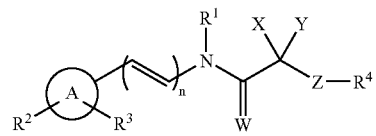

methods for preparing these compounds, compositions, intermediates and derivatives thereof, and methods for treating inflammatory and serine protease mediated disorders.

58 Claims, 2 Drawing Sheets

OTHER PUBLICATIONS

Lindstedt et al., "Chymase in Exocytosed Rat Mast Cell Granules Effectively Proteolyzes Apoliopoprotein A1-containing Lipoproteins, So Reducing the Cholesterol Efflux-inducing Ability of Serum and Aortic Intimal Fluid," J Clin Invest, 1996, pp. 2174-2182, vol. 97, No. 10, The American Society for Clinical Investigation, Inc.

Gould et al., "Salt Selection for basic drugs," International Journal Of Pharmaceutics, 1986, pp. 201-217, vol. 33, Elsevier Science Publichers, B.V.

De Paulis et al., "Novel Autocrine and Paracrine Loops of the Stem Cell Factor/Chymase Network," Int Arch Allergy Immunol, 1999, pp. 422-425, vol. 118.

Ehara et al., "Contribution of mast cells to the tubulointerstitial lesions in IgA nephritis," Kidney International, 1998, pp. 1675-83, vol. 54, International Society of Nephrology.

Graham et al., "Topically Active Carbonic Anhydrase Inhibitors," J Med Chem., 1989, pp. 2548-2554, vol. 32, No. 12, American Chemical Society.

Henning et al., "Synthesis and Neuroleptic Activity of a Series of 1-[-1-(Benzo-1, 4-dioxan-2-ylmethyl)-4-piperidinyl]benzimidazolone Derivatives," J Med Chem., 1987, pp. 814-19, vol. 30, American Chemical Society.

Egfange et al., "Modified Ibogaine Fragments: Synthesis and Preliminary Pharmacological Characterization of 3-Ethyl-5-phenly-1,2,3,4,5,6-hexahydroazepino[4,5-b] benzothiophenes," J Med Chem, 1998, pp. 4486-91, vol. 41, American Chemical Society.

Ple et al., Synthesis of Substituted Benzo [b]thiophenes by Acid-Catalyzed.

Cyclization of Thiophenylacetals and Ketones, J. Heterocyclic Chem, 1988, pp. 1271, 25.

Steininger, "Uber die Herstellung von Bis-phosphiinigsaureestern und anderer Bix-phosphorverbindungen," Chem Berg, 1963, pp. 3184-94, 96.

Cory et al., "Extended Chains of Six-Membered Rings 1. Model Studies and Key Intermediates," Synthetic Communications, 1994, pp. 799-807, vol. 24, No. 6, Marcel Dekker, Inc.

Deprele et al., "Palladium-Catalyzed Hydrophosphinylation of Aikenes and Alkynes," J. Am Chem Soc., 2002, pp. 9386-87, vol. 124, American Chemical Society.

Yamashiro et al., "Distribution of intrahepatic mast cells in various hepatolbiliary disorders," Virchows Arch, 1998, pp. 471-79, vol. 433, Springer-Verlag.

Michele Reboud-Ravaux et al., Journal De La Societe De Biologie, Issn 1295-0661, 2001, pp. 143-150, vol. 195, No. 2.

Matsumoto et al., "Chymase Inhibition Prevents Cardiac Fibrosis and Improves Diastolic Dysfunction in the Progression of Heart Failure," Circulation, pp. 2555-2558.

Paananen et al., "Proteolysis and Fusion of Low Density Lipoprotein Particles Independently Strengthen their Binding to Exocytosed Mast Cell Granules," The Journal Of Biological Chemisty, 1994, pp. 2023-2031, vol. 269, No. 3, The American Society For Biochemistry And Molecular Biology, Inc., USA.

Longley et al., "Chymase cleavage of stem factor yields a bioactive soluble product," Proc. National Acad., 1997, pp. 9017-9021, vol. 94, Biochemistry.

Froestl et al., "Phosphinic Acid Analogues of GABA. 1. New Potent and Selective $GABA_B$," J Med Chem, 1995, pp. 3297-3312, vol. 38, American Chemical Society.

Depaulis et al., "Novel Autocrine and Paracrine Loops of the Stem Cell Factor/Chymase Network," Int Arch Allergy Immunol, 1999, pp. 4252-4425, vol. 118, Biology Of Inflammatory Products: Cytokines and Mediators.

Denney et al., "Osomeric Five-Membered Ring Phosphites and Phosphates," Journal Of American Chemical Society, 1969, pp. 6838-6841, vol. 91, 24.

Deprele et al., "A novel and convenient preparation of hypophosphite esters," Journal of Organometallic Chemistry, 2002, pp. 154-163, 643-644, Elsevier Science.

Garabadzhiu et al., "Actions of Perfluoroalkyl Iodides Phosphorus (III) esters kinetics and mechanism of the reactions heptafluoropropyl with ethyl phosphonous eters," Journal Of General Chemistry Ussr, 1982, pp. 1905-1910, Plenum Publishing Corporation.

Grasa et al., "Amination Reactions of Aryl Halides with Nitrogen-Containing Reagents Mediated by Palladium/Imidazolium Salt Systems," J Org Chem, pp. 7729-7737, vol. 66.

Belley et al., "Synthesis of the Nanomolar Photoaffinity $GABA_B$ Receptor Ligand CGP 71872 Reveals Diversity in the Tissue Distribution of $GABA_B$ Receptor Forms," Bioorganic and Medicinal Chemistry, 1999, pp. 2697-2704, vol. 7, Elsevier Science Ltd.

Martinez et al., "New 3-[4-(aryl)piperazin-1-yl]-1-(benzol[b]thiophen-3-yl)propane derivatives with dual action at $5-HT_{1A}$ serotonin receptors and serotonin transporter as a new class of antidepressants," Eur J Med Chem, 2001, pp. 55-61, vol. 36, Elsevier.

Berge et al., "Pharmaceutical Salts," Journal Of Pharmaceutical Sciences, 1977, pp. 1-19, vol. 66, No. 1.

Abraham et al., "Pharmacology of Allergen-Induced Early and Late Airway Responses and Antigen-Induced Hyperresponsiveness in Allergic Sheep," Pulmonary Pharmacology, 1989, pp. 33-40, vol. 2, Longman Group UK Ltd.

Hara et al "Evidence for a Role of Mast Cells in the Evolution to Congestive Heart Failure," J Exp Med., 2002, pp. 375-381, vol. 195, No. 3, The rockafeller University Press.

Katritzky et al., "A One-Pot Porcedure for the Preparation of Phosphonic Accids from Alkyl Halides," Organic Preparations and Procedures Int., 1990, pp. 209-213, vol. 22, No. 2.

Borch et al., "The Cyanohydridoborate Anion as A Selective Reducing Agent," Journal of the American Chemical Society, 1971, pp. 2897-2904, vol. 93, No. 12. Cyanohydridoborate Anion.

Taft et al., "Fluorine Nuclear Magnetic Resonance Shielding in *meta*-Substituted Fluobenzenes. The Effect of Solvent on the Inductive Order," Journal of the American Chemical Society, 1963, vol. 85, No. 6, pp. 711-716.

Seto et al., "Molecular Self-Assembly through Hydrogen Bonding: Aggregation of Five Molecules to Form a Discrete Supramolecular Structure," J Am. Chem Society, 1993, pp. 1321-1329, vol. 115, American Chemical Society.

Collins et al., "Organophosphorus Compounds, XIX+ Synthesis of 2,3 Dihydro-1H-1,2-benzaza-phosphole 2-oxides, variously substituted on nitrogen and phosphorus, by N-P Cyclization of Zqitterionic Intermediates," Aust. J. Chem, 1983, pp. 2517-2536, No. 36.

Greco et al., "Discovery of Potent, Selective, Orally Active, Nonpeptide Inhibitors of Human Mast Cell Chymase," J Med Chem, 2007, pp. 1727-1730, vol. 50, American Chemical Society.

Maryanoff et al., "Protease inhibitors for treating pulmonary inflammatory disorders: Focus on chymase and cathepsin G," Abstracts of Papers, 234th ACS National Meeting, Aug. 19-23, 2007. Medi-247, Coden: 69JNR2 An 2007:883608. Caplus.

Hawkins et al., "Structure-based design of serine protease inhibitors: Discovery of selective chymase inhibitors containing a novel beta-amidophosphonic acid recognition motif," Abstracts of Papers, 232nd ACS National Meeting, San Francisco, Ca, United States, Sep. 10-14, 2006 (2006) Orgn-623, Coden: 691hrd and 2006:862763 Caplus.

Hawkins et al., "Structure-based design of serine protesase inhibitors: Discovery of selective chymase inhibitors containing a novel β-amidophosphonic acid recognition motifs," Abstracts of Papers, 230th ACS National Meeting, Washington, DC, United States, Aug. 28-Sep. 1, 2005 (2005) Medi-336. Cohen: 69hfcl an2005:739844 Caplus.

Goodman & Gilman Pharmacological Basis of Therapeutics, 1996, 9th Ed., vol. 1, 47, 58, McGraw Hill.

INHIBITORS OF CHYMASE

This application claims priority from application 60/538,663, filed Jan. 23, 2004, which is incorporated herein by reference.

FIELD OF THE INVENTION

The present invention relates to certain novel compounds, methods for preparing compounds, compositions, intermediates and derivatives thereof and methods for treating inflammatory and serine protease mediated disorders. More particularly, the compounds of the present invention are serine protease inhibitors useful for treating inflammatory and serine protease mediated disorders.

BACKGROUND OF THE INVENTION

Serine proteases represent a broad class of proteolytic enzymes that are involved in physiological processes such as blood coagulation, complement activation, phagocytosis and turnover of damaged cell tissue. Human chymase (EC.3.4.21.39) is a glycosylated monomeric chymotrypsin-like serine protease (MW=30 kDa) localized mainly in mast cell secretory granules. Chymase is thought to have a variety of functions, including degradation of extracellular matrix proteins, cleavage of angiotensin I to angiotensin II (except in the rat), and activation of matrix proteases and cytokines. Endogenously, chymase is regulated by the serpins α1-antichymotrypsin and α1-proteinase.

Although the precise patho-physiological roles of chymase have yet to be determined, chymase has been implicated in microvascular leakage, neutrophil accumulation, the stimulation of mucus secretion, and the modulation of cytokines. A potent, chymase-selective inhibitor may be indicated in mast cell-mediated diseases such as asthma, pulmonary inflammation, and chronic obstructive pulmonary diseases (COPD). Because chymase can play a role in the generation of cardiac and vascular wall angiotensin II, an inhibitor may have potential use as an antihypertensive treatment for vascular wall injury and inflammation (atherosclerosis/restenosis), as well as cardiac hypertrophy. Thus, small molecule inhibitors of chymase are likely to represent useful therapeutic agents.

U.S. Pat. No. 5,508,273 to Beers, et al. and *Bioorganic & Med. Chem. Lett.,* 1995, 5 (16), 1801-1806 describe phosphonic acid compounds useful in treating bone wasting diseases. In particular, 1-napthylmethylphosphonic acid derivatives have been described as osteoclastic acid phosphatase inhibitors of the formula:

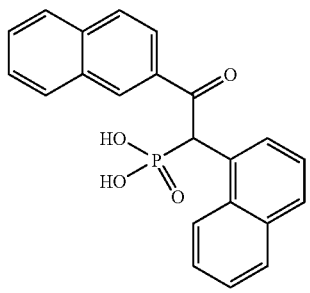

Accordingly, it is an object of the present invention to provide phosphonic acid and phosphinic acid compounds that are serine protease inhibitors, in particular, inhibitors of chymase, useful for treating inflammatory and serine protease mediated disorders. It is another object of the invention to provide a process for preparing phosphonic or phosphinic acid compounds, compositions, intermediates and derivatives thereof. It is a further object of the invention to provide methods for treating inflammatory and serine protease mediated disorders.

SUMMARY OF THE INVENTION

The present invention is directed to a compound of Formula (I)

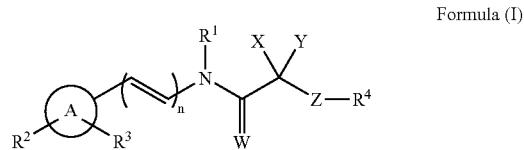

Formula (I)

wherein $R^1$ is selected from the group consisting of hydrogen and $C_{1-4}$alkyl;

is selected from the group consisting of aryl, heteroaryl, benzo fused heterocyclyl, cyclopropyl when n is 0 and one of $R^2$ or $R^3$ is phenyl, and benzo fused cycloalkyl, and ring A is optionally substituted with $R^2$ and $R^3$;

$R^2$ is one to two substituents independently selected from the group consisting of $C_{1-6}$alkyl, $C_{2-6}$alkenyl, $C_{2-6}$alkynyl, methoxy, $C_{2-6}$alkoxy, $C_{1-6}$alkylthio, —$OCF_3$, —$NH_2$, —$NH(C_{1-6})$alkyl, —$N(C_{1-6})$dialkyl, aryl, heteroaryl, aryloxy, heteroaryloxy, halogen, hydroxy, and nitro; furthermore, $R^2$ is optionally oxo when ring A is heteroaryl or benzo fused heterocyclyl; and, wherein any aryl-containing substituent of $R^2$ is optionally substituted with a substituent independently selected from the group consisting of $C_{1-6}$alkyl, $C_{1-6}$alkoxy, $C_{2-6}$ alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, halogen, hydroxy, and nitro;

and, wherein any of the foregoing $C_{1-6}$alkyl or $C_{2-6}$alkoxy containing substituents of $R^2$ are optionally substituted with a substituent independently selected from the group consisting of —$NR^{11}R^{12}$, aryl, heteroaryl, one to three halogens and hydroxy; wherein $R^{11}$ and $R^{12}$ are independently hydrogen; $C_{1-6}$ alkyl optionally substituted with hydroxy, aryl, —$C(=O)C_{1-4}$alkoxy, or —$NR^{15}R^{16}$; or aryl;

$R^{15}$ and $R^{16}$ are substituents independently selected from the group consisting of hydrogen, $C_{1-6}$ alkyl, and aryl, and said $R^{15}$ and $R^{16}$ are optionally taken together with the atoms to which they are attached to form a ring of five to seven members;

$R^3$ is one to three substituents independently selected from the group consisting of $C_{1-6}$alkyl, $C_{2-6}$alkenyl, $C_{2-6}$alkynyl, $C_{1-6}$alkoxy, $C_{1-6}$alkylthio, —$OCF_3$, —$OCH_2(C_{2-6})$alkenyl, —$NH_2$, —$NH(C_{1-6})$alkyl, —$N(C_{1-6})$dialkyl, —$NHC(=O)Cy$, —$N(C_{1-6}$alkyl$)C(=O)Cy$, —$(NC(=O))_2NH_2$, —$C(=O)C_{1-4}$alkoxy, —$C(=O)NR^{17}R^{18}$, —$C(=O)NHcycloalkyl$, —$C(=O)N(C_{1-6}$alkyl$)$cycloalkyl, —C(=O)NHCy, —C(=O)N($C_{1-6}$alkyl)Cy, —C(=O)Cy, —OC(=O)$C_{1-6}$alkyl, —OC(=O)NR$^{19}$R$^{20}$, —C(=O)Oaryl, —C(=O)Oheteroaryl, —CO$_2$H, ureido, halogen, hydroxy, nitro, cyano, aryl, heteroaryl, heteroaryloxy, and aryloxy;

wherein any of the foregoing $C_{1-6}$alkyl or $C_{1-6}$alkoxy containing substituents of of R$^3$ are optionally substituted with one to three substituents independently selected from the group consisting of —NR$^{21}$R$^{22}$, —NH(cycloalkyl), —N($C_{1-6}$alkyl)(cycloalkyl), —NHCy, —N($C_{1-6}$alkyl)Cy, aryl, heteroaryl, hydroxy, halogen, —C(=O)NR$^{23}$R$^{24}$, —OC(=O)NR$^{25}$R$^{26}$, —C(=O)$C_{1-4}$alkoxy, and —C(=O)Cy;

wherein said R$^{17}$, R$^{18}$, R$^{19}$, R$^{20}$, R$^{21}$, R$^{22}$, R$^{23}$, R$^{24}$, R$^{25}$, R$^{26}$ are substituents independently selected from the group consisting of hydrogen, $C_{1-6}$ alkyl, and aryl, wherein $C_{1-6}$ alkyl is optionally substituted with hydroxy, aryl, —C(=O)$C_{1-4}$alkoxy, NH$_2$, NH($C_{1-6}$alkyl), or —N($C_{1-6}$)dialkyl; and R$^{17}$ and R$^{18}$, R$^{19}$ and R$^{20}$, R$^{21}$ and R$^{22}$, R$^{23}$ and R$^{24}$ and R$^{25}$ and R$^{26}$ are optionally taken together with the atoms to which they are attached to form a ring of five to seven members;

Cy is a heterocyclyl optionally substituted with a substituent selected from the group consisting of $C_{1-6}$alkyl, $C_{1-6}$alkylC(=O)$C_{1-6}$alkyl, —$C_{1-6}$alkylC(=O)$C_{1-6}$alkoxy, $C_{1-6}$alkylC(=O)aryl, —C(=O)($C_{1-6}$)alkyl, —C(=O)($C_{1-6}$)alkoxy, —C(=O)aryl, —SO$_2$aryl, aryl, heteroaryl, and heterocyclyl; wherein the aryl portion of any aryl-containing substituent of Cy is optionally substituted with one to three substituents independently selected from the group consisting of $C_{1-6}$alkyl, $C_{1-6}$alkoxy, $C_{1-6}$alkylthio, halogen, hydroxy, NH$_2$, NH($C_{1-6}$alkyl), and —N($C_{1-6}$)dialkyl; and wherein heterocyclyl is optionally substituted with aryl, one to three halogen atoms, or one to three oxo substituents; and heterocyclyl is optionally spiro-fused to said Cy;

and wherein the $C_{1-6}$alkenyl and $C_{1-6}$alkynyl substituents of R$^3$ are optionally substituted with aryl or —C(=O)NR$^{27}$R$^{28}$; wherein said R$^{27}$ and R$^{28}$ are independently hydrogen; $C_{1-6}$ alkyl optionally substituted with hydroxy, aryl, —C(=O)$C_{1-4}$alkoxy, NH$_2$, NH($C_{1-6}$alkyl), or —N($C_{1-6}$)dialkyl; or aryl; and R$^{27}$ and R$^{28}$ are optionally taken together with the atoms to which they are attached to form a ring of five to seven members;

wherein the aryl, heteroaryl, and cycloalkyl substituents of R$^3$ are optionally substituted with one to three substituents independently selected from R$^{14}$;

wherein R$^{14}$ is independently hydrogen, $C_{1-6}$alkyl, $C_{1-6}$alkoxy, $C_{2-6}$alkenyl, $C_{1-6}$alkylthio, —NH$_2$, —NH($C_{1-6}$)alkyl, —N($C_{1-6}$)dialkyl, aryl, heteroaryl, aryloxy, heteroaryloxy, halogen, hydroxy, or nitro;

and any one of the foregoing $C_{1-6}$alkyl- or $C_{1-6}$alkoxy-containing substituents of R$^{14}$ is optionally substituted on a terminal carbon atom with a substituent selected from —NR$^{29}$R$^{30}$, aryl, heteroaryl, one to three halogen atoms, or hydroxy; wherein R$^{29}$ and R$^{30}$ are independently hydrogen; $C_{1-6}$ alkyl optionally substituted with hydroxy, aryl, —C(=O)$C_{1-4}$alkoxy, NH$_2$, NH($C_{1-6}$alkyl), or —N($C_{1-6}$)dialkyl; or aryl; and R$^{29}$ and R$^{30}$ are optionally taken together with the atoms to which they are attached to form a ring of five to seven members;

n is 0 or 1;

W is O or S;

X is hydrogen or $C_{1-3}$alkyl;

Y is independently selected from the group consisting of $C_{1-6}$alkyl substituted with —OSO$_2$NH$_2$ or hydroxy; SO$_3$H, CO$_2$H, heteroaryl, —OC(=O)NH$_2$, and P(=O)OR$^5$R$^6$ provided that when Y is CO$_2$H, A and Z must both be bicyclic ring systems;

R$^5$ is selected from the group consisting of hydrogen; $C_{1-6}$alkyl optionally substituted with NH$_2$, —NH($C_{1-6}$)alkyl, —N($C_{1-6}$)dialkyl, 1,3-dioxolan-2-yl, $C_{1-6}$alkylcarbonyloxy, $C_{1-6}$alkoxycarbonyloxy, $C_{1-6}$alkylcarbonylthio, ($C_{1-6}$)alkylaminocarbonyl, di($C_{1-6}$)alkylaminocarbonyl, one to three halogens, or hydroxy; and aryl optionally substituted with $C_{1-6}$alkyl, $C_{1-6}$alkoxy, $C_{1-6}$alkylthio, $C_{2-6}$alkenyl, —NH$_2$, —NH($C_{1-6}$)alkyl, —N($C_{1-6}$)dialkyl, aryl, heteroaryl, aryloxy, heteroaryloxy, halogen, hydroxy, or nitro; alternatively, when R$^6$ is $C_{1-8}$alkoxy, R$^5$ and R$^6$ are taken together with the atoms to which they are attached to form a 5-8 membered monocyclic ring;

provided that R$^5$ is other than $C_{1-6}$alkyl substituted with di($C_{1-6}$)alkylamino-carbonyl when ring system A is 3,4-difluoro-phenyl, n is 1, R$^6$ is OH, and Z-R$^4$ is 5-chloro-benzothiophen-3-yl; and provided that R$^5$ is other than $C_{1-6}$alkyl substituted with $C_{1-6}$alkylcarbonylthio when ring system A is 3,4-difluoro-phenyl, n is 1, R$^6$ is CH$_3$, and Z-R$^4$ is 5-chloro-benzothiophen-3-yl;

R$^6$ is selected from the group consisting of $C_{1-8}$alkyl, $C_{1-8}$alkoxy, $C_{2-8}$alkenyl, heteroaryl, aryl, and hydroxy; wherein $C_{1-8}$alkyl, $C_{1-8}$alkoxy, and $C_{2-8}$alkenyl are optionally substituted with a substituent selected from the group consisting of $C_{1-6}$alkoxy, aryl, heterocyclyl, heteroaryl, NH$_2$, —NH($C_{1-6}$)alkyl, —N($C_{1-6}$)dialkyl, $C_{1-6}$alkylcarbonyloxy, $C_{1-6}$alkylcarbonylthio, $C_{1-6}$alkoxycarbonyloxy, ($C_{1-6}$)alkylaminocarbonyl, di($C_{1-6}$)alkylaminocarbonyl, one to three halogen atoms, and hydroxy; and when R$^6$ is $C_{1-8}$alkyl, said $C_{1-8}$alkyl is optionally substituted with one to four additional halogen atoms such that one to three halogen atoms are optionally chlorine and one to, seven of the halogen atoms are optionally fluorine;

wherein the heteroaryl and aryl substituents of R$^6$ are optionally substituted with a substituent independently selected from the group consisting of $C_{1-6}$alkyl, $C_{1-6}$alkoxy, $C_{2-6}$ alkenyl, $C_{1-6}$alkylthio, —NH$_2$, —NH($C_{1-6}$)alkyl, —N($C_{1-6}$)dialkyl, aryl, heteroaryl, aryloxy, heteroaryloxy, halogen, hydroxy, and nitro;

Z is a seven to fifteen membered monocyclic or polycyclic ring system selected from the group consisting aryl, heteroaryl, benzo fused heterocyclyl, or benzo fused cycloalkyl, optionally substituted with R$^4$;

R$^4$ is one to three substituents selected from the group consisting of $C_{1-6}$alkyl, $C_{1-6}$alkenyl, $C_{1-6}$alkoxy, $C_{1-6}$alkylthio, aryl($C_{1-6}$)alkyl, aryl($C_{2-6}$)alkenyl, halogen, —C(=O)Cy, —C(=O)NR$^{31}$R$^{32}$, aryl, —CO$_2$H, oxo, and cyano; wherein $C_{1-6}$alkyl, $C_{1-6}$alkenyl and $C_{1-6}$alkoxy are optionally substituted with —NR$^{33}$R$^{34}$, aryl, heteroaryl, cycloalkyl, one to three halogen atoms, or hydroxy; and aryl and heteroaryl are each optionally substituted with a substituent independently selected from the group consisting of $C_{1-6}$alkyl, $C_{1-6}$alkoxy, $C_{2-6}$ alkenyl, $C_{1-6}$alkylthio, —NH$_2$, —NH($C_{1-6}$)alkyl, —N($C_{1-6}$)dialkyl, aryl, heteroaryl, aryloxy, heteroaryloxy, one to three halogen atoms, hydroxy, and nitro;

wherein said R$^{31}$, R$^{32}$, R$^{33}$, and R$^{34}$ are substituents independently selected from the group consisting of hydrogen, $C_{1-6}$ alkyl, and aryl, wherein alkyl is optionally substituted with hydroxy, aryl, —C(=O)$C_{1-4}$alkoxy, NH$_2$, NH($C_{1-6}$alkyl), or —N($C_{1-6}$)dialkyl; and R$^{31}$ with R$^{32}$ and R$^{33}$ with R$^{34}$ are optionally taken together with the atoms to which they are attached to form a ring of five to seven members;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

The present invention is also directed to methods for producing the instant compounds and pharmaceutical compositions and medicaments thereof.

The present invention is further directed to methods for treating or ameliorating a serine protease-mediated disorder. In particular, the method of the present invention is directed to treating or ameliorating a chymase mediated disorder such as, but not limited to, allergic rhinitis, viral rhinitis, asthma, chronic obstructive pulmonary diseases, bronchitis, pulmonary emphysema, acute lung injury, psoriasis, arthritis, reperfusion injury, ischemia, hypertension, hypercardia myocardial infarction, heart failure damage associated with myocardial infarction, cardiac hypertrophy, arteriosclerosis, saroidosis, vascular stenosis or restenosis (e.g., associated with vascular injury, angioplasty, vascular stents or vascular grafts), pulmonary fibrosis, kidney fibrosis (e.g., associated with glomerulonephritis), liver fibrosis, post surgical adhesion formation, systemic sclerosis, keloid scars, rheumatoid arthritis, bullous pemphigiod, and atherosclerosis. Additionally, these compounds can be used for modulating wound healing and remodeling (e.g., cardiac hypertrophy) as well as immune modulation.

Figure 1:
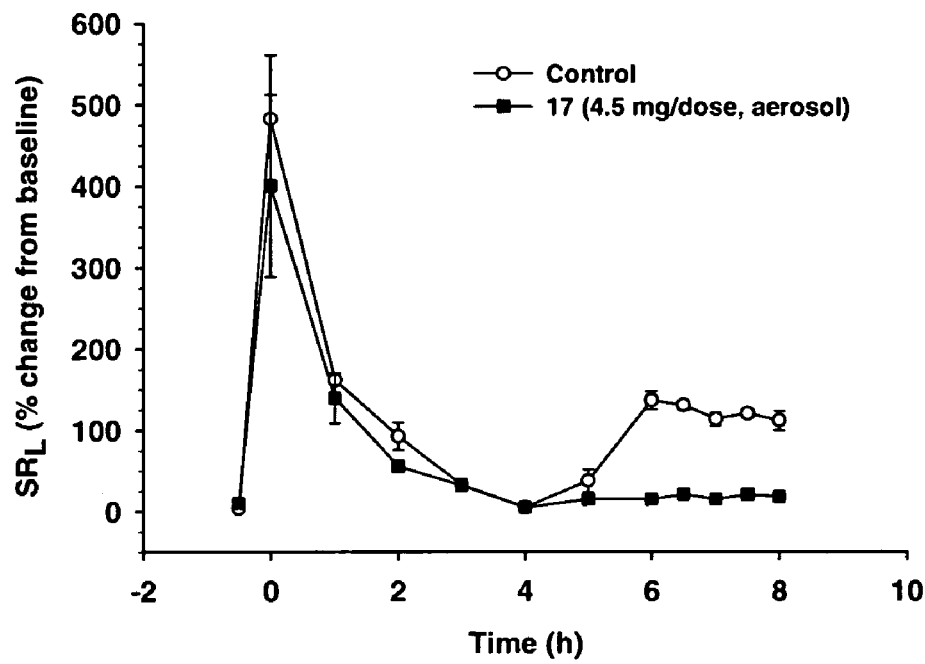
FIG. 1 shows the percent change in specific lung resistance ($SR_L$) from baseline for Compound 17 when administered via aerosol inhalation compared to control in a spontaneous *Ascaris suum* antigen-induced model of asthma in sheep over an 8 hour period.

FIG. 2 shows the change in the cumulative carbachol dose required to increase $SR_L$ 400% (PC 400) from a baseline value (BSL) measured at 24 hours post-dosing of Compound 17 via aerosol inhalation delivery in the spontaneous *Ascaris suum* antigen-induced model of asthma in sheep compared to a 24 hour post-dosing challenge with carbachol (Post Antigen).

FIG. 3 shows the percent change in specific lung resistance ($SR_L$) from baseline for Compound 17 when administered via oral administration compared to control in a spontaneous *Ascaris suum* antigen-induced model of asthma in sheep over an 8 hour period.

FIG. 4 shows the change in the cumulative carbachol dose required to increase $SR_L$ 400% (PC 400) from a baseline value (BSL) measured at 24 hours post-dosing of Compound 17 via oral administration in the spontaneous *Ascaris suum* antigen-induced model of asthma in sheep compared to a 24 hour post-dosing challenge with carbachol (Post Antigen).

DETAILED DESCRIPTION OF THE INVENTION

Preferred embodiments of the present invention include compounds of Formula (I) wherein:

(I)

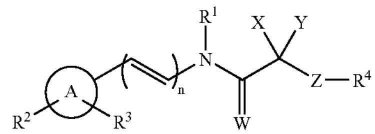

$R^1$ is selected from the group consisting of hydrogen and $C_{1-4}$alkyl.

More preferably, $R^1$ is hydrogen.

Preferred embodiments of the present invention include compounds of Formula (I) wherein:

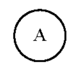

is selected from the group consisting of aryl, heteroaryl, benzo fused heterocyclyl and benzo fused cycloalkyl optionally substituted with $R^2$ and $R^3$.

Preferably, ring system A is selected from the group consisting of heteroaryl, benzo fused heterocyclyl, or aryl.

Preferably when A is a bicyclic ring system of the formula:

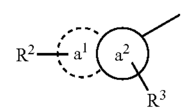

wherein the $a^1$ portion of said $a^1a^2$ is optionally substituted with $R^2$; and the $a^2$ portion is optionally substituted with $R^3$.

Preferably $a^2$ is an aromatic ring.

Preferably, ring system A is selected from the group consisting of naphthyl, benzothiazolyl, benzothiophenyl, quinolinyl, isoquinolinyl, dihydronaphthyl, indanyl, tetralinyl, and benzodioxolyl when n is equal to zero; and A is phenyl, pyridin-2-yl, or pyridin-3-yl when n is equal to one. In embodiments of the present invention wherein a bicyclic ring system is used for A, the $a^2$ ring will be aromatic. More preferably, ring system A is selected from the group consisting of naphthyl, benzothiazolyl, and benzothiophenyl, when n is equal to zero, and A is selected from phenyl, pyridin-2-yl, and pyridin-3-yl when n is equal to one.

A preferred embodiment of the present invention includes compounds of Formula (I) wherein n is equal to one.

Preferred embodiments of the present invention include compounds of Formula (I) wherein $R^2$ is one to three substituents independently selected from the group consisting of $C_{1-6}$alkyl, methoxy, $C_{2-6}$alkoxy, —$NH_2$, $NH(C_{1-6}alkyl)$, —$N(C_{1-6})$dialkyl, aryl, heteroaryl, halogen, hydroxy, and nitro; wherein $C_{1-6}$alkyl and $C_{2-6}$alkoxy are optionally substituted with a substituent selected from —$NR^{11}R^{12}$, aryl, heteroaryl, one to three halogens, and hydroxy.

More preferably, $R^2$ is a substituent independently selected from the group consisting of $C_{1-4}$alkyl, methoxy, $C_{2-4}$alkoxy, hydroxy, halogen, and —$NH_2$.

Most preferably, $R^2$ is $C_{1-4}$alkyl, halogen, or —$NH_2$.

Preferred embodiments of the present invention include compounds of Formula (I) wherein $R^3$ is one to three substituents independently selected from the group consisting of $C_{1-6}$alkyl, $C_{2-6}$alkenyl, $C_{1-6}$alkoxy, —$OCH_2(C_{2-6})$alkenyl, $NH_2$, —$NH(C_{1-6}alkyl)$, —$N(C_{1-6})$dialkyl, —NHC(=O)Cy, —N($C_{1-6}$alkyl)C(=O)Cy, —C(=O)$C_{1-4}$alkoxy, —C(=O)NR$^{17}$R$^{18}$, C(=O)NHcycloalkyl, —C(=O)N($C_{1-6}$alkyl)cycloalkyl, —C(=O)NHCy, —C(=O)N($C_{1-6}$alkyl)Cy, —C(=O)Cy, —OC(=O)NR$^{19}$R$^{20}$, halogen, hydroxy, nitro, cyano, aryl, and aryloxy; wherein alkyl and alkoxy are optionally substituted with one to three substituents independently selected from the group consisting of —NR$^{21}$R$^{22}$, —NHcycloalkyl, —N($C_{1-6}$alkyl)cycloalkyl, —NHCy, —N($C_{1-6}$alkyl)Cy, aryl, heteroaryl, halogen, —C(=O)NR$^{23}$R$^{24}$, —OC(=O)NR$^{25}$R$^{26}$, —C(=O)($C_{1-4}$)alkoxy, and —C(=O)Cy; wherein alkenyl is optionally substituted on a terminal carbon with aryl and —C(=O)NR$^{27}$R$^{28}$; and wherein aryl and cycloalkyl are optionally substituted with one to three substituents independently selected from R$^{14}$.

More preferably, R$^3$ is one to three substituents independently selected from the group consisting of $C_{1-6}$alkyl, $C_{1-6}$alkoxy, —NR$^{19}$R$^{20}$, —NHC(=O)Cy, —C(=O)NR$^{17}$R$^{18}$, —C(=O)NHcycloalkyl, —C(=O)N($C_{1-6}$alkyl)cycloalkyl, halogen, and aryl; wherein alkyl and alkoxy are optionally substituted on a terminal carbon atom with one to three fluorine atoms, —NH$_2$, —NHCy, or —N($C_{1-4}$alkyl)Cy; and wherein aryl and cycloalkyl are optionally substituted with a group independently selected from R$^{14}$.

Even more preferably, R$^3$ is one to two substituents independently selected from trifluoromethyl, $C_{1-4}$alkoxy optionally substituted with one to three fluorine atoms, —NH$_2$, —NHC(=O)Cy, or halogen.

Preferably when R$^3$ is NHC(=O)Cy then Cy is preferably piperadinyl, and substituted with a substituent selected from the group consisting of $C_{1-4}$alkyl, $C_{1-4}$alkylC(=O)$C_{1-4}$alkyl, —$C_{1-4}$alkylC(=O)$C_{1-4}$alkoxy, $C_{1-4}$alkylC(=O)aryl, —C(=O)($C_{1-4}$)alkyl, —C(=O)($C_{1-4}$)alkoxy, —C(=O)aryl, —SO$_2$aryl, aryl, heteroaryl, and heterocyclyl; wherein aryl and the aryl portion of the $C_{1-4}$alkylC(=O)aryl, —C(=O)aryl, and —SO$_2$aryl is optionally substituted with one to three substituents independently selected from the group consisting of $C_{1-4}$alkyl, $C_{1-4}$alkoxy, halogen, hydroxy, NH$_2$, NH($C_{1-6}$alkyl), and —N($C_{1-4}$)dialkyl; and wherein heterocyclyl is optionally substituted with aryl, one to three halogen atoms, or one oxo substituents.

Most preferably, R$^3$ is trifluoromethyl, one to two fluorine atoms, chloro, methoxy, trifluoromethoxy, or NH$_2$; furthermore, when A is naphthyl and n is equal to zero, R$^3$ is (4-{[1-(naphthalene-2-carbonyl)-piperadine-4-carbonyl]-amino}-naphthalene-2-yl.

Preferred embodiments of the present invention include compounds of Formula (I) wherein X is hydrogen or $C_{1-3}$alkyl.

More preferably, X is hydrogen.

Preferred embodiments of the present invention include compounds of Formula (I) wherein Y is independently selected from a group consisting of $C_{1-3}$alkyl, SO$_3$H, CO$_2$H, heteroaryl, —OC(=O)NH$_2$, and P(=O)OR$^5$R$^6$; wherein alkyl is substituted with a substituent selected from the group consisting of —OS$_2$NH$_2$ and hydroxy.

More preferably, Y is independently SO$_3$H or P(=O)OR$^5$R$^6$.

Most preferably, Y is P(=O)OR$^5$R$^6$.

Preferred embodiments of the present invention include compounds of Formula (I) wherein R$^5$ is selected from the group consisting of hydrogen; $C_{1-3}$alkyl optionally substituted with NH$_2$, —NH($C_{1-6}$)alkyl, —N($C_{1-6}$)dialkyl, $C_{1-6}$alkylcarbonyloxy, $C_{1-6}$alkoxycarbonyloxy, $C_{1-6}$alkylcarbonylthio, ($C_{1-6}$)alkylaminocarbonyl, di($C_{1-6}$)alkylaminocarbonyl, one to three halogens, or hydroxy; and aryl optionally substituted with $C_{1-6}$alkyl, $C_{1-6}$alkoxy, $C_{1-6}$alkylthio, $C_{2-6}$ alkenyl, —NH$_2$, —NH($C_{1-6}$)alkyl, —N($C_{1-6}$)dialkyl, aryl, heteroaryl, aryloxy, heteroaryloxy, halogen, hydroxy, or nitro; alternatively, when R$^6$ is $C_{1-6}$alkoxy, R$^5$ and R$^6$ are taken together with the atoms to which they are attached to form a 5-8 membered monocyclic ring;

provided that R$^5$ is other than $C_{1-6}$alkyl substituted with di($C_{1-6}$)alkylaminocarbonyl when ring system A is 3,4-difluoro-phenyl, n is 1, R$^6$ is OH, and Z-R$^4$ is 5-chloro-benzothiophen-3-yl; and provided that R$^5$ is other than $C_{1-6}$alkyl substituted with $C_{1-6}$alkylcarbonylthio when ring system A is 3,4-difluoro-phenyl, n is 1, R$^6$ is CH$_3$, and Z-R$^4$ is 5-chloro-benzothiophen-3-yl.

More preferably, R$^5$ is selected from the group consisting of hydrogen, $C_{1-3}$alkyl optionally substituted with $C_{1-6}$alkylcarbonyloxy, $C_{1-6}$alkoxycarbonyloxy, $C_{1-6}$alkylcarbonylthio, ($C_{1-6}$)alkylaminocarbonyl, di($C_{1-6}$)alkylaminocarbonyl, one to three halogens, or hydroxyl; and aryl; alternatively, when R$^6$ is $C_{1-8}$alkoxy, R$^5$ and R$^6$ are taken together with the atoms to which they are attached to form a 6-7 membered monocyclic ring; provided that R$^5$ is other than $C_{1-3}$alkyl substituted with di($C_{1-6}$)alkylaminocarbonyl when ring system A is 3,4-difluoro-phenyl, n is 1, R$^6$ is OH, and Z-R$^4$ is 5-chloro-benzothiophen-3-yl; and provided that R$^5$ is other than $C_{1-3}$alkyl substituted with $C_{1-6}$alkylcarbonylthio when ring system A is 3,4-difluoro-phenyl, n is 1, R$^6$ is CH$_3$, and Z-R$^4$ is 5-chloro-benzothiophen-3-yl.

Most preferably, R$^5$ is hydrogen or $C_{1-3}$alkyl optionally substituted with $C_{1-6}$alkylcarbonyloxy, $C_{1-6}$alkoxycarbonyloxy, $C_{1-6}$alkylcarbonylthio, ($C_{1-6}$)alkylamino-carbonyl, or di($C_{1-6}$)alkylaminocarbonyl; and alternatively, when R$^6$ is $C_{1-8}$alkoxy, R$^5$ and R$^6$ are taken together with the atoms to which they are attached to form a 6-membered monocyclic ring; provided that R$^5$ is other than $C_{1-3}$alkyl substituted with di($C_{1-6}$)alkylaminocarbonyl when ring system A is 3,4-difluoro-phenyl, n is 1, R$^6$ is OH, and Z-R$^4$ is 5-chloro-benzothiophen-3-yl; and provided that R$^5$ is other than $C_{1-3}$alkyl substituted with $C_{1-6}$alkylcarbonylthio when ring system A is 3,4-difluoro-phenyl, n is 1, R$^6$ is CH$_3$, and Z-R$^4$ is 5-chloro-benzothiophen-3-yl.

Preferred embodiments of the present invention include compounds of Formula (I) wherein R$^6$ is selected from the group consisting of $C_{1-8}$alkyl, $C_{1-8}$alkoxy, $C_{2-8}$alkenyl, heteroaryl, aryl, and hydroxy; wherein alkyl, alkoxy, and alkenyl are optionally substituted on a terminal carbon atom with a substituent independently selected from the group consisting of $C_{1-4}$alkoxy, aryl, heteroaryl, heterocyclyl, $C_{1-6}$alkylcarbonyloxy, $C_{1-6}$alkylcarbonylthio, $C_{1-6}$alkoxycarbonyloxy, ($C_{1-6}$)alkylaminocarbonyl, di($C_{1-6}$)alkylaminocarbonyl, and hydroxy; and wherein heteroaryl and aryl are optionally substituted with one to three substituents independently selected from the group consisting of aryl, hydroxy, $C_{1-6}$alkoxy, and halogen.

More preferably, R$^6$ is selected from the group consisting of $C_{1-6}$alkyl, $C_{1-8}$alkoxy, heteroaryl, aryl, and hydroxy; wherein alkyl and is optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkyl-aminocarbonyl; and wherein heteroaryl and aryl are optionally substituted with one to three substituents independently selected from the group consisting of aryl, hydroxy, $C_{1-6}$alkoxy, and halogen.

Most preferably, R$^6$ is selected from the group consisting of methyl, ethyl, methoxypropyl, phenethyl, benzo[1,3]dioxol-5-yl-propyl, hydroxy, and $C_{1-3}$alkoxy optionally substituted with $C_{1-6}$alkylcarbonyloxy, and di($C_{1-6}$)alkylaminocarbonyl.

Preferred embodiments of the present invention include compounds of Formula (I) wherein Z is a bicyclic aryl or bicyclic heteroaryl; wherein aryl and heteroaryl are optionally substituted with the group $R^4$; provided that when Y is $CO_2H$, A must be a bicycle.

More preferably, Z is selected from the group consisting of indolyl, benzothiophenyl, naphthalenyl, quinolinyl, isoquinolinyl and benzothiazolone.

Most preferably, Z is selected from the group consisting of indolyl, benzothiophenyl, and naphthalenyl.

Embodiments of the present invention include compounds of Formula (I) wherein $R^4$ is one to three substituents selected from the group consisting of hydrogen, $C_{1-6}$alkyl, $C_{1-6}$alkenyl, $C_{1-6}$alkoxy, aryl($C_{2-6}$)alkenyl, halogen, —C(=O)Cy, —C(=O)NR$^{31}$R$^{32}$, aryl, —CO$_2$H, oxo, and cyano; wherein alkyl and alkoxy are optionally substituted on a terminal carbon atom with a substituent selected from aryl, —NR$^{33}$R$^{34}$, one to three halogens, or hydroxy; wherein aryl is optionally substitututed with one to three substituents independently selected from from the group consisting of hydrogen, $C_{1-6}$alkyl, $C_{1-6}$alkoxy, $C_{2-6}$ alkenyl, —NH$_2$, —NH($C_{1-6}$)alkyl, —N($C_{1-6}$)dialkyl, aryl, heteroaryl, aryloxy, heteroaryloxy, halogen, hydroxy, and nitro.

Preferably, $R^4$ is one to three substituents selected from the group consisting of $C_{1-6}$alkyl, $C_{1-6}$alkenyl, $C_{1-6}$alkoxy, aryl($C_{2-6}$)alkenyl, halogen, —C(=O)Cy, —C(=O)NR$^{31}$R$^{32}$, aryl, —CO$_2$H, oxo, and cyano; wherein alkyl and alkoxy are optionally substituted with a substituent independently selected from —NR$^{33}$R$^{34}$, aryl, one to three halogen atoms, or hydroxy; wherein aryl is optionally substitututed with a substituent independently selected from the group consisting of hydrogen, $C_{1-6}$alkyl, $C_{1-6}$alkoxy, aryl, halogen, hydroxy, and nitro.

More preferably, $R^4$ is one to three substituents selected from the group consisting of $C_{1-6}$alkyl, $C_{1-6}$alkenyl, aryl($C_{2-6}$)alkenyl, halogen, and —C(=O)Cy; wherein aryl is optionally substituted with a substituent selected from halogen and $C_{1-4}$alkoxy.

Most preferably, $R^4$ is one to two substituents selected from the group consisting of fluorine, chlorine, bromine, methyl, phenyl($C_{2-6}$)alkenyl, and —C(=O)(2-(4-phenyl-piperidin-1-ylcarbonyl)).

Embodiments of the phosphonic and phosphinic acids of the present invention include those compounds of Formula (Ia) wherein the substituents are as previously defined (including the previously listed preferred substitutions in any combination). Examples of embodiments of the present invention are shown in Table I:

TABLE I (Ia)

| Cpd | R² | R³ | R⁵ | R⁶ | n | W | Z-R⁴ |
|---|---|---|---|---|---|---|---|
| 1 | naphthalen-2-yl | | H | CH₃ | 0 | O | 5-Cl-N-methyl-indol-3-yl |
| 2 | 3,4-difluoro-phenyl | | H | OH | 1 | O | 5-Cl-benzothiophen-3-yl |
| 3 | naphthalen-2-yl | | H | OH | 0 | O | 5-Cl-N-methyl-indol-3-yl |
| 4 | 4-fluoro-phenyl | | H | OH | 1 | O | 5-Cl-N-methyl-indol-3-yl |
| 5 | naphthalen-2-yl | | H | OH | 0 | O | 5-Me-benzothiophen-2-yl |
| 6 | 3-fluoro-phenyl | | H | CH₃ | 1 | O | 5-Cl-N-methyl-indol-3-yl |
| 7 | 3,4-difluoro-phenyl | | H | CH₃ | 1 | O | 5-Cl-N-methyl-indol-3-yl |
| 8 | 4-{[1-(naphthalen-2-ylcarbonyl)-piperadin-4-ylcarbonyl]-amino}naphthalen-2-yl | | H | OH | 0 | O | naphthalen-1-yl |
| 9 | naphthalen-2-yl | | H | OH | 0 | O | 5-Cl-benzothiophen-3-yl |
| 10 | naphthalen-2-yl | | H | OH | 0 | O | 5-F-benzothiophen-3-yl |
| 11 | naphthalen-2-yl | | H | OH | 0 | O | 5-F-N-methyl-indol-3-yl |
| 12 | 4-amino-phenyl | | H | OH | 1 | O | 5-Cl-benzothiophen-3-yl |
| 13 | naphthalen-2-yl | | H | OH | 0 | O | 5-Br-N-methyl-indol-3-yl |
| 14 | Phenyl | | H | CH₃ | 1 | O | 5-Cl-benzothiophen-3-yl |
| 15 | 3-fluoro-phenyl | | H | CH₃ | 1 | O | 5-Cl-benzothiophen-3-yl |
| 16 | 3,4-trifluoro-phenyl | | H | CH₃ | 1 | O | 5-Cl-benzothiophen-3-yl |
| 17 | 3,4-difluoro-phenyl | | H | CH₃ | 1 | O | 5-Cl-benzothiophen-3-yl |
| 18 | phenyl | | H | OH | 1 | O | 5-Cl-benzothiophen-2-yl |
| 19 | 4-fluoro-phenyl | | H | OH | 1 | O | 5-Cl-benzothiophen-3-yl |
| 20 | naphthalen-2-yl | | H | CH₃ | 0 | O | 5-Cl-benzothiophen-3-yl |
| 21 | 2-fluoro-phenyl | | H | CH₃ | 1 | O | 5-Cl-benzothiophen-3-yl |
| 22 | naphthalen-2-yl | | H | OH | 0 | O | N-methyl-indol-3-yl |
| 23 | naphthalen-2-yl | | H | OH | 0 | O | 5-Br-benzothiophen-3-yl |
| 24 | 4-fluoro-phenyl | | H | CH₃ | 1 | O | 5-Cl-benzothiophen-3-yl |
| 25 | pyridin-3-yl | | H | OH | 1 | O | 5-Cl-benzothiophen-3-yl |

TABLE I-continued

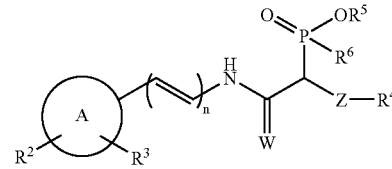

(Ia)

| Cpd | R² | R³ | R⁵ | R⁶ | n | W | Z-R⁴ |
|---|---|---|---|---|---|---|---|
| 26 | naphthalen-2-yl | | H | OH | 0 | O | benzothiophen-3-yl |
| 27 | naphthalen-2-yl | | H | OH | 0 | O | N-(3-phenyl-allyl)-indol-3-yl |
| 28 | naphthalen-2-yl | | H | CH₂CH₃ | 0 | O | 5-Cl-benzothiophen-3-yl |
| 29 | 3,4-difluoro-phenyl | | H | CH₂CH₃ | 1 | O | 5-Cl-benzothiophen-3-yl |
| 30 | benzothiazol-6-yl | | H | OH | 0 | O | 5-Cl-benzothiophen-3-yl |
| 31 | naphthalen-2-yl | | H | OH | 0 | O | naphthalen-1-yl |
| 32 | naphthalen-2-yl | | H | CH₃ | 0 | O | 2-(4-phenyl-piperidin-1-ylcarbonyl)-benzothiophen-3-yl |
| 33 | naphthalen-2-yl | | H | CH₃ | 0 | O | naphthalen-1-yl |
| 34 | naphthalen-2-yl | | H | 3-methoxy-propyl | 0 | O | 5-Cl-benzothiophen-3-yl |
| 35 | naphthalen-2-yl | | H | CH₃ | 0 | O | 2-(4-(4-methoxyphenyl)-piperidin-1-ylcarbonyl)-benzothiophen-3-yl |
| 36 | naphthalen-2-yl | | H | phenethyl | 0 | O | 5-Cl-benzothiophen-3-yl |
| 37 | phenyl | | H | OH | 1 | O | naphthalen-1-yl |
| 38 | 4-methoxy-phenyl | | H | OH | 1 | O | 5-Cl-benzothiophen-3-yl |
| 39 | naphthalen-2-yl | | H | 3-(benzo[1,3]dioxol-5-yl)-propyl | 0 | O | 5-Cl-benzothiophen-3-yl |
| 40 | naphthalen-2-yl | | H | 3-(naphthylen-1yl) propyl | 0 | O | 5-Cl-benzothiophen-3-yl |
| 41 | naphthalen-2-yl | | H | CH₃ | 0 | O | 2-(4-(Benzyloxycarbonyl)-piperazin-1-ylcarbonyl))-benzothiophen-3-yl |
| 42 | 4-methyl-phenyl | | H | OH | 1 | O | 5-Cl-benzothiophen-2-yl |
| 43 | naphthalen-2-yl | | H | 3-(4-hydroxy phenyl) propyl | 0 | O | 5-Cl-benzothiophen-3-yl |
| 44 | 3-((N-benzoyl-piperidin-4-ylamino)-methyl)-naphthalen-2-yl | | H | OH | 0 | O | naphthalen-1-yl |
| 45 | naphthalen-2-yl | | H | OH | 0 | S | 5-Cl-benzothiophen-3-yl |
| 46 | 3-[(1-phenyl)-cyclohex 1-enyl-N-methyl-aminocarbonyl]-naphthalen-2-yl | | H | OH | 0 | O | naphthalen-1-yl |
| 47 | naphthalen-2-yl | | H | CH₃ | 0 | O | 2-((4-F-phenyl)-piperidin-1-ylcarbonyl)-benzothiophen-3-yl |
| 48 | naphthalen-2-yl | | H | (3-phenyl) propyl | 0 | O | 5-Cl-benzothiophen-3-yl |
| 49 | 3,4-dimethoxy-phenyl | | H | OH | 1 | O | 5-Cl-benzothiophen-3-yl |
| 51 | naphthalen-2-yl | | H | (4-phenyl) butyl | 0 | O | 5-Cl-benzothiophen-3-yl |
| 52 | naphthalen-2-yl | | H | OH | 0 | O | 6-Cl-N-methyl-indol-3-yl |
| 53 | naphthalen-2-yl | | H | 3-(4-methoxy-phenyl) propyl | 0 | O | 5-Cl-benzothiophen-3-yl |
| 54 | 3-[4-((3-phenethyl)-pyrrolidin-1-ylcarbonyl)]-naphthalen-2-yl | | H | OH | 0 | O | naphthalen-1-yl |
| 55 | benzothiophen-5-yl | | H | OH | 0 | O | 5-Cl-benzothiophen-3-yl |
| 56 | naphthalen-2-yl | | H | OH | 0 | O | 5-carboxy-N-Me-indol-3-yl- |
| 57 | quinolin-3-yl | | H | OH | 0 | O | naphthalen-1-yl |
| 58 | naphthalen-2-yl | | H | OH | 0 | O | 7-Cl-N-methyl-indol-3-yl |

TABLE I-continued (Ia)

| Cpd | R² / A / R³ | R⁵ | R⁶ | n | W | Z-R⁴ |
|---|---|---|---|---|---|---|
| 59 | benzo[b]thiophen-6-yl | H | OH | 0 | O | naphthalen-1-yl |
| 60 | 3-[4-(6-chloro-2-oxo-2,3-dihydro-benzoimidazol-1-yl)-piperidin-1-ylcarbonyl]-naphthalen-2-yl | H | OH | 0 | O | naphthalen-1-yl |
| 61 | 4-biphenyl | H | OH | 0 | O | naphthalen-1-yl |
| 62 | naphthalen-2-yl | H | OH | 0 | O | N-cyclopropyl methyl-indol-3-yl |
| 63 | naphthalen-2-yl | H | OH | 0 | O | 4-Cl-N-methyl-indol-3-yl |
| 64 | benzothiophen-2-yl | H | OH | 0 | O | naphthalen-1-yl |
| 65 | naphthalen-2-yl | H | OH | 0 | O | 5-cyano-N-methyl-indol-3-yl |
| 66 | 4-hydroxy-phenyl | H | OH | 1 | O | 5-Cl-benzothiophen-3-yl |
| 67 | (6-Br)-naphthalen-2-yl | H | OH | 0 | O | 5-Cl-benzothiophen-3-yl |
| 68 | naphthalen-2-yl | H | OH | 0 | O | Indol-3-yl |
| 69 | 2-amino-benzothiazol-6-yl | H | OH | 0 | O | 5-Cl-benzothiophen-3-yl |
| 70 | 3-(Cyclohexylamino)methyl-naphthalen-2-yl | H | OH | 0 | O | naphthalen-1-yl |
| 71 | naphthalen-2-yl | H | OH | 0 | O | 5-Ph-benzothiophen-3-yl |
| 72 | 3-(N-benzyl-amino-carbonyloxymethyl)naphthalen-2-yl | H | OH | 0 | O | naphthalen-1-yl |
| 73 | 3-(pyridin-4-yl-pyrrolidin-1-ylcarbonyl)-naphthalen-2-yl | H | OH | 0 | O | naphthalen-1-yl |
| 74 | naphthalen-2-yl | H | OH | 0 | O | 5-methoxy-N-methyl-indol-3-yl |
| 75 | 3-(methoxycarbonyl)-naphthalen-2-yl | H | OH | 0 | O | naphthalen-1-yl |
| 76 | naphthalen-2-yl | H | OH | 0 | O | 6-Br-benzothiophen-3-yl |
| 77 | naphthalen-2-yl | H | OH | 0 | O | N-isopropyl-indol-3-yl |
| 78 | 4-chloro-phenyl | H | CH₃ | 1 | O | 5-Cl-benzothiophen-3-yl |
| 79 | quinolin-6-yl | H | OH | 0 | O | naphthalen-1-yl |
| 81 | 4-trifluoromethyl-phenyl | H | OH | 1 | O | 5-Cl-benzothiophen-3-yl |
| 82 | naphthalen-2-yl | H | OH | 0 | O | N-phenyl-indol-3-yl |
| 83 | 4-(1H-indol-3-yl)-piperidin-1-ylcarbonyl)-naphthalen-2-yl | H | OH | 0 | O | naphthalen-1-yl |
| 85 | indanyl | H | OH | 0 | O | naphthalen-1-yl |
| 86 | naphthalen-2-yl | H | OH | 0 | O | 5-Cl-1,1-dioxo benzothiophen-3-yl |
| 87 | ((3-phenyl)pyrrolidin-1-ylcarbonyl)-naphthalen-2-yl | H | OH | 0 | O | naphthalen-1-yl |
| 89 | naphthalen-2-yl | H | Ph | 0 | O | 5-Cl-benzothiophen-3-yl |
| 90 | ((3-methyl)-cyclohexylamino)methyl-naphthalen-2-yl | H | OH | 0 | O | naphthalen-1-yl |
| 91 | 3-(cyclopentyl-N-methylamino-carbonyl)-naphthalen-2-yl | H | OH | 0 | O | naphthalen-1-yl |
| 92 | 3-((5-methoxy carbonyl)aminomethyl)-naphthalen-2-yl | H | OH | 0 | O | naphthalen-1-yl |
| 93 | 3-(4-(2-oxo-2,3-dihydro-benzoimidazol 1-yl)-piperidin-1-yl-carbonyl)-naphthalen 2-yl | H | OH | 0 | O | naphthalen-1-yl |

TABLE I-continued (Ia)

Structure: A ring with R2, R3 substituents connected via CH=CH (n) to NH-C(W)-CH(Z-R4)-P(=O)(OR5)(R6)

| Cpd | R² | R⁵ | R⁶ | n | W | Z-R⁴ |
|---|---|---|---|---|---|---|
| 94 | 3-(phenylamino-carbonyloxy)methyl)-naphthalen-2-yl | H | OH | 0 | O | naphthalen-1-yl |
| 95 | 3-(phenylamino-carbonyl)methyl)-naphthalen-2-yl | H | OH | 0 | O | naphthalen-1-yl |
| 96 | quinolin-2-yl | H | OH | 0 | O | naphthalen-1-yl |
| 97 | 3-((4-phenoxy-phenyl)-aminocarbonyloxy methyl)naphthalen-2-yl | H | OH | 0 | O | naphthalen-1-yl |
| 98 | naphthalen-2-yl | H | OH | 0 | O | 5-(4-F-pheny)-N-methyl-indol-3-yl |
| 99 | naphthalen-2-yl | H | OH | 0 | O | 4-Br-benzo thiophen-3-yl |
| 100 | 3-[(4-benzotriazol-1-yl piperidin-1-ylcarbonyl)]-naphthalen-2-yl | H | OH | 0 | O | naphthalen-1-yl |
| 101 | 3-(4-phenyl)-piperidin-1-ylcarbonyl)-naphthalen-2-yl | H | OH | 0 | O | naphthalen-1-yl |
| 102 | 3-((naphthalen-2-ylcarbonyl)piperidin-4-ylmethylamino-methyl)-naphthalen-2-yl | H | OH | 0 | O | naphthalen-1-yl |
| 103 | 3-((3-benzenesulfonyl)-pyrrolidin-1-ylcarbonyl)-naphthalen-2-yl | H | OH | 0 | O | naphthalen-1-yl |
| 104 | 3-(N-[3-(4-oxo-1-phenyl-1,3,8-triaza-spiro[4.5]decane-8-carbonyl)-naphthalen-2-yl | H | OH | 0 | O | naphthalen-1-yl |
| 105 | 3-(naphthalen-2-ylaminocarbonyloxy-methyl)naphthalen-2-yl | H | OH | 0 | O | naphthalen-1-yl |
| 106 | 2-fluorenyl | H | OH | 0 | O | naphthalen-1-yl |
| 107 | 3-(benzylaminomethyl)-naphthalen-2-yl | H | OH | 0 | O | naphthalen-1-yl |
| 108 | (3-OH)naphthalen-2-yl | H | OH | 0 | O | naphthalen-1-yl |
| 109 | 3-(N-benzyl-3-acrylamide)naphthalen-2-yl | H | OH | 0 | O | naphthalen-1-yl |
| 110 | 3-((5-phenyl)-pentylamino)-naphthaten-2-yl | H | OH | 0 | O | naphthalen-1-yl |
| 111 | 3-(N-benzyl-N-methyl-aminocarbonyl)-naphthalen-2-yl | H | OH | 0 | O | naphthalen-1-yl |
| 112 | 3-[(5H-dibenzo-[a,d]cyctohepten-5-yl)-propyl]-methyl-amino-methyl-naphthalen-2-yl | H | OH | 0 | O | naphthalen-1-yl |
| 113 | 3-(4-(benzothiazol-2-yl-piperidin-1-ylcarbonyl))-naphthalen-2-yl | H | OH | 0 | O | naphthalen-1-yl |
| 114 | 1-(2-oxo-2-(4-phenyl-piperidin-1-yl)-ethoxy)-naphthalen-2-yl | H | OH | 0 | O | naphthalen-1-yl |
| 115 | 3-([2-(3,4-dimethoxy-phenyl)-ethyl]-N-methylaminocarbonyl)-naphthalen-2-yl | H | OH | 0 | O | naphthalen-1-yl |

TABLE I-continued

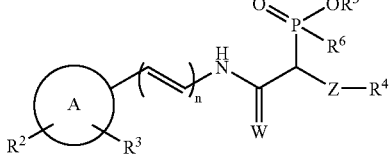

(Ia)

| Cpd | R² R³ | R⁵ | R⁶ | n | W | Z-R⁴ |
|---|---|---|---|---|---|---|
| 116 | naphthalen-2-yl | H | OH | 0 | O | 1-Me-1H-pyrrolo[2,3-b]pyridine |
| 117 | 3-((4-OH-cyclohexylamino)-methyl)naphthalen-2-yl | H | OH | 0 | O | naphthalen-1-yl |
| 118 | naphthalen-2-yl | H | CH₃ | 0 | O | 2-carboxy-benzothiophen-3-yl |
| 119 | 3-(benzyl aminocarbonyl)-naphthalen-2-yl | H | OH | 0 | O | naphthalen-1-yl |
| 121 | 3-(3-phenyl-allyloxy)-naphthalen-2-yl | H | OH | 0 | O | naphthalen-1-yl |
| 122 | 3-(benzyloxy)-naphthalen-2-yl | H | OH | 0 | O | naphthalen-1-yl |
| 123 | 3-(methoxycarbonyl-methoxy)naphthalen-2-yl | H | OH | 0 | O | naphthalen-1-yl |
| 124 | 3-(cyclopentylamino-methyl)naphthalen-2-yl | H | OH | 0 | O | naphthalen-1-yl |
| 125 | naphthalen-2-yl | H | OH | 0 | O | 5-Cl-benzothiophen-2-yl |
| 126 | 3-(phenethyl-methylaminomethyl) naphthalen-2-yl | H | OH | 0 | O | naphthalen-1-yl |
| 127 | naphthalen-2-yl | H | CH₃ | 0 | O | 2-(benzylaminocarbonyl)-benzothiophen-3-yl |
| 128 | naphthalen-2-yl | H | OH | 0 | O | N-phenyl-indol-4-yl |
| 129 | indol-5-yl | H | OH | 0 | O | naphthalen-1-yl |
| 130 | 3-(3-phenyl-propytcarbamoyl) methoxy)-naphthalen-2-yl | H | OH | 0 | O | naphthalen-1-yl |
| 131 | 3-(2-phenyl-pyrrolidin-1-ylcarbonyl)-naphthalen-2-yl | H | OH | 0 | O | naphthalen-1-yl |
| 132 | 3-amino-naphthalen-2-yl | H | OH | 0 | O | naphthalen-1-yl |
| 133 | 3-((5-hydroxy-pentylamino)-methyl)-naphthalen-2-yl | H | OH | 0 | O | naphthalen-1-yl |
| 134 | 1-(methoxycarbonyl-methoxy)-naphthalen-2-yl | H | OH | 0 | O | naphthalen-1-yl |
| 135 | benzo[1,3]dioxolyl | H | OH | 0 | O | naphthalen-1-yl |
| 137 | isoquinolin-3-yl | H | OH | 0 | O | naphthalen-1-yl |
| 138 | 3-phenoxy-phenyl | H | OH | 0 | O | naphthalen-1-yl |
| 139 | 3-(isopropyloxy-carbonyl)-naphthalen-2-yl | H | OH | 0 | O | naphthalen-1-yl |
| 140 | naphthalen-2-yl | H | OH | 0 | O | benzothiophen-2-yl |
| 141 | 3-{[1-(naphthalen-2-ylcarbonyl)-piperidin-4-ylcarbonyl]-amino}-naphthalen-2-yl | H | OH | 0 | O | naphthalen-1-yl |
| 142 | 3-(benzylmethyl aminomethyl)-naphthalen-2-yl | H | OH | 0 | O | naphthalen-1-yl |
| 143 | naphthalen-2-yl | H | OH | 0 | O | 6-(4-butylphenyl)-benzothiophen-3-yl |
| 144 | trans 2-phenylcycloprop-1-yl | H | CH₃ | 0 | O | 5-Cl-benzothiophen-3-yl |
| 145 | 2-methoxy-phenyl | H | CH₃ | 1 | O | 5-Cl-benzothiophen-3-yl |
| 146 | benzofuran-2-yl | H | CH₃ | 0 | O | 5-Cl-benzothiophen-3-yl |
| 147 | 2-nitro-phenyl | H | CH₃ | 1 | O | 5-Cl-benzothiophen-3-yl |

TABLE I-continued

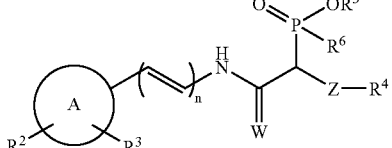

(Ia)

| Cpd | R² | R⁵ | R⁶ | n | W | Z-R⁴ |
|---|---|---|---|---|---|---|
| 148 | 2-methylcarbonyloxy-phenyl | H | CH₃ | 1 | O | 5-Cl-benzothiophen-3-yl |
| 149 | 2-hydroxy-phenyl | H | CH₃ | 1 | O | 5-Cl-benzothiophen-3-yl |
| 150 | pyridin-2-yl | H | CH₃ | 1 | O | 5-Cl-benzothiophen-3-yl |
| 151 | 2-amino-phenyl | H | CH₃ | 1 | O | 5-Cl-benzothiophen-3-yl |
| 152 | 3-trifluoromethyl-phenyl | H | CH₃ | 1 | O | 5-Cl-benzothiophen-3-yl |
| 153 | 3-trifluoromethoxy-phenyl | H | CH₃ | 1 | O | 5-Cl-benzothiophen-3-yl |
| 154 | 3-methoxy-phenyl | H | CH₃ | 1 | O | 5-Cl-benzothiophen-3-yl |
| 155 | 2-methyl-phenyl | H | CH₃ | 1 | O | 5-Cl-benzothiophen-3-yl |
| 156 | 2,6-difluoro-phenyl | H | CH₃ | 1 | O | 5-Cl-benzothiophen-3-yl |
| 157 | 4-cyano-phenyl | H | CH₃ | 1 | O | 5-Cl-benzothiophen-3-yl |
| 158 | 2-ureido-phenyl | H | CH₃ | 1 | O | 5-Cl-benzothiophen-3-yl |
| 159 | 2-(NHC(=O))₂NH₂—phenyl | H | CH₃ | 1 | O | 5-Cl-benzothiophen-3-yl |
| 160 | 2-chloro-phenyl | H | CH₃ | 1 | O | 5-Cl-benzothiophen-3-yl |
| 161 | 3-chloro-phenyl | H | CH₃ | 1 | O | 5-Cl-benzothiophen-3-yl |
| 162 | 3,5-difluoro-phenyl | H | CH₃ | 1 | O | 5-Cl-benzothiophen-3-yl |
| 163 | 2,3-difluoro-phenyl | H | CH₃ | 1 | O | 5-Cl-benzothiophen-3-yl |
| 164 | 2-bromo-phenyl | H | CH₃ | 1 | O | 5-Cl-benzothiophen-3-yl |
| 165 | 2,3-dimethoxy-phenyl | H | CH₃ | 1 | O | 5-Cl-benzothiophen-3-yl |
| 166 | 3-nitro-phenyl | H | CH₃ | 1 | O | 5-Cl-benzothiophen-3-yl |
| 167 | 3-bromo-phenyl | H | CH₃ | 1 | O | 5-Cl-benzothiophen-3-yl |
| 168 | 3,5-dimethoxy-phenyl | H | CH₃ | 1 | O | 5-Cl-benzothiophen-3-yl |
| 169 | 2,5-difluoro-phenyl | H | CH₃ | 1 | O | 5-Cl-benzothiophen-3-yl |
| 170 | 3,5-dichloro-phenyl | H | CH₃ | 1 | O | 5-Cl-benzothiophen-3-yl |
| 171 | 2,4-difluoro-phenyl | H | CH₃ | 1 | O | 5-Cl-benzothiophen-3-yl |
| 172 | 3-amino-phenyl | H | CH₃ | 1 | O | 5-Cl-benzothiophen-3-yl |
| 173 | phenyl | —CH₂C(Me)₂CH₂O— | | 1 | O | naphthalen-1-yl |
| 174 | phenyl | 3-methoxy-prop-1-yl | OH | 1 | O | naphthalen-1-yl |
| 175 | phenyl | 3-methoxy-prop-1-yl | 3-methoxy-prop-1-yl-oxy | 1 | O | naphthalen-1-yl |
| 176 | phenyl | 2-(1,3-dioxolan-2-yl)-eth-1-yl | OH | 1 | O | naphthalen-1-yl |
| 177 | phenyl | —CH₂OC(=O)t-butyl | OH | 1 | O | naphthalen-1-yl |
| 178 | phenyl | —CH₂CH₂CH₂O— | | 1 | O | naphthalen-1-yl |
| 179 | phenyl | (2-dimethylamino)-eth-1-yl | 2-dimethyl-amino-ethoxy | 1 | O | naphthalen-1-yl |
| 180 | phenyl | —CH₂C(=O)NEt₂ | —OCH₂O(=O)NEt₂ | 1 | O | naphthalen-1-yl |
| 181 | phenyl | —(CH₂)₂SC(=O)t-butyl | —O(CH₂)₂SC(=O)t-butyl | 1 | O | naphthalen-1-yl |
| 182 | 3,4-difluoro-phenyl | —CH₂OC(=O)t-butyl | CH₃ | 1 | O | 5-Cl-benzothiophen-3-yl |
| 183 | 3,4-difluoro-phenyl | (2-dimethylamino)-eth-1-yl | CH₃ | 1 | O | 5-Cl-benzothiophen-3-yl |
| 184 | 3,4-difluoro-phenyl | (2-amino)-eth-1-yl | CH₃ | 1 | O | 5-Cl-benzothiophen-3-yl |
| 185 | 3,4-difluoro-phenyl | —CH₂C(=O)NEt₂ | CH₃ | 1 | O | 5-Cl-benzothiophen-3-yl |
| 186 | 3,4-difluoro-phenyl | —CH₂OC(=O)t-butyl | —OCH₂OC(=O)t-butyl | 1 | O | 5-Cl-benzothiophen-3-yl |
| 187 | 3,4-difluoro-phenyl | —CH₂OC(=O)t-butyl | OH | 1 | O | 5-Cl-benzothiophen-3-yl |

TABLE I-continued (Ia)

| Cpd | R² | R⁵ | R⁶ | n | W | Z-R⁴ |
|---|---|---|---|---|---|---|
| 188 | 3,4-difluoro-phenyl | —CH₂C(=O)NEt₂ | —OCH₂O(=O)NEt₂ | 1 | O | 5-Cl-benzothiophen-3-yl |
| 189 | 3,4-difluoro-phenyl | —CH₂CH₂CH₂O— | | 1 | O | 5-Cl-benzothiophen-3-yl |
| 190 | 3,4-difluoro-phenyl | —CH₂OC(=O)methyl | OH | 1 | O | 5-Cl-benzothiophen-3-yl |
| 191 | 3,4-difluoro-phenyl | —CH₂OC(=O)isopropyloxy | OH | 1 | O | 5-Cl-benzothiophen-3-yl |
| 192 | 2-methoxy-phenyl | H | OH | 1 | O | 5-Cl-benzothiophen-3-yl |
| 193 | pyridin-2-yl | H | OH | 1 | O | 5-Cl-benzothiophen-3-yl |
| 194 | 3-trifluoromethoxy-phenyl | H | OH | 1 | O | 5-Cl-benzothiophen-3-yl |
| 195 | 3-methoxy-phenyl | H | OH | 1 | O | 5-Cl-benzothiophen-3-yl |
| 196 | 2,6-difluoro-phenyl | H | OH | 1 | O | 5-Cl-benzothiophen-3-yl |
| 197 | 2-chloro-phenyl | H | OH | 1 | O | 5-Cl-benzothiophen-3-yl |
| 198 | 3-chloro-phenyl | H | OH | 1 | O | 5-Cl-benzothiophen-3-yl |
| 199 | 3,5-difluoro-phenyl | H | OH | 1 | O | 5-Cl-benzothiophen-3-yl |
| 200 | 2,3-difluoro-phenyl | H | OH | 1 | O | 5-Cl-benzothiophen-3-yl |
| 201 | 2-bromo-phenyl | H | OH | 1 | O | 5-Cl-benzothiophen-3-yl |
| 202 | 2,3-dimethoxy-phenyl | H | OH | 1 | O | 5-Cl-benzothiophen-3-yl |
| 203 | 3-nitro-phenyl | H | OH | 1 | O | 5-Cl-benzothiophen-3-yl |
| 204 | 3-bromo-phenyl | H | OH | 1 | O | 5-Cl-benzothiophen-3-yl |
| 205 | 3,5-dimethoxy-phenyl | H | OH | 1 | O | 5-Cl-benzothiophen-3-yl |
| 206 | 2,5-difluoro-phenyl | H | OH | 1 | O | 5-Cl-benzothiophen-3-yl |
| 207 | 3,5-dichloro-phenyl | H | OH | 1 | O | 5-Cl-benzothiophen-3-yl |
| 208 | 2,4-difluoro-phenyl | H | OH | 1 | O | 5-Cl-benzothiophen-3-yl |
| 209 | 3-amino-phenyl | H | OH | 1 | O | 5-Cl-benzothiophen-3-yl |
| 210 | 2-methoxy-phenyl | —CH₂OC(=O)t-butyl | CH₃ | 1 | O | 5-Cl-benzothiophen-3-yl |
| 211 | pyridin-2-yl | —CH₂OC(=O)t-butyl | CH₃ | 1 | O | 5-Cl-benzothiophen-3-yl |
| 212 | 3-trifluoromethoxy-phenyl | —CH₂OC(=O)t-butyl | CH₃ | 1 | O | 5-Cl-benzothiophen-3-yl |
| 213 | 3-methoxy-phenyl | —CH₂OC(=O)t-butyl | CH₃ | 1 | O | 5-Cl-benzothiophen-3-yl |
| 214 | 2,6-difluoro-phenyl | —CH₂OC(=O)t-butyl | CH₃ | 1 | O | 5-Cl-benzothiophen-3-yl |
| 215 | 2-chloro-phenyl | —CH₂OC(=O)t-butyl | CH₃ | 1 | O | 5-Cl-benzothiophen-3-yl |
| 216 | 3-chloro-phenyl | —CH₂OC(=O)t-butyl | CH₃ | 1 | O | 5-Cl-benzothiophen-3-yl |
| 217 | 3,5-difluoro-phenyl | —CH₂OC(=O)t-butyl | CH₃ | 1 | O | 5-Cl-benzothiophen-3-yl |
| 218 | 2,3-difluoro-phenyl | —CH₂OC(=O)t-butyl | CH₃ | 1 | O | 5-Cl-benzothiophen-3-yl |
| 219 | 2-bromo-phenyl | —CH₂OC(=O)t-butyl | CH₃ | 1 | O | 5-Cl-benzothiophen-3-yl |
| 220 | 2,3-dimethoxy-phenyl | —CH₂OC(=O)t-butyl | CH₃ | 1 | O | 5-Cl-benzothiophen-3-yl |
| 221 | 3-nitro-phenyl | —CH₂OC(=O)t-butyl | CH₃ | 1 | O | 5-Cl-benzothiophen-3-yl |
| 222 | 3-bromo-phenyl | —CH₂OC(=O)t-butyl | CH₃ | 1 | O | 5-Cl-benzothiophen-3-yl |
| 223 | 3,5-dimethoxy-phenyl | —CH₂OC(=O)t-butyl | CH₃ | 1 | O | 5-Cl-benzothiophen-3-yl |
| 224 | 2,5-difluoro-phenyl | —CH₂OC(=O)t-butyl | CH₃ | 1 | O | 5-Cl-benzothiophen-3-yl |
| 225 | 3,5-dichloro-phenyl | —CH₂OC(=O)t-butyl | CH₃ | 1 | O | 5-Cl-benzothiophen-3-yl |
| 226 | 2,4-difluoro-phenyl | —CH₂OC(=O)t-butyl | CH₃ | 1 | O | 5-Cl-benzothiophen-3-yl |
| 227 | 3-amino-phenyl | —CH₂OC(=O)t-butyl | CH₃ | 1 | O | 5-Cl-benzothiophen-3-yl |

TABLE I-continued (Ia)

| Cpd | R² | R⁵ | R⁶ | n | W | Z-R⁴ |
|---|---|---|---|---|---|---|
| 228 | 2-methoxy-phenyl | —CH₂OC(=O)t-butyl | —OCH₂OC(=O)t-butyl | 1 | O | 5-Cl-benzothiophen-3-yl |
| 229 | pyridin-2-yl | —CH₂OC(=O)t-butyl | —OCH₂OC(=O)t-butyl | 1 | O | 5-Cl-benzothiophen-3-yl |
| 230 | 3-trifluoromethoxy-phenyl | —CH₂OC(=O)t-butyl | —OCH₂OC(=O)t-butyl | 1 | O | 5-Cl-benzothiophen-3-yl |
| 231 | 3-methoxy-phenyl | —CH₂OC(=O)t-butyl | —OCH₂OC(=O)t-butyl | 1 | O | 5-Cl-benzothiophen-3-yl |
| 232 | 2,6-difluoro-phenyl | —CH₂OC(=O)t-butyl | —OCH₂OC(=O)t-butyl | 1 | O | 5-Cl-benzothiophen-3-yl |
| 233 | 2-chloro-phenyl | —CH₂OC(=O)t-butyl | —OCH₂OC(=O)t-butyl | 1 | O | 5-Cl-benzothiophen-3-yl |
| 234 | 3-chloro-phenyl | —CH₂OC(=O)t-butyl | —OCH₂OC(=O)t-butyl | 1 | O | 5-Cl-benzothiophen-3-yl |
| 235 | 3,5-difluoro-phenyl | —CH₂OC(=O)t-butyl | —OCH₂OC(=O)t-butyl | 1 | O | 5-Cl-benzothiophen-3-yl |
| 236 | 2,3-difluoro-phenyl | —CH₂OC(=O)t-butyl | —OCH₂OC(=O)t-butyl | 1 | O | 5-Cl-benzothiophen-3-yl |
| 237 | 2-bromo-phenyl | —CH₂OC(=O)t-butyl | —OCH₂OC(=O)t-butyl | 1 | O | 5-Cl-benzothiophen-3-yl |
| 238 | 2,3-dimethoxy-phenyl | —CH₂OC(=O)t-butyl | —OCH₂OC(=O)t-butyl | 1 | O | 5-Cl-benzothiophen-3-yl |
| 239 | 3-nitro-phenyl | —CH₂OC(=O)t-butyl | —OCH₂OC(=O)t-butyl | 1 | O | 5-Cl-benzothiophen-3-yl |
| 240 | 3-bromo-phenyl | —CH₂OC(=O)t-butyl | —OCH₂OC(=O)t-butyl | 1 | O | 5-Cl-benzothiophen-3-yl |
| 241 | 3,5-dimethoxy-phenyl | —CH₂OC(=O)t-butyl | —OCH₂OC(=O)t-butyl | 1 | O | 5-Cl-benzothiophen-3-yl |
| 242 | 2,5-difluoro-phenyl | —CH₂OC(=O)t-butyl | —OCH₂OC(=O)t-butyl | 1 | O | 5-Cl-benzothiophen-3-yl |
| 243 | 3,5-dichloro-phenyl | —CH₂OC(=O)t-butyl | —OCH₂OC(=O)t-butyl | 1 | O | 5-Cl-benzothiophen-3-yl |
| 244 | 2,4-difluoro-phenyl | —CH₂OC(=O)t-butyl | —OCH₂OC(=O)t-butyl | 1 | O | 5-Cl-benzothiophen-3-yl |
| 245 | 3-amino-phenyl | —CH₂OC(=O)t-butyl | —OCH₂OC(=O)t-butyl | 1 | O | 5-Cl-benzothiophen-3-yl |
| 246 | 2-methoxy-phenyl | —CH₂OC(=O)t-butyl | OH | 1 | O | 5-Cl-benzothiophen-3-yl |
| 247 | pyridin-2-yl | —CH₂OC(=O)t-butyl | OH | 1 | O | 5-Cl-benzothiophen-3-yl |
| 248 | 3-trifluoromethoxy-phenyl | —CH₂OC(=O)t-butyl | OH | 1 | O | 5-Cl-benzothiophen-3-yl |
| 249 | 3-methoxy-phenyl | —CH₂OC(=O)t-butyl | OH | 1 | O | 5-Cl-benzothiophen-3-yl |

TABLE I-continued (Ia)

| Cpd | R² | R⁵ | R⁶ | n | W | Z-R⁴ |
|---|---|---|---|---|---|---|
| 250 | 2,6-difluoro-phenyl | —CH₂OC(=O)t-butyl | OH | 1 | O | 5-Cl-benzothiophen-3-yl |
| 251 | 2-chloro-phenyl | —CH₂OC(=O)t-butyl | OH | 1 | O | 5-Cl-benzothiophen-3-yl |
| 252 | 3-chloro-phenyl | —CH₂OC(=O)t-butyl | OH | 1 | O | 5-Cl-benzothiophen-3-yl |
| 253 | 3,5-difluoro-phenyl | —CH₂OC(=O)t-butyl | OH | 1 | O | 5-Cl-benzothiophen-3-yl |
| 254 | 2,3-difluoro-phenyl | —CH₂OC(=O)t-butyl | OH | 1 | O | 5-Cl-benzothiophen-3-yl |
| 255 | 2-bromo-phenyl | —CH₂OC(=O)t-butyl | OH | 1 | O | 5-Cl-benzothiophen-3-yl |
| 256 | 2,3-dimethoxy-phenyl | —CH₂OC(=O)t-butyl | OH | 1 | O | 5-Cl-benzothiophen-3-yl |
| 257 | 3-nitro-phenyl | —CH₂OC(=O)t-butyl | OH | 1 | O | 5-Cl-benzothiophen-3-yl |
| 258 | 3-bromo-phenyl | —CH₂OC(=O)t-butyl | OH | 1 | O | 5-Cl-benzothiophen-3-yl |
| 259 | 3,5-dimethoxy-phenyl | —CH₂OC(=O)t-butyl | OH | 1 | O | 5-Cl-benzothiophen-3-yl |
| 260 | 2,5-difluoro-phenyl | —CH₂OC(=O)t-butyl | OH | 1 | O | 5-Cl-benzothiophen-3-yl |
| 261 | 3,5-dichloro-phenyl | —CH₂OC(=O)t-butyl | OH | 1 | O | 5-Cl-benzothiophen-3-yl |
| 262 | 2,4-difluoro-phenyl | —CH₂OC(=O)t-butyl | OH | 1 | O | 5-Cl-benzothiophen-3-yl |
| 263 | 3-amino-phenyl | —CH₂OC(=O)t-butyl | OH | 1 | O | 5-Cl-benzothiophen-3-yl |
| 264 | 2-methoxy-phenyl | —CH₂CH₂CH₂O— | | 1 | O | 5-Cl-benzothiophen-3-yl |
| 265 | pyridtn-2-yl | —CH₂CH₂CH₂O— | | 1 | O | 5-Cl-benzothiophen-3-yl |
| 266 | 3-trifluoromethoxy-phenyl | —CH₂CH₂CH₂O— | | 1 | O | 5-Cl-benzothiophen-3-yl |
| 267 | 3-methoxy-phenyl | —CH₂CH₂CH₂O— | | 1 | O | 5-Cl-benzothiophen-3-yl |
| 268 | 2,6-difluoro-phenyl | —CH₂CH₂CH₂O— | | 1 | O | 5-Cl-benzothiophen-3-yl |
| 269 | 2-chloro-phenyl | —CH₂CH₂CH₂O— | | 1 | O | 5-Cl-benzothiophen-3-yl |
| 270 | 3-chloro-phenyl | —CH₂CH₂CH₂O— | | 1 | O | 5-Cl-benzothiophen-3-yl |
| 271 | 3,5-difluoro-phenyl | —CH₂CH₂CH₂O— | | 1 | O | 5-Cl-benzothiophen-3-yl |
| 272 | 2,3-difluoro-phenyl | —CH₂CH₂CH₂O— | | 1 | O | 5-Cl-benzothiophen-3-yl |
| 273 | 2-bromo-phenyl | —CH₂CH₂CH₂O— | | 1 | O | 5-Cl-benzothiophen-3-yl |
| 274 | 2,3-dimethoxy-phenyl | —CH₂CH₂CH₂O— | | 1 | O | 5-Cl-benzothiophen-3-yl |
| 275 | 3-nitro-phenyl | —CH₂CH₂CH₂O— | | 1 | O | 5-Cl-benzothiophen-3-yl |
| 276 | 3-bromo-phenyl | —CH₂CH₂CH₂O— | | 1 | O | 5-Cl-benzothiophen-3-yl |
| 277 | 3,5-dimethoxy-phenyl | —CH₂CH₂CH₂O— | | 1 | O | 5-Cl-benzothiophen-3-yl |
| 278 | 2,5-difluoro-phenyl | —CH₂CH₂CH₂O— | | 1 | O | 5-Cl-benzothiophen-3-yl |
| 279 | 3,5-dichloro-phenyl | —CH₂CH₂CH₂O— | | 1 | O | 5-Cl-benzothiophen-3-yl |
| 280 | 2,4-difluoro-phenyl | —CH₂CH₂CH₂O— | | 1 | O | 5-Cl-benzothiophen-3-yl |
| 281 | 3-amino-phenyl | —CH₂CH₂CH₂O— | | 1 | O | 5-Cl-benzothiophen-3-yl |
| 282 | 2-methoxy-phenyl | —CH₂OC(=O)isopropyloxy | OH | 1 | O | 5-Cl-benzothiophen-3-yl |
| 283 | pyridin-2-yl | —CH₂OC(=O)isopropyloxy | OH | 1 | O | 5-Cl-benzothiophen-3-yl |
| 284 | 3-trifluoromethoxy-phenyl | —CH₂OC(=O)isopropyloxy | OH | 1 | O | 5-Cl-benzothiophen-3-yl |
| 285 | 3-methoxy-phenyl | —CH₂OC(=O)isopropyloxy | OH | 1 | O | 5-Cl-benzothiophen-3-yl |
| 286 | 2,6-difluoro-phenyl | —CH₂OC(=O)isopropyloxy | OH | 1 | O | 5-Cl-benzothiophen-3-yl |
| 287 | 2-chloro-phenyl | —CH₂OC(=O)isopropyloxy | OH | 1 | O | 5-Cl-benzothiophen-3-yl |
| 288 | 3-chloro-phenyl | —CH₂OC(=O)isopropyloxy | OH | 1 | O | 5-Cl-benzothiophen-3-yl |
| 289 | 3,5-difluoro-phenyl | —CH₂OC(=O)isopropyloxy | OH | 1 | O | 5-Cl-benzothiophen-3-yl |

TABLE I-continued

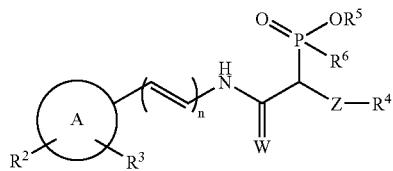

(Ia)

| Cpd | R² | R⁵ | R⁶ | n | W | Z-R⁴ |
|---|---|---|---|---|---|---|
| 290 | 2,3-difluoro-phenyl | —CH₂OC(=O)isopropyloxy | OH | 1 | O | 5-Cl-benzothiophen-3-yl |
| 291 | 2-bromo-phenyl | —CH₂OC(=O)isopropyloxy | OH | 1 | O | 5-Cl-benzothiophen-3-yl |
| 292 | 2,3-dimethoxy-phenyl | —CH₂OC(=O)isopropyloxy | OH | 1 | O | 5-Cl-benzothiophen-3-yl |
| 293 | 3-nitro-phenyl | —CH₂OC(=O)isopropyloxy | OH | 1 | O | 5-Cl-benzothiophen-3-yl |
| 294 | 3-bromo-phenyl | —CH₂OC(=O)isopropyloxy | OH | 1 | O | 5-Cl-benzothiophen-3-yl |
| 295 | 3,5-dimethoxy-phenyl | —CH₂OC(=O)isopropyloxy | OH | 1 | O | 5-Cl-benzothiophen-3-yl |
| 296 | 2,5-difluoro-phenyl | —CH₂OC(=O)isopropyloxy | OH | 1 | O | 5-Cl-benzothiophen-3-yl |
| 297 | 3,5-dichloro-phenyl | —CH₂OC(=O)isopropyloxy | OH | 1 | O | 5-Cl-benzothiophen-3-yl |
| 298 | 2,4-difluoro-phenyl | —CH₂OC(=O)isopropyloxy | OH | 1 | O | 5-Cl-benzothiophen-3-yl |
| 299 | 3-amino-phenyl | —CH₂OC(=O)isopropyloxy | OH | 1 | O | 5-Cl-benzothiophen-3-yl |
| 300 | 3-fluoro-5-chloro-phenyl | H | CH₃ | 1 | O | 5-Cl-benzothiophen-3-yl |
| 301 | 2-fluoro-3-chloro-phenyl | H | CH₃ | 1 | O | 5-Cl-benzothiophen-3-yl |
| 302 | 4-fluoro-3-chloro-phenyl | H | CH₃ | 1 | O | 5-Cl-benzothiophen-3-yl |
| 303 | 2-fluoro-5-chloro-phenyl | H | CH₃ | 1 | O | 5-Cl-benzothiophen-3-yl |
| 304 | 3,5-dibromo-phenyl | H | CH₃ | 1 | O | 5-Cl-benzothiophen-3-yl |
| 305 | 3-cyano-phenyl | H | CH₃ | 1 | O | 5-Cl-benzothiophen-3-yl |
| 306 | 2-cyano-phenyl | H | CH₃ | 1 | O | 5-Cl-benzothiophen-3-yl |
| 307 | 3-fluoro-5-trifluoromethyl-phenyl | H | CH₃ | 1 | O | 5-Cl-benzothiophen-3-yl |
| 308 | 3-fluoro-5-chloro-phenyl | H | OH | 1 | O | 5-Cl-benzothiophen-3-yl |
| 309 | 2-fluoro-3-chloro-phenyl | H | OH | 1 | O | 5-Cl-benzothiophen-3-yl |
| 310 | fluoro-3-chloro-phenyl | H | OH | 1 | O | 5-Cl-benzothiophen-3-yl |
| 311 | 2-fluoro-5-chloro-phenyl | H | OH | 1 | O | 5-Cl-benzothiophen-3-yl |
| 312 | 3,5-dibromo-phenyl | H | OH | 1 | O | 5-Cl-benzothiophen-3-yl |
| 313 | 3-cyano-phenyl | H | OH | 1 | O | 5-Cl-benzothiophen-3-yl |
| 314 | 2-cyano-phenyl | H | OH | 1 | O | 5-Cl-benzothiophen-3-yl |
| 315 | 3-fluoro-5-trifluoromethyl-phenyl | H | OH | 1 | O | 5-Cl-benzothiophen-3-yl |
| 316 | 3-fluoro-5-chloro-phenyl | —CH₂OC(=O)t-butyl | CH₃ | 1 | O | 5-Cl-benzothiophen-3-yl |
| 317 | 2-fluoro-3-chloro-phenyl | —CH₂OC(=O)t-butyl | CH₃ | 1 | O | 5-Cl-benzothiophen-3-yl |
| 318 | 4-fluoro-3-chloro-phenyl | —CH₂OC(=O)t-butyl | CH₃ | 1 | O | 5-Cl-benzothiophen-3-yl |
| 319 | 2-fluoro-5-chloro-phenyl | —CH₂OC(=O)t-butyl | CH₃ | 1 | O | 5-Cl-benzothiophen-3-yl |
| 320 | 3,5-dibromo-phenyl | —CH₂OC(=O)t-butyl | CH₃ | 1 | O | 5-Cl-benzothiophen-3-yl |
| 321 | 3-cyano-phenyl | —CH₂OC(=O)t-butyl | CH₃ | 1 | O | 5-Cl-benzothiophen-3-yl |
| 322 | 2-cyano-phenyl | —CH₂OC(=O)t-butyl | CH₃ | 1 | O | 5-Cl-benzothiophen-3-yl |
| 323 | 3-fluoro-5-trifluoromethyl-phenyl | —CH₂OC(=O)t-butyl | CH₃ | 1 | O | 5-Cl-benzothiophen-3-yl |

TABLE I-continued

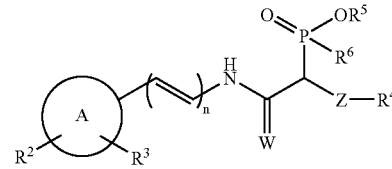

| Cpd | R² | R⁵ | R⁶ | n | W | Z-R⁴ |
|---|---|---|---|---|---|---|
| 324 | 3-fluoro-5-chloro phenyl | —CH₂OC(=O)t-butyl | —OCH₂OC(=O)t-butyl | 1 | O | 5-Cl-benzothiophen-3-yl |
| 325 | 2-fluoro-3-chloro phenyl | —CH₂OC(=O)t-butyl | —OCH₂OC(=O)t-butyl | 1 | O | 5-Cl-benzothiophen-3-yl |
| 326 | 4-fluoro-3-chloro phenyl | —CH₂OC(=O)t-butyl | —OCH₂OC(=O)t-butyl | 1 | O | 5-Cl-benzothiophen-3-yl |
| 327 | 2-fluoro-5-chloro-phenyl | —CH₂OC(=O)t-butyl | —OCH₂OC(=O)t-butyl | 1 | O | 5-Cl-benzothiophen-3-yl |
| 328 | 3,5-dibromo-phenyl | —CH₂OC(=O)t-butyl | —OCH₂OC(=O)t-butyl | 1 | O | 5-Cl-benzothiophen-3-yl |
| 329 | 3-cyano-phenyl | —CH₂OC(=O)t-butyl | —OCH₂OC(=O)t-butyl | 1 | O | 5-Cl-benzothiophen-3-yl |
| 330 | 2-cyano-phenyl | —CH₂OC(=O)t-butyl | —OCH₂OC(=O)t-butyl | 1 | O | 5-Cl-benzothiophen-3-yl |
| 331 | 3-fluoro-5-trifluoromethyl-phenyl | —CH₂OC(=O)t-butyl | —OCH₂OC(=O)t-butyl | 1 | O | 5-Cl-benzothiophen-3-yl |
| 332 | 3-fluoro-5-chloro phenyl | —CH₂OC(=O)t-butyl | OH | 1 | O | 5-Cl-benzothiophen-3-yl |
| 333 | 2-fluoro-3-chloro-phenyl | —CH₂OC(=O)t-butyl | OH | 1 | O | 5-Cl-benzothiophen-3-yl |
| 334 | 4-fluoro-3-chloro-phenyl | —CH₂OC(=O)t-butyl | OH | 1 | O | 5-Cl-benzothiophen-3-yl |
| 335 | 2-fluoro-5-chloro-phenyl | —CH₂OC(=O)t-butyl | OH | 1 | O | 5-Cl-benzothiophen-3-yl |
| 336 | 3,5-dibromo-phenyl | —CH₂OC(=O)t-butyl | OH | 1 | O | 5-Cl-benzothiophen-3-yl |
| 337 | 3-cyano-phenyl | —CH₂OC(=O)t-butyl | OH | 1 | O | 5-Cl-benzothiophen-3-yl |
| 338 | 2-cyano-phenyl | —CH₂OC(=O)t-butyl | OH | 1 | O | 5-Cl-benzothiophen-3-yl |
| 339 | 3-fluoro-5-trifluoromethyl-phenyl | —CH₂OC(=O)t-butyl | OH | 1 | O | 5-Cl-benzothiophen-3-yl |
| 340 | fluoro-5-chloro-phenyl | —CH₂CH₂CH₂O— | | 1 | O | 5-Cl-benzothiophen-3-yl |
| 341 | 2-fluoro-3-chloro-phenyl | —CH₂CH₂CH₂O— | | 1 | O | 5-Cl-benzothiophen-3-yl |
| 342 | 4-fluoro-3-chloro-phenyl | —CH₂CH₂CH₂O— | | 1 | O | 5-Cl-benzothiophen-3-yl |
| 343 | 2-fluoro-5-chloro-phenyl | —CH₂CH₂CH₂O— | | 1 | O | 5-Cl-benzothiophen-3-yl |
| 344 | 3,5-dibromo-phenyl | —CH₂CH₂CH₂O— | | 1 | O | 5-Cl-benzothiophen-3-yl |
| 345 | 3-cyano-phenyl | —CH₂CH₂CH₂O— | | 1 | O | 5-Cl-benzothiophen-3-yl |
| 346 | 2-cyano-phenyl | —CH₂CH₂CH₂O— | | 1 | O | 5-Cl-benzothiophen-3-yl |
| 347 | 3-fluoro-5-trifluoromethyl-phenyl | —CH₂CH₂CH₂O— | | 1 | O | 5-Cl-benzothiophen-3-yl |
| 348 | 3-fluoro-5-chloro-phenyl | —CH₂OC(=O)isopropyloxy | OH | 1 | O | 5-Cl-benzothiophen-3-yl |
| 349 | 2-fluoro-3-chloro-phenyl | —CH₂OC(=O)isopropyloxy | OH | 1 | O | 5-Cl-benzothiophen-3-yl |
| 350 | 4-fluoro-3-chloro-phenyl | —CH₂OC(=O)isopropyloxy | OH | 1 | O | 5-Cl-benzothiophen-3-yl |
| 351 | 2-fluoro-5-chloro-phenyl | —CH₂OC(=O)isopropyloxy | OH | 1 | O | 5-Cl-benzothiophen-3-yl |
| 352 | 3,5-dibromo-phenyl | —CH₂OC(=O)isopropyloxy | OH | 1 | O | 5-Cl-benzothiophen-3-yl |

TABLE I-continued (Ia)

| Cpd | R² | R⁵ | R⁶ | n | W | Z-R⁴ |
|---|---|---|---|---|---|---|
| 353 | 3-cyano-phenyl | —CH₂OC(=O)isopropyloxy | OH | 1 | O | 5-Cl-benzothiophen-3-yl |
| 354 | 2-cyano-phenyl | —CH₂OC(=O)isopropyloxy | OH | 1 | O | 5-Cl-benzothiophen-3-yl |
| 355 | 3-fluoro-5-trifluoromethyl-phenyl | —CH₂OC(=O)isopropyloxy | OH | 1 | O | 5-Cl-benzothiophen-3-yl |

Embodiments of the present invention include those compounds of Formula (II) own in Table II:

TABLE II (II)

| Cpd | Y |
|---|---|
| 50 | —SO₃H |
| 80 | —OC(=O)NH₂ |
| 84 | —CO₂H |
| 88 | (tetrazol-5-yl) |

TABLE II-continued (II)

| Cpd | Y |
|---|---|
| 120 | —CH₂OSO₂NH₂ |
| 136 | —CH₂OH |

Preferred embodiments of the phosphonic and phosphinic acids of the present invention include those compounds of Formula (Ib) wherein the substituents are as previously defined (including any combinations of the preferred embodiments). Examples of some of these embodiments are shown in Table III:

TABLE III (Ib)

| Cpd | | R⁶ | Z-R⁴ |
|---|---|---|---|
| 1 | naphthalen-2-yl | CH₃ | 5-Cl-N-methyl-indol-3-yl |
| 3 | naphthalen-2-yl | OH | 5-Cl-N-methyl-indol-3-yl |

TABLE III-continued (Ib)

| Cpd | (R² a¹ a² R³) | R⁶ | Z-R⁴ |
|---|---|---|---|
| 5 | naphthalen-2-yl | OH | 5-Me-benzothiophen-2-yl |
| 8 | 4-{[1-(naphthalen-2-carbonyl)-piperidin-4-ylcarbonyl]-amino}-naphthalen-2-yl | OH | naphthalen-1-yl |
| 9 | naphthalen-2-yl | OH | 5-Cl-benzothiophen-3-yl |
| 10 | naphthalen-2-yl | OH | 5-F-benzothiophen-3-yl |
| 11 | naphthalen-2-yl | OH | 5-F-N-methyl-indol-3-yl |
| 13 | naphthalen-2-yl | OH | 5-Br-N-methyl-indol-3-yl |
| 20 | naphthalen-2-yl | $CH_3$ | 5-Cl-benzothiophen-3-yl |
| 22 | naphthalen-2-yl | H | N-methyl-indol-3-yl |
| 23 | naphthalen-2-yl | H | 5-Br-benzothiophen-3-yl |
| 26 | naphthalen-2-yl | OH | benzothiophen-3-yl |
| 27 | naphthalen-2-yl | OH | N-(3-phenyl-allyl)-indol-3-yl |
| 28 | naphthalen-2-yl | $CH_2CH_3$ | 5-Cl-benzothiophen-3-yl |
| 30 | benzothiazol-6-yl | OH | 5-Cl-benzothiophen-3-yl |
| 31 | naphthalen-2-yl | OH | naphthalen-1-yl |
| 32 | naphthalen-2-yl | $CH_3$ | 2-(4-phenyl-piperidine-1-carbonyl)-benzothiophen-3-yl |
| 33 | naphthalen-2-yl | $CH_3$ | naphthalen-1-yl |
| 34 | naphthalen-2-yl | 3-methoxy-propyl | 5-Cl-benzothiophen-3-yl |
| 35 | naphthalen-2-yl | $CH_3$ | 2-(4-(4-methoxyphenyl)-piperidin-1-ylcarbonyl)-benzothiophen-3-yl |
| 36 | naphthalen-2-yl | phenethyl | 5-Cl-benzothiophen-3-yl |
| 39 | naphthalen-2-yl | 3-(benzo[1,3]dioxol-5-yl)-propyl | 5-Cl-benzothiophen-3-yl |
| 40 | naphthalen-2-yl | 3-(naphthylen-1yl)propyl | 5-Cl-benzothiophen-3-yl |
| 41 | naphthalen-2-yl | $CH_3$ | 2-(4-(Benzyloxycarbonyl)-piperazin-1-ylcarbonyl))-benzothiophen-3-yl |
| 43 | naphthalen-2-yl | 3-(4-hydroxy phenyl)propyl | 5-Cl-benzothiophen-3-yl |
| 44 | 3-((benzoyl-piperidin-4-yl amino)-methyl)-naphthalen-2-yl | OH | naphthalen-1-yl |
| 45 | naphthalen-2-yl | OH | 5-Cl-benzothiophen-3-yl |
| 46 | 3-((1-phenyl)-cyclohex-1-enyl-4-N-methylamino-carbonyl)]-naphthalen-2-yl | OH | naphthalen-1-yl |
| 47 | naphthalen-2-yl | $CH_3$ | 2-((4-F-phenyl)-piperidin-1-ylcarbonyl)-benzothiophen-3-yl |
| 48 | naphthalen-2-yl | (3-phenyl)propyl | 5-Cl-benzothiophen-3-yl |
| 51 | naphthalen-2-yl | (4-phenyl)butyl | 5-Cl-benzothiophen-3-yl |
| 52 | naphthalen-2-yl | OH | 6-Cl-N-methyl-indol-3-yl |
| 53 | naphthalen-2-yl | 3-(4-methoxy phenyl)propyl | 5-Cl-benzothiophen-3-yl |
| 54 | 3-[4-((3-phenethyl)-pyrrolidin-1 ylcarbonyl)]-naphthalen-2-yl | OH | naphthalen-1-yl |
| 55 | benzothiophen-5-yl | OH | 5-Cl-benzothiophen-3-yl |
| 56 | naphthalen-2-yl | OH | 5-carboxy-N-Me-indol-3-yl- |
| 57 | quinolin-3-yl | OH | naphthalen-1-yl |

TABLE III-continued (Ib)

| Cpd | a¹–a² (R², R³) | R⁶ | Z–R⁴ |
|---|---|---|---|
| 58 | naphthalen-2-yl | OH | 7-Cl-N-methyl-indol-3-yl |
| 59 | benzo[b]thiophen-6-yl | OH | naphthalen-1-yl |
| 60 | 3-[4-(6-Chloro-2-oxo-2,3-dihydro-benzoimidazol-1-yl)-piperidin-1-ylcarbonyl]-naphthalen-2-yl | OH | naphthalen-1-yl |
| 61 | p-biphenyl | OH | naphthalen-1-yl |
| 62 | naphthalen-2-yl | OH | N-cyclopropylmethyl-indol-3-yl |
| 63 | naphthalen-2-yl | OH | 4-Cl-N-methyl-indol-3-yl |
| 64 | benzothiophen-2-yl | OH | naphthalen-1-yl |
| 65 | naphthalen-2-yl | OH | 5-cyano-N-methyl-indol-3-yl |
| 67 | (6-Br)-naphthalen-2-yl | OH | 5-Cl-benzothiophen-3-yl |
| 68 | naphthalen-2-yl | OH | Indol-3-yl |
| 69 | 2-amino-benzothiazol-6-yl | OH | 5-Cl-benzothiophen-3-yl |
| 70 | 3-(cyclohexylamino)methyl-naphthalen-2-yl | OH | naphthalen-1-yl |
| 71 | naphthalen-2-yl | OH | 5-Ph-benzothiophen-3-yl |
| 72 | 3-(N-benzyl-aminocarbonyloxy methyl) naphthalen-2-yl | OH | naphthalen-1-yl |
| 73 | 3-(pyridin-4-yl-pyrrolidin-1-ylcarbonyl)-naphthalen-2-yl | OH | naphthalen-1-yl |
| 74 | naphthalen-2-yl | OH | 5-methoxy-N-methyl-indol-3-yl |
| 75 | 3-(methoxycarbonyl)-naphthalen-2-yl | OH | naphthalen-1-yl |
| 76 | naphthalen-2-yl | OH | 6-Br-benzothiophen-3-yl |
| 77 | naphthalen-2-yl | OH | N-isopropyl-indol-3-yl |
| 79 | quinolin-6-yl | OH | naphthalen-1-yl |
| 82 | naphthalen-2-yl | OH | N-phenyl-indol-3-yl |
| 83 | (4-(1H-indol-3-yl)-piperidin-1-ylcarbonyl)-naphthalen-2-yl | OH | naphthalen-1-yl |
| 85 | Indanyl | OH | naphthalen-1-yl |
| 86 | naphthalen-2-yl | OH | 5-Cl-1,1-dioxo-benzothiophen-3-yl |
| 87 | ((3-phenyl)pyrrolidin-1-ylcarbonyl)-naphthalen-2-yl | OH | naphthalen-1-yl |
| 89 | naphthalen-2-yl | Ph | 5-Cl-benzothiophen-3-yl |
| 90 | ((3-methyl)-cyclohexyl-amino)methyl-naphthalen-2-yl | OH | naphthalen-1-yl |
| 91 | 3-(cyclopentyl-N-methylamino-carbonyl)-naphthalen-2-yl | OH | naphthalen-1-yl |
| 92 | 3-((Hexanoic acid methyl ester)aminomethyl)-naphthalen-2-yl | OH | naphthalen-1-yl |
| 93 | 3-(4-(2-oxo-2,3-dihydro-benzoimidazol-1-yl)-piperidin-1-ylcarbonyl)-naphthalen-2-yl | OH | naphthalen-1-yl |
| 94 | 3-(phenyl-aminocarbonyloxy)-methyl)-naphthalen-2-yl | OH | naphthalen-1-yl |
| 95 | 3-(phenyl-aminocarbonyl)-methyl-naphthalen-2-yl | OH | naphthalen-1-yl |
| 96 | quinolin-2-yl | OH | naphthalen-1-yl |
| 97 | 3-((4-phenoxy-phenyl)-aminocarbonyloxymethyl)-naphthalen-2-yl | OH | naphthalen-1-yl |
| 98 | naphthalen-2-yl | OH | 5-(4-F-phenyl)-N-methyl-indol-3-yl |
| 99 | naphthalen-2-yl | OH | 4-Br-benzothiophen-3-yl |
| 100 | 3-[(4-benzotriazol-1-yl-piperidin-1-ylcarbonyl)]-naphthalen-2-yl | OH | naphthalen-1-yl |

TABLE III-continued (Ib)

| Cpd | R³ substituent | R⁶ | Z-R⁴ |
|---|---|---|---|
| 101 | 3-(4-phenyl)-piperidin-1-ylcarbonyl)-naphthalen-2-yl | OH | naphthalen-1-yl |
| 102 | 3-((naphthalene-2-carbonyl)-piperidin-4-ylmethylamino-methyl)-naphthalen-2-yl | OH | naphthalen-1-yl |
| 103 | 3-((3-benzenesulfonyl)-pyrrolidin-1-ylcarbonyl)-naphthalen-2-yl | OH | naphthalen-1-yl |
| 104 | 3-(N-[3-(4-oxo-1-phenyl-1,3,8-triaza-spiro[4.5]decane-8-carbonyl)-naphthalen-2-yl | OH | naphthalen-1-yl |
| 105 | 3-(naphthalen-2-ylaminocarbonyloxy-methyl)-naphthalen-2-yl | OH | naphthalen-1-yl |
| 106 | 2-fluorenyl | OH | naphthalen-1-yl |
| 107 | 3-(benzylaminomethyl)-naphthalen-2-yl | OH | naphthalen-1-yl |
| 108 | (3-OH)naphthalen-2-yl | OH | naphthalen-1-yl |
| 109 | 3-(N-benzyl-3-acrylamide)naphthalen-2-yl | OH | naphthalen-1-yl |
| 110 | 3-((5-phenyl)pentylamino)-naphthalen-2-yl | OH | naphthalen-1-yl |
| 111 | 3-(N-benzyl-N-methyl-amino-carbonyl)-naphthalen-2-yl | OH | naphthalen-1-yl |
| 112 | 3-[[5H-dibenzo[a,d]cyclohepten-5-yl)-propyl]-methyl-amino-methyl-naphthalen-2-yl | OH | naphthalen-1-yl |
| 113 | 3-(4-(benzothiazol-2-yl-piperidine-1-carbonyl))-naphthalen-2-yl | OH | naphthalen-1-yl |
| 114 | 1-(2-oxo-2-(4-phenyl-piperidin-1-yl)-ethoxy)-naphthalen-2-yl | OH | naphthalen-1-yl |
| 115 | 3-[2-(3,4-dimethoxy-phenyl)-ethyl]-N-methyl-aminocarbonyl)-naphthalen-2-yl | OH | naphthalen-1-yl |
| 116 | naphthaten-2-yl | OH | 1-Me-1H-pyrrolo[2,3-b]pyridine |
| 117 | 3-((4-OH-cyclohexylamino)-methyl)-naphthalen-2-yl | OH | naphthalen-1-yl |
| 118 | naphthalen-2-yl | CH₃ | 2-carboxy-benzothiophen-3-yl |
| 119 | 3-(benzylaminocarbonyl)-naphthalen-2-yl | OH | naphthalen-1-yl |
| 121 | 3-(3-phenyl-allyloxy)-naphthalen-2-yl | OH | naphthalen-1-yl |
| 122 | 3-(benzyloxy)-naphthalen-2-yl | OH | naphthalen-1-yl |
| 123 | 3-(methoxycarbonyl-methoxy)-naphthalen-2-yl | OH | naphthalen-1-yl |
| 124 | 3-cyclopentylamino-methyl)-naphthalen-2-yl | OH | naphthalen-1-yl |
| 125 | naphthalen-2-yl | OH | 5-Cl-benzothiophen-2-yl |
| 126 | 3-(phenethyl-methylamino-methyl)naphthalen-2-yl | OH | naphthalen-1-yl |
| 127 | naphthalen-2-yl | CH₃ | 2-(benzylaminocarbonyl)-benzothiophen-3-yl |
| 128 | naphthalen-2-yl | OH | N-phenyl-indol-4-yl |
| 129 | indol-5-yl | OH | naphthalen-1-yl |
| 130 | 3-(3-phenyl-propylcarbamoyl)-methoxy)-naphthalen-2-yl | OH | naphthalen-1-yl |
| 131 | 3-(2-phenyl-pyrrolidin-1-ylcarbonyl)-naphthalen-2-yl | OH | naphthalen-1-yl |
| 132 | 3-amino-naphthalen-2-yl | OH | naphthalen-1-yl |

TABLE III-continued (Ib)

| Cpd | R² a¹ a² R³ | R⁶ | Z-R⁴ |
|---|---|---|---|
| 133 | 3-((5-hydroxypentylamino)-methyl)-naphthalen-2-yl | OH | naphthalen-1-yl |
| 134 | 1-(1-oxy-acetic acid methyl ester)-naphthalen-2-yl | OH | naphthalen-1-yl |
| 135 | benzo[1,3]dioxolyl | OH | naphthalen-1-yl |
| 137 | isoquinolin-3-yl | OH | naphthalen-1-yl |
| 138 | 3-phenoxy-phenyl | OH | naphthalen-1-yl |
| 139 | 3-(isopropyloxycarbonyl)-naphthalen-2-yl | OH | naphthalen-1-yl |
| 140 | naphthalen-2-yl | OH | benzothiophen-2-yl |
| 141 | 3-{(1-(naphthalen-2-ylcarbonyl)-piperidin-4-ylcarbonyl]-amino}-naphthalen-2-yl | OH | naphthalen-1-yl |
| 142 | 3-(benzylmethyl aminomethyl)-naphthalen-2-yl | OH | naphthalen-1-yl |
| 143 | naphthalen-2-yl | OH | 6-(4-butylphenyl)-benzothiophen-3-yl |
| 146 | benzofuran-2-yl | CH₃ | 5-Cl-benzothiophen-3-yl |

Preferred embodiments of the phosphonic and phosphinic acids of the present invention include those compounds of Formula (Ic) shown in Table IV:

TABLE IV (Ic)

| Cpd | R³ | R⁵ | R⁶ | Z—R⁴ |
|---|---|---|---|---|
| 2 | 3,4-difluoro-phenyl | H | OH | 5-Cl-benzothiophen-3-yl |
| 4 | 4-fluoro-phenyl | H | OH | 5-Cl-N-methyl-indol-3-yl |
| 6 | 3-fluoro-phenyl | H | CH₃ | 5-Cl-N-methyl-indol-3-yl |
| 7 | 3,4-difluoro-phenyl | H | CH₃ | 5-Cl-N-methyl-indol-3-yl |
| 12 | 4-amino-phenyl | H | OH | 5-Cl-benzothiophen-3-yl |
| 14 | phenyl | H | CH₃ | 5-Cl-benzothiophen-3-yl |
| 15 | 3-fluoro-phenyl | H | CH₃ | 5-Cl-benzothiophen-3-yl |
| 16 | 3,4-trifluoro-phenyl | H | CH₃ | 5-Cl-benzothiophen-3-yl |
| 17 | 3,4-difluoro-phenyl | H | CH₃ | 5-Cl-benzothiophen-3-yl |
| 18 | phenyl | H | OH | 5-Cl-benzothiophen-2-yl |
| 19 | 4-fluoro-phenyl | H | OH | 5-Cl-benzothiophen-3-yl |
| 21 | 2-fluoro-phenyl | H | CH₃ | 5-Cl-benzothiophen-3-yl |
| 24 | 4-fluoro-phenyl | H | CH₃ | 5-Cl-benzothiophen-3-yl |
| 25 | pyridin-3-yl | H | OH | 5-Cl-benzothiophen-3-yl |
| 29 | 3,4-difluoro-phenyl | H | CH₂CH₃ | 5-Cl-benzothiophen-3-yl |
| 37 | phenyl | H | OH | naphthalen-1-yl |
| 38 | 4-methoxy-phenyl | H | OH | 5-Cl-benzothiophen-3-yl |
| 42 | 4-methyl-phenyl | H | OH | 5-Cl-benzothiophen-2-yl |
| 49 | 3,4-dimethoxy-phenyl | H | OH | 5-Cl-benzothiophen-3-yl |
| 66 | 4-hydroxy-phenyl | H | OH | 5-Cl-benzothiophen-3-yl |

TABLE IV-continued (Ic)

$$\text{R}^3-a^2-\overset{H}{N}-\underset{O}{C}-\overset{R^6}{\underset{Z-R^4}{C}}-\overset{O}{\underset{OR^5}{P}}$$

| Cpd | a²  R³ | R⁵ | R⁶ | Z—R⁴ |
|---|---|---|---|---|
| 78 | 4-chloro-phenyl | H | CH₃ | 5-Cl-benzothiophen-3-yl |
| 81 | 4-trifluoromethyl-phenyl | H | OH | 5-Cl-benzothiophen-3-yl |
| 145 | 2-methoxy-phenyl | H | CH₃ | 5-Cl-benzothiophen-3-yl |
| 146 | benzofuran-2-yl | H | CH₃ | 5-Cl-benzothiophen-3-yl |
| 147 | 2-nitro-phenyl | H | CH₃ | 5-Cl-benzothiophen-3-yl |
| 148 | 2-methylcarbonyloxy-phenyl | H | CH₃ | 5-Cl-benzothiophen-3-yl |
| 149 | 2-hydroxy-phenyl | H | CH₃ | 5-Cl-benzothiophen-3-yl |
| 150 | pyridin-2-yl | H | CH₃ | 5-Cl-benzothiophen-3-yl |
| 151 | 2-amino-phenyl | H | CH₃ | 5-Cl-benzothiophen-3-yl |
| 152 | 3-trifluoromethyl-phenyl | H | CH₃ | 5-Cl-benzothiophen-3-yl |
| 153 | 3-trifluoromethoxy-phenyl | H | CH₃ | 5-Cl-benzothiophen-3-yl |
| 154 | 3-methoxy-phenyl | H | CH₃ | 5-Cl-benzothiophen-3-yl |
| 155 | 2-methyl-phenyl | H | CH₃ | 5-Cl-benzothiophen-3-yl |
| 156 | 2,6-difluoro-phenyl | H | CH₃ | 5-Cl-benzothiophen-3-yl |
| 157 | 4-cyano-phenyl | H | CH₃ | 5-Cl-benzothiophen-3-yl |
| 158 | 2-ureido-phenyl | H | CH₃ | 5-Cl-benzothiophen-3-yl |
| 159 | 2-(NHO(=O))₂NH₂-phenyl | H | CH₃ | 5-Cl-benzothiophen-3-yl |
| 160 | 2-chloro-phenyl | H | CH₃ | 5-Cl-benzothiophen-3-yl |
| 161 | 3-chloro-phenyl | H | CH₃ | 5-Cl-benzothiophen-3-yl |
| 162 | 3,5-difluoro-phenyl | H | CH₃ | 5-Cl-benzothiophen-3-yl |
| 163 | 2,3-difluoro-phenyl | H | CH₃ | 5-Cl-benzothiophen-3-yl |
| 164 | 2-bromo-phenyl | H | CH₃ | 5-Cl-benzothiophen-3-yl |
| 165 | 2,3-dimethoxy-phenyl | H | CH₃ | 5-Cl-benzothiophen-3-yl |
| 166 | 3-nitro-phenyl | H | CH₃ | 5-Cl-benzothiophen-3-yl |
| 167 | 3-bromo-phenyl | H | CH₃ | 5-Cl-benzothiophen-3-yl |
| 168 | 3,5-dimethoxy-phenyl | H | CH₃ | 5-Cl-benzothiophen-3-yl |
| 169 | 2,5-difluoro-phenyl | H | CH₃ | 5-Cl-benzothiophen-3-yl |
| 170 | 3,5-dichloro-phenyl | H | CH₃ | 5-Cl-benzothiophen-3-yl |
| 171 | 2,4-difluoro-phenyl | H | CH₃ | 5-Cl-benzothiophen-3-yl |
| 172 | 3-amino-phenyl | H | CH₃ | 5-Cl-benzothiophen-3-yl |
| 173 | phenyl | —CH₂C(Me)₂CH₂O— | | naphthalen-1-yl |
| 174 | phenyl | 3-methoxy-prop-1-yl | OH | naphthalen-1-yl |
| 175 | phenyl | 3-methoxy-prop-1-yl | 3-methoxy-prop-1-yl-oxy | naphthalen-1-yl |
| 176 | phenyl | 2-(1,3-dioxolan-2-yl)-eth-1-yl | OH | naphthalen-1-yl |
| 177 | phenyl | —CH₂OC(=O)t-butyl | OH | naphthalen-1-yl |
| 178 | phenyl | —CH₂CH₂CH₂O— | | naphthalen-1-yl |
| 179 | phenyl | (2-dimethylamino)-eth-1-yl | 2-dimethyl amino-ethoxy | naphthalen-1-yl |
| 180 | phenyl | —CH₂C(=O)NEt₂ | —OCH₂C(=O)NEt₂ | naphthalen-1-yl |
| 181 | phenyl | —(CH₂)₂SC(=O)t-butyl | —O(CH₂)₂SC(=O)t-butyl | naphthalen-1-yl |
| 182 | 3,4-difluoro-phenyl | 1-CH₂OC(=O)t-butyl | CH₃ | 5-Cl-benzothiophen-3-yl |
| 183 | 3,4-difluoro-phenyl | (2-dimethylamino)-eth-1-yl | CH₃ | 5-Cl-benzothiophen-3-yl |
| 184 | 3,4-difluoro-phenyl | (2-amino)-eth-1-yl | CH₃ | 5-Cl-benzothiophen-3-yl |
| 185 | 3,4-difluoro-phenyl | —CH₂C(=O)NEt₂ | CH₃ | 5-Cl-benzothiophen-3-yl |
| 186 | 3,4-difluoro-phenyl | —CH₂OC(=O)t-butyl | —OCH₂OC(=O)t-butyl | 5-Cl-benzothiophen-3-yl |
| 187 | 3,4-difluoro-phenyl | —CH₂OC(=O)t-butyl) | OH | 5-Cl-benzothiophen-3-yl |
| 188 | 3,4-difluoro-phenyl | —CH₂C(=O)NEt₂ | —OCH₂C(=O)NEt₂ | 5-Cl-benzothiophen-3-yl |

TABLE IV-continued (Ic)

| Cpd | a², R³ | R⁵ | R⁶ | Z—R⁴ |
|---|---|---|---|---|
| 189 | 3,4-difluoro-phenyl | —CH₂CH₂CH₂O— | | 5-Cl-benzothiophen-3-yl |
| 190 | 3,4-difluoro-phenyl | —CH₂OC(=O) methyl | OH | 5-Cl-benzothiophen-3-yl |
| 191 | 3,4-difluoro-phenyl | —CH₂OC(=O) isopropyloxy | OH | 5-Cl-benzothiophen-3-yl |
| 192 | 2-methoxy-phenyl | H | OH | 5-Cl-benzothiophen-3-yl |
| 193 | pyridin-2-yl | H | OH | 5-Cl-benzothiophen-3-yl |
| 194 | 3-trifluoromethoxy-phenyl | H | OH | 5-Cl-benzothiophen-3-yl |
| 195 | 3-methoxy-phenyl | H | OH | 5-Cl-benzothiophen-3-yl |
| 196 | 2,6-difluoro-phenyl | H | OH | 5-Cl-benzothiophen-3-yl |
| 197 | 2-chloro-phenyl | H | OH | 5-Cl-benzothiophen-3-yl |
| 198 | 3-chloro-phenyl | H | OH | 5-Cl-benzothiophen-3-yl |
| 199 | 3,5-difluoro-phenyl | H | OH | 5-Cl-benzothiophen-3-yl |
| 200 | 2,3-difluoro-phenyl | H | OH | 5-Cl-benzothiophen-3-yl |
| 201 | 2-bromo-phenyl | H | OH | 5-Cl-benzothiophen-3-yl |
| 202 | 2,3-dimethoxy-phenyl | H | OH | 5-Cl-benzothiophen-3-yl |
| 203 | 3-nitro-phenyl | H | OH | 5-Cl-benzothiophen-3-yl |
| 204 | 3-bromo-phenyl | H | OH | 5-Cl-benzothiophen-3-yl |
| 205 | 3,5-dimethoxy-phenyl | H | OH | 5-Cl-benzothiophen-3-yl |
| 206 | 2,5-difluoro-phenyl | H | OH | 5-Cl-benzothiophen-3-yl |
| 207 | 3,5-dichloro-phenyl | H | OH | 5-Cl-benzothiophen-3-yl |
| 208 | 2,4-difluoro-phenyl | H | OH | 5-Cl-benzothiophen-3-yl |
| 209 | 3-amino-phenyl | H | OH | 5-Cl-benzothiophen-3-yl |
| 210 | 2-methoxy-phenyl | —CH₂OC(=O) t-butyl | CH₃ | 5-Cl-benzothiophen-3-yl |
| 211 | pyridin-2-yl | —CH₂OC(=O) t-butyl | CH₃ | 5-Cl-benzothiophen-3-yl |
| 212 | 3-trifluoromethoxy phenyl | —CH₂OC(=O) t-butyl | CH₃ | 5-Cl-benzothiophen-3-yl |
| 213 | 3-methoxy-phenyl | —CH₂OC(=O) t-butyl | CH₃ | 5-Cl-benzothiophen-3-yl |
| 214 | 2,6-difluoro-phenyl | —CH₂OC(=O) t-butyl | CH₃ | 5-Cl-benzothioph,en-3-yl |
| 215 | 2-chloro-phenyl | —CH₂OC(=O) t-butyl | CH₃ | 5-Cl-benzothiophen-3-yl |
| 216 | 3-chloro-phenyl | —CH₂OC(=O) t-butyl | CH₃ | 5-Cl-benzothiophen-3-yl |
| 217 | 3,5-difluoro-phenyl | —CH₂OC(=O) t-butyl | CH₃ | 5-Cl-benzothiophen-3-yl |
| 218 | 2,3-difluoro-phenyl | —CH₂OC(=O) t-butyl | CH₃ | 5-Cl-benzothiophen-3-yl |
| 219 | 2-bromo-phenyl | —CH₂OC(=O) t-butyl | CH₃ | 5-Cl-benzothiophen-3-yl |
| 220 | 2,3-dimethoxy-phenyl | —CH₂OC(=O) t-butyl | CH₃ | 5-Cl-benzothiophen-3-yl |
| 221 | 3-nitro-phenyl | —CH₂OC(=O) t-butyl | CH₃ | 5-Cl-benzothiophen-3-yl |
| 222 | 3-bromo-phenyl | —CH₂OC(=O) t-butyl | CH₃ | 5-Cl-benzothiophen-3-yl |
| 223 | 3,5-dimethoxy-phenyl | —CH₂OC(=O) t-butyl | CH₃ | 5-Cl-benzothiophen-3-yl |
| 224 | 2,5-difluoro-phenyl | —CH₂OC(=O) t-butyl | CH₃ | 5-Cl-benzothiophen-3-yl |
| 225 | 3,5-dichloro-phenyl | —CH₂OC(=O) t-butyl | CH₃ | 5-Cl-benzothiophen-3-yl |
| 226 | 2,4-difluoro-phenyl | —CH₂OC(=O) t-butyl | CH₃ | 5-Cl-benzothiophen-3-yl |
| 227 | 3-amino-phenyl | —CH₂OC(=O) t-butyl | CH₃ | 5-Cl-benzothiophen-3-yl |
| 228 | 2-methoxy-phenyl | —CH₂OC(=O) t-butyl | —OCH₂OC(=O) t-butyl | 5-Cl-benzothiophen-3-yl |

TABLE IV-continued (Ic)

| Cpd | a² R³ | R⁵ | R⁶ | Z—R⁴ |
|---|---|---|---|---|
| 229 | pyridin-2-yl | —CH₂OC(=O)t-butyl | —OCH₂OC(=O)t-butyl | 5-Cl-benzothiophen-3-yl |
| 230 | 3-trifluoromethoxy phenyl | —CH₂OC(=O)t-butyl | —OCH₂OC(=O)t-butyl | 5-Cl-benzothiophen-3-yl |
| 231 | 3-methoxy-phenyl | —CH₂OC(=O)t-butyl | —OCH₂OC(=O)t-butyl | 5-Cl-benzothiophen-3-yl |
| 232 | 2,6-difluoro-phenyl | —CH₂OC(=O)t-butyl | —OCH₂OC(=O)t-butyl | 5-Cl-benzothiophen-3-yl |
| 233 | 2-chloro-phenyl | —CH₂OC(=O)t-butyl | —OCH₂OC(=O)t-butyl | 5-Cl-benzothiophen-3-yl |
| 234 | 3-chloro-phenyl | —CH₂OC(=O)t-butyl | —OCH₂OC(=O)t-butyl | 5-Cl-benzothiophen-3-yl |
| 235 | 3,5-difluoro-phenyl | —CH₂OC(=O)t-butyl | —OCH₂OC(=O)t-butyl | 5-Cl-benzothiophen-3-yl |
| 236 | 2,3-difluoro-phenyl | —CH₂OC(=O)t-butyl | —OCH₂OC(=O)t-butyl | 5-Cl-benzothiophen-3-yl |
| 237 | 2-bromo-phenyl | —CH₂OC(=O)t-butyl | —OCH₂OC(=O)t-butyl | 5-Cl-benzothiophen-3-yl |
| 238 | 2,3-dimethoxy-phenyl | —CH₂OC(=O)t-butyl | —OCH₂OC(=O)t-butyl | 5-Cl-benzothiophen-3-yl |
| 239 | 3-nitro-phenyl | —CH₂OC(=O)t-butyl | —OCH₂OC(=O)t-butyl | 5-Cl-benzothiophen-3-yl |
| 240 | 3-bromo-phenyl | —CH₂OC(=O)t-butyl | —OCH₂OC(=O)t-butyl | 5-Cl-benzothiophen-3-yl |
| 241 | 3,5-dimethoxy-phenyl | —CH₂OC(=O)t-butyl | —OCH₂OC(=O)t-butyl | 5-Cl-benzothiophen-3-yl |
| 242 | 2,5-difluoro-phenyl | —CH₂OC(=O)t-butyl | —OCH₂OC(=O)t-butyl | 5-Cl-benzothiophen-3-yl |
| 243 | 3,5-dichloro-phenyl | —CH₂OC(=O)t-butyl | —OCH₂OC(=O)t-butyl | 5-Cl-benzothiophen-3-yl |
| 244 | 2,4-difluoro-phenyl | —CH₂OC(=O)t-butyl | —OCH₂OC(=O)t-butyl | 5-Cl-benzothiophen-3-yl |
| 245 | 3-amino-phenyl | —CH₂OC(=O)t-butyl | —OCH₂OC(=O)t-butyl | 5-Cl-benzothiophen-3-yl |
| 246 | 2-methoxy-phenyl | —CH₂OC(=O)t-butyl | OH | 5-Cl-benzothiophen-3-yl |
| 247 | pyridin-2-yl | —CH₂OC(=O)t-butyl | OH | 5-Cl-benzothiophen-3-yl |
| 248 | 3-trifluoromethoxy phenyl | —CH₂OC(=O)t-butyl | OH | 5-Cl-benzothiophen-3-yl |
| 249 | 3-methoxy-phenyl | —CH₂OC(=O)t-butyl | OH | 5-Cl-benzothiophen-3-yl |
| 250 | 2,6-difluoro-phenyl | —CH₂OC(=O)t-butyl | OH | 5-Cl-benzothiophen-3-yl |
| 251 | 2-chloro-phenyl | —CH₂OC(=O)t-butyl | OH | 5-Cl-benzothiophen-3-yl |
| 252 | 3-chloro-phenyl | —CH₂OC(=O)t-butyl | OH | 5-Cl-benzothiophen-3-yl |

TABLE IV-continued

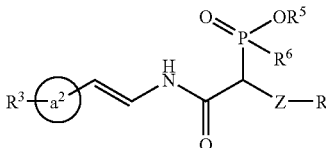

(Ic)

| Cpd | a²<br>R³ | R⁵ | R⁶ | Z—R⁴ |
|---|---|---|---|---|
| 253 | 3,5-difluoro-phenyl | —CH₂OC(=O)t-butyl | OH | 5-Cl-benzothiophen-3-yl |
| 254 | 2,3-difluoro-phenyl | —CH₂OC(=O)t-butyl | OH | 5-Cl-benzothiophen-3-yl |
| 255 | 2-bromo-phenyl | —CH₂OC(=O)t-butyl | OH | 5-Cl-benzothiophen-3-yl |
| 256 | 2,3-dimethoxy-phenyl | —CH₂OC(=O)t-butyl | OH | 5-Cl-benzothiophen-3-yl |
| 257 | 3-nitro-phenyl | —CH₂OC(=O)t-butyl | OH | 5-Cl-benzothiophen-3-yl |
| 258 | 3-bromo-phenyl | —CH₂OC(=O)t-butyl | OH | 5-Cl-benzothiophen-3-yl |
| 259 | 3,5-dimethoxy-phenyl | —CH₂OC(=O)t-butyl | OH | 5-Cl-benzothiophen-3-yl |
| 260 | 2,5-difluoro-phenyl | —CH₂OC(=O)t-butyl | OH | 5-Cl-benzothiophen-3-yl |
| 261 | 3,5-dichloro-phenyl | —CH₂OC(=O)t-butyl | OH | 5-Cl-benzothiophen-3-yl |
| 262 | 2,4-difluoro-phenyl | —CH₂OC(=O)t-butyl | OH | 5-Cl-benzothiophen-3-yl |
| 263 | 3-amino-phenyl | —CH₂OC(=O)t-butyl | OH | 5-Cl-benzothiophen-3-yl |
| 264 | 2-methoxy-phenyl | —CH₂CH₂CH₂O— | | 5-Cl-benzothiophen-3-yl |
| 265 | pyridin-2-yl | —CH₂CH₂CH₂O— | | 5-Cl-benzothiophen-3-yl |
| 266 | 3-trifluoromethoxy-phenyl | —CH₂CH₂CH₂O— | | 5-Cl-benzothiophen-3-yl |
| 267 | 3-methoxy-phenyl | —CH₂CH₂CH₂O— | | 5-Cl-benzothiophen-3-yl |
| 268 | 2,6-difluoro-phenyl | —CH₂CH₂CH₂O— | | 5-Cl-benzothiophen-3-yl |
| 269 | 2-chloro-phenyl | —CH₂CH₂CH₂O— | | 5-Cl-benzothiophen-3-yl |
| 270 | 3-chloro-phenyl | —CH₂CH₂CH₂O— | | 5-Cl-benzothiophen-3-yl |
| 271 | 3,5-difluoro-phenyl | —CH₂CH₂CH₂O— | | 5-Cl-benzothiophen-3-yl |
| 272 | 2,3-difluoro-phenyl | —CH₂CH₂CH₂O— | | 5-Cl-benzothiophen-3-yl |
| 273 | 2-bromo-phenyl | —CH₂CH₂CH₂O— | | 5-Cl-benzothiophen-3-yl |
| 274 | 2,3-dimethoxy-phenyl | —CH₂CH₂CH₂O— | | 5-Cl-benzothiophen-3-yl |
| 275 | 3-nitro-phenyl | —CH₂CH₂CH₂O— | | 5-Cl-benzothiophen-3-yl |
| 276 | 3-bromo-phenyl | —CH₂CH₂CH₂O— | | 5-Cl-benzothiophen-3-yl |
| 277 | 3,5-dimethoxy-phenyl | —CH₂CH₂CH₂O— | | 5-Cl-benzothiophen-3-yl |
| 278 | 2,5-difluoro-phenyl | —CH₂CH₂CH₂O— | | 5-Cl-benzothiophen-3-yl |
| 279 | 3,5-dichloro-phenyl | —CH₂CH₂CH₂O— | | 5-Cl-benzothiophen-3-yl |
| 280 | 2,4-difluoro-phenyl | —CH₂CH₂CH₂O— | | 5-Cl-benzothiophen-3-yl |
| 281 | 3-amino-phenyl | —CH₂CH₂CH₂O— | | 5-Cl-benzothiophen-3-yl |
| 282 | 2-methoxy-phenyl | —CH₂OC(=O)isopropyloxy | OH | 5-Cl-benzothiophen-3-yl |
| 283 | pyridin-2-yl | —CH₂OC(=O)isopropyloxy | OH | 5-Cl-benzothiophen-3-yl |
| 284 | 3-trifluoromethoxy-phenyl | —CH₂OC(=O)isopropyloxy | OH | 5-Cl-benzothiophen-3-yl |
| 285 | 3-methoxy-phenyl | —CH₂OC(=O)isopropyloxy | OH | 5-Cl-benzothiophen-3-yl |
| 286 | 2,6-difluoro-phenyl | —CH₂OC(=O)isopropyloxy | OH | 5-Cl-benzothiophen-3-yl |
| 287 | 2-chloro-phenyl | —CH₂OC(=O)isopropyloxy | OH | 5-Cl-benzothiophen-3-yl |
| 288 | 3-chloro-phenyl | —CH₂OC(=O)isopropyloxy | OH | 5-Cl-benzothiophen-3-yl |
| 289 | 3,5-difluoro-phenyl | —CH₂OC(=O)isopropyloxy | OH | 5-Cl-benzothiophen-3-yl |
| 290 | 2,3-difluoro-phenyl | —CH₂OC(=O)isopropyloxy | OH | 5-Cl-benzothiophen-3-yl |
| 291 | 2-bromo-phenyl | —CH₂OC(=O)isopropyloxy | OH | 5-Cl-benzothiophen-3-yl |
| 292 | 2,3-dimethoxy-phenyl | —CH₂OC(=O)isopropyloxy | OH | 5-Cl-benzothiophen-3-yl |
| 293 | 3-nitro-phenyl | —CH₂OC(=O)isopropyloxy | OH | 5-Cl-benzothiophen-3-yl |

TABLE IV-continued

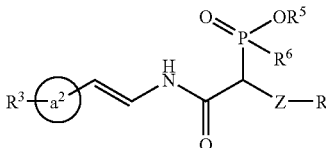

(Ic)

| Cpd | a²/R³ | R⁵ | R⁶ | Z—R⁴ |
|---|---|---|---|---|
| 294 | 3-bromo-phenyl | —CH₂OC(=O)isopropyloxy | OH | 5-Cl-benzothiophen-3-yl |
| 295 | 3,5-dimethoxy-phenyl | —CH₂OC(=O)isopropyloxy | OH | 5-Cl-benzothiophen-3-yl |
| 296 | 2,5-difluoro-phenyl | —CH₂OC(=O)isopropyloxy | OH | 5-Cl-benzothiophen-3-yl |
| 297 | 3,5-dichloro-phenyl | —CH₂OC(=O)isopropyloxy | OH | 5-Cl-benzothiophen-3-yl |
| 298 | 2,4-difluoro-phenyl | —CH₂OC(=O)isopropyloxy | OH | 5-Cl-benzothiophen-3-yl |
| 299 | 3-amino-phenyl | —CH₂OC(=O)isopropyloxy | OH | 5-Cl-benzothiophen-3-yl |
| 300 | 3-fluoro-5-chloro-phenyl | H | CH₃ | 5-Cl-benzothiophen-3-yl |
| 301 | 2-fluoro-3-chloro-phenyl | H | CH₃ | 5-Cl-benzothiophen-3-yl |
| 302 | 4-fluoro-3-chloro-phenyl | H | CH₃ | 5-Cl-benzothiophen-3-yl |
| 303 | 2-fluoro-5-chloro-phenyl | H | CH₃ | 5-Cl-benzothiophen-3-yl |
| 304 | 3,5-dibromo-phenyl | H | CH₃ | 5-Cl-benzothiophen-3-yl |
| 305 | 3-cyano-phenyl | H | CH₃ | 5-Cl-benzothiophen-3-yl |
| 306 | 2-cyano-phenyl | H | CH₃ | 5-Cl-benzothiophen-3-yl |
| 307 | 3-fluoro-5-trifluoromethyl-phenyl | H | CH₃ | 5-Cl-benzothiophen-3-yl |
| 308 | 3-fluoro-5-chloro-phenyl | H | OH | 5-Cl-benzothiophen-3-yl |
| 309 | 2-fluoro-3-chloro-phenyl | H | OH | 5-Cl-benzothiophen-3-yl |
| 310 | 4-fluoro-3-chloro-phenyl | H | OH | 5-Cl-benzothiophen-3-yl |
| 311 | 2-fluoro-5-chloro-phenyl | H | OH | 5-Cl-benzothiophen-3-yl |
| 312 | 3,5-dibromo-phenyl | H | OH | 5-Cl-benzothiophen-3-yl |
| 313 | 3-cyano-phenyl | H | OH | 5-Cl-benzothiophen-3-yl |
| 314 | 2-cyano-phenyl | H | OH | 5-Cl-benzothiophen-3-yl |
| 315 | 3-fluoro-5-trifluoromethyl-phenyl | H | OH | 5-Cl-benzothiophen-3-yl |
| 316 | 3-fluoro-5-chloro-phenyl | —CH₂OC(=O)t-butyl | CH₃ | 5-Cl-benzothiophen-3-yl |
| 317 | 2-fluoro-3-chloro-phenyl | —CH₂OC(=O)t-butyl | CH₃ | 5-Cl-benzothiophen-3-yl |
| 318 | 4-fluoro-3-chloro-phenyl | —CH₂OC(=O)t-butyl | CH₃ | 5-Cl-benzothiophen-3-yl |
| 319 | 2-fluoro-5-chloro-phenyl | —CH₂OC(=O)t-butyl | CH₃ | 5-Cl-benzothiophen-3-yl |
| 320 | 3,5-dibromo-phenyl | —CH₂OC(=O)t-butyl | CH₃ | 5-Cl-benzothiophen-3-yl |
| 321 | 3-cyano-phenyl | —CH₂OC(=O)t-butyl | CH₃ | 5-Cl-benzothiophen-3-yl |
| 322 | 2-cyano-phenyl | —CH₂OC(=O)t-butyl | CH₃ | 5-Cl-benzothiophen-3-yl |
| 323 | 3-fluoro-5-trifluoromethyl-phenyl | —CH₂OC(=O)t-butyl | CH₃ | 5-Cl-benzothiophen-3-yl |
| 324 | 3-fluoro-5-chloro-phenyl | —CH₂OC(=O)t-butyl | —OCH₂OC(=O)t-butyl | 5-Cl-benzothiophen-3-yl |
| 325 | 2-fluoro-3-chloro-phenyl | —CH₂OC(=O)t-butyl | —OCH₂OC(=O)t-butyl | 5-Cl-benzothiophen-3-yl |
| 326 | 4-fluoro-3-chloro-phenyl | —CH₂OC(=O)t-butyl | —OCH₂OC(=O)t-butyl | 5-Cl-benzothiophen-3-yl |
| 327 | 2-fluoro-5-chloro-phenyl | —CH₂OC(=O)t-butyl | —OCH₂OC(=O)t-butyl | 5-Cl-benzothiophen-3-yl |
| 328 | 3,5-dibromo-phenyl | —CH₂OC(=O)t-butyl | —OCH₂OC(=O)t-butyl | 5-Cl-benzothiophen-3-yl |
| 329 | 3-cyano-phenyl | —CH₂OC(=O)t-butyl | —OCH₂OC(=O)t-butyl | 5-Cl-benzothiophen-3-yl |

TABLE IV-continued (Ic)

| Cpd | R³ | R⁵ | R⁶ | Z—R⁴ |
|---|---|---|---|---|
| 330 | 2-cyano-phenyl | —CH₂OC(=O) t-butyl | —OCH₂OC(=O) t-butyl | 5-Cl-benzothiophen-3-yl |
| 331 | 3-fluoro-5-trifluoromethyl-phenyl | —CH₂OC(=O) t-butyl | —OCH₂OC(=O) t-butyl | 5-Cl-benzothiophen-3-yl |
| 332 | 3-fluoro-5-chloro-phenyl | —CH₂OC(=O) t-butyl | OH | 5-Cl-benzothiophen-3-yl |
| 333 | 2-fluoro-3-chloro-phenyl | —CH₂OC(=O) t-butyl | OH | 5-Cl-benzothiophen-3-yl |
| 334 | 4-fluoro-3-chloro-phenyl | —CH₂OC(=O) t-butyl | OH | 5-Cl-benzothiophen-3-yl |
| 335 | 2-fluoro-5-chloro-phenyl | —CH₂OC(=O) t-butyl | OH | 5-Cl-benzothiophen-3-yl |
| 336 | 3,5-dibromo-phenyl | —CH₂OC(=O) t-butyl | OH | 5-Cl-benzothiophen-3-yl |
| 337 | 3-cyano-phenyl | —CH₂OC(=O) t-butyl | OH | 5-Cl-benzothiophen-3-yl |
| 338 | 2-cyano-phenyl | —CH₂OC(=O) t-butyl | OH | 5-Cl-benzothiophen-3-yl |
| 339 | 3-fluoro-5-trifluoromethyl-phenyl | —CH₂OC(=O) t-butyl | OH | 5-Cl-benzothiophen-3-yl |
| 340 | 3-fluoro-5-chloro-phenyl | —CH₂CH₂CH₂O— | | 5-Cl-benzothiophen-3-yl |
| 341 | 2-fluoro-3-chloro-phenyl | —CH₂CH₂CH₂O— | | 5-Cl-benzothiophen-3-yl |
| 342 | 4-fluoro-3-chloro-phenyl | —CH₂CH₂CH₂O— | | 5-Cl-benzothiophen-3-yl |
| 343 | 2-fluoro-5-chloro-phenyl | —CH₂CH₂CH₂O— | | 5-Cl-benzothiophen-3-yl |
| 344 | 3,5-dibromo-phenyl | —CH₂CH₂CH₂O— | | 5-Cl-benzothiophen-3-yl |
| 345 | 3-cyano-phenyl | —CH₂CH₂CH₂O— | | 5-Cl-benzothiophen-3-yl |
| 346 | 2-cyano-phenyl | —CH₂CH₂CH₂O— | | 5-Cl-benzothiophen-3-yl |
| 347 | 3-fluoro-5-trifluoromethyl-phenyl | —CH₂CH₂CH₂O— | | 5-Cl-benzothiophen-3-yl |
| 348 | 3-fluoro-5-chloro-phenyl | —CH₂OC(=O) isopropyloxy | OH | 5-Cl-benzothiophen-3-yl |
| 349 | 2-fluoro-3-chloro-phenyl | —CH₂OC(=O) isopropyloxy | OH | 5-Cl-benzothiophen-3-yl |
| 350 | 4-fluoro-3-chloro-phenyl | —CH₂OC(=O) isopropyloxy | OH | 5-Cl-benzothiophen-3-yl |
| 351 | 2-fluoro-5-chloro-phenyl | —CH₂OC(=O) isopropyloxy | OH | 5-Cl-benzothiophen-3-yl |
| 352 | 3,5-dibromo-phenyl | —CH₂OC(=O) isopropyloxy | OH | 5-Cl-benzothiophen-3-yl |
| 353 | 3-cyano-phenyl | —CH₂OC(=O) isopropyloxy | OH | 5-Cl-benzothiophen-3-yl |
| 354 | 2-cyano-phenyl | —CH₂OC(=O) isopropyloxy | OH | 5-Cl-benzothiophen-3-yl |
| 355 | 3-fluoro-5-trifluoromethyl-phenyl | —CH₂OC(=O) isopropyloxy | OH | 5-Cl-benzothiophen-3-yl |

A preferred embodiment of the present invention includes the representative compounds presented in Table V.

TABLE V
| Cpd | |
|---|---|
| 1 | 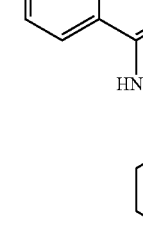 |
| 2 | 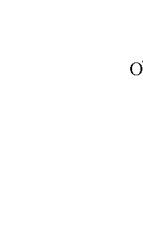 |
| 3 | 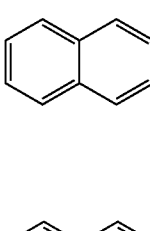 |
| 4 | 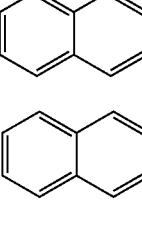 |
| 5 |  |
| 6 | 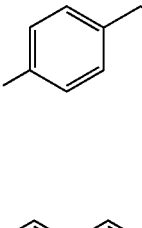 |
| 7 | 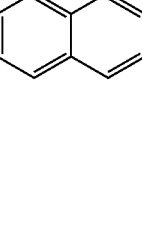 |
| 8 |  |
| 9 | |
| 10 | |
| 11 | |
| 12 | |
| 13 | |

TABLE V-continued

| Cpd | Structure |
|---|---|
| 14 | (E)-2-(5-chlorobenzo[b]thiophen-3-yl)-2-(methyl(hydroxy)phosphoryl)-N-styrylacetamide |
| 15 | (E)-2-(5-chlorobenzo[b]thiophen-3-yl)-N-(3-fluorostyryl)-2-(methyl(hydroxy)phosphoryl)acetamide |
| 16 | (E)-2-(5-chlorobenzo[b]thiophen-3-yl)-2-(methyl(hydroxy)phosphoryl)-N-(3,4,5-trifluorostyryl)acetamide |
| 17 | (E)-2-(5-chlorobenzo[b]thiophen-3-yl)-N-(3,4-difluorostyryl)-2-(methyl(hydroxy)phosphoryl)acetamide |
| 18 | 2-(5-chlorobenzo[b]thiophen-3-yl)-2-(dihydroxyphosphoryl)-N-styrylacetamide |
| 19 | 2-(5-chlorobenzo[b]thiophen-3-yl)-2-(dihydroxyphosphoryl)-N-(4-fluorostyryl)acetamide |
| 20 | 2-(5-chlorobenzo[b]thiophen-3-yl)-2-(methyl(hydroxy)phosphoryl)-N-(naphthalen-2-yl)acetamide |
| 21 | (E)-2-(5-chlorobenzo[b]thiophen-3-yl)-N-(2-fluorostyryl)-2-(methyl(hydroxy)phosphoryl)acetamide |
| 22 | 2-(dihydroxyphosphoryl)-2-(1-methyl-1H-indol-3-yl)-N-(naphthalen-2-yl)acetamide |
| 23 | 2-(5-bromobenzo[b]thiophen-3-yl)-2-(dihydroxyphosphoryl)-N-(naphthalen-2-yl)acetamide |
| 24 | (E)-2-(5-chlorobenzo[b]thiophen-3-yl)-N-(4-fluorostyryl)-2-(methyl(hydroxy)phosphoryl)acetamide |
| 25 | (E)-2-(5-chlorobenzo[b]thiophen-3-yl)-2-(methyl(hydroxy)phosphoryl)-N-(2-(pyridin-3-yl)vinyl)acetamide |
| 145 | (E)-2-(5-chlorobenzo[b]thiophen-3-yl)-N-(2-methoxystyryl)-2-(methyl(hydroxy)phosphoryl)acetamide |
| 149 | (E)-2-(5-chlorobenzo[b]thiophen-3-yl)-N-(2-hydroxystyryl)-2-(methyl(hydroxy)phosphoryl)acetamide |
| 150 | (E)-2-(5-chlorobenzo[b]thiophen-3-yl)-2-(methyl(hydroxy)phosphoryl)-N-(2-(pyridin-2-yl)vinyl)acetamide |
| 153 | (E)-2-(5-chlorobenzo[b]thiophen-3-yl)-2-(methyl(hydroxy)phosphoryl)-N-(3-(trifluoromethoxy)styryl)acetamide |

TABLE V-continued

| Cpd | Structure |
|---|---|
| 154 | (E)-2-(5-chlorobenzo[b]thiophen-3-yl)-N-(3-methoxystyryl)-2-(methyl(hydroxy)phosphoryl)acetamide |
| 156 | (E)-2-(5-chlorobenzo[b]thiophen-3-yl)-N-(2,6-difluorostyryl)-2-(methyl(hydroxy)phosphoryl)acetamide |
| 160 | (E)-2-(5-chlorobenzo[b]thiophen-3-yl)-N-(2-chlorostyryl)-2-(methyl(hydroxy)phosphoryl)acetamide |
| 161 | (E)-2-(5-chlorobenzo[b]thiophen-3-yl)-N-(3-chlorostyryl)-2-(methyl(hydroxy)phosphoryl)acetamide |
| 162 | (E)-2-(5-chlorobenzo[b]thiophen-3-yl)-N-(3,5-difluorostyryl)-2-(methyl(hydroxy)phosphoryl)acetamide |
| 163 | (E)-2-(5-chlorobenzo[b]thiophen-3-yl)-N-(2,3-difluorostyryl)-2-(methyl(hydroxy)phosphoryl)acetamide |
| 164 | (E)-N-(2-bromostyryl)-2-(5-chlorobenzo[b]thiophen-3-yl)-2-(methyl(hydroxy)phosphoryl)acetamide |
| 165 | (E)-2-(5-chlorobenzo[b]thiophen-3-yl)-N-(2,3-dimethoxystyryl)-2-(methyl(hydroxy)phosphoryl)acetamide |
| 166 | (E)-2-(5-chlorobenzo[b]thiophen-3-yl)-2-(methyl(hydroxy)phosphoryl)-N-(3-nitrostyryl)acetamide |
| 167 | (E)-N-(3-bromostyryl)-2-(5-chlorobenzo[b]thiophen-3-yl)-2-(methyl(hydroxy)phosphoryl)acetamide |
| 168 | (E)-2-(5-chlorobenzo[b]thiophen-3-yl)-N-(3,5-dimethoxystyryl)-2-(methyl(hydroxy)phosphoryl)acetamide |
| 169 | (E)-2-(5-chlorobenzo[b]thiophen-3-yl)-N-(2,5-difluorostyryl)-2-(methyl(hydroxy)phosphoryl)acetamide |
| 170 | (E)-2-(5-chlorobenzo[b]thiophen-3-yl)-N-(3,5-dichlorostyryl)-2-(methyl(hydroxy)phosphoryl)acetamide |

TABLE V-continued

| Cpd | Structure |
|---|---|
| 171 | (structure) |
| 172 | (structure) |
| 177 | (structure) |
| 182 | (structure) |
| 186 | (structure) |
| 187 | (structure) |
| 189 | (structure) |
| 191 | (structure) |

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic, and trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tris(hydroxymethyl)methylamine, tromethamine), ammonia, benzathine, t-butylamine, calcium, chloroprocaine, choline, cyclohexylamine, diethanolamine, ethylenediamine, lithium, L-lysine, magnesium, meglumine, $NH_3$, $NH_4OH$, N-methyl-D-glucamine, piperidine, potassium, procaine, quinine, SEH, sodium, triethanolamine (TEA), imidazole, and zinc.

Compounds of the present invention may be contacted with a pharmaceutically acceptable cation selected from the group consisting of aluminum, 2-amino-2-hydroxymethyl-propane-1,3-diol (also known as tris(hydroxymethyl)aminomethane, tris(hydroxymethyl)methylamine, tromethamine), ammonia, benzathine, t-butylamine, calcium, chloroprocaine, choline, cyclohexylamine, diethanolamine, ethylenediamine, lithium, L-lysine, magnesium, meglumine, $NH_3$, $NH_4OH$, N-methyl-D-glucamine, piperidine, potassium, procaine, quinine, SEH, sodium, triethanolamine (TEA), imidazole, and zinc to form a salt.

Preferred cations for use with the instant compounds are selected from the group consisting of benzathine, t-butylamine, calcium, choline, cyclohexylamine, diethanolamine, ethylenediamine, L-lysine, $NH_3$, $NH_4OH$, N-methyl-D-glucamine, piperidine, potassium, procaine, quinine, sodium, triethanolamine, imidazole, and tris(hydroxymethyl)methylamine (tromethamine).

More preferably, cations for use with the instant compounds are selected from the group consisting of t-butylamine, $NH_4OH$, imidazole, sodium, and tris(hydroxymethyl)methylamine(tromethamine).

Most preferably, the cations for use with the instant compounds are tromethamine and sodium.

The present invention includes within its scope prodrugs of the compounds of this invention. In general, such prodrugs will be functional derivatives of the compounds, which are readily convertible in vivo into an active compound. Thus, in the methods of treatment of the present invention, the term "administering" shall encompass the treatment of the various disorders described with the compound specifically disclosed or a prodrug compound which would be obviously included within the scope of the invention although not specifically disclosed. Conventional procedures for the selection and preparation of suitable prodrug derivatives are described, for example, in "*Design of Prodrugs*", ed. H. Bundgaard, Elsevier, 1985. Phosphonic acid prodrugs (as described in De Lombaert S., et al, Non-Peptidic Inhibitors of Neutral Endopeptidase 24.11; Design and Pharmacology of Orally Active Phosphonate Prodrugs, *Bioorganic and Medicinal Chemistry Letters*, 1995, 5(2), 151-154; and, De Lombaert S., et al, N-Phosphonomethyl Dipeptides and Their Phosphonate Prodrugs, a New Generatrion Neutral Endopeptidase (NEP, EC 3.424.11) Inhibitors, *J. Med. Chem.*, 1994, 37, 498-511) and phosphinic acid prodrugs are intended to be included within the scope of the present invention.

The compounds according to this invention may have at least one chiral center and thus may exist as enantiomers. In addition, the compounds of the present invention may also possess two or more chiral centers and thus may also exist as diastereomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active base, followed by fractional crystallization and regeneration of the compounds of this invention. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a terminal carbon atom or, when acting as a linking group, within the carbon chain.

The term "cycloalkyl" refers to saturated or partially unsaturated, moncyclic or polycyclic hydrocarbon rings of from 3 to 20 carbon atom members (preferably from 3 to 14 carbon atom members). Further, a cycloalkyl ring may optionally be fused to one or more cycloalkyl rings. Examples of such rings include, and are not limited to, cyclopropyl, cyclobutyl, cyclopentyl, cyclohexyl, cycloheptyl, and adamantyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. Alternatively, the heterocyclyl ring may be fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, the heterocyclyl can be bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl, and piperazinyl.

The term "aryl" refers to an unsaturated, aromatic monocyclic ring of 6 carbon members or to an unsaturated, aromatic polycyclic ring of from 10 to 20 carbon members. Examples of such aryl rings include, and are not limited to, phenyl, naphthalenyl and anthracenyl. Preferred aryl groups for the practice of this invention are phenyl and naphthalenyl.

The term "benzo fused cycloalkyl" refers to a bicyclic or tricyclic ring structure wherein at least one of the ring substituents is phenyl or naphthalenyl and at least one of the other substituents is a cycloalkyl ring (as cycloalkyl was previously defined). For the purpose of these definitions, the cycloalkyl rings may be fused to an additional benzene ring (to provide fused multiple ring systems such as fluorene). Example of such benzo fused cycloalkyls include, but are not limited to, indanyl, 1,2,3,4-tetrahydronaphthalenyl and fluorenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. Optionally, the heteroaryl ring is fused to a benzene ring (benzo fused heteroaryl), a 5 or 6 membered heteroaryl ring (containing one of O, S or N and, optionally, one additional nitrogen), a 5 to 7 membered cycloalkyl ring or a 5 to 7 membered heterocyclo ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl, and quinazolinyl.

The term "arylalkyl" means an alkyl group substituted with an aryl group (e.g., benzyl and phenethyl). Similarly, the term "arylalkoxy" indicates an alkoxy group substituted with an aryl group (e.g., benzyloxy).

The term "halogen" refers to fluorine, chlorine, bromine, and iodine. Substituents that are substituted with multiple halogens are substituted in a manner that provides compounds which are stable.

Whenever the term "alkyl" or "aryl" or either of their prefix roots appear in a name of a substituent (e.g., arylalkyl and alkylamino), it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.). However, for clarity in the terms "$C_9$-$C_{14}$ benzo fused cycloalkyl", "$C_9$-$C_{14}$ benzo fused cycloalkenyl", "$C_9$-$C_{14}$ benzo fused aryl"; $C_9$-$C_{14}$ refers to the number of carbon atoms both in the benzene ring (6) and the number of atoms in the ring fused to the benzene ring, but does not include carbon atoms that may be pendent from these multiple ring systems. The amount of substituents attached to a moiety "optionally substituted with one to five substituents" is limited to that amount of open valences on the moiety available for substitution.

In general, under standard nomenclature rules used throughout this disclosure, the terminal portion of the designated side chain is described first followed by the adjacent functionality toward the point of attachment. Thus, for example, a. "phenyl$C_1$-$C_6$ alkylamido$C_1$-$C_6$alkyl" substituent refers to a group of the formula:

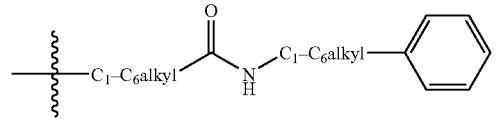

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Illustrative of the invention is a composition comprising a pharmaceutically acceptable carrier and any of the compounds described above. Also illustrative of the invention is a composition made by mixing any of the compounds described above and a pharmaceutically acceptable carrier. A further illustration of the invention is a process for making a composition comprising mixing any of the compounds described above and a pharmaceutically acceptable carrier. The present invention also provides compositions comprising one or more compounds of this invention in association with a pharmaceutically acceptable carrier.

The compounds of the present invention are useful serine protease inhibitors (in particular, inhibitors of chymase) useful for treating inflammatory, and serine protease mediated disorders. Serine proteases such as chymase produced by mast cells have been recognized to be involved in a variety of inflammatory and wound healing events (e.g., angiogenesis, collagen deposition and cell proliferation). Chymase plays these roles by activating a variety of pre-existing factors present in the microenvironment surrounding the mast cells. For example, just to name a few of these interactions chymase activates SCF, angiotensin I to angiotensin II, endothelin 1, type 1 procollagen, metalloprotienases, IL-1B, TGF-β, as well as, degrades the extracellular matrix (de Paulis et al. Int Arch Allerg Immunol 118 (1999) 422-425; Longley et al. Proc Natl Acad Sci USA 94 (1997) 9017-9021). Consequently, the release of chymase plays significant role in a variety of pathological conditions associated with vascular proliferation, fibrosis, tissue remodeling, inflammation, and the like.

Some of these, inflammatory and serine protease mediated disorders include, and are not limited to, allergic rhinitis, viral rhinitis, asthma, chronic obstructive pulmonary diseases, bronchitis, pulmonary emphysema, acute lung injury (e.g. adult (acute) respiratory distress syndrome) psoriasis, arthritis, reperfusion injury, ischemia, hypertension, hypercardia myocardial infarction, heart failure damage associated with myocardial infarction, cardiac, hypertrophy, arteriosclerosis, saroidosis, vascular stenosis or restenosis (e.g., associated with vascular injury, angioplasty, vascular stents or vascular grafts), pulmonary fibrosis, kidney fibrosis (e.g., associated with glomerulonephritis), liver fibrosis, post surgical adhesion formation, systemic sclerosis, keloid scars rheumatoid arthritis, bullous pemphigiod and atherosclerosis. Additionally, these compounds can be used for modulating wound healing and remodeling (e.g., cardiac hypertrophy) as well as immune modulation. The utility of the compounds to treat inflammatory and serine protease mediated disorders is illustrated by the following non-limiting discussions of the proposed mechanisms of actions of chymase. Other disorders that can be treated with chymase inhibitors can be determined according to the procedures described herein and the use of, animal knock-out models and the like.

As mentioned above, chymase coverts angiotensin I into angiotensin II, and this activity has been associated with vascular proliferation. In human vascular extracts only about 8% of angiotensin II activity is inhibited with an angiotensin converting enzyme inhibitor (lisinopril) while 95% is inhibited by a chymase inhibitor. In vein grafts, vascular injury associated with catheter or balloon injury, chymase induces vascular hyperplasia and restenosis in dogs (Takai and Miyazaki, 21 (2003) 185-189). This same mechanism of action would also be expected to apply to restenosis associated with the use of vascular stents. Pathological serine protease mediated disorders associated with angiotensin II, including but not limited to hypertension, hypercardia myocardial infarction, arteriosclerosis, saroidosis, vascular stenosis or restenosis (e.g., associated with vascular injury, angioplasty, vascular stents or vascular grafts), and the like.

Pathological fibrosis can be associated with the degeneration of organs (e.g., skin, heart, kidneys or liver) or as an undesirable outcome of surgery. Preventing the formation of pathological fibrosis would be beneficial in a variety of diseases. For example mast cell chymase has been implicated in pulmonary fibrosis, kidney fibrosis, liver fibrosis, post surgical adhesion formation, systemic sclerosis, keloid scars, and the like.

In the heart mast cells have been implicated in cardiac hypertrophy, which involves both fibrosis and remodeling. Cardiac hypertrophy develops to preserve its function by normalizing chamber wall stress. Mast cells have been implicated as being involved in the development of myocardial fibrosis and systolic pressure over load induced hypertrophy (Hara et al, J. Exp. Med. 195 (2002) 375-381). The remodeling of the heart associated under these conditions is believed to involve mast cell chymase, which activates endothelin 1, matrix metalloproteinases and TGF-β. Chymase inhibitors have been shown to exert favorable cardioprotective action in a dog model of hypertrophy (Matsumoto et al., Circulation 107 (2003) 2555-2558).

In the kidneys mast cell chymase has also been implicated in pathological firbrosis. For example, glomerulonephritis has also been reported to involve mast cells (Ehara and Shigematsu, Kidney Inter. 54 (1998) 1675-1683). The results of this found that mast cells were one of the constitutive cell types in the interstitium of IgA nephritis patients and contributed to interstitial fibrosis resulting in deterioration of renal function. Similarly, liver fibrosis has been associated with mast cells (Yamashiro et al., Virchows Arch. 433 (1998) 471-479). Although, the mechanisms for fibrosis in the kidney and liver have not been as well defined as for coronary fibrosis, it is very likely that chymase is operating through similar signaling pathways to cause fibrosis (especially in liver fibrosis where fibrosis seem to be occurring more frequently where mast cells stained positive for chymase).

Chymase is also involved in the formation of fibrous adhesions associated with surgery. Chymase inhibitors have been tested in two different animals models and found to reduce the number of adhesions (Okamoto et al., J. Surg. Res. 107 (2002) 219-222 and Lucas et al., J. Surg. Res. 65 (1999) 135). It has been suggested that the prevention of adhesions is associated with blocking the activation of latent TGF-β by chymase (Yoa et al., J. Surg. Res. 92 (2000) 40-44).

Collagen induced arthritic mice show increased numbers of mast cells and expression of chymase in fibroproliferative inflammation (Kakizoe et al., Inflamm. Res. 48 (1999) 318-324). In human rheumatoid arthritis increased mast cell density in the superficial synovium is associated with the severity of the disease (Grotis-Graham and McNeil, Arthritis & Rheumatism 40 (1997) 479-489). It was theorized by these authors that chymase and its ability to activate metalloprotinases plays a significant role in the rapid functional deterioration observed in rheumatoid arthritis.

Mast cell chymase has been implicated in artherosclerosis via its ability to cleave apolipoprotein B-100 of LDL which facilitates lipoprotein aggregations and uptake by macrophages (Paananen et al., J. Biol. Chem. 269 (1994) 2023-2031). Chymase also degrades apolipoprotein A of HDL, which would reduce cholesterol efflux and increases lipid deposition (Lindstedt et al., J. Clin. Invest. 97 (1996) 2174-2182). Thus chymase is involved in two different pathways to atherosclerosis.

An embodiment of the invention is a method for treating inflammatory and serine protease mediated disorders in a subject in need thereof which comprises administering to the subject a therapeutically effective amount of any of the compounds or compositions described above. Also included in the invention is the use of a compound of Formula (I) for the preparation of a medicament for treating an inflammatory or serine protease mediated disorder in a subject in need thereof. The term "treating" as used herein refers to a method for improving, halting, retarding or palliating an inflammatory or serine protease mediated disorder in the subject in need thereof. All such methods of treatment are intended to be within the scope of the present invention.

In accordance with the methods of the present invention, the individual components of the compositions described herein can also be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal (preferably, a mammal; most preferably, a human) who has been the object of treatment, observation, or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare the compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a composition of the present invention in liquid dosage form for oral, topical, inhalation/insufflation and parenteral administration, any of the usual pharmaceutical media or excipients may be employed. Thus, for liquid dosage forms, such as suspensions (i.e., colloids, emulsions and dispersions) and solutions, suitable carriers and additives include but are not limited to pharmaceutically acceptable wetting agents, dispersants, flocculation agents, thickeners, pH control agents (i.e., buffers), osmotic agents, coloring agents, flavors, fragrances, preservatives (i.e., to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents, and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid compositions such as tablets, the principal active ingredient is mixed with a pharmaceutical carrier, e.g., conventional tabletting ingredients such as diluents, binders, adhesives, disintegrants, lubricants, antiadherents, and glidants. Suitable diluents include, but are not limited to, starch (i.e., corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e., AVICEL™ microcrystalline cellulose available from FMC Corp.), dicalcium phosphate, calcium sulfate dihydrate, calcium lactate trihydrate, and the like. Suitable binders and adhesives include, but are not limited to accacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e., alginic acid and salts thereof, magnesium aluminum silicate, hydroxyethylcellulose (i.e. TYLOSE™ available from Hoechst Celanese), polyethylene glycol, polysaccharide acids, bentonites, polyvinylpyrrolidone, polymethacrylates and pregelatinized starch), and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e., corn starch, etc.), gums (i.e., agar, guar, locust bean, karaya, pectin, and tragacanth gum), cross-linked polyvinylpyrrolidone, and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate, and the like. Suitable gildants include, but are not limited to, talc, cornstarch, silica (i.e., CAB-O-SIL™ silica available from Cabot, SYLOID™ silica available from W.R. Grace/Davison, and AEROSIL™ silica available from Degussa), and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation, and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate, cellulose acetate phthalate, polyvinyl acetate phthalate, hydroxypropyl methylcellulose phthalate, hydroxypropyl methylcellulose acetate succinate, methacrylate and ethylacrylate copolymers, and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e., beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e., propylene alginate, sodium alginate, and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e., carboxypolymethylene), and polyethylene glycol; clays such as bentonite, hectorite, attapulgite or sepiolite; and other pharmaceutically acceptable suspending agents such as lecithin, gelatin, or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235, and combinations thereof. Suitable deflocculating or dispersing agent include pharmaceutical grade lecithins. Suitable flocculating agent include but are not limited to simple neutral electrolytes (i.e., sodium chloride, potassium, chloride, and the like), highly charged insoluble polymers and polyelectrolyte species, water soluble divalent or trivalent ions (i.e., calcium salts, alums or sulfates, citrates and phosphates (which can be used jointly in formulations as pH buffers and flocculating agents). Suitable preservatives include but are not limited to parabens (i.e., methyl, ethyl, n-propyl and n-butyl), sorbic acid, thimerosal, quaternary ammonium salts, benzyl alcohol, benzoic acid, chlorhexidine gluconate, phenylethanol, and the like. There are many liquid vehicles that may be used in liquid pharmaceutical dosage forms, however, the liquid vehicle that is used in a particular dosage form must be compatible with the suspending agent(s). For example, non-polar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers, and the like. Conversely, polar liquids such as water, alcohols, polyols and glycols are best used with suspending agents such as higher HLB surfactants, clays silicates, gums, water soluble cellulosics, water soluble polymers, and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in a form suitable for intranasal or inhalation therapy. For such therapy, compounds of the present invention are conveniently delivered in the form of a solution or suspension from a pump spray container that is squeezed or pumped or as an aerosol spray from a pressurized container or a nebulizer (such as, a metered dose inhaler, a dry powder inhaler or other conventional or non-conventional modes or devices for inhalation delivery) using a suitable propellant (such as, dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (such as, those made from gelatin) for use in an inhaler or insufflator may be formulated containing a powder mix of a compound of the invention and a suitable powder base such as lactose or starch.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines, and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, and polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, poly-orthoesters, polyacetals, polydihydropyrans, polycyanoacrylates, and cross-linked or amphipathic block copolymers of hydrogels and blends thereof.

The therapeutically effective amount of a compound or composition thereof may be from about 0.001 mg/kg/dose to about 300 mg/kg/dose. Preferably, the therapeutically effective amount may be from about 0.001 mg/kg/dose to about 100 mg/kg/dose. More preferably, the therapeutically effective amount may be from about 0.001 mg/kg/dose to about 50 mg/kg/dose. Most preferably, the therapeutically effective amount may be from about 0.001 mg/kg/dose to about 30 mg/kg/dose. Therefore, the therapeutically effective amount of the active ingredient contained per dosage unit (e.g., tablet, capsule, powder, injection, suppository, teaspoonful, and the like) as described herein will be in the range of from about 1 mg/day to about 21,000 mg/day for a subject, for example, having an average weight of 70 kg. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. Advantageously, compounds of the present invention may be administered in a single daily dose or the total daily dosage may be administered in divided doses of two, three or four times daily.

Representative IUPAC names for the compounds of the present invention were derived using the ACD/LABS SOFTWARE™ Index Name Pro Version 4.5 nomenclature software program provided by Advanced Chemistry Development, Inc., Toronto, Ontario, Canada or AutoNom Version 2.1 provided by Beilstein Informationssysteme.

Abbreviations used in the instant specification, particularly the Schemes and Examples, are as follows:
Boc=tert-butoxycarbonyl
BOC-ON=2-(tert-butoxycarbonyloxyimino)-2-phenylacetonitrile
BuLi=n-butyllithium
t-BuOH=tert-butanol
Cpd or Cpd=compound
d=day/days
DCC=dicyclohexylcarbodiimide
DIPEA=diisopropylethylamine
EtOH=ethanol
h=hour/hours
HOBt=hydroxybenzotriazole
KH=potassium hydride
LDA=lithium diisopropyamide
M=molar
MeI=methyliodide
MeOH=methanol
min=minutes
NT=not tested
PPA=polyphosphoric acid
rt/RT=room temperature
THF=tetrahydrofuran
TFA=trifluoroacetic acid
TMSBr=bromotrimethylsilane.

GENERAL SYNTHETIC METHODS

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds and stereoisomers, racemic mixtures, diasteromers and enantiomers thereof can be synthesized using the intermediates prepared in accordance to the general schemes and other materials, compounds and reagents known to those skilled in the art. All such compounds, stereoisomers, racemic mixtures, diasteromers and enantiomers thereof are intended to be encompassed within the scope of the present invention. Since the scheme is an illustration, the invention should not be construed as being limited by the chemical reactions and conditions expressed. The preparation of the various starting materials used in the scheme is well within the skill of persons versed in the art.

Scheme A illustrates the general method for the preparation of compounds of the present invention by the reaction of a phosphonate or phosphinate anion (prepared from its corresponding phosphonate or phosphinate Compound A2 and an organometallic base such as n-butyllithium) to isocyanate A1 in a solvent such as THF to afford an amidophosphonate or amidophosphinate compound A3. One versed in the art will recognize that conventional chemical transformations may be utilized to prepare certain $R^2$ and $R^3$ substituents of the present invention. For example, for the preparation of a compound wherein $R^3$ is amino, a nitro group may be reduced with hydrazine hydrate in the presence of a palladium catalyst; or, for the preparation of a compound wherein $R^3$ is ureido, a compound in which $R^3$ is an amino group may be reacted with a cyanate salt or the like.

Compound A2, wherein $R^5$ and $R^6$ are as previously defined, may be made according to known methods (Katritsky et. al. *Org. Prep. Proced. Int.*, 1990, 22(2), 209-213; *J. Am. Chem. Soc.*, 2002, 124, 9386-9387; and *Chem. Ber.*, 1963, 96, 3184-3194). Fluorinated $R^6$ compounds can be made following methods known in the art such as the methods similar those set forth in Garabadzhia et al., Journal General Chemistry USSR, English translation, 1981, pages 1905-1910. Compound A3 may be dealkylated with bromotrimethylsilane in a solvent such as pyridine, followed by treatment with dilute HCl to afford Compound A4.

Scheme A

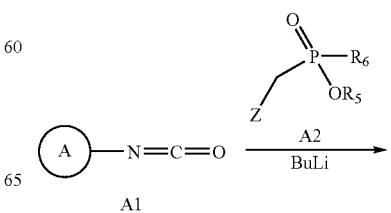

-continued

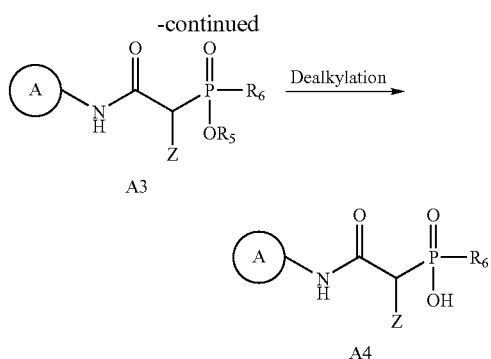

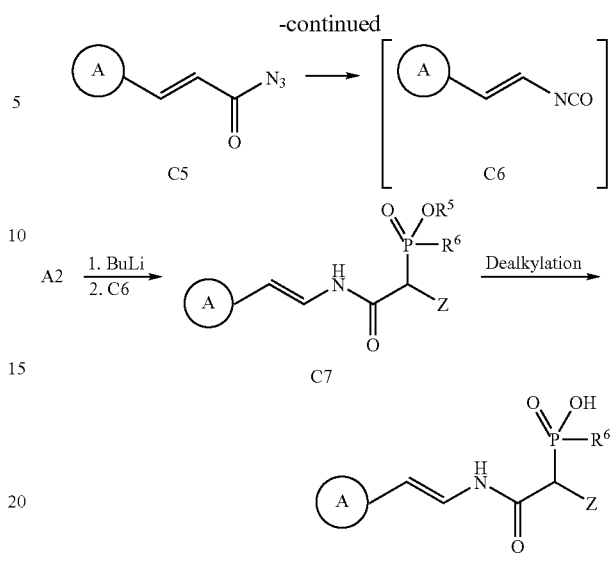

Compound A2, wherein Z is a heteroaryl or aryl ring, may be prepared from a commercially available or known haloalkyl substituted heteroaryl ring. Another method for preparing Compound A2 uses a quaternary ammonium salt rather than an alkyl halide.

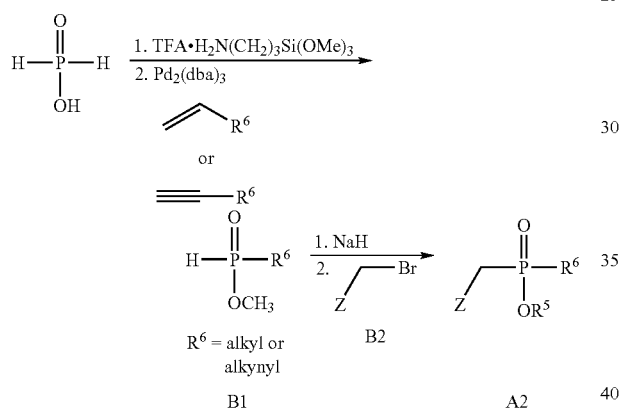

Scheme B shows a method for preparing Compound A2 wherein $R^6$ is an alkyl or alkenyl substituent using methods described in the literature (*J. Organomet. Chem.* 2002, 643-644,154-163; *J. Amer. Chem. Soc.* 2002, 124, 9386-9387). An alternate method for preparing such compounds is described in the literature (*Med. Chem.* 1995, 38(17), 3297-3312; *Bioorg. Med. Chem.* 1999, 7, 2697-2704).

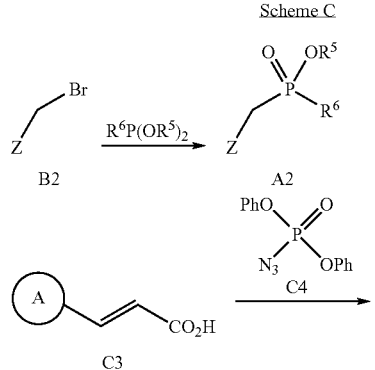

Scheme C illustrates a general method for the preparation of compounds of the present invention wherein ring system A of Formula (I) is an aryl substituent and n of Formula (I) is equal to 1. Reaction of an α/β-unsaturated carboxylic acid, Compound C3, with phosphorazidic acid dialkyl ester Compound C4 provides Compound C5. Compound C5 may subsequently undergo a Curtius rearrangement to afford an isocyanate intermediate, Compound C6. Compound C6 may be treated with a phosphonate or phosphinate anion (as previously described in Scheme A) in an aprotic solvent such as THF to yield amidophosphonate or amidophosphinate Compound C7. Compound C7 may be dealkylated with bromotrimethylsilane, followed by treatment with dilute HCl to afford Compound C8.

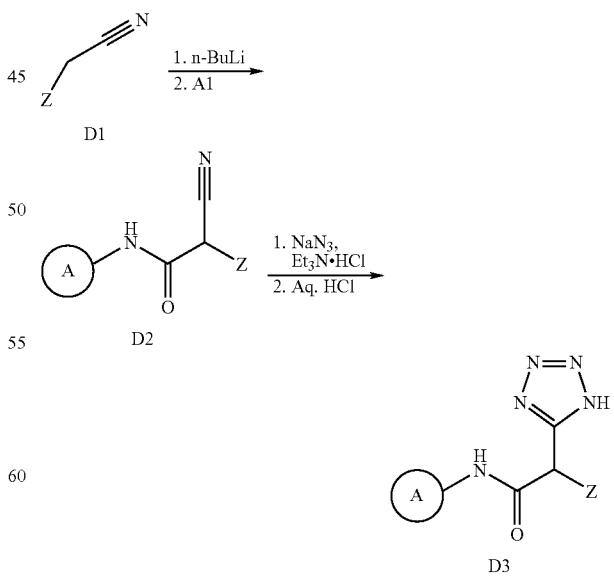

Scheme D further illustrates the preparation of compounds of the present invention wherein Y of Formula (I) is a heteroaryl substituent. Compound D1 may be dissolved in an aprotic solvent, treated with an organometallic base such as n-BuLi, and subsequently reacted with isocyanate Compound A1 to afford Compound D2. Compound D2 may undergo a cycloaddition reaction with sodium azide to provide Compound D3.

A1 to give Compound F4. Compound F4 is converted into its corresponding carboxylic acid Compound F5 by treatment with TFA.

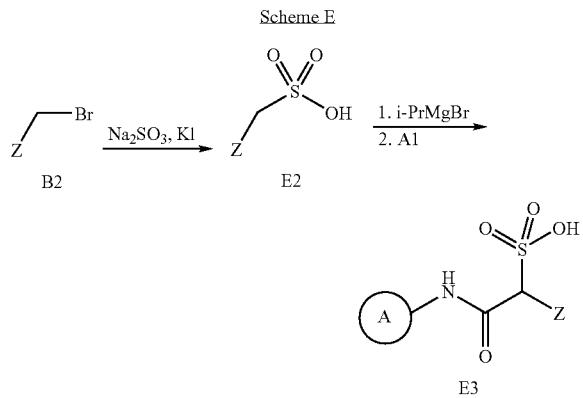

Scheme E shows the preparation of compounds of the present invention wherein Y of Formula (I) is a sulfonic acid. Compound B2 may be treated with sodium sulfite to afford Compound E2. Compound E2 may then be treated with an organometallic base such as isopropylmagnesium bromide and reacted with isocyanate Compound A1 to yield Compound E3.

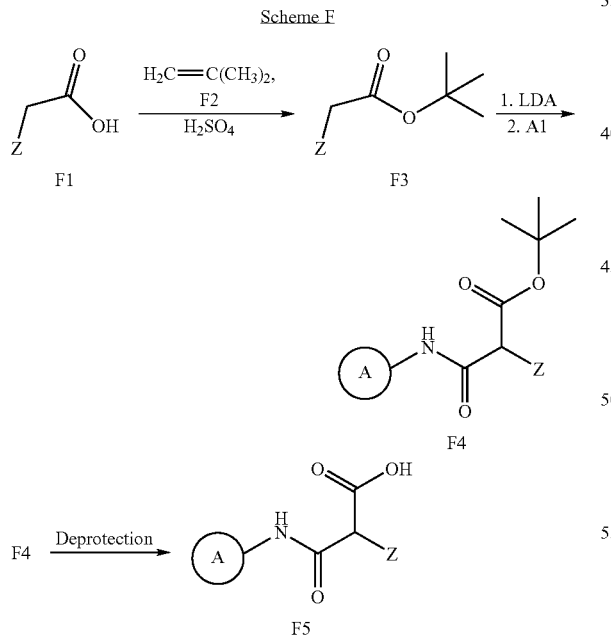

Scheme F illustrates the preparation of compounds of the present invention wherein Y of Formula (I) is a carboxylic acid. Compound F1 may be reacted with isobutylene under acidic conditions to provide ester Compound F3. Compound F3 may then be treated with a strong base such as lithium diethylamide and further reacted with isocyanate Compound

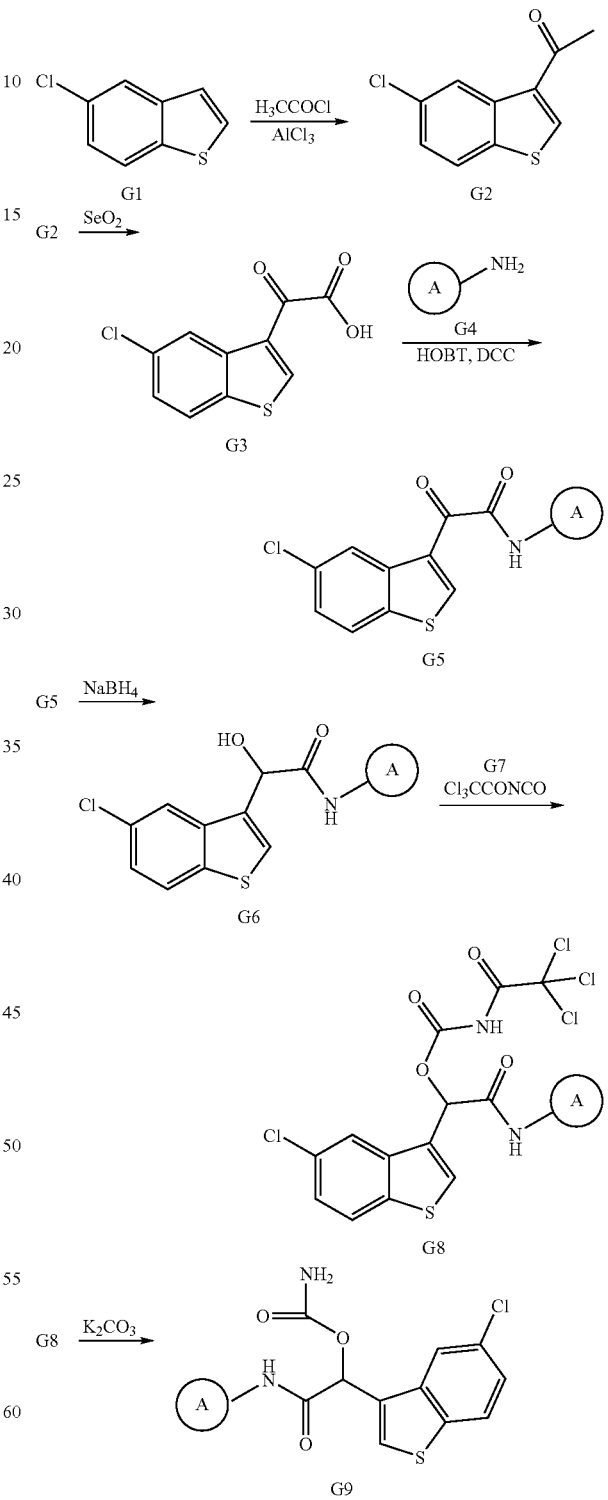

Scheme G illustrates the preparation of compounds of the present invention wherein Y of Formula (I) is a carbamate.

Compound G1 may be prepared by the methods described in the literature (*J. Med. Chem.* 1989, 32(12), 2548-2554, *J. Het. Chem.* 1998, 25, 1271). Compound G1 may be converted to Compound G2 by the method described in the literature (*Eur. J. Med. Chem.* 2001, 36(1), 55-62). Compound G2 may be oxidized using selenium dioxide to yield resultant carboxylic acid Compound G3. Compound G3 may be coupled with amine Compound G4 in the presence of an appropriate coupling agent, base, activating agent, and solvent to afford amide Compound G5. In the present invention, Compound G3 is coupled to Compound G4 in the presence of DCC and HOBt to form Compound G5. Compound G5 may be reduced in the presence of a hydride source such as sodium borohydride to give alcohol Compound G6, which may be treated with isocyanate Compound G7 to form Compound G8. Compound G8 may be deprotected in the presence of t-butyl alcohol and potassium carbonate to yield carbamate Compound G9.

Scheme H

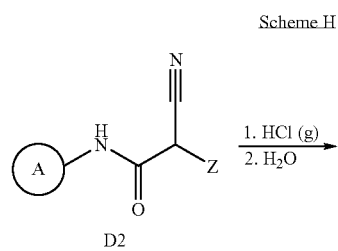

D2

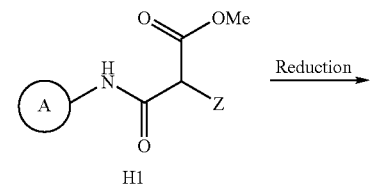

H1

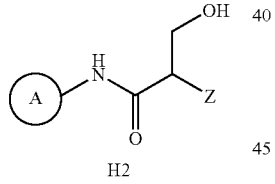

H2

Scheme H illustrates the preparation of compounds of the present invention wherein Y of Formula (I) is hydroxymethyl. Nitrile Compound D2 may be converted to an imidate in the presence of HCl gas, followed by hydrolysis to yield Compound H1. Compound H1 may be reduced to a primary alcohol in the presence of hydride source, such as sodium borohydride, to give methyl alcohol Compound H2.

Scheme I

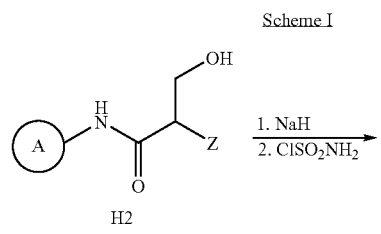

H2

-continued

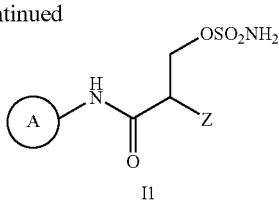

I1

Scheme I illustrates the preparation of compounds of the present invention wherein Y of Formula (I) is a sulfamic acid methyl group. Compound H2 may be treated with a base such as sodium hydride, followed by the addition of sulfamoyl chloride to yield Compound I1.

Scheme J

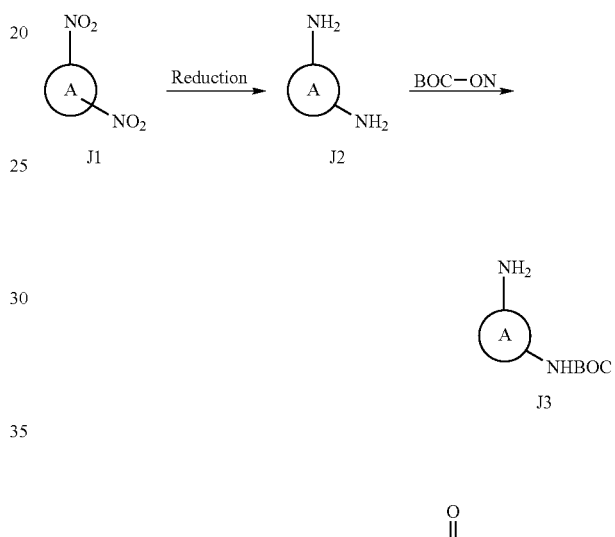

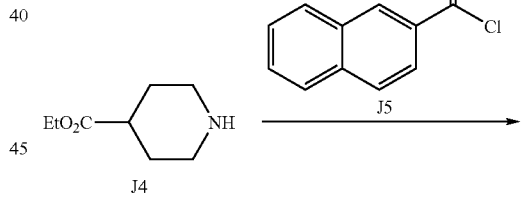

J4

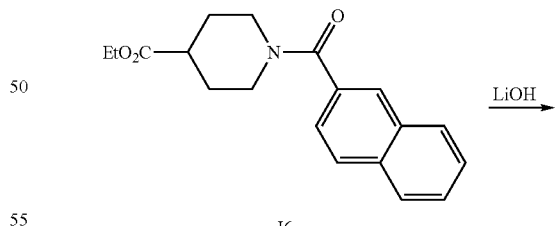

J6

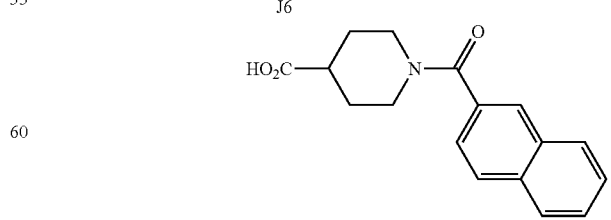

J7

-continued

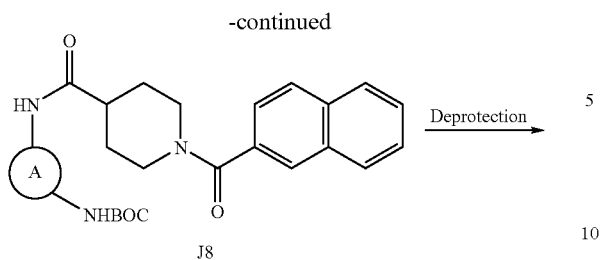

J8

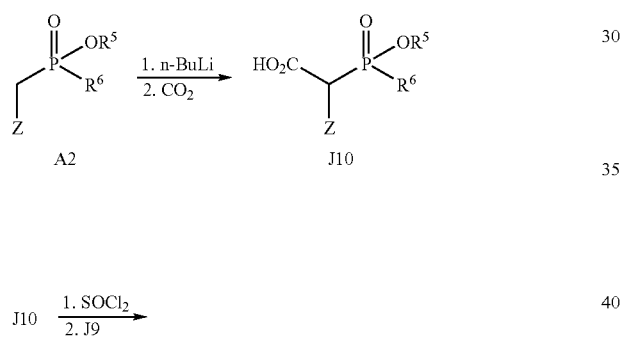

J9

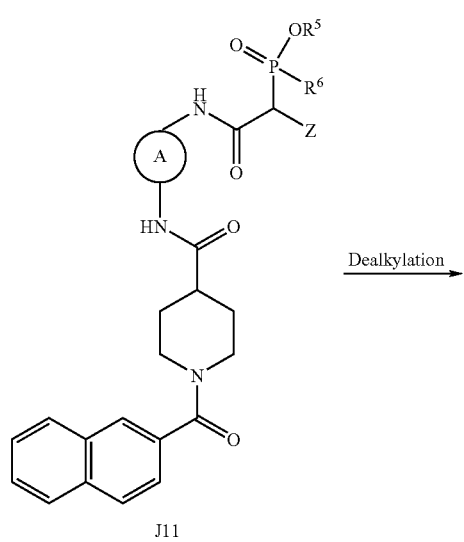

J11

-continued

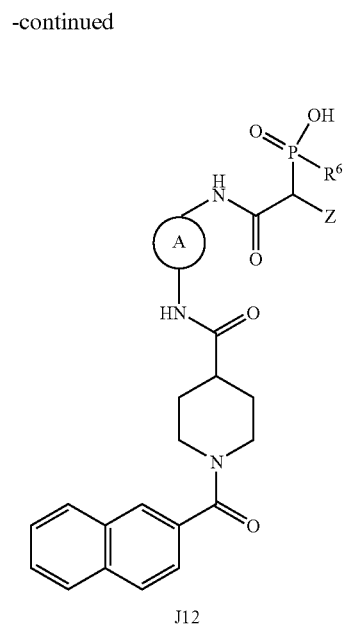

J12

Scheme J illustrates the general method for the preparation of compounds of the present invention wherein $R^3$ is an amide substituent on ring A as defined by the invention. Dinitro-substituted Compound J1 may be reduced by hydrogenation in the presence of a palladium catalyst to give Compound J2 which then may be acylated with BOC-ON to provide Compound J3.

Compound J4 may be acylated with acid chloride Compound J5 to yield Compound J6, followed by saponification of Compound J6 to provide carboxylic acid Compound J7. Compound J8 may be prepared by coupling Compound J3 to Compound J7 using an appropriate coupling agent, activating agent, and solvent.

The Boc protecting group of Compound J8 was removed under acidic conditions to afford the free amine, Compound J9. Treatment of Compound A2 with an organometallic base such as n-butyllithium, followed by reaction with carbon dioxide afforded the carboxylated phosphonic ester, Compound J10. Compound J10 was converted to its acid chloride by treatment with thionyl chloride followed, by condensation with amine Compound J9 to afford amide Compound J11. Compound J11 was dealkylated using bromotrimethylsilane and treated with HCl to provide Compound J12.

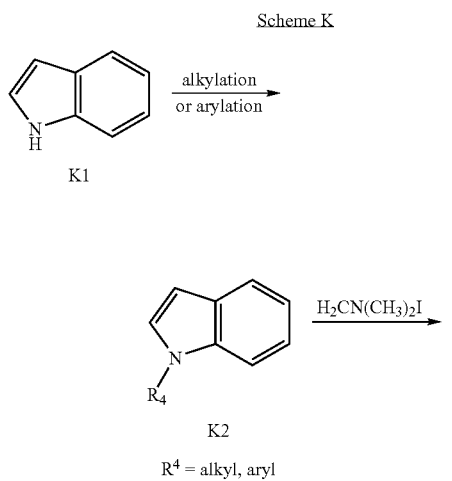

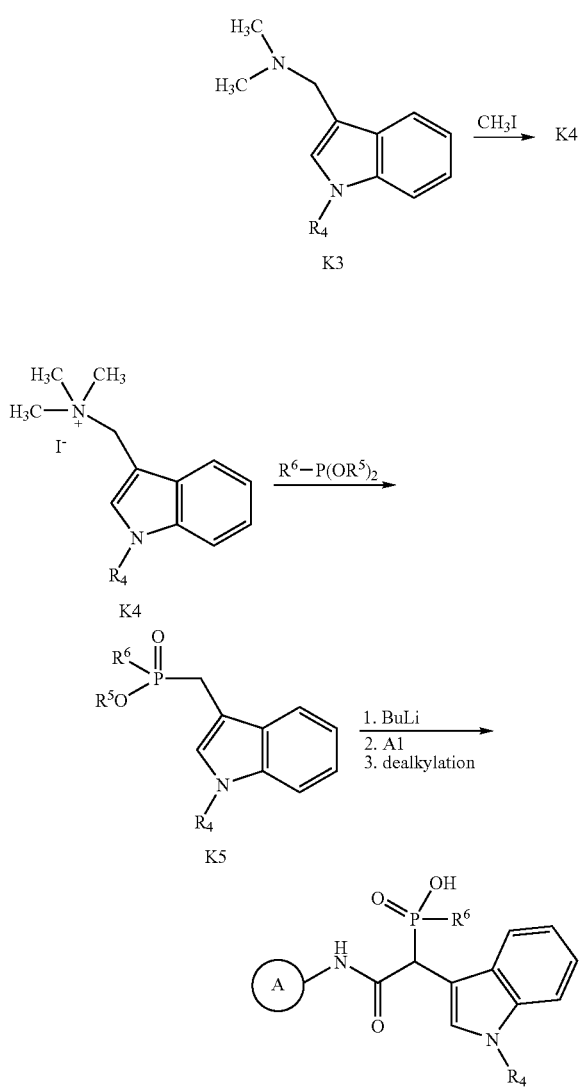

Scheme K illustrates a general method for the preparation of compounds of the present invention wherein Z is an N-substituted indole as previously defined. Compound K1 may be reacted with an alkylating agent such as methyl iodide or an arylating agent such as bromobenzene with copper oxide, Compound K2. Compound K2 may be treated with N,N-dimethylmethyleneammonium iodide to afford Compound K3. Compound K3 may be converted to Compound K4 using methyl iodide, and then reacted with a phosphite or phosphonite to provide Compound K5. Compound K5 may be reacted with Compound A1 and dealkylated as previously described to yield Compound K6.

Optionally, the phenyl portion of Compound K2 may be substituted with an alkoxycarbonyl. In this instance, the ester may be reduced to its corresponding methyl alcohol, and converted to a methyl halide using techniques and reagents known to those skilled in the art. The halide may then be converted to Compound A2 wherein Z is an indole as previously defined in the present invention. Compound A2 may be subsequently reacted according to Scheme A to form a compound of Formula (I) wherein the phosphonic attached through the aryl portion of indole Z.

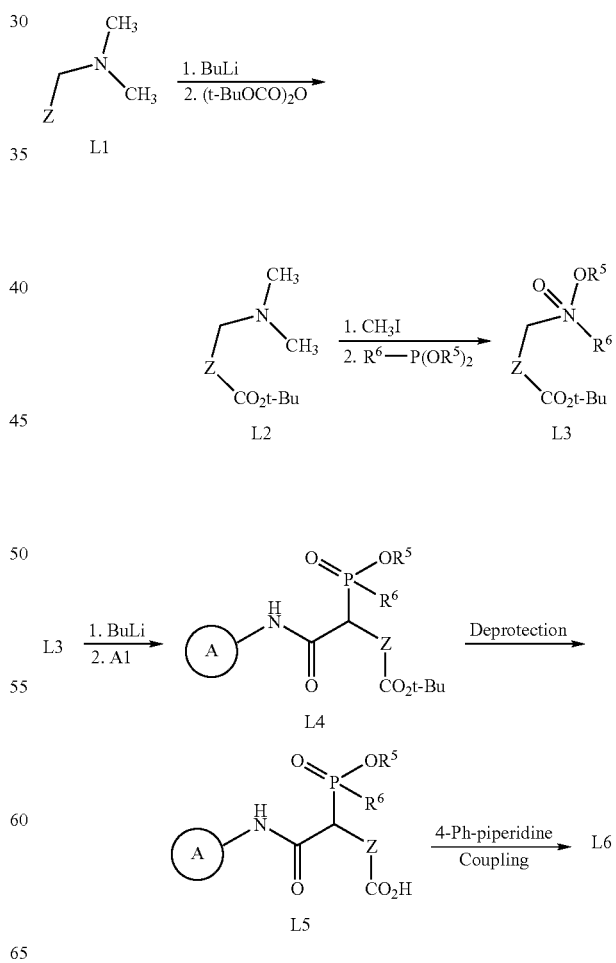

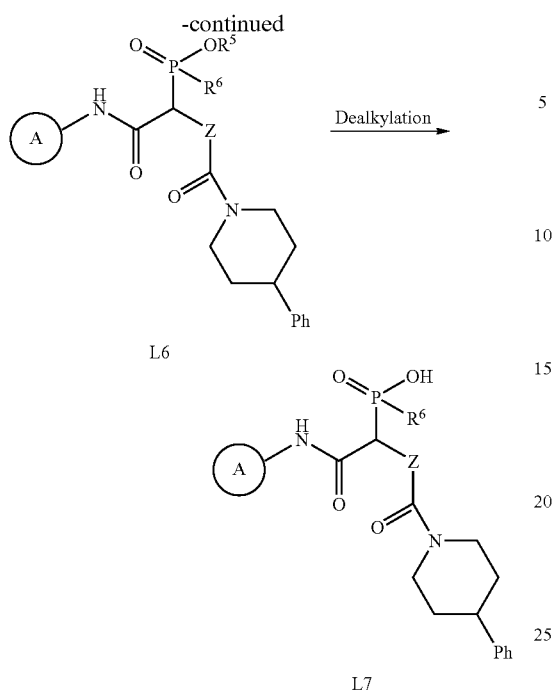

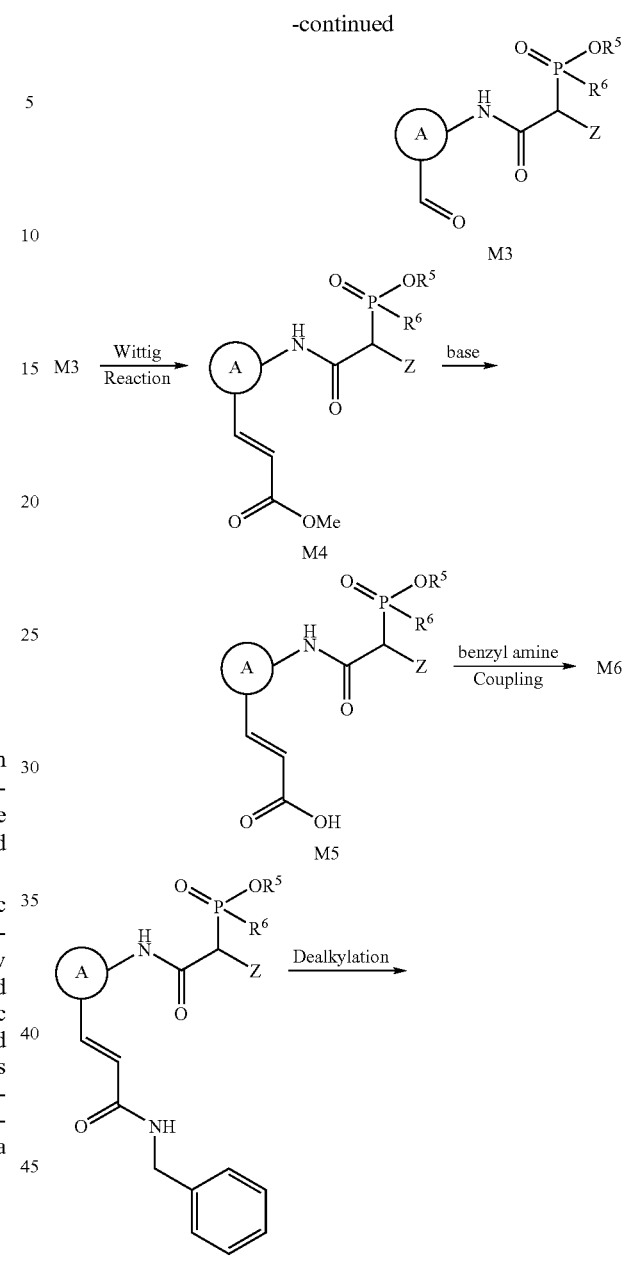

Scheme L illustrates the general method for the preparation of compounds of the present invention wherein $R^4$ is a heterocyclylcarbonyl substituent. Compound L1 may be made by the procedures described in *JACS* 1963, 6, 711-716 and *JACS* 1971, 93(12), 2897-2904.

Compound L1 may be reacted with an organometallic base, such as butyllithium, followed by treatment with di-tert-butyldicarbonate to give Compound L2. Compound L2 may be converted to Compound L4 using the methods described previously. Compound L4 may be deprotected under acidic conditions to afford Compound L5. The carboxylic acid group of Compound L5 may be treated with an amine, such as 4-phenylpiperidine, in the presence of an appropriate coupling agent, base, activating agent, and solvent to afford Compound L6. Dealkylation of Compound L6 as described supra yields Compound L7.

Scheme M illustrates a general method for the preparation of compounds of the present invention. A Compound M1, wherein $R^3$ is an alkoxycarbonyl substituent, may be reduced in the presence of a hydride source to the corresponding alcohol, Compound M2. Compound M2 may be oxidized to aldehyde Compound M3. Reaction of Compound M3 with a Wittig reagent affords alkene Compound M4. Saponification of Compound M4 provides carboxylic acid Compound M5, which may be coupled with an amine, such as benzyl amine, in the presence of an appropriate coupling agent as described supra, to give amide Compound M6. Compound M6 may be dealkylated using the procedure previously described in Scheme A to yield Compound M7.

Alternatively, other compounds of the present invention wherein $R^3$ is alkoxy or —C(=O)$NR^{11}R^{12}$ may be derived from Compound M2. The hydroxy group of Compound M2 may be alkylated using reagents and methods known to one skilled in the art to afford compounds wherein $R^3$ is alkoxy. Alternatively, the hydroxy group of Compound M2 may be reacted with a variety of acylating agents known to one skilled in the art, such as isocyanates, to arrive at compounds of the present invention wherein $R^3$ is a carbamate.

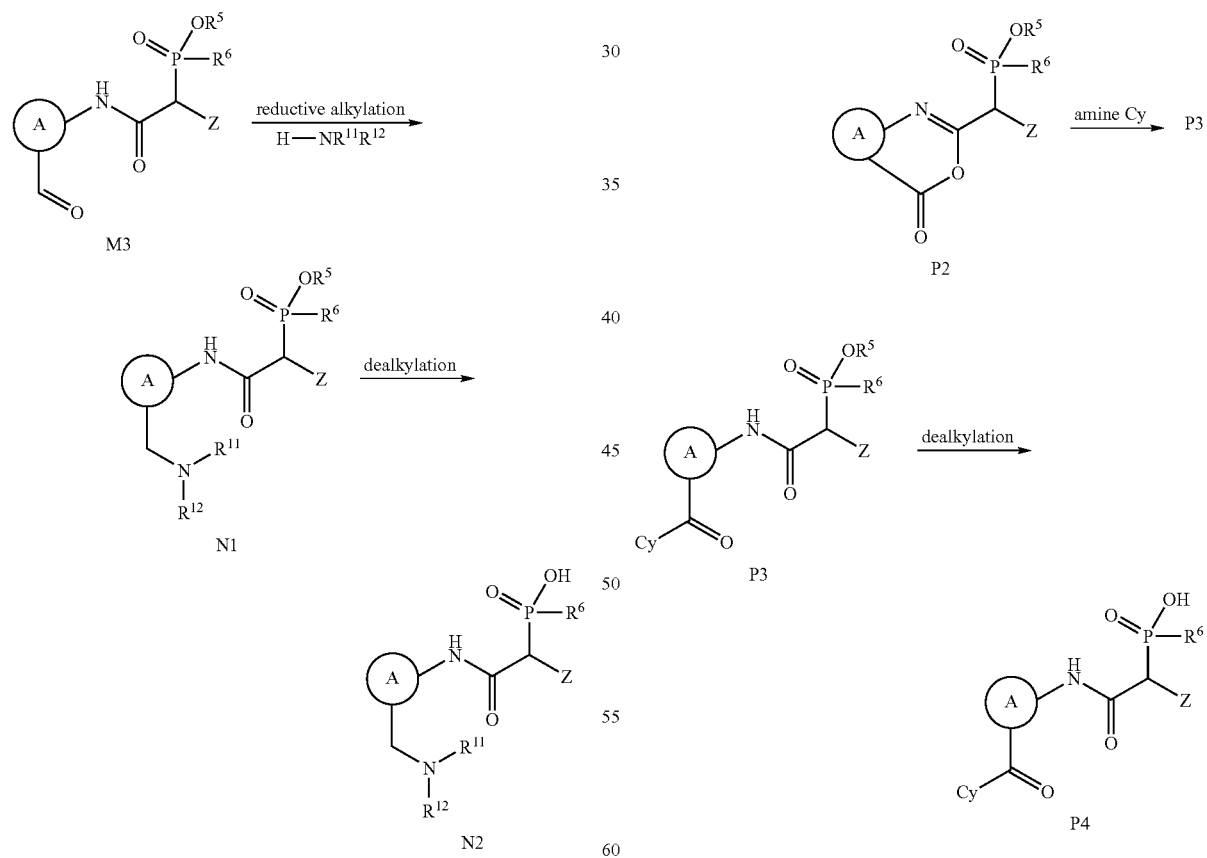

As shown in Scheme N, Compound M3 may be reacted with a variety of amines in the presence of a hydride source under acidic conditions to yield Compound N1. Dealkylation of Compound N1 by the method described in Scheme A affords Compound N2.

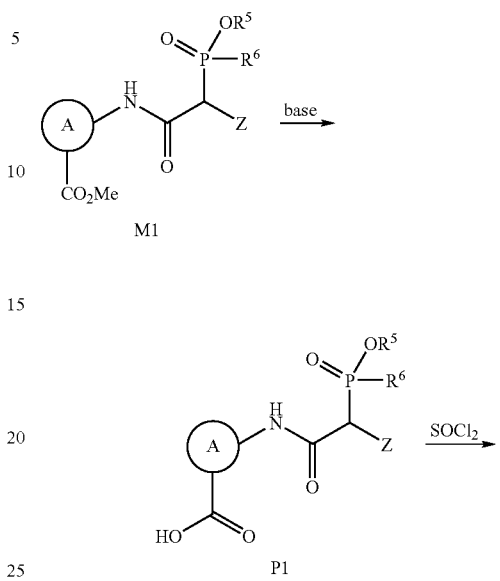

The preparation of compounds of the present invention wherein $R^3$ is —C(=O)Cy as previously defined, and said Cy is attached through a nitrogen atom, is shown in Scheme P. Compound M1 may be saponified under basic conditions to provide Compound P1, which may be treated with thionyl chloride to give Compound P2. Compound P2 may be reacted with a heterocyclic amine to provide Compound P3. Dealkylation of Compound P3 using methods previously described affords Compound P4.

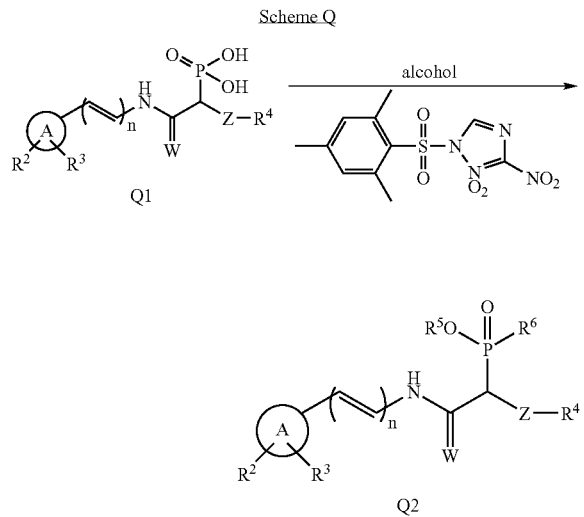

Scheme Q illustrates a method for the preparation of compounds of the present invention wherein $R^5$ and $R^6$ are appropriately substituted alkoxy substituents as defined herein. A compound of formula Q1 wherein $R^5$ is hydrogen and $R^6$ is hydroxyl may be coupled with an appropriately substituted alcohol in the presence of MSNT (1-(mesitylene-2-sulfonyl)-3-nitro-1,2,4-triazole) to afford a compound of formula Q2 wherein $R^5$ is a substituted alkyl and $R^6$ is a substituted alkoxy as defined herein.

Alternatively, compounds of formula Q1 may be elaborated using an appropriately substituted alkylating agent to provide compounds of the present invention where either one or both hydroxyl groups of the phosphonic acid are alkylated. An alkylating agent in this instance is an alkyl substituent that is optionally substituted as defined for $R^5$ or $R^6$, and said alkyl substituent is substituted with a leaving group. A leaving group is defined as a substituent that is activated toward nucleophilic displacement, including halides, tosylates, and the like.

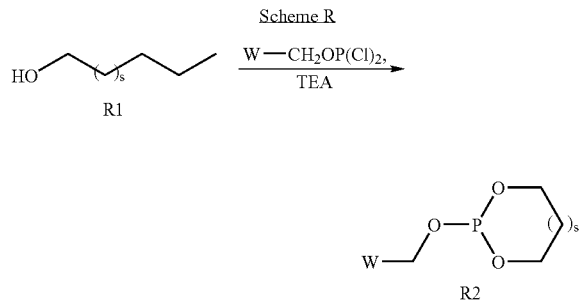

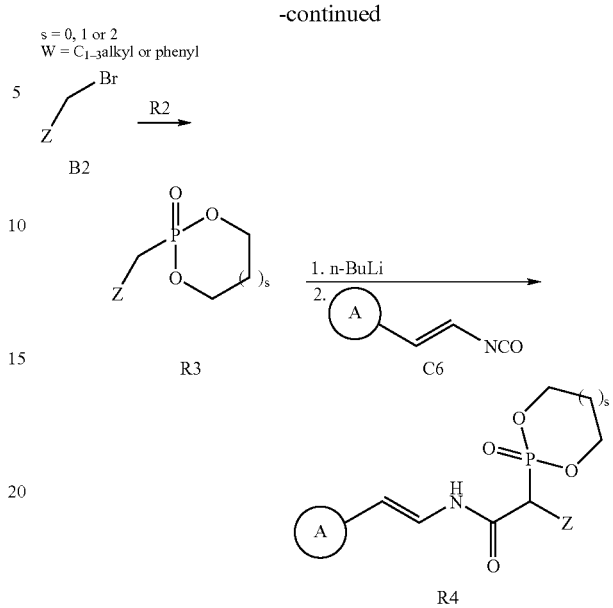

Scheme R illustrates the preparation of compounds of the present invention wherein $R^5$ and $R^6$ (when $R^6$ is alkoxy) are taken together with the atoms to which they are both attached to form a monocyclic ring. A diol of formula R1 may be treated with a benzyl- or lower alkyl-dichlorophosphite to form a cyclic phosphonate of formula R2. A compound of formula R2 may be condensed under refluxing conditions with a compound of formula B2 to form a compound of formula R3. The elaboration of a compound of formula R3 to a compound of formula R4 may be achieved using the methods described for Scheme A.

SPECIFIC SYNTHETIC EXAMPLES

The following Examples are set forth to aid in the understanding of the invention, and are not intended and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

All chemicals were obtained from commercial suppliers and used without further purification. $^1$H and $^{13}$C NMR spectra were recorded on a Bruker, AC® 300B (300 MHz proton) or a Bruker® AM-400 (400 MHz proton) spectrometer with Me$_4$Si as an internal standard (s=singlet, d=doublet, m=multiplet, t=triplet, br=broad). ES-MS were recorded on a Micromass® mass spectrometer or on an Agilent® HPLC mass spectrometer. TLC was performed with Whatman® 250-μm silica gel plates. Preparative TLC was performed with Analtech® tapered silica gel GF plates. Preparative. HPLC separations were carried out on a Gilson® HPLC using a Phenomenex® Kromasil 100A C18 column (25 cm×50 mm, or 10 cm×21.2 mm) using gradients of CH$_3$CN/water/0.2% TFA; Analytical HPLC separations were carried out on a Supelco® ABZ+Plus column (5 cm×2.1 mm) or a YMC® J'Sphere H80 S4 column (5 cm×2 mm) with detection at 220 nm and 254 nm on a Hewlett Packard® 1100 UV detector. The gradient used was 10% to 90% CH$_3$CN/water/0.1% TFA in 6 min. Reported percent purity data is based on the 220 nm data. Microanalysis was performed by Robertson Microlit Laboratories, Inc.

Representative Chemical Abstracts Service (CAS) Index-like names for the compounds of the present invention were derived using the Autonom Version 2.1 nomenclature software.

Example 1

[(5-Chloro-benzo[b]thiophen-3-yl)-(naphthalen-2-ylcarbamoyl)-methyl]-phosphonic acid, Cpd 9

A solution of Compound 1a (5.01 g, 19.2 mmol) and Compound 1b (10 mL) was refluxed for 105 min. The solution was concentrated under high vacuum at 90° C. to yield 6.01 g of Compound 1c as a pale yellow viscous oil; HPLC: 3.51 min; MS (ES) m/z 319 (MH$^+$).

To a solution of 2.5 M n-BuLi in hexanes (4.73 mL, 12 mmol) in THF (30 mL) at −78° C. was added dropwise a solution of Compound 1c (3.77 g, 12 mmol) in THF (30 mL) over 15 min. After stirring for an additional 30 min, Compound 1d (naphthalen-2-yl isocyanate) (2.0 g, 12 mmol) in THF (30 mL) was added dropwise to the mixture over 5 min. After the addition was complete, the solution was allowed to reach rt and stirred overnight. Excess saturated NH$_4$Cl (aq) was added, and the layers were separated. The aqueous portion was extracted with EtOAc (3×20 mL). The combined organic extracts were dried (Na$_2$SO$_4$), filtered, and concentrated under reduced pressure at rt. The residue was taken up in CH$_3$CN (10 mL) the solid was collected and dried under N$_2$/vacuum to afford Compound 1e (4.3 g) as a white powder: HPLC: 4.25 min; MS (ES) m/z 488 (MH$^+$).

Procedure A: General Method for Deethylation of Phosphonates and Phosphinates

To a solution of the phosphonate or phospinate (x mmol) in pyridine (5 mL/mmol of phosphonate or phosphinate) is added excess bromotrimethylsilane (5× to 8× mmol) in three portions at 15 min intervals. The mixture is stirred for 60 min after the last addition, then concentrated under reduced pressure. The residue is stirred with excess 1N HCl (aq) for 60 min. The white precipitate is collected and rinsed sequentially with 1N HCl (aq) and water, then dried under N$_2$/vacuum. The crude product may be purified by trituration with appropriate solvents, salt formation, recrystallization, or reverse phase chromatography.

Compound 1e (4.3 g, 8.8 mmol) was deethylated according to Procedure A. The crude product was further purified: the white solid was stirred with CH$_3$CN for 60 min, collected, rinsed with CH$_3$CN, and dried under N$_2$/vacuum to afford 3.2 g of Cpd 9 as a white powder: HPLC 4.47 min; MS (ES) m/z 432 (MH$^+$).

To a solution of Cpd 9 (2.68 g, 6.2 mmol) in CH$_3$OH (10 mL) was added a solution of tris(hydroxymethyl)aminomethane (1.5 g, 12.4 mmol) in CH$_3$OH (10 mL). The solution was concentrated, and the resulting white solid was recrystallized from i-PrOH to yield 4.0 g of the tromethamine salt of Cpd 9 as an off-white solid. HPLC: 4.4 min, 94%; MS (ES) m/z (MH$^+$)=432; $^1$H NMR (DMSO-d$_6$) δ 3.32 (s, 10H), 4.59 (d, 1H), 7.30-7.42 (overlapping m, 3H), 7.56 (d, 1H), 7.71-7.80 (overlapping m, 3H), 7.94-7.05 (overlapping m, 3H), 8.28 (s, 1H), 11.40 (s, 1H); Anal. Calc'd for C$_{20}$H$_{15}$NO$_4$PSCl·1.6C$_4$H$_{11}$NO$_3$·1.0 i-PrOH·0.25H$_2$O: C, 51.16; H, 6.01; N, 5.28; H$_2$O, 0.66. Found: C, 51.21; H, 5.92; N, 5.22; H$_2$O, 0.74.

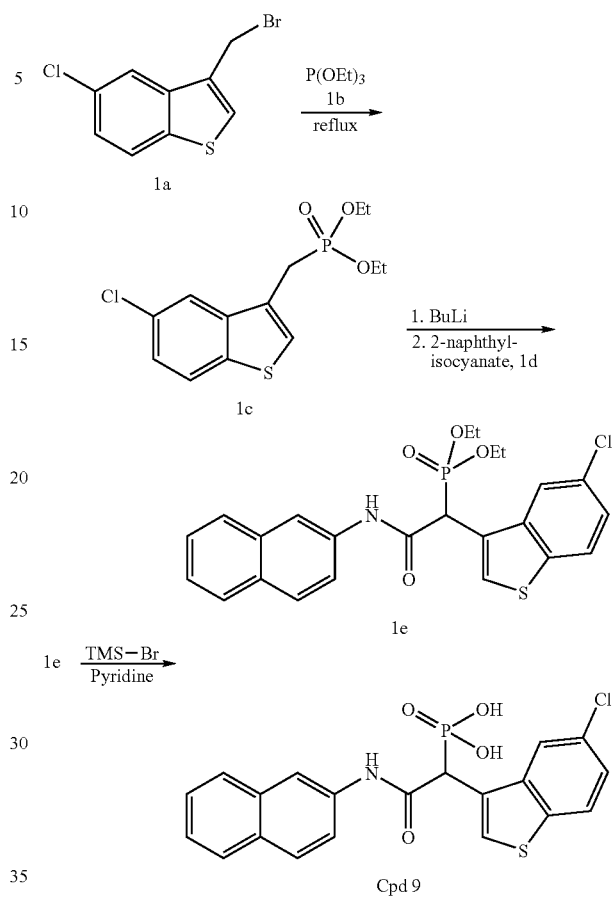

Other compounds of the present invention may be prepared by those skilled in the art by varying the starting materials, reagent(s) and conditions used. Using the procedure for Example 1, the following compounds were prepared without further purification:

| Cpd | MS (MH$^+$) | Cpd | MS (MH$^+$) |
|---|---|---|---|
| 30 | 439 | 76 | 476 |
| 31 | 392 | 82 | 382 |
| 55 | 436 (MH−) | 96 | 393 |
| 57 | 393 | 106 | 430 |
| 59 | 398 | 129 | 381 |
| 64 | 398 | 135 | 386 |
| 67 | 510 (MH−) | 137 | 393 |
| 68 | 379 (MH−) | 138 | 434 |
| 79 | 393 | | |

Example 2

[(Benzo[b]thiophen-2-yl)-(naphthalen-2-ylcarbamoyl)-methyl]-phosphonic acid, Cpd 140

To a solution of Cpd 2a (3.5 g, 26.1 mmol) in 25 mL of THF at −78° C. was added a solution of 2.5 M n-BuLi in hexanes (13 mL, 32.6 mmol). The reaction was warmed to 0° C. and stirred for 25 min, then 4 mL of DMF was added slowly. The solution was heated to reflux for 1 h. The reaction was cooled to rt, poured into water and extracted three times with Et$_2$O. The combined organic extracts were washed with brine, dried (Na$_2$SO$_4$), filtered, and concentrated under reduced pressure at rt. The crude oil was dissolved in 25 mL of MeOH, cooled to 0° C., and NaBH$_4$ (1.6 g, 42 mmol) was added and stirred for 2 h. After quenching with excess acetone, the mixture was concentrated, and the residue was partitioned between EtOAc and brine. The brine was extracted twice with EtOAc, and the combined organic extracts were washed twice with brine, dried (Na$_2$SO$_4$), filtered and concentrated under reduced pressure at rt. The crude solid was stirred with 6:1 CH$_2$Cl$_2$/hexane, then collected to afford Compound 2b (2.52 g) as an off-white powder: HPLC: 2.85 min.

To Compound 2b (2.52 g, 16.8 mmol) was added 10 mL of thionyl chloride and refluxed for 1.5 h. The reaction was concentrated under reduced pressure at rt, and the residue was treated with hexanes. After concentration, the residue was treated with excess triethylphosphite Compound 1 b and refluxed for 1.5 h. The reaction was concentrated under reduced pressure at 90° C. and purified by flash column chromatography (silica, 0 to 40% EtOAc/Hexane) to yield Compound 2c (2.5 g) as an oil: HPLC: 3.32 min; MS (ES) m/z 285 (MH$^+$).

From Compound 2c (0.64 g, 2.25 mmol) was prepared Compound 140 according to Procedure A: HPLC: 3.87 min; MS (ES) m/z 398 (MH$^+$).

Example 4

[1-(5-Chloro-benzo[b]thiophen-3-yl)-1-(naphthalen-2-ylcarbamoyl)-ethyl]-phosphonic acid, Cpd 125

To a solution of 2.5 M n-BuLi in hexanes (0.44 mL, 12 mmol) in THF (7 mL) at −78° C. was added dropwise a solution of Compound 1c (3.77 g, 1.1 mmol) in THF (7 mL). After stirring for 30 min, methyl iodide (0.068 mL, 1.1 mmol) was added dropwise by syringe. The reaction was warmed to 0° C. and then to rt. The solution was returned to −78° C. and a solution of 2.5 M n-BuLi in hexanes (0.44 mL, 12 mmol) was added dropwise. After stirring for 30 min, Compound 1d (0.19, 1.1 mmol) in THF (7 mL) was added dropwise to the mixture. After the addition was complete, the solution was allowed to reach rt and stirred overnight. Excess saturated NH$_4$Cl (aq) was added, and the layers were separated. The aqueous portion was extracted with EtOAc (3×5 mL). The combined organic extracts were dried (Na$_2$SO$_4$), filtered, and concentrated under reduced pressure at rt. The residue was dissolved in CH$_3$CN (5 mL), and filtered. The filtrate was purified by flash column chromatography (silica, CH$_2$Cl$_2$) to yield Compound 4a (0.036 g) HPLC: 4.62 min; MS (ES) m/z 502 (MH$^+$).

Compound 4a was converted to Compound 125 using Procedure A: HPLC: 4.34 min (94%); MS (ES) m/z 444 (MH$^-$).

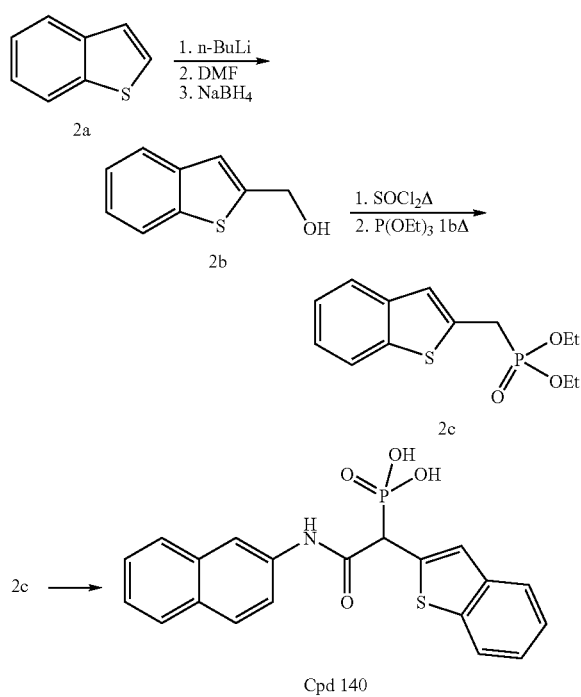

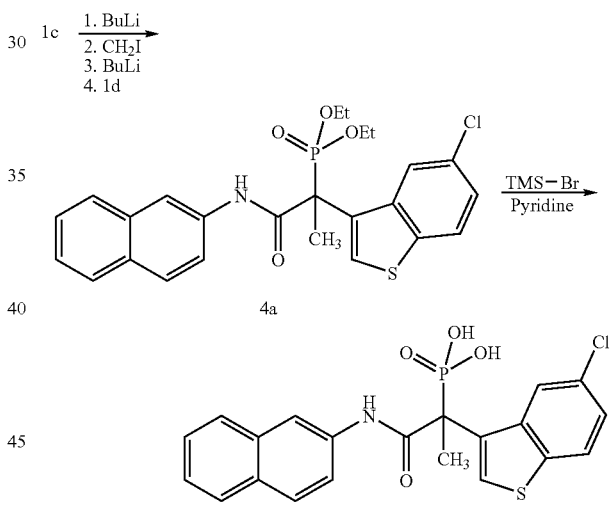

Example 3

[(5-Chloro-benzo[b]thiophen-3-yl)-(naphthalen-2-ylthiocarbamoyl)-methyl]-phosphonic acid, Cpd 45

Using the procedure described in Example 1 and substituting 2-napthylthioisocyanate for 2-naphthylisocyanate, Compound 45 was synthesized as a pale yellow powder: HPLC: 4.89 min; MS (ES) m/z 448 (MH$^+$).

Example 5

[(5-Chloro-1,1-dioxo-1H-1λ$^6$-benzo[b]thiophen-3-yl)-(naphthalen-2-ylcarbamoyl)-methyl]-phosphonic acid, Cpd 86

Compound 1e (0.20 g, 0.41 mmol) was suspended in acetic acid (5 mL) and heated to 47.5° C. and sodium perborate tetrahydrate Compound 5a (0.31 g, 2.0 mmol) was added portionwise over 15 min, and the reaction was stirred at 47.5° C. overnight. The reaction was partitioned between water and EtOAc, and the layers were separated. The aqueous phase was extracted with EtOAc, and the combined organic phases were washed sequentially with saturated NaHCO$_3$ (aq), brine, and then dried (Na$_2$SO$_4$), filtered, and concentrated under reduced pressure at rt. The residue was purified by flash column chromatography (silica, 0-40% EtOAc/hexane) to yield Compound 5b (0.052 g): HPLC: 3.87 min; MS (ES) m/z 520 (MH+).

Compound 5b (0.052 g, 0.10 mmol) was converted Compound 86 (0.0185 g) by Procedure A: HPLC: 3.25 min, 95%; MS (ES) m/z 462 (MH-).

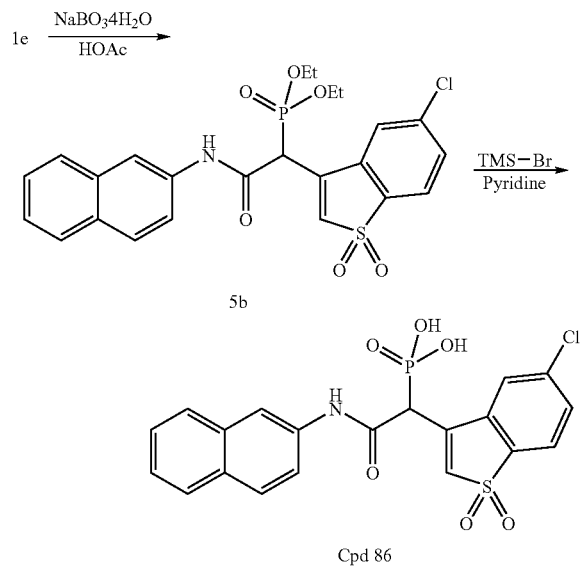

Example 6

{[(5-Chloro-benzo[b]thiophen-3-yl)-[2-(3,4-difluoro-phenyl)-vinylcarbamoyl]-methyl}-methyl-phosphinic acid, Cpd 17

A solution of Compound 1a (1.96 g, 7.48 mmol) in excess diethylmethylphosphonite was refluxed for 3 h. The solution was concentrated under high vacuum at 90° C., and the residue was purified by flash column chromatography (silica, 0-100% EtOAc/hexanes) to yield 1.88 g of Compound 6a as a slightly cloudy pale yellow viscous oil: HPLC: 3.19 min; MS (ES) m/z 290 (MH+).

To a suspension of Compound 6b (5.0 g, 27.2 mmol) in dry benzene (20 mL) was added triethylamine (3.74 mL, 27.2 mmol). The solution cooled to 0° C., and Compound 6c (5.86 mL, 27.2 mmol) was added rapidly dropwise, and the cooling was removed. The reaction was stirred 18 h, then poured into $H_2O$. The mixture was extracted three times with EtOAc, and the combined organic extracts were washed once with brine, dried ($Na_2SO_4$), filtered, and concentrated under reduced pressure at rt. The residue was purified by flash column chromatography (silica, 0-100% EtOAc/hexanes) to yield 4.88 g of Compound 6d as a white solid: HPLC: 3.65 min.

Compound 6d (3.4 g, 16.3 mmol) was dissolved in benzene (30 mL) and refluxed for 3 h. The solution was concentrated under reduced pressure at rt and the resulting crude Compound 6e was used without purification in the next reaction.

To a solution of 2.5M n-BuLi in hexanes (8.9 mL, 22.3 mmol) in THF (30 mL) at −78° C. was added dropwise a solution of Compound 6a (4.7 g, 16.3 mmol) in THF (30 mL) over 15 min. After stirring for an additional 30 min, a solution of Compound 6d (3.4 g, 16.3 mmol) in THF (30 mL) was added dropwise to the mixture over 5 min. After the addition was complete, the solution was stirred at −78° C. for 30 min, then quenched cold with excess $NH_4Cl$ (saturated, aq.), and stirred overnight at rt. The layers were separated, and the aqueous portion was extracted with EtOAc (2×20 mL). The combined organic extracts were washed once with brine, dried ($Na_2SO_4$), filtered, and concentrated under reduced pressure at rt. The residue was purified by flash column chromatography (silica, 0-50% EtOAc/hexanes) to yield 4.1 g of a pale yellow solid, which was stirred with 15 mL $CH_3CN$, collected, and dried under $N_2$/vacuum to afford 3.5 g of Compound 6f as a white powder: HPLC: 4.04 min., 97%, broad; MS (ES) m/z 470 (MH+).

Compound 6f (3.5 g, 7.46 mmol) was deethylated following Procedure A. The solid was further purified by taking it up in MeOH, followd by collection of the precipitate to afford Compound 17 (2.93 g) as a white powder: HPLC 4.0 min.

To a mixture of Compound 17 (2.93 g, 6.2 mmol) in $CH_3OH$ (10 mL) was added a solution of tris(hydroxymethyl)aminomethane (0.75 g, 6.2 mmol) in $CH_3OH$ (1.0 mL). The solution was filtered and concentrated under reduced pressure at rt, and the resulting white solid was recrystallized from $CH_3CN$/EtOAc to yield the tromethamine salt of Compound 17 (3.35 g) as a white solid. HPLC: 4.02 min, 100%; MS (ES) 442 (MH+); $^1$H NMR (DMSO-$d_6$) δ 1.07 (d, 3H), 3.45 (s, 6H), 4.48 (d, 1H), 6.12 (d, 1H), 7.12-7.18 (br m, $^1$H), 7.24-7.45 (overlapping m, 4H), 7.92-8.00 (overlapping m, 3H), 10.92 (d, 1H); Anal. Calc'd for $C_{19}H_{15}NO_3PSCl$ $F_2$.1.0 $C_4H_{11}NO_3$.0.15$H_2O$: C, 48.84; H, 4.69; N, 4.96; $H_2O$, 0.48. Found: C, 48.99; H, 4.62; N, 4.97; $H_2O$, 0.42.

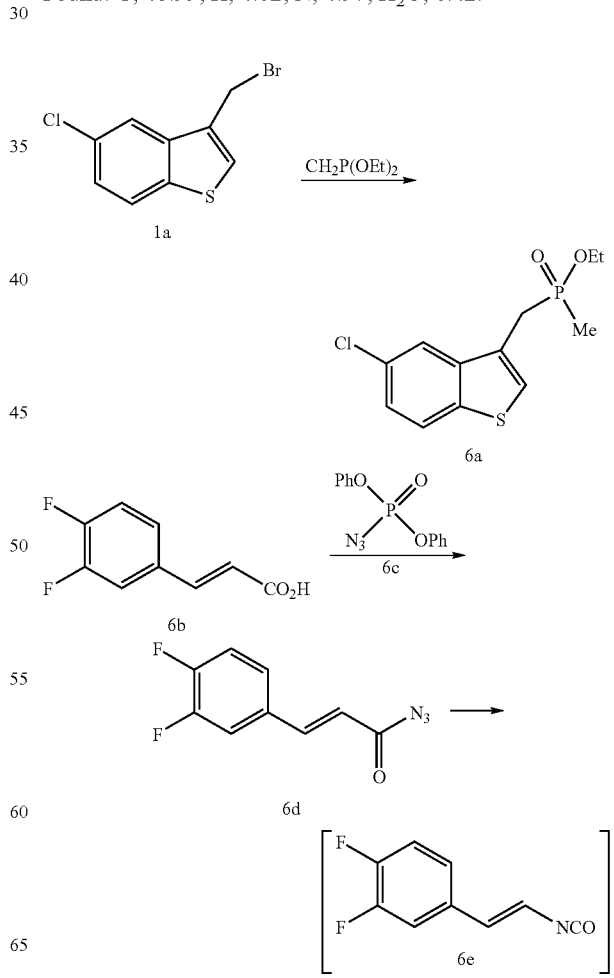

-continued

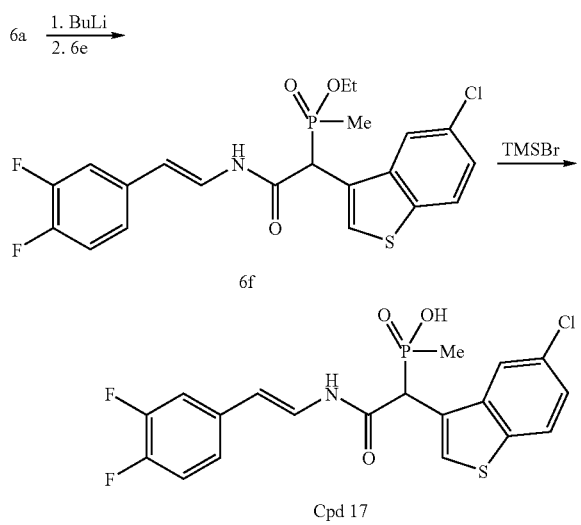

Other compounds of the present invention may be prepared by those skilled in the art by varying the starting materials, reagent(s) and conditions used. Using the procedure of Example 6, the following compounds were prepared without further purification:

| Cpd | MS (MH+) |
|---|---|
| 14 | 406 |
| 15 | 422 (MH−) |
| 16 | 460 |
| 20 | 430 |
| 21 | 422 (MH−) |
| 24 | 422 (MH−) |
| 28 | 444 |
| 29 | 456 |
| 33 | 389 |
| 66 | 422 (MH−) |
| 144 | 382 |
| 145 | 436 |
| 146 | 420 |
| 147 | 451 |
| 148 | 464 |
| 150 | 407 |
| 152 | 474 |
| 153 | 490 |
| 154 | 436 |
| 155 | 420 |
| 156 | 442 |
| 157 | 431 |
| 160 | 440 |
| 161 | 440 |
| 162 | 442 |
| 163 | 442 |
| 164 | 485 |
| 165 | 466 |
| 166 | 451 |
| 167 | 485 |
| 168 | 464 (MH−) |
| 169 | 442 |
| 170 | 475 |
| 171 | 442 |

The following compounds can be made by those skilled in the art by using Example 6 and varying the starting materials, reagent(s) and conditions used: compounds 300, 301, 302, 303, 304, 305, 306, and 307.

Example 7

[(5-Chloro-benzo[b]thiophen-3-yl)-(2-amino-4-benzothioazol-6-ylcarbamoyl)-methyl]-phosphonic acid, Cpd 69

Using the procedure described in Example 6 for the conversion of Compound 6b to Compound 17, Compound 7a was converted to Compound 7b. Compound 7b was suspended in a small volume of 1,4-dioxane and gaseous HCl was bubbled in to yield a clear yellow solution and the solution was stirred for 1 h. The reaction was concentrated under reduced pressure at rt, the residue stirred with 1N HCl (aq) for 45 min, and the solid was collected to yield Compound 69 as a yellow powder: HPLC: 2.58 min; MS (ES) m/z 454(MH+).

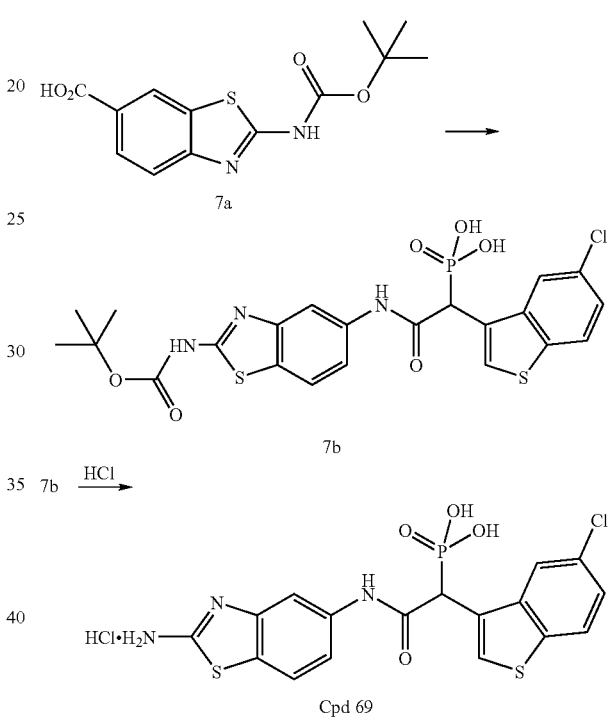

Example 8

2-(5-Chloro-benzo[b]thiophen-3-yl)-n-naphthalen-2-yl-2-(1h-tetrazol-5-yl)-acetamide, Cpd 88

A solution of Compound 8a (1.15 g, 5.53 mmol) in THF (10 mL) was added dropwise to a solution of 2.5M n-BuLi in hexanes (2.40 mL, 6.08 mmol) in THF (10 mL) at −78° C. After stirring for 30 min at −78° C., a solution of Compound 1d (0.94 g, 5.60 mmol) in THF (10 mL) was added dropwise. After 1 h, the reaction was quenched at −78° C. with excess $NH_4Cl$ (aq). After warming to rt gradually, the layers were separated, and the aqueous phase was extracted with EtOAc (3×10 mL). The combined organic extracts were dried ($Na_2SO_4$), filtered, and concentrated under reduced pressure at rt. The residue was stirred with MeOH, and the precipitate was collected to yield Compound 8b (1.5 g) as an off-white powder: HPLC: 4.39 min.

A suspension of Compound 8b (0.28 g, 0.75 mmol), sodium azide (0.15 g, 2.24 mmol), and triethylamine hydrochloride (0.31 g, 2.24 mmol) in toluene (7 mL) was refluxed overnight. Upon cooling to rt, EtOAc (10 mL) and 1 N HCl (10 mL) were added and the mixture was stirred vigorously. The biphasic mixture was filtered and a tan solid was collected. The layers were separated, and the organic layer was concentrated under reduced pressure at rt. The residue was treated with CH₃CN, and a tan solid was collected. The combined solids were treated with hot CH₃CN (100 mL), cooled, and the solid was collected to afford Compound 88: HPLC: 4.11 min; MS (ES) m/z 420 (MH⁺)=420; ¹H NMR (DMSO-d₆) δ 6.15 (s, 1H), 7.41-7.62 (overlapping m, 4H), 7.82-7.93 (overlapping m, 5H), 8.10 (d, 1H, J=8.6 Hz), 8.32 (s, 1H), 10.92 (s, 1H).

minimum volume of CH₃CN and allowed to stand overnight. The solution was filtered, and the filtrate was concentrated under reduced pressure and the residue was purified by reverse phase HPLC (20-90% CH₃CN/H₂O). The resulting white powder was dissolved in CH₃CN, filtered, and concentrated under reduced pressure at rt to yield Compound 50 (0.14 g) as a white solid: HPLC: 3.14 min; MS (ES) m/z 430 (MH⁻); ¹H NMR (DMSO-d₆) δ 5.35 (s, 1H), 7.28-7.51 (overlapping m, 4H), 7.72-7.80 (m, 3H), 7.92-8.05 (overlapping m, 3H), 8.24 (s, 1H), 10.40 (s, 1H), 10.40

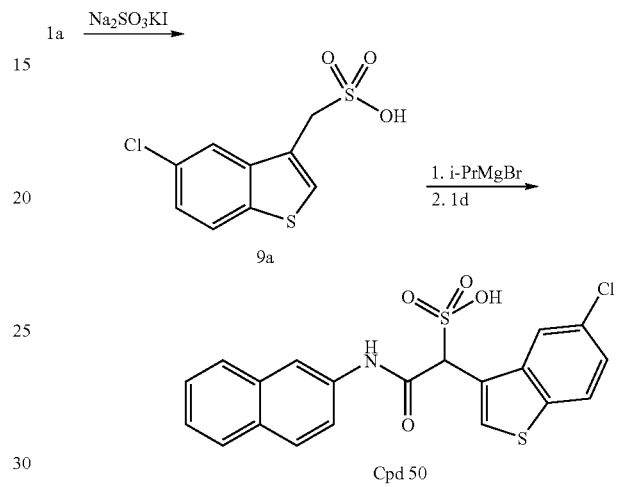

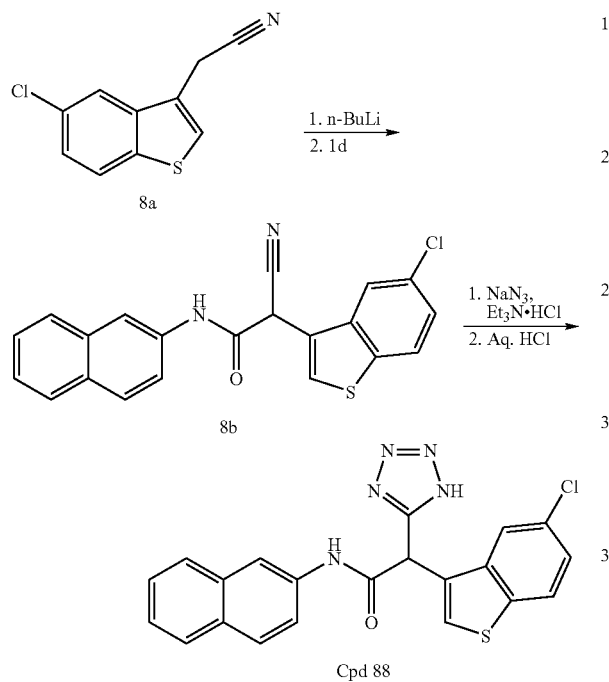

Example 9

[(5-Chloro-benzo[b]thiophen-3-yl)-(naphthalen-2-ylcarbamoyl)-methyl]-sulfonic acid, Cpd 50'

To a solution of Compound 1a (1.0 g, 3.85 mmol) in acetone (5 mL) was added a solution of sodium sulfite (0.49 g, 3.85 mmol) and KI (potassium iodide) (0.13 g, 0.77 mmol) in water (10 mL). The solution was refluxed for 3.5 h, then cooled to rt and concentrated under reduced pressure. The residue was treated with 1N HCl (15 mL), filtered, and the filtrate was extracted with EtOAc (3×10 mL). The combined organic extracts were filtered, and concentrated under reduced pressure at rt to yield 0.60 g of Compound 9a as a white powder: HPLC: 3.38 min; MS (ES) m/z 261 (MH⁻).

To a suspension of Compound 9a (0.29 g, 1.11 mmol) in THF (7 mL) at −5° C. was added a solution of 2 M i-PrMgBr in Et₂O (1.39 mL, 2.77 mmol). The mixture was stirred for 2 h at rt, then cooled to −10° C. before treatment with a solution of Compound 1d (0.20 g, 1.17 mmol) in THF (7 mL). After stirring overnight at rt, the reaction was quenched with 3 mL of 1N HCl (aq), and extracted with EtOAc (3×10 mL). The combined organic layers were washed with brine (10 mL), dried (Na₂SO₄), filtered, and concentrated under reduced pressure at rt. The resulting tan foam was dissolved in a

Example 10

{[(5-Chloro-benzo[b]thiophen-3-yl)-[2-(4-aminophenyl)-vinylcarbamoyl]-methyl}-methyl-phosphonic acid, Cpd 12

Using the procedure described in Example 6, substituting p-nitro-cinnamic acid for 3,4-difluorocinnamic acid and substituting Compound 1c for Compound 6a, Compound 10a was prepared. To a solution of Compound 10a (0.115 g, 0.226 mmol) in 6 mL of 1:1 EtOH/CH₂Cl₂ was added 10% Pd/C (0.060 g) and hydrazine hydrate (0.173 mL, 3.35 mmol). After 2 h, the reaction mixture was filtered, concentrated under reduced pressure at rt, and the resulting yellow solid was taken up in hot acetonitrile and filtered. The filtrate was concentrated under reduced pressure at rt, and the residue was purified by flash column chromatography (silica, 1% CH₃OH/CH₂Cl₂) to yield Compound 10b (0.064 g) as a bright yellow solid: HPLC: 2.94 min; MS (ES) m/z 479 (MH⁺).

Compound 10b (0.064 g, 0.134 mmol) was deethylated by Procedure A to yield Compound 12 (0.036 g) as an orange solid: HPLC: 2.41 min; MS (ES) m/z 423 (MH⁺).

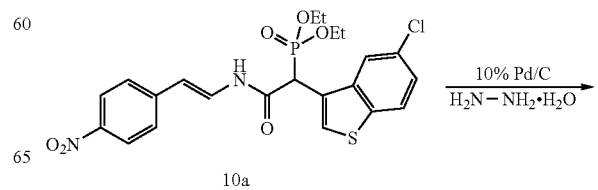

-continued

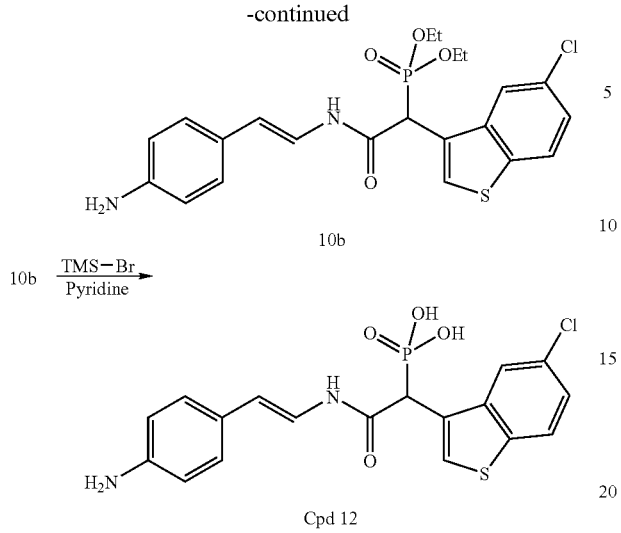

Example 11

{[(5-Chloro-benzo[b]thiophen-3-yl)-[2-(3,4-difluoro-phenyl)-vinylcarbamoyl]-methyl}-methyl-phosphonic acid, Cpd 2

Using the procedure described in Example 6, substituting phosphonate Compound 1c (0.75 g, 2.34 mmol) for Compound 6a, followed by deethylation by Procedure A, Compound 2 (0.116 g) was prepared as a white solid: HPLC: 3.98 min; MS (ES) m/z 444 (MH$^+$); Anal. Calc'd for $C_{18}H_{13}NO_3PSCl$ $F_2 \cdot 1.0 C_4H_{11}NO_3 \cdot 0.10 H_2O$ $C_4H_{11}NO_3 \cdot 0.33 C_2H_6O$: C, 46.34; H, 4.43; N, 4.87; $H_2O$, 1.04. Found: C, 46.47; H, 4.09; N, 4.65; $H_2O$, 1.34.

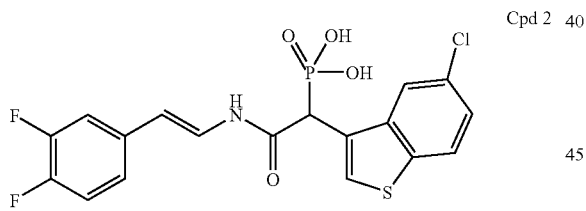

Cpd 2

Other compounds of the present invention may be prepared by those skilled in the art by varying the starting materials, reagent(s) and conditions used. Using the procedure of Example 11, the following compounds were prepared without further purification:

| Cpd | MS (MH$^+$) |
|---|---|
| 18 | 407 (MH−) |
| 19 | 424 (MH−) |
| 25 | 409 |
| 37 | 368 |
| 38 | 437 |
| 42 | 422 |
| 49 | 468 |
| 78 | 440 |
| 81 | 476 |
| 199 | 442 (MH−) |

The following compounds can be made by those skilled in the art by using Example 11 and varying the starting materials, reagent(s) and conditions used: compounds 192, 193, 194, 195, 196, 197, 198, 200, 201, 202, 203, 204, 205, 206, 207, 208, 209, 308, 309, 310, 311, 312, 313, 314, and 315.

Example 12

[(5-Chloro-benzo[b]thiophen-3-yl)-(naphthalen-2-ylcarbamoyl)-methyl]-phenyl-phosphinic acid, Cpd 89

Compound 12a (0.35 g, 1.17 mmol) was prepared by the method described in Aust. J. Chem. 1983, 36, 2517-2536. Using the procedure described in Example 1 and Procedure A, substituting Compound 12a for Compound 1c, Compound 89 was prepared as a white solid: HPLC: 4.19 min; MS (ES) m/z 490 (MH$^-$).

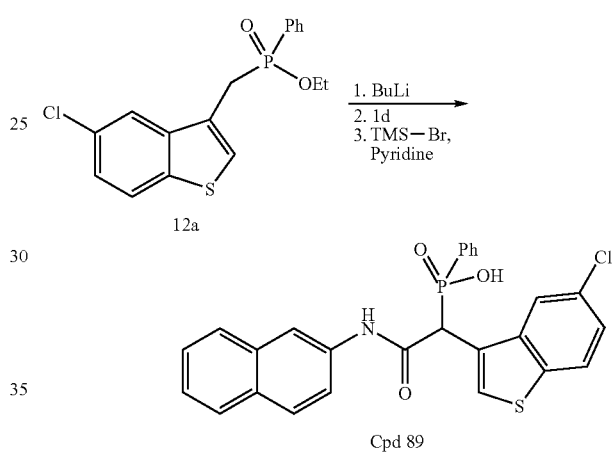

Example 13

[(5-Chloro-benzo[b]thiophen-3-yl)-(naphthalen-2-ylcarbamoyl)-methyl]-carboxylic acid, Cpd 84

A stream of isobutylene (g) Compound 13b was introduced into a suspension of Compound 13a (1.07 g, 4.71 mmol) in acetone (15 mL) containing $H_2SO_4$ (0.026 mL, 0.94 mmol). After 40 min, the cloudy solution was stoppered and stirred overnight. The reaction was poured into 1N NaOH (aq), and the layers were separated. The aqueous portion was extracted with $CH_2Cl_2$ (2×10 mL). The combined organic extracts were washed with brine (10 mL), dried ($Na_2SO_4$), filtered, and concentrated under reduced pressure at rt to yield Compound 13c (1.20 g): HPLC: 4.37 min.

To a solution of diisopropylamine (0.26 mL, 1.84 mmol) in THF (7 mL) at −40° C. was added a 2.5M solution of n-BuLi in hexanes (0.74 mL, 1.84 mmol). The temperature lowered to −70° C., and a solution of Compound 13c (0.38 g, 1.34 mmol) in THF (7 mL) was added slowly dropwise. The mixture was stirred for 30 min, at which time a solution of Compound 1d (0.24 g, 1.41 mmol) in THF (7 mL) was added dropwise. After 45 min the reaction was quenched with 3 mL of $NH_4Cl$ (aq), then extracted with EtOAc (2×10 mL). The combined organic extracts were washed with brine (10 mL), dried ($Na_2SO_4$), filtered, and concentrated under reduced pressure at rt. The residue was purified by flash column chromatography (silica, 0-10% EtOAc/hexanes) to afford Compound 13d (0.18 g): HPLC: 4.73 min; MS (ES) m/z 452 (MH⁺).

A solution of Compound 13d (0.10 g, 0.22 mmol) in 1 mL of 1:1 CH$_2$Cl$_2$/TFA was allowed to stand for 65 min. The solution was concentrated under reduced pressure at rt and the residue was held under vacuum at rt overnight. The residue was dissolved in CH$_3$CN, filtered and concentrated under reduced pressure at rt. The residue was triturated from diethyl ether at rt, and the white solid was collected to yield Compound 84 (0.023 g) as a tan solid: HPLC: 4.16 min; MS (ES) m/z 396 (MH⁺); ¹H NMR (DMSO-d$_6$) δ 5.33 (s, 1H), 7.39-7.59 (overlapping m, 4H), 7.82-7.91 (overlapping m, 4H), 8.02-8.08 (overlapping m, 2H), 8.31 (s, 1H), 10.63

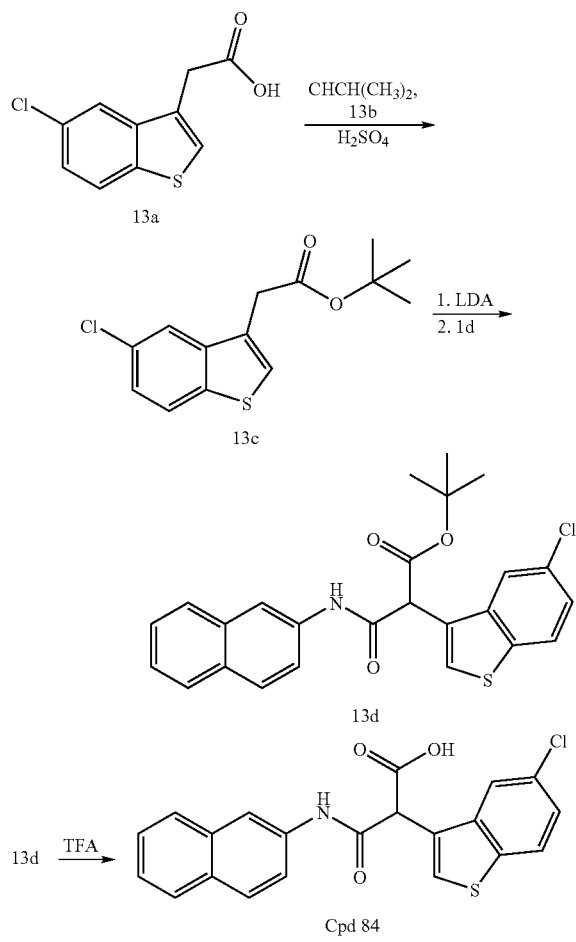

To a solution of Compound 14f (2.0 g, 8.22 mmol), Compound 14g (1.18 g, 8.22 mmol), and HOBT (1.11 g, 8.22 mmol) in DMF (15 mL) was added DCC (1.69 g, 8.22 mmol) and the reaction was stirred for 48 h. The slurry was filtered, and the filtrate concentrated under high vacuum at rt. The residue was purified by trituration from boiling CH$_3$CN to yield Compound 14h (1.41 g) as a bright yellow powder: HPLC: 4.91 min; MS (ES) m/z 364 (MH⁻).

To a suspension of Compound 14h (1.02 g, 2.79 mmol) in 20 mL of 1:1 THF/MeOH was added NaBH$_4$ (0.32 g, 8.42 mmol). The reaction was stirred for 1 h, then quenched with 1N HCl (5 mL). The volume was reduced approximately 50% under reduced pressure at rt and the solution was extracted with EtOAc (2×10 mL). The combined organic extracts were washed with brine (10 mL), dried (Na$_2$SO$_4$), filtered, and concentrated under reduced pressure at rt. The residue was purified by recrystallization from CH$_3$CN, to yield Compound 14i (0.70 g): HPLC: 4.18 min; MS (ES) m/z 368 (MH⁺).

To a suspension of Compound 14i (0.25 g, 0.68 mmol) in CH$_2$Cl$_2$ (10 mL) at 0° C., was added Compound 14j (0.11 mL, 0.88 mmol). After stirring for 3 h at rt, a white solid was collected and rinsed with a minimal volume of CH$_2$Cl$_2$, then dried under N$_2$/vacuum to yield 0.36 g of Compound 14k: HPLC: 4.56 min; MS (ES) m/z 554 (MH⁻).

A suspension of Compound 14k (0.36 g, 0.65 mmol) in saturated aqueous K$_2$CO$_3$ (6 mL) and t-BuOH (3 mL) was refluxed for 2 h, then stirred at rt for 24 h. The reaction was concentrated under reduced pressure at rt, treated with aqueous 1N HCl (10 mL), and extracted with EtOAc (3×10 mL). The combined organic extracts were washed with brine (10 mL), dried (Na$_2$SO$_4$), filtered, and concentrated under reduced pressure at rt to yield Compound 80 (0.105 g): HPLC: 4.29 min; MS (ES) m/z 410 (MH⁻); ¹H NMR (DMSO-d$_6$) δ 6.16 (s, 1H), 7.38-7.49 (overlapping m, 3H), 7.57-7.61 (m, 1H), 7.77-4.86 (overlapping m; 3H), 7.97 (s, 1H), 8.07 (d, 1H J=8.7 Hz), 8.13 (s, 1H), 8.22 (d, 1H, J=2 Hz), 10.02 (s, 1H).

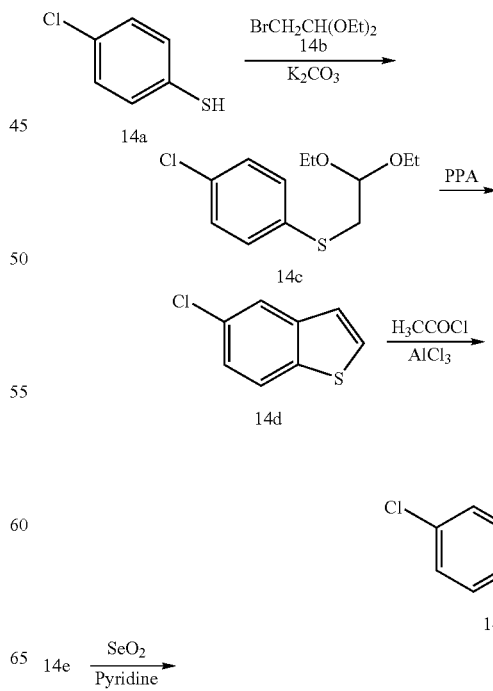

Example 14

[(5-Chloro-benzo[b]thiophen-3-yl)-(naphthalen-2-ylcarbamoyl)-methyl]-carbamate, Cpd 80

Compound 14d was prepared from Compound 14a by the methods described in *J. Med. Chem.* 1989, 32(12), 2548-2554 and *J. Het. Chem.* 1998, 25, 1271: HPLC: 3.95 min.

Compound 14d was converted to Compound 14e using the method described in *Eur. J. Med. Chem.* 2001, 36(1), 55-62). Compound 14e was oxidized with selenium dioxide, to yield Compound 14f using the method described in British patent 1399089(1971): HPLC: 3.78 min; MS (ES) m/z 239 (MH⁻).

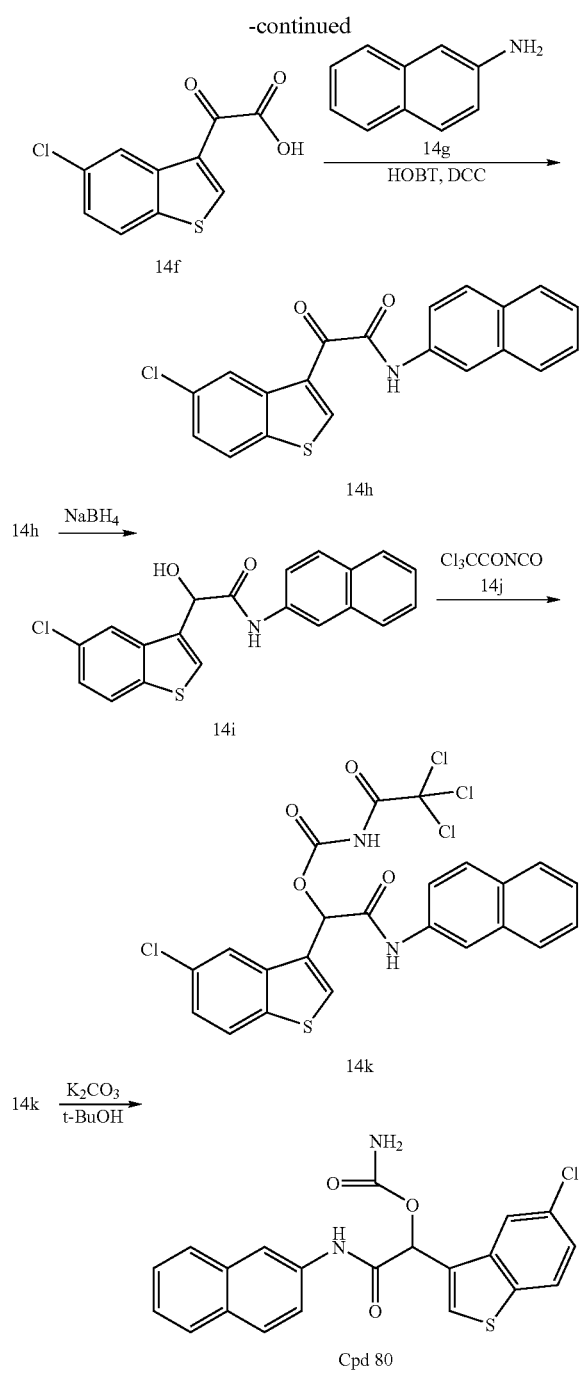

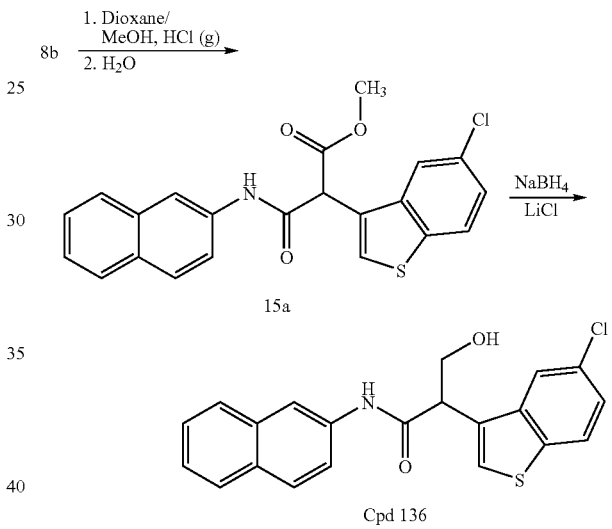

reduced pressure at rt, and the resulting residue was recrystallized from CH₃CN to afford Compound 15a (1.47 g) as a white powder: HPLC: 4.31 min.

To a solution of Compound 15a (0.23 g, 0.56 mmol) in THF (5 mL) was added NaBH₄ (0.043 g, 1.12 mmol), LiCl (0.048 g, 1.12 mmol), and EtOH (10 mL). The reaction was stirred for 90 min, then quenched with several drops of 1N HCl (aq). The mixture was cooled to −10° C., and treated with 10 mL of 1N HCl. The mixture was extracted with EtOAc (4×) and the combined organic extracts were washed with brine (4×), dried (Na₂SO₄), filtered, and concentrated under reduced pressure at rt to yield a white solid. The solid was triturated with CH₃CN to yield Compound 136 (0.14 g) as a snow-white solid: HPLC: 4.11 min; MS (ES) m/z 382 (MH⁺); $^1$H NMR (DMSO-d₆) δ 3.69-3.75 (m, 1H), 4.11-4.19 (m, 1H), 4.33-4.37 (m, 1H), 5.17 (t, 1H, J=5 Hz), 7.37-7.49 (m, 3H), 7.59-7.63 (m, 1H), 7.76 (s, 1H), 7.80-7.88 (m, 3H), 8.05 (d, 1H, J=8 Hz), 8.18 (d, 1H, J=2 Hz), 8.35 (s, 1H), 10.46 (s, 1H).

Example 15

2-(5-Chloro-benzo[b]thiophen-3-yl)-3-hydroxy-N-naphthalen-2-yl-propionamide, Cpd 136

A suspension of Compound 8b (1.23 g, 3.27 mmol) in 1,4-dioxane/methanol (1:1, 50 mL) at −78° C. was saturated with HCl (g). The mixture was maintained at −20° C. overnight, then concentrated under vacuum, such that the temperature remained below 20° C. The residue was partitioned between EtOAc (10 mL) and water (10 mL). The organic layer was dried (Na₂SO₄), filtered, and concentrated under

Example 16

Sulfamic acid 2-(5-chloro-benzo[b]thiophen-3-yl)-2-(naphthalen-2-ylcarbamoyl)-ethyl ester, Cpd 120

To a suspension of 95% NaH (0.017 g, 0.68 mmol) in DMF (2 mL) at 0° C. was added a solution of Compound 136 (0.10 g, 0.26 mmol) in DMF (2 mL) dropwise. The suspension was stirred at 0° C. for 1 h, then sulfamoyl chloride (0.067 g, 0.58 mmol) was added as a solid. After stirring for 1 h at 0° C., the mixture was treated with excess sulfamoyl chloride. After stirring overnight, the reaction was, quenched with water and extracted with EtOAc (3×5 mL). The combined organic phases were washed with brine, dried (Na₂SO₄), filtered and concentrated under reduced pressure at rt. The residue was purified by flash column chromatography (silica, 0-40% EtOAc/hexanes) to yield Compound 120 (0.1.0 g) as a white foam: HPLC: 4.12 min; MS (ES) m/z 461 (MH⁺); $^1$H NMR (DMSO-d₆) δ 4.29-4.34 (m, 1H), 4.65-4.75 (m, 2H), 7.39-7.50 (m, 3H), 7.57-7.64 (m, 1H), 7.81-7.90 (m, 4H), 8.09 (d, 1H, J=8.5 Hz), 8.215 (d, 1H, J=2 Hz), 8.34 (s, 1H), 10.55 (s, 1H).

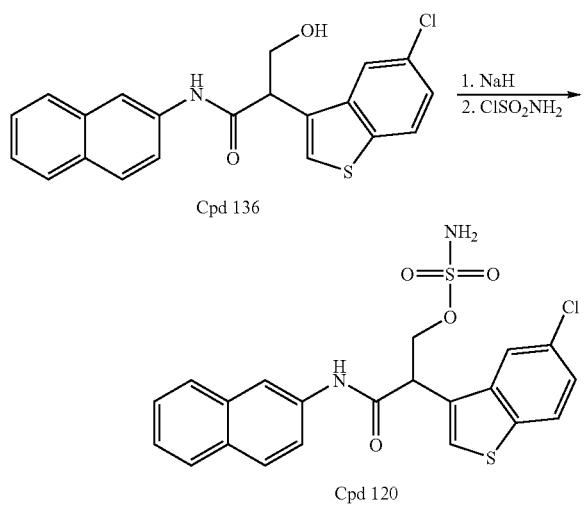

Cpd 136

Cpd 120

Example 17

[(4-{[1-(Naphthalene-2-carbonyl)-piperidine-4-carbonyl]-amino}-naphthalen-2-ylcarbamoyl)-naphthalen-1-yl-methyl]-phosphonic acid, Cpd 8

A solution of Compound 17a (10 g, 45.9 mmol) in MeOH (200 mL) was added to 10% Pd/C and hydrogenated for 3.5 h at 40-50 psi. The mixture was filtered (Celite) and concentrated under reduced pressure at rt, and the resulting material was triturated with EtOAc to yield Compound 17b as a crude black solid. Compound 17b (1.36 g, approx. 8.61 mmol) was dissolved in DMF (20 mL) and TEA (1.32 mL, 9.46 mmol). To this solution was added 2-(tert-butoxycarbonyloxyimino)-2-phenylacetonitrile, (BOC-ON) (2.33 g, 9.46 mmol), and the reaction was heated at 55° C. overnight. The solution was concentrated under reduced pressure at rt and filtered through a plug of silica gel. The crude product was stirred with $CH_2Cl_2$ and filtered to yield 0.18 g of Compound 17c: HPLC: 2.68 min; MS (ES) m/z 259 (MH$^+$).

A solution of ethyl isonipecotamate, Compound 17d (2.04 g, 13.0 mmol), and DIPEA (2.3 mL, 13.0 mmol) in 10 mL of $CH_2Cl_2$ was treated with 2-naphthoyl chloride, Compound 17e (2.48 g, 13.0 mmol). After stirring for 1.5 h, the mixture was sequentially washed with 1N HCl (2×10 mL), saturated $Na_2CO_3$ (aq) (2×10 mL), and brine (10 mL). The organic phase was dried ($Na_2SO_4$), filtered, and concentrated under reduced pressure at rt. The residue was dissolved in 1,4-dioxane (41 mL) and treated with a solution of LiOH.$H_2O$ (1.63 g, 39 mmol) in 5 mL of water. After 2 h, the reaction was concentrated under reduced pressure at rt, and the residue was acidified with 1N HCl (aq), and extracted with $CH_2Cl_2$ (3×10 mL). The combined organic extracts were washed with brine (10 mL), dried ($Na_2SO_4$), filtered, and concentrated under reduced pressure at rt to yield 3.57 g of Compound 17g: HPLC: 2.77 min; MS (ES) m/z 284 (MH$^+$).

To a solution of Compound 17c (0.18 g, 0.70 mmol), Compound 17g (0.20 g, 0.70 mmol), and HOBT (0.094 g, 0.70 mmol) in DMF (8 mL) was added DCC (0.14 g, 0.70 mmol) and the reaction was stirred for 6 d. The mixture was filtered, concentrated under reduced pressure at rt, and the residue suspended in a minimal volume of $CH_2Cl_2$, and filtered again. The clear solution was washed with 1N KHSO$_4$ (aq) and the organic phase was filtered and washed sequentially with saturated $Na_2CO_3$ (aq) and brine. The organic phase was then dried ($Na_2SO_4$), filtered, and concentrated under reduced pressure at rt. The residue was purified by flash column chromatography (silica, 0-3% MeOH/$CH_2Cl_2$) to afford Compound 17h (0.20 g, 0.382 mmol). A solution of 17h in TFA (3 mL) was stirred for 50 min. The mixture was concentrated under reduced pressure at rt and the residue was suspended in $CH_2Cl_2$, washed with saturated $Na_2CO_3$ (2×5 mL), dried ($Na_2SO_4$), filtered, and concentrated under reduced pressure at rt to yield 0.17 g of Compound 17i.

To 100 mL of THF and 2.5 M n-BuLi (79.2 mL, 0.198 mol) at −78° C. was added dropwise a solution of Compound 17j (50 g, 0.18 mol). After 30 min, $CO_2$ was bubbled through the reaction for 1 h, after which point the mixture was warmed to rt. The ice bath-cooled mixture was quenched with excess saturated $Na_2CO_3$ (aq), and the volatile solvents were removed under reduced pressure at rt. The resulting solution was washed with Et$_2$O (3×), acidified with 3N HCl (aq), and extracted with EtOAc (4×). The combined organic extracts were washed once with water, dried ($Na_2SO_4$), filtered (Celite), and concentrated under reduced pressure at rt to yield 32.59 g of Compound 17k: HPLC: 3.06 min, MS (ES) m/z 323 (MH$^+$).

Compound 17k (0.13 g, 0.40 mmol) was stirred with 1 mL of thionyl chloride for 30 min and the mixture was concentrated under reduced pressure at rt. The residue was treated with hexanes and concentrated under reduced pressure at rt again. The residue was dissolved in THF (5 mL), at −78° C., treated with a solution of Compound 17i (0.17 g, 0.40 mmol) in pyridine (3.5 mL). The solution was stirred at rt overnight, then concentrated under reduced pressure at rt. The residue was taken up in $CH_2Cl_2$ (5 mL) and washed sequentially with 1N KHSO$_4$ (aq), saturated $Na_2CO_3$ (aq) (3×5 mL), and brine (5 mL), dried ($Na_2SO_4$), filtered, and concentrated under reduced pressure at rt. The residue was purified by prep-plate chromatography (75% EtOAc/hexanes) to yield 0.11 g of Compound 17l: HPLC: 4.02 min; MS (ES) m/z 728 (MH$^+$).

Compound 17l was deethylated by Procedure A to yield Compound 8 (0.063 g): HPLC: 3.91 min; MS (ES) m/z 424 {M-[COCH(1-Naph)P(=O)(OH)$_2$]}; $^1$H NMR (DMSO-d$_6$) δ 1.6-2.2 (br overlapping m, 4H), 2.7-3.3 (br overlapping m, 3H), 3.6-4.0 (br m, 1H), 4.45-4.75 (br m, 1H), 5.32 (d, 1H, J=24 Hz), 7.39-7.60 (overlapping m, 8H), 7.79-8.0 (overlapping m, 9H), 8.24 (s, 1H), 8.31 (d, 1H, J=7 Hz), 8.38 (d, 1H, J=10 Hz), 9.95 (s, 1H), 10.6 (s, 1H).

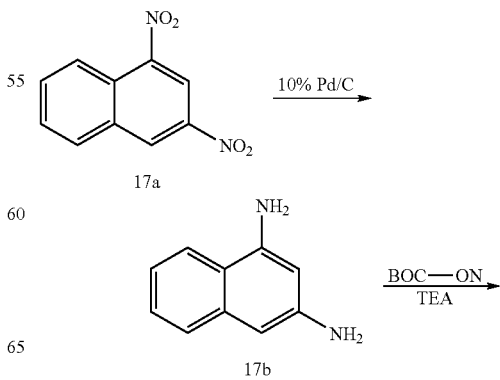

-continued

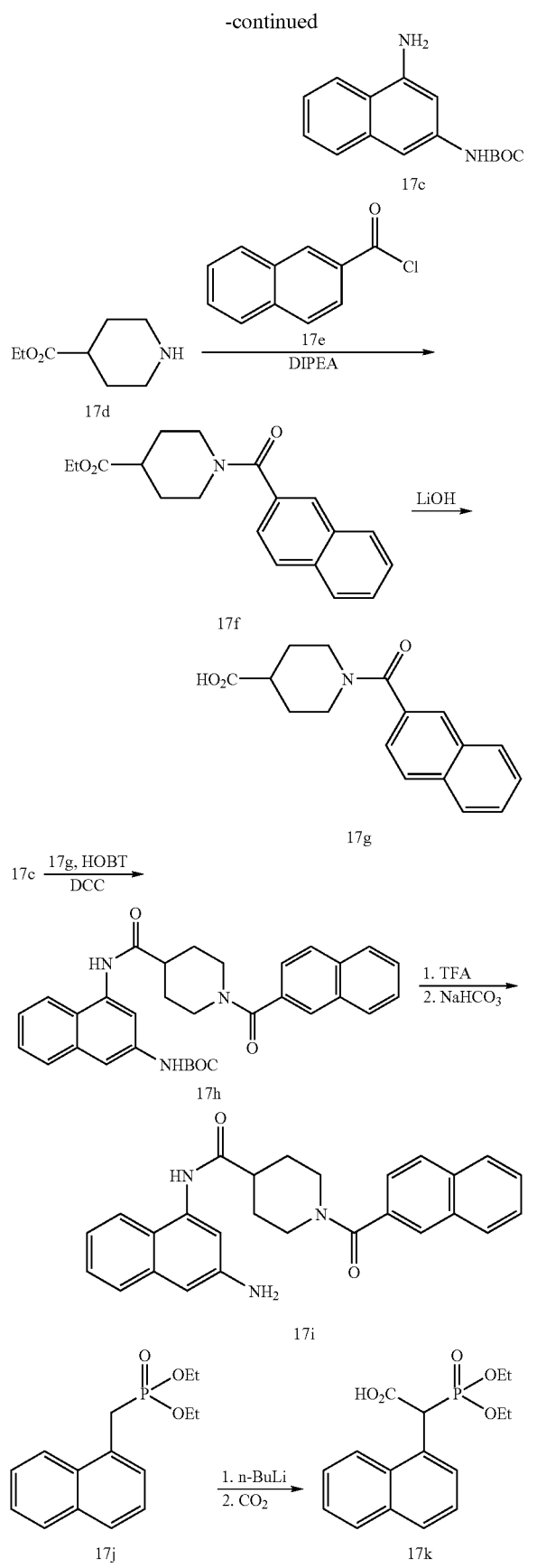

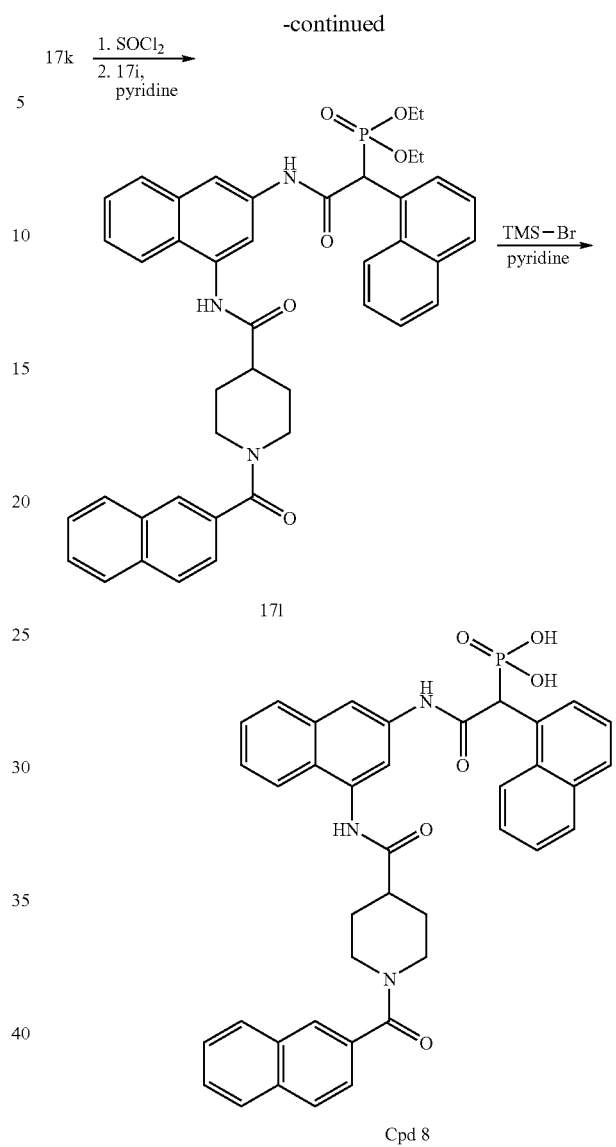

Cpd 8

Example 18

[(4-Chloro-1-methyl-1H-indol-3-yl)-(naphthalen-2-ylcarbamoyl)-methyl]-phosphonic acid, Cpd 63

To a stirred mixture of 95% sodium hydride (0.35 g, 13.85 mmol) in THF (3 mL) at 0° C. was added a solution of 4-chloroindole Compound 18a (0.35 g, 6.59 mmol) in THF (3 mL), and the mixture was stirred for 15 min. Methyl iodide (1.03 g, 7.26 mmol) was added and the reaction was stirred overnight. The reaction was quenched with saturated $NaHCO_3$ (aq), the volatiles were removed under reduced pressure at rt, and the resulting mixture was extracted with EtOAc (3×). The combined organic extracts were washed with brine, dried ($Na_2SO_4$), filtered (Celite), and concentrated under reduced pressure at rt to yield 1.11 g of Compound 18b as an oil: HPLC: 3.37 min, 77%.

To a stirred suspension of Compound 18b (1.09 g, 6.59 mmol) in $CH_2Cl_2$ (10 mL) was added Compound 18c (1.58 g, 8.57 mmol). After stirring overnight, the solid was collected and rinsed sequentially with $CH_2Cl_2$ and $Et_2O$. The solid was dissolved in 1N NaOH (aq) and extracted with CH₂Cl₂ (3×). The combined organic extracts were washed with brine, dried (Na₂SO₄), filtered (Celite), and concentrated under reduced pressure at rt to yield 0.95 g Compound 18d as a clear oil: HPLC: 1.18 min, 97%; MS (ES) m/z 223 (MH⁺).

To a stirred solution of Compound 18b (0.944 g, 4.24 mmol) in EtOH (10 mL) at 0° C. was added methyl iodide (0.66 g, 4.66 mmol). After stirring at room temperature overnight, a solid was collected by filtration and rinsed sequentially with EtOH and Et₂O to yield 1.46 g of Compound 18e as a white solid: HPLC: 1.93 min, 68%.

A mixture of Compound 18e (1.0 g, 2.74 mmol) in triethyl phosphite (8 mL) was refluxed overnight and concentrated under high vacuum at 90° C. The residue was dissolved in EtOAc, washed with H₂O, dried (Na₂SO₄), filtered (Celite), and concentrated under reduced pressure at rt. The residue was purified by flash column chromatography (silica, 0-1% MeOH/CH₂Cl₂) to yield 0.82 g of Compound 18f as an oil: HPLC: 3.39 min; MS (ES) m/z 316 (MH⁺).

Using the procedure described in Example 1 for the conversion of Compound 1c to Compound 9, including deethylation by Procedure A, Compound 18f was converted to Compound 63.

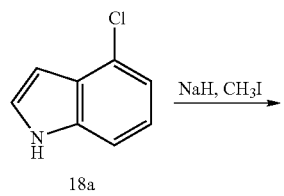
18a

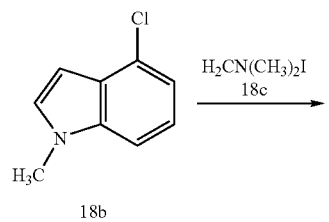
18b

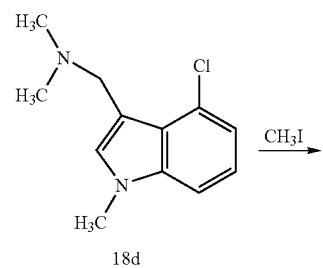
18d

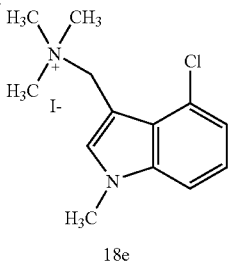
18e

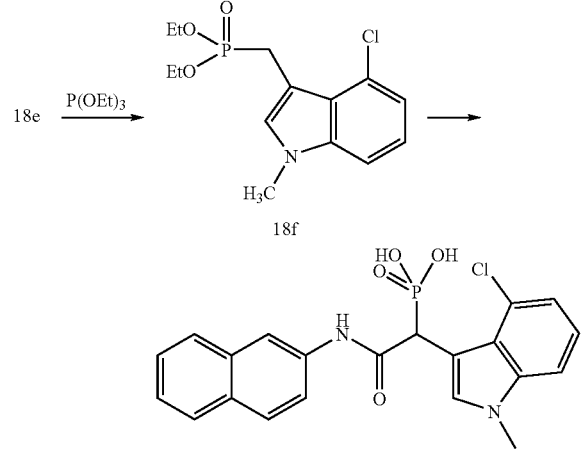

Cpd 63

Other compounds of the present invention may be prepared by those skilled in the art by varying the starting materials, reagent(s) and conditions used. Using the procedure of Example 18, the following compounds were prepared without further purification:

| Cpd | MS (MH⁺) |
|---|---|
| 3 | 429 |
| 11 | 413 |
| 13 | 471 (MH−) |
| 22 | 395 |
| 27 | 497 |
| 52 | 451 (M + Na) |
| 58 | 429 |
| 62 | 433 (MH−) |
| 65 | 420 |
| 74 | 425 |
| 77 | 423 |
| 116 | 396 |

Example 19

{(5-Chloro-1-methyl-1H-indol-3-yl)-[2-(4-fluorophenyl)-vinylcarbamoyl]-methyl}-phosphonic acid, Cpd 4

Using the procedure described in Example 18, substituting 5-chloroindole for 4-chloroindole, Compound 19a was prepared.

Using the procedure described in Example 11, Compound 4 was prepared: HPLC: 360 min; MS (ES) m/z 423 (MH⁺).

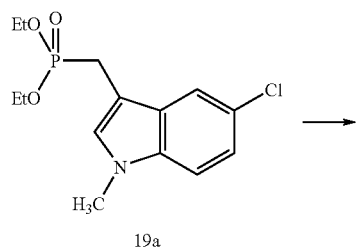

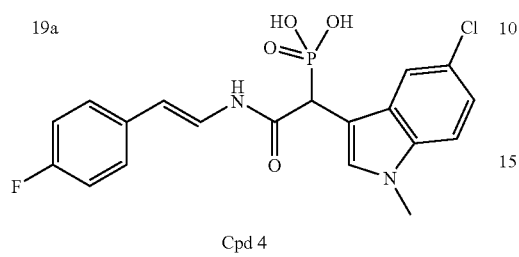

Cpd 4

Example 20

[(5-Chloro-1-methyl-1H-indol-3-yl)-(naphthalen-2-ylcarbamoyl)-methyl]-methyl-phosphinic acid, Cpd 1

Using the procedure described in Example 18, substituting 5-chloroindole for 4-chloroindole, Compound 20a was prepared.

Using the procedure described in Example 18, substituting Compound 20a for Compound 18b, Compound 20b was prepared.

Using the procedure described in Example 1 followed by deethylation by Procedure A, Compound 20b was converted to Compound 1: HPLC: 3.77 min, 97%; MS (ES) m/z 427 (MH+).

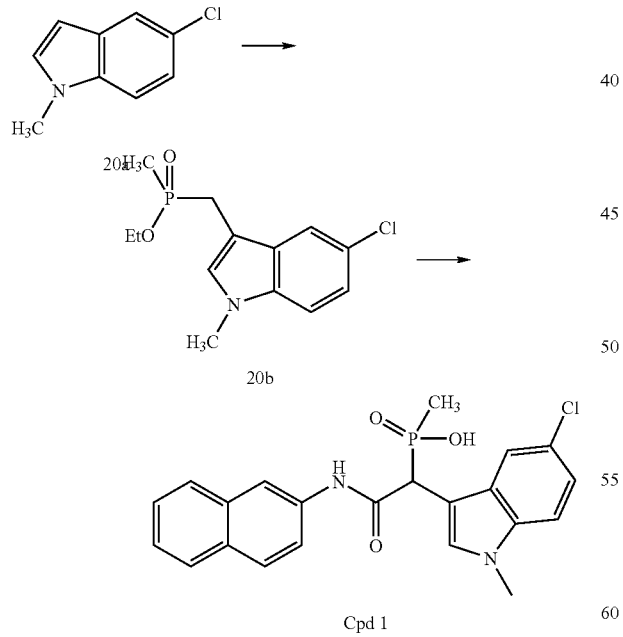

Other compounds of the present invention may be prepared by those skilled in the art by varying the starting materials, reagent(s) and conditions used. Using the procedure of Example 20, the following compounds were prepared without further purification:

| Cpd | MS (MH+) |
|---|---|
| 6 | 419 (MH−) |
| 7 | 439 |

Example 21

1-Methyl-3-[(naphthalen-2-ylcarbamoyl)-phosphono-methyl]-1H-indole-5-carboxylic acid, Cpd 56

Using the procedure described in Example 18, Compound 21a was prepared. To a solution of 2.5 M n-BuLi in hexanes (0.56 mL, 1.40 mmol) in THF (2 mL) at −78° C. was added dropwise a solution of Compound 21a (0.27 g, 0.79 mmol) in THF (1 mL). After stirring for an additional 45 min, Compound 1d (0.15 g, 0.87 mmol) in THF (1.5 mL) was added dropwise to the mixture. After the addition was complete, the solution was stirred at −78° C. for 2 h. The mixture was warmed to rt, excess saturated NaHCO₃ (aq) was added, and the solid was collected by filtration. The solid was rinsed (THF), and air dried to yield Compound 21b (0.12 g): HPLC: 3.77 min.

Compound 21b (0.060 g, 0.12 mmol) was deethylated by Procedure A to yield Compound 56 (0.042 g): HPLC: 3.19 min; MS (ES) m/z 420 (M-H₂O).

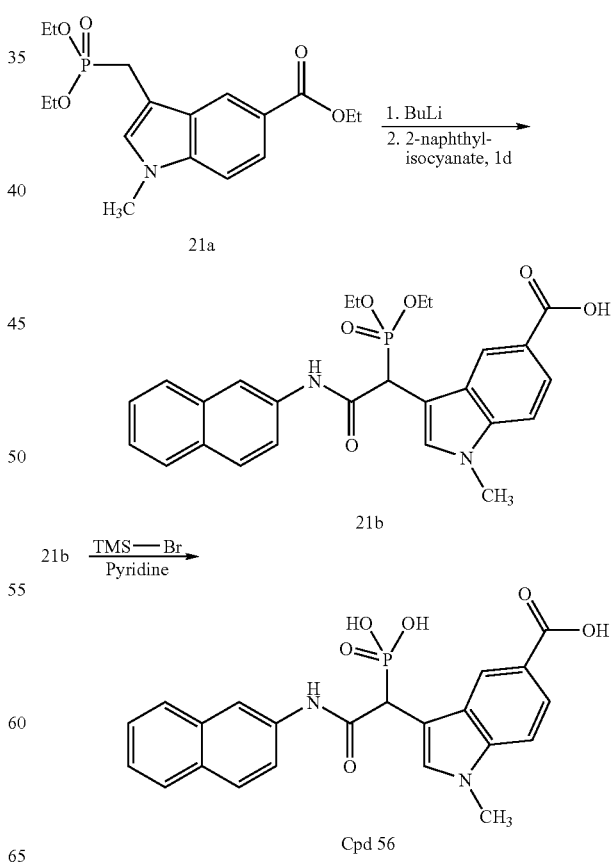

Example 22

[[5-(4-Fluoro-phenyl)-1-methyl-1H-indol-3-yl]-(naphthalen-2-ylcarbamoyl)-methyl]-phosphonic acid, Cpd 98

Compound 22a (0.27 g, 0.75 mmol), prepared by the method of *Synlett* January 1994, 93, was methylated as described in Example 18 to yield 0.27 g of Compound 22b: HPLC: 3.65 min, 96.5%; MS (ES) m/z 362 (MH$^+$).

Using the procedure described in Example 1, followed by deethylation Procedure A, Compound 22b converted to Compound 98: HPLC: 4.46 min; MS (ES) m/z 487 (MH$^-$).

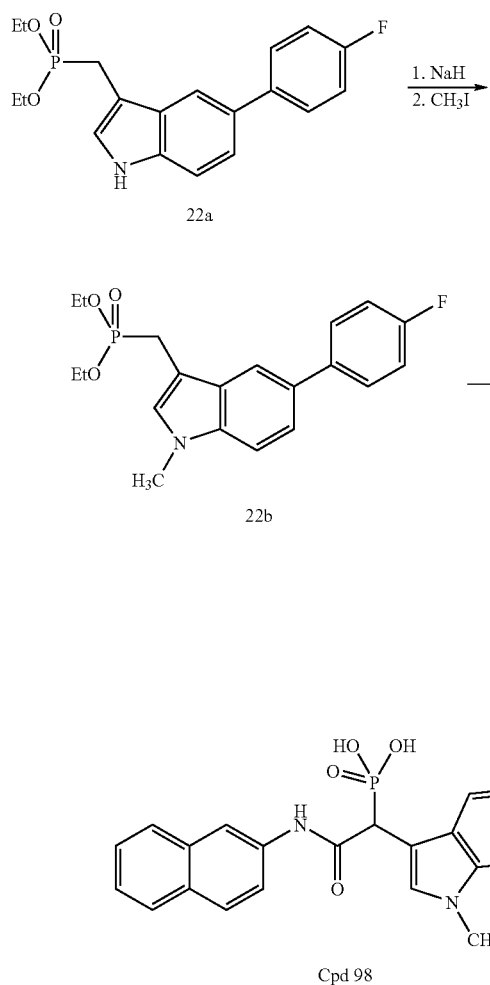

Example 23

[(Naphthalen-2-ylcarbamoyl)-(1-phenyl-1H-indol-3-yl)-methyl]-phosphonic acid, Cpd 128

A mixture of Compound 23a (5.0 g, 29 mmol), copper(II) oxide (4.9 g, 63 mmol), potassium carbonate (5.0 g, 36 mmol), and bromobenzene (30 mL) was refluxed for 13 h. After cooling to rt, the mixture was filtered (dicalite) and concentrated under reduced pressure at rt. The residue was triturated with hexanes to yield 5.2 g of Compound 23b as a brown solid: HPLC: 4.44 min, 93%; MS (ES) m/z 252 (MH$^+$).

To a suspension of lithium aluminum hydride (1.0 g, 26 mmol) in THF (30 mL) was added Compound 23b (5.2 g, 20 mmol) in THF (25 mL) at 0° C. The reaction was stirred for 1 h, then quenched at 0° C. with moist Na$_2$SO$_4$. The mixture was diluted with THF and filtered (dicalite). The filtrate was concentrated under reduced pressure at rt, and the residue was purified by flash column chromatography (silica, 25% EtOAc/hexanes) to yield 2.7 g of Compound 23c as a white solid: HPLC: 3.62 min, 99%; MS (ES) m/z 224 (MH$^+$).

To a solution of Compound 23c in DMF (15 mL) and CCl$_4$ (4 mL) at 0° C. was added triphenylphosphine (3.4 g, 13 mmol) and the mixture was stirred at rt overnight. The reaction was concentrated under reduced pressure at rt, dissolved in EtOAc and passed through a short plug of silica gel (30% EtOAc/hexanes) to yield 1.3 g of Compound 23d: HPLC: 4.19 min, 91%; MS (ES) m/z 513 (MH$^+$).

Using the procedure described in Example 1, substituting Compound 23d for Compound 1a, Compound 128 was prepared: HPLC: 4.23 min, 83%, MS (ES) m/z 479 (M+Na).

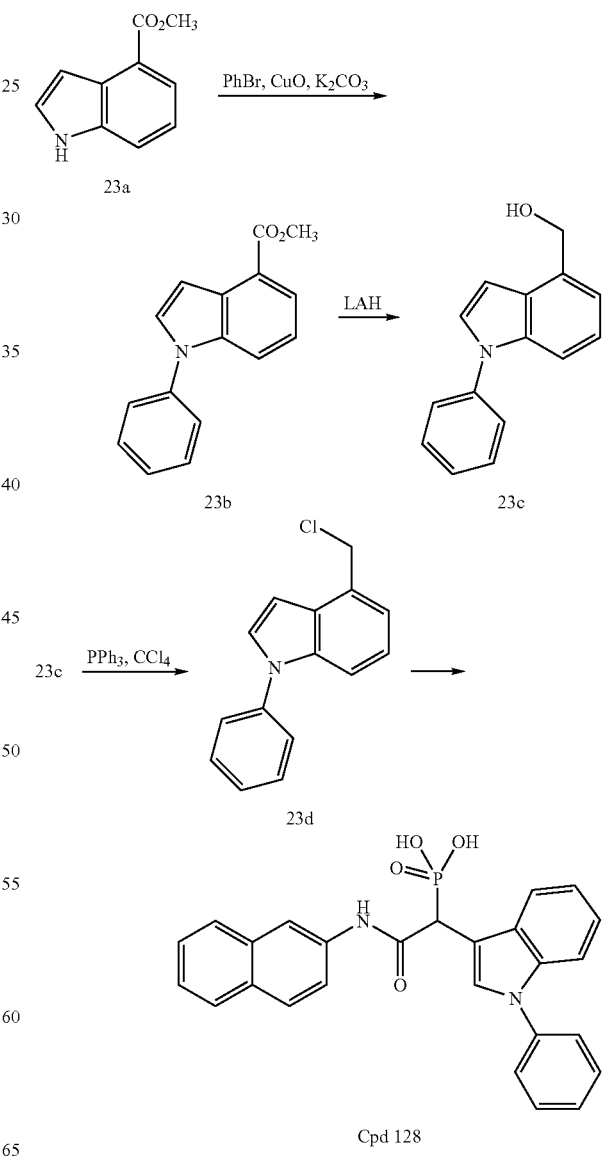

Example 24

Methyl-{(naphthalen-2-ylcarbamoyl)-[2-(4-phenyl-piperidine-1-carbonyl)-benzo[b]thiophen-3-yl]-methyl}-phosphinic acid, Cpd 32

Compound 24a was prepared according to the procedures described in *JACS* 1963, 6, 711-716 and *JACS* 1971, 93(12), 2897-2904.

To a solution of 2.5 M n-BuLi in hexanes (8.5 mL, 21.2 mmol) and THF (33 mL) at −78° C. was added dropwise a solution of Compound 24a (3.52 g, 18.4 mmol) in THF (33 mL). After stirring the resulting yellow slurry for 45 min, di-tert-butyidicarbonate (4.14 g, 19.0 mmol) in THF (33 mL) was added dropwise to the mixture. After the addition was complete, the solution was allowed to reach rt then quenched with 50 mL of saturated NH$_4$Cl (aq). The layers were separated, and the aqueous portion was extracted with EtOAc (2×20 mL). The combined organic phases were dried (Na$_2$SO$_4$), filtered, and concentrated under reduced pressure at rt. The residue was purified by flash column chromatography (silica, 0 to 75% EtOAc/hexanes) to yield 3.68 g of Compound 24b: HPLC: 2.74 min, 90%; MS (ES) M/Z (MH$^+$) 292.

Using the procedure described in Example 18, substituting Compound 24b (3.68 g, 12.65 mmol) for Compound 18d, and diethylmethylphosphonite for triethylphosphite, Compound 24c (3.36 g) was prepared: HPLC: 3.67 min.

Using the procedure described in Example 1, followed by deethylation Procedure A, Compound 24c (3.36 g, 9.5 mmol) was converted to Compound 24d (2.18 g): HPLC: 4.24 min; MS (ES) m/z 524 (MH$^+$).

To Compound 24d (2.18 g, 4.17 mmol) was added 5 mL of TFA. After 50 min, the mixture was concentrated under reduced pressure at rt and the residue was purified by flash column chromatography (silica, 0 to 20% MeOH/EtOAc) to yield 0.30 g of Compound 24e: HPLC: 3.63 min, 91%; MS (ES) m/z 468 (MH$^+$).

To a solution of Compound 24e (0.20 g, 0.43 mmol), Compound 24f (0.07 g, 0.45 mmol), and HOBT (0.061 g, 0.45 mmol) in DMF (2 mL) was added DCC (0.093 g, 0.45 mmol). After 1 h, the reaction mixture was filtered, the residue was suspended in a minimal volume of CH$_2$Cl$_2$ and filtered. The filitrate was washed sequentially with 1N HCl (2×), 10% aqueous Na$_2$CO$_3$, and brine, then dried (Na$_2$SO$_4$), filtered, and concentrated under reduced pressure at rt. The residue was purified by flash column chromatography (silica, 0-60% EtOAc/heptane) to yield 0.12 g of Compound 24g: HPLC: 4.44 min; MS (ES) m/z 611 (MH$^+$).

Compound 24g (0.12 g, 0.197 mmol) was deethylated by Procedure A to afford Compound 32 (0.086 g): HPLC: 4.49 min, 92%; MS (ES) m/z 583 (MH$^+$).

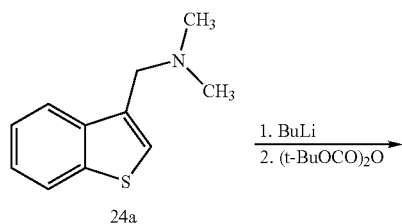

24a

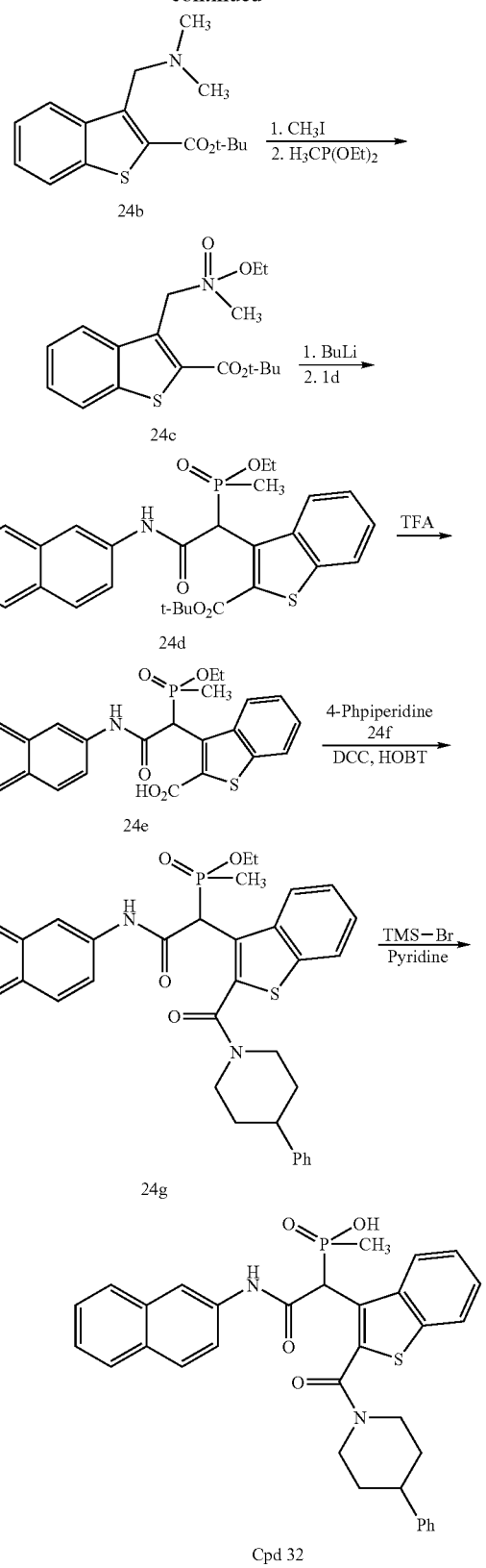

Cpd 32

Other compounds of the present invention may be prepared by those skilled in the art by varying the starting materials, reagent(s) and conditions used. Using the procedure of Example 24, the following compounds were prepared without further purification:

| Cpd | MS (MH+) |
|---|---|
| 38 | 611 (MH−) |
| 44 | 640 (MH−) |
| 50 | 599 (MH−) |
| 121 | 438 (MH−) |
| 130 | 529 |

Example 25

[(5-Chloro-benzo[b]thiophen-3-yl)-(naphthalen-2-ylcarbamoyl)-methyl]-(3-phenyl-propyl)-phosphinic acid, Cpd 36

Compound 25a was prepared according to the procedures described in *JACS* 2002, 124, 9386-9387 and *J. Organomet. Chem* 2002, 643-644, 154-163.

To a solution of Compound 25a (0.51 g, 2.58 mmol) in THF (10 mL) at −78° C. was added a solution of 2.5 M n-BuLi in hexanes (1.29 mL, 3.22 mmol). After stirring for 30 min, a solution of Compound 1a (0.225 g, 0.86 mmol) in THF (7 mL) was added dropwise. After 35 min, the reaction was quenched with excess saturated NH$_4$Cl (aq), and the layers were separated. The aqueous layer was extracted with EtOAc (3×) and the combined organic extracts were washed with brine, dried (Na$_2$SO$_4$), filtered and concentrated under reduced pressure at rt. The residue was purified by flash column chromatography (silica, 0-30% EtOAc/hexanes) to yield 0.070 g of Compound 25b: HPLC: 3.93 min, 88%; MS (ES) m/z 379 (MH+).

Using the procedure described in Example 1 with deethylation Procedure A, Compound 25b was converted to Compound 36: HPLC: 4.70 min 90%; MS (ES) m/z 520 (MH+).

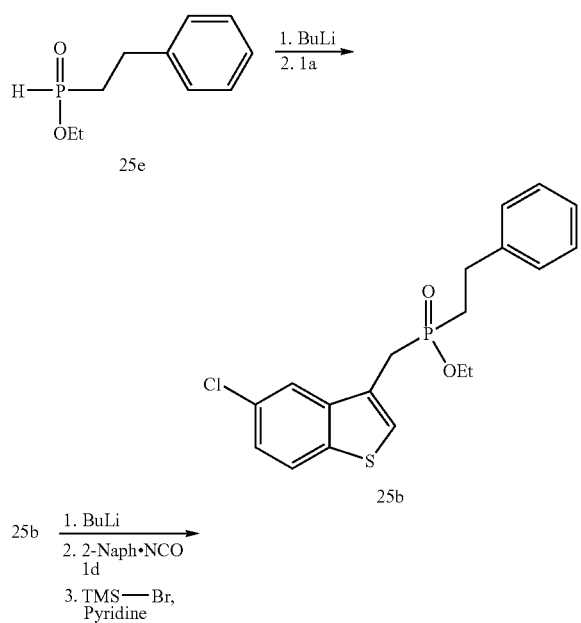

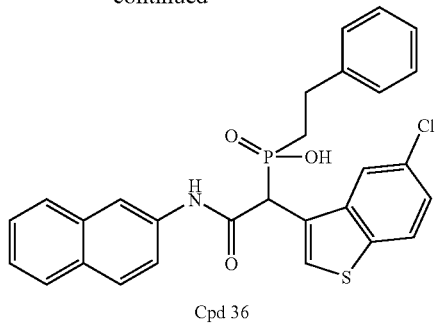

Cpd 36

Other compounds of the present invention may be prepared by those skilled in the art by varying the starting materials, reagent(s) and conditions used. Using the procedure of Example 25, the following compounds were prepared without further purification:

| Cpd | MS (MH+) |
|---|---|
| 34 | 488 |
| 39 | 578 |
| 40 | 582 |
| 43 | 548 (MH−) |
| 48 | 534 |
| 51 | 548 |
| 53 | 562 (MH−) |

Example 26

3-(2-Naphthalen-1-yl-2-phosphono-acetylamino)-naphthalene-2-carboxylic acid methyl ester, Cpd 75

Using the procedure described in Example 17, Compound 17k was converted to Compound 75: HPLC: 4.13 min; MS (ES) m/z 450 (MH+).

Other compounds of the present invention may be prepared by those skilled in the art by varying the starting materials, reagent(s) and conditions used. Using the procedure of Example 26, the following compounds were prepared without further purification:

| Cpd | MS (MH+) |
|---|---|
| 139 | 478 |

Example 27

[(3-Benzylcarbamoyloxymethyl-naphthalen-2-ylcarbamoyl)-naphthalen-1-yl-methyl]-phosphonic acid, Cpd 72

To a suspension of Compound 75 (7.6 g, 15.03 mmol) in THF (150 mL) at 0° C. was added dropwise a 1M solution of diisobutyl aluminum hydride in toluene (90 mL) and stirred at rt overnight. The reaction was cooled to 0° C., quenched with saturated NH$_4$Cl (aq), and extracted with EtOAc (2×). The combined organic extracts were filtered (Celite), washed with brine, dried (Na$_2$SO$_4$), filtered, and concentrated under reduced pressure at rt. The residue was purified by flash column chromatography (0-3% MeOH/CH$_2$Cl$_2$). The product was recrystallized from MeOH to yield Compound 27a (1.85 g) as a crystalline solid: HPLC: 3.66 min; MS (ES) m/z 478 (MH$^+$).

To a solution of Compound 27a (0.30 g, 0.63 mmol) in THF (4 mL) was added triethylamine (28 µl, 0.20 mmol) followed by benzylisocyanate (0.084 g, 0.63 mmol) in THF (2 mL) dropwise. The flask was wrapped with foil and stirred at rt for 96 h. Additional benzylisocyanate (0.042 g, 0.032 mmol) and triethylamine (60 µl, 0.43 mmol) were added and the reaction was stirred for an additional 48 h. The mixture was concentrated under reduced pressure at rt and the residue was taken up in CH$_2$Cl$_2$ and washed sequentially with 1N KHSO$_4$ (aq) (2×), brine, dried (Na$_2$SO$_4$), then filtered, and concentrated under reduced pressure at rt. The residue was purified by flash column chromatography (silica, 0-3% MeOH/CH$_2$Cl$_2$) to yield 0.22 g of Compound 27b: HPLC: 4.19 min, 95%; MS (ES) m/z 611 (MH$^+$).

Compound 27b (0.22 g, 0.36 mmol) was deethylated by Procedure A to yield Compound 72 (0.16 g): HPLC: 3.80 min; MS (ES) m/z 555 (MH$^+$).

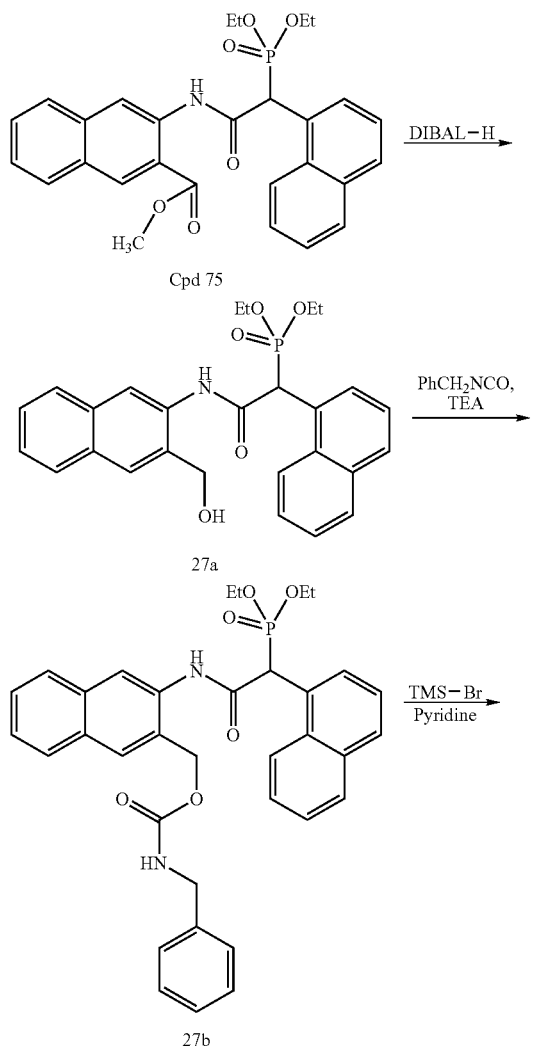

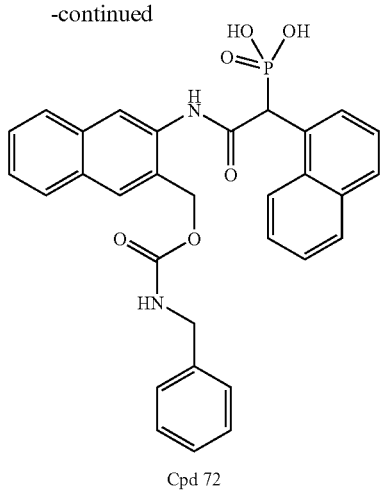

Other compounds of the present invention may be prepared by those skilled in the art by varying the starting materials, reagent(s) and conditions used. Using the procedure of Example 27, the following compounds were prepared without further purification:

| Cpd | MS (MH$^+$) |
| --- | --- |
| 97 | 541 |
| 100 | 631 (MH−) |
| 108 | 591 |

Example 28

{[3-(2-Benzylcarbamoyl-vinyl)-naphthalen-2-ylcarbamoyl]-naphthalen-1-yl-methyl}-phosphonic acid, Cpd 109

A solution of Compound 27a (3.9 g, 8.1 mmol) in CHCl$_3$ (50 mL) was treated with activated MnO$_2$ (7.0 g 780 mmol) and stirred for 48 h. The mixture was filtered (Celite), and concentrated under reduced pressure at rt. The residue was triturated with Et$_2$O to obtain 3 g of Compound 28a as a yellow powder: HPLC: 4.35 min; MS (ES) m/z 476 (MH$^+$).

A solution of Compound 28a (1.0 g, 2.0 mmol), methyltriphenylphosphoranylidene acetate (1.5 g, 4.5 mmol), and THF (25 mL) was refluxed for 7 h, then concentrated under reduced pressure at rt. The residue was purified by flash column chromatography (silica, 5% MeOH/CH$_2$Cl$_2$) to obtain 1.4 g of Compound 28b: HPLC: 4.33 min; MS (ES) m/z 531 (MH$^+$).

To a solution of Compound 28b (1.0 g, 1.89 mmol) in 3:1 dioxane-H$_2$O (20 mL) was added LiOH (0.18 g, 7.50 mmol) and the mixture was stirred for 3 h. The layers were separated, and the aqueous layer was acidified with 3N HCl and extracted repeatedly with EtOAc. The combined organic extracts were dried (Na$_2$SO$_4$), and filtered. The filtrate was concentrated under reduced pressure at rt to afford 0.52 g of Compound 28c as a white foam: HPLC: 3.89 min, 70%; MS (ES) m/z 518 (MH$^+$).

A solution of Compound 28c (0.40 g), benzylamine (0.10 g, 0.93 mmol) and HOBt (0.104 g, 0.77 mmol) in DMF (5 mL) was treated DCC (0.16 g, 0.77 mmol) in DMF (1 mL).

The mixture was stirred for 24 h, then filtered (Celite) and concentrated under reduced, pressure at rt. The residue was taken up in CH$_2$Cl$_2$ and washed sequentially with saturated NaHCO$_3$ (aq), H$_2$O, 1 N KHSO$_4$ (aq) and H$_2$O, then dried (Na$_2$SO$_4$) and filtered. The residue was purified by flash column chromatography (silica, 5% MeOH/CH$_2$Cl$_2$) to yield 0.22 g of Compound 28d: MS (ES) m/z 607 (MH$^+$).

Compound 28d was deethylated by Procedure A to afford Compound 109: HPLC: 3.64 min; MS (ES) m/z (MH+)=551.

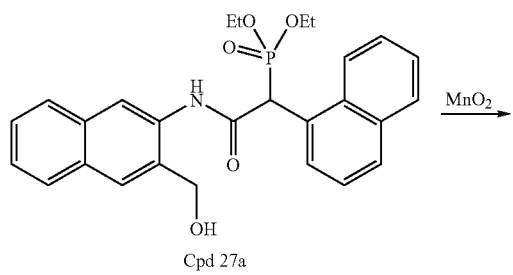

Example 29

[(3-Cyclohexylaminomethyl-naphthalen-2-ylcarbamoyl)-naphthalen-1-yl-methyl]-phosphonic acid, Cpd 70

To a stirred solution of Compound 28a (0.125 g, 0.263 mmol) and cyclohexyl amine (0.031 g, 0.316 mmol) in DCE (4 mL) was added NaB(OAc)$_3$H (0.111 g, 0.526 mmol) and glacial acetic acid (0.017 g, 0.316 mmol) and the mixture was stirred for 48 h. The reaction was treated with 3N NaOH, and the layers were separated. The aqueous layer was extracted with CH$_2$Cl$_2$ (3×) and the combined organic extracts were washed with water, dried (Na$_2$SO$_4$), filtered (Celite), and concentrated under reduced pressure at rt. The residue was treated with 1N HCl (aq), and the solid was collected, rinsed with water, and air-dried. The product was dissolved in CH$_3$CN, precipitated with Et$_2$O, and the solid was collected and rinsed with Et$_2$O to yield 0.084 g of Compound 29a: HPLC: 3.27 min; MS (ES) m/z 559 (MH$^+$).

From Compound 29a (0.079 g) was prepared Compound 70 by deethylation Procedure A. The crude product was dissolved in 1:1 CH$_2$Cl$_2$/TFA and concentrated. The residue was stirred with Et$_2$O, and the solid was collected and rinsed with Et$_2$O to yield Compound 70 (0.046 g): HPLC: 2.91 min; MS (ES) m/z 503 (MH$^+$).

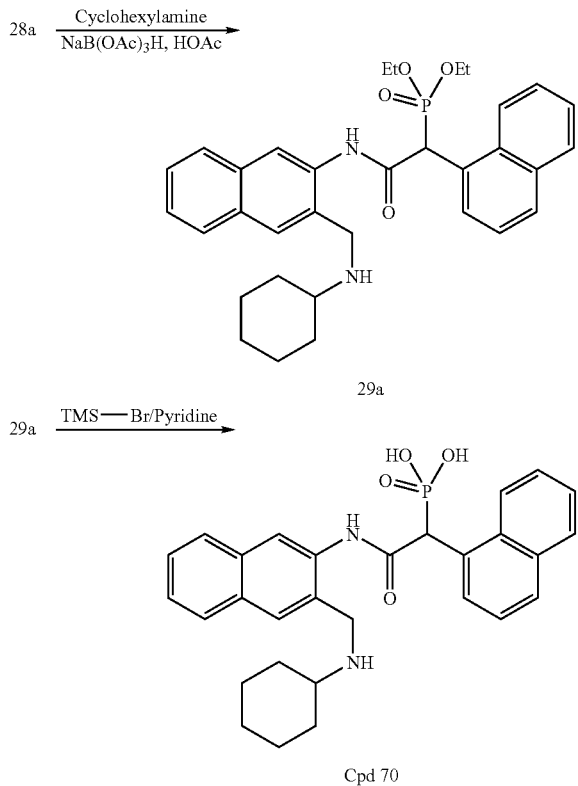

Cpd 70

Other compounds of the present invention may be prepared by those skilled in the art by varying the starting materials, reagent(s) and conditions used. Using the procedure of Example 29, the following compounds were prepared without further purification:

| Cpd | MS (MH$^+$) |
|---|---|
| 90 | 517 |
| 92 | 549 |
| 107 | 511 |
| 110 | 575 (M + Na) |
| 112 | 667 |
| 117 | 541 |
| 124 | 489 |
| 126 | 539 |
| 133 | 507 |
| 142 | 525 |

Example 30

{[3-({Methyl-[1-(naphthalene-2-carbonyl)-piperidin-4-yl]-amino}-methyl)-naphthalen-2-ylcarbamoyl]-naphthalen-1-yl-methyl}-phosphonic acid, Cpd 102

Using the procedure of Example 29, substituting (4-methylamino-piperidin-1-yl)-naphthalen-2-yl-methanone for cyclohexylamine, Compound 102 was prepared: HPLC: 3.12 min; MS (ES) m/z 672 (MH$^+$).

Example 31

({3-[(1-Benzoyl-piperidin-4-ylamino)-methyl]-naphthalen-2-ylcarbamoyl}-naphthalen-1-yl-methyl)-phosphonic acid, Cpd 44

Using the procedure of Example 29, substituting (4-amino-piperidin-1-yl)-phenyl-methanone for cyclohexylamine, Compound 44 was prepared: HPLC: 2.84 min; MS (ES) m/z 608 (MH$^+$).

Example 32

({3-[4-(6-Chloro-2-oxo-2,3-dihydro-benzoimidazol-1-yl)-piperidine-1-carbonyl]-naphthalen-2-ylcarbamoyl}-naphthalen-1-yl-methyl)-phosphonic acid, Cpd 60

Using the procedure of Example 17, Compound 17k was converted to Compound 32a.

To a suspension of Compound 32a (9.02 g, 17.9 mmol) in 1,4-dioxane (200 mL) was added a mixture of LiOH.H$_2$O (2.25 g, 53.6 mmol) in water (25 mL). The mixture was stirred for 4.5 h, then concentrated under reduced pressure at rt. The residue was partitioned between 1N HCl and EtOAc, and the aqueous portion was extracted with EtOAc (5x). The combined organic extracts were washed with brine, dried (Na$_2$SO$_4$), filtered and concentrated under reduced pressure at rt. The solid was suspended in MeOH, collected, washed with MeOH, and dried under N$_2$/vacuum to yield 6.87 g of Compound 32b as a white powder: HPLC: 3.99 min.

A mixture of Compound 32b (2.85 g, 9.79 mmol) and excess thionyl chloride was stirred until the solution became clear. The solution was concentrated under reduced pressure at rt, and the residue was taken up in hexanes and concentrated under reduced pressure at rt. The residue was stirred with CH$_3$CN, and the solid was collected and dried under N$_2$/vacuum to yield 2.45 g of Compound 32c: HPLC: 4.10 min, 87%.

A mixture of Compound 32c (0.31 g, 0.66 mmol) Compound 32d (0.33 g, 1.311 mmol; J. Med. Chem. 1987, 30(5), 814-819) in CH$_3$CN (15 mL) was refluxed for 1 h. The mixture was cooled to rt, filtered, and concentrated under reduced pressure at rt. The residue was purified by flash column chromatography (silica, 0-3% MeOH/CH$_2$Cl$_2$) to yield 0.38 g of Compound 32e: HPLC: 3.98 min.

Compound 32e (0.18 g, 0.25 mmol) was deethylated by Procedure A to yield Compound 60 (0.14 g): HPLC: 3.65 min; MS (ES) m/z 669 (MH$^+$).

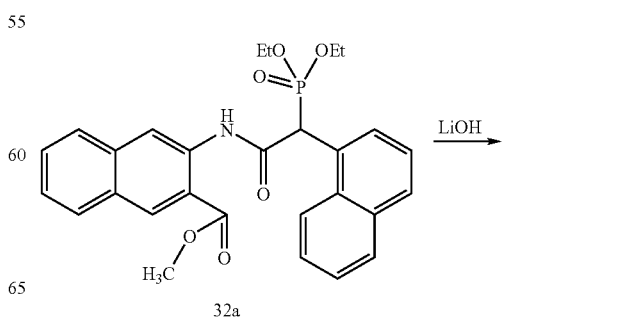

32a

-continued

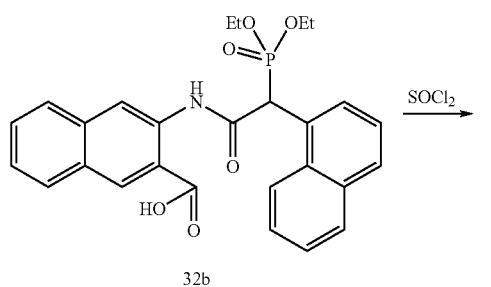
32b

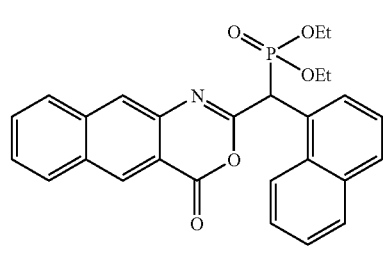
32c

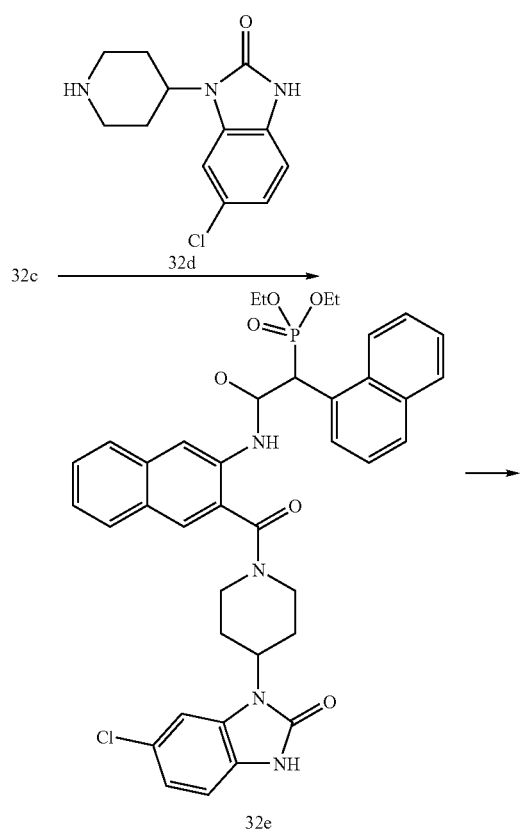
32e

-continued

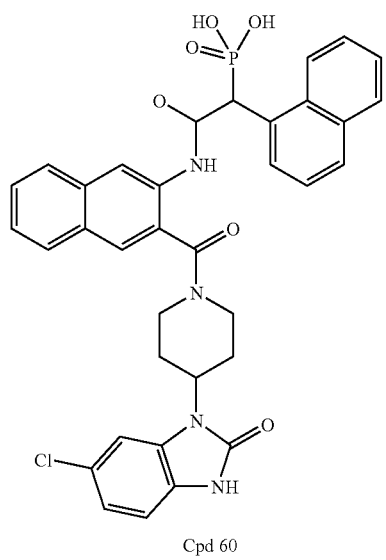
Cpd 60

Other compounds of the present invention may be prepared by those skilled in the art by varying the starting materials, reagent(s) and conditions used. Using the procedure of Example 32, the following compounds were prepared without further purification:

| Cpd | MS (MH$^+$) |
| --- | --- |
| 54 | 593 |
| 73 | 566 |
| 83 | 618 |
| 87 | 565 |
| 91 | 517 |
| 93 | 635 |
| 100 | 620 |
| 101 | 579 |
| 103 | 629 |
| 104 | 649 |
| 111 | 539 |
| 113 | 636 |
| 115 | 613 |
| 131 | 565 |

Example 33

({3-[Methyl-(4-phenyl-cyclohex-3-enyl)-carbamoyl]-naphthalen-2-ylcarbamoyl}-naphthalen-1-yl-methyl)-phosphonic acid, Cpd 46

To a stirred solution of Compound 33a (0.68 g, 3.96 mmol; *Syn. Comm.* 1994, 24(6), 799-808) and a 2 mL of a 2M solution of methyl amine in THF (6 mL) was added sodium triacetoxyborohydride (1.30 g, 5.94 mmol) followed by glacial acetic acid (0.24 g, 3.96 mmol). After stirring for 2.5 h, the mixture was treated with water and extracted with $CH_2Cl_2$ (3×). The combined organic extracts were dried ($Na_2SO_4$), filtered (Celite) and concentrated under reduced pressure at rt. The residue was purified by flash column chromatography (silica, 0-10% MeOH/$CH_2Cl_2$) to yield 0.25 g of Compound 33b as a light brown tacky solid: HPLC: 1.91 min; MS (ES) m/z 188 (MH+).

Using the procedure described in Example 32, Compound 33b was converted to Compound 46: HPLC: 3.97 min; MS (ES) m/z 605 (MH+).

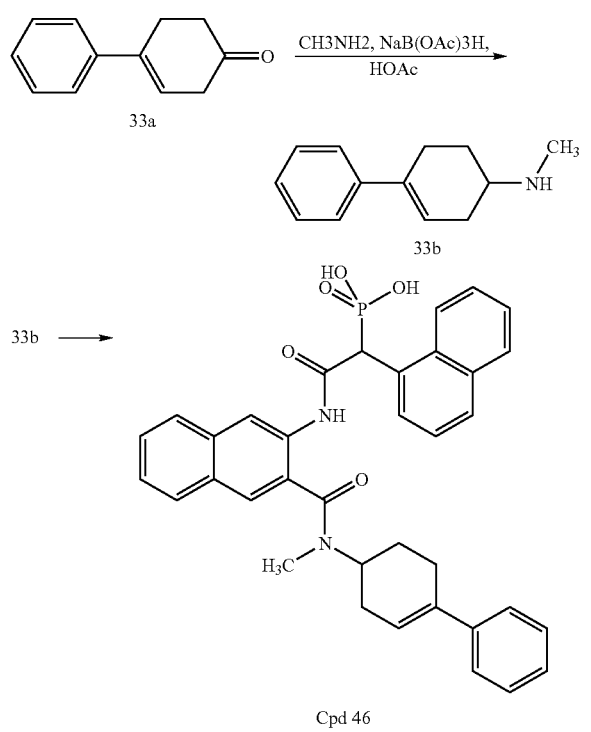

Example 34

[(3-Benzylcarbamoyl-naphthalen-2-ylcarbamoyl)-naphthalen-1-yl-methyl]-phosphonic acid, Cpd 119

Compound 119 was prepared from Compound 32b via a standard BOP-Cl/TEA coupling and deethylation by Procedure A: HPLC: 3.81 min, 90%; MS (ES) m/z 525 (MH+).

Example 35

[(5-Bromo-benzo[b]thiophen-3-yl)-(naphthalen-2-ylcarbamoyl)-methyl]-phosphonic acid, Cpd 23

Compound 35a (6-bromobenzothiophene) was prepared by the method described in *J. Med. Chem* 1998, 41, 4486-4491. Compound 35a (3.45 g, 16.2 mmol) was converted to 3.68 g of crude Compound 35b by the method described in the reference cited supra: HPLC: 4.14 min, 53%.

Following the procedure of Example 1 for the conversion of Compound 1c to Compound 9, Compound 35b was converted to Compound 23: HPLC: 4.53 min; MS (ES) m/z 475 (MH−).

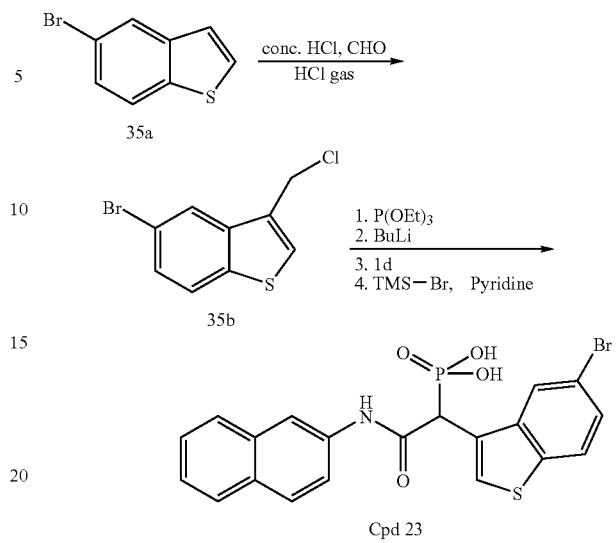

Other compounds of the present invention may be prepared by those skilled in the art by varying the starting materials, reagent(s) and conditions used. Using the procedure of Example 35, the following compounds were prepared without further purification:

| Cpd | MS (MH+) |
|-----|----------|
| 5   | 412      |
| 10  | None (verified by NMR) |
| 29  | 396 (MH−) |
| 76  | 474 (MH−) |
| 99  | 476/478  |

Example 36

[(5-phenyl-benzo[b]thiophen-3-yl)-(naphthalen-2-ylcarbamoyl)-methyl]-phosphonic acid, Cpd 71

To a heat-gun dried flask under Ar was sequentially added toluene (15 mL), Compound 35a (0.33 g, 0.91 mmol) and then tetrakis triphenylphosphine Pd(0) (0.053 g, 0.046 mmol). After stirring for 30 min, the mixture was treated with a solution of phenyl boronic acid, Compound 36a (0.17 g, 1.36 mmol) in EtOH (5 mL) followed by saturated $NaHCO_3$ (aq) (7.5 mL). After 4 h at reflux, the mixture was cooled to rt and treated with brine (15 mL). The layers were separated, and the aqueous portion was extracted with EtOAc (3×) and the combined organic extracts were washed sequentially with 0.1 N NaOH (aq) (3×), brine, dried ($Na_2SO_4$), filtered and concentrated under reduced pressure at rt. The residue was purified by flash column chromatography (silica, 0-3% MeOH/$CH_2Cl_2$) to yield 0.27 g of Compound 36b: HPLC: 3.91 min, 95%; MS (ES) m/z 361 (MH+).

Following the procedure of Example 35 for the conversion of Compound 35a to Compound 35b, Compound 36b was converted to Compound 36c.

Following the procedure of Example 1 with Procedure A for the conversion of Compound 1c to Compound 9, Compound 36c was converted to Compound 71: HPLC: 4.84 min; MS (ES) m/z 572 (MH⁻).

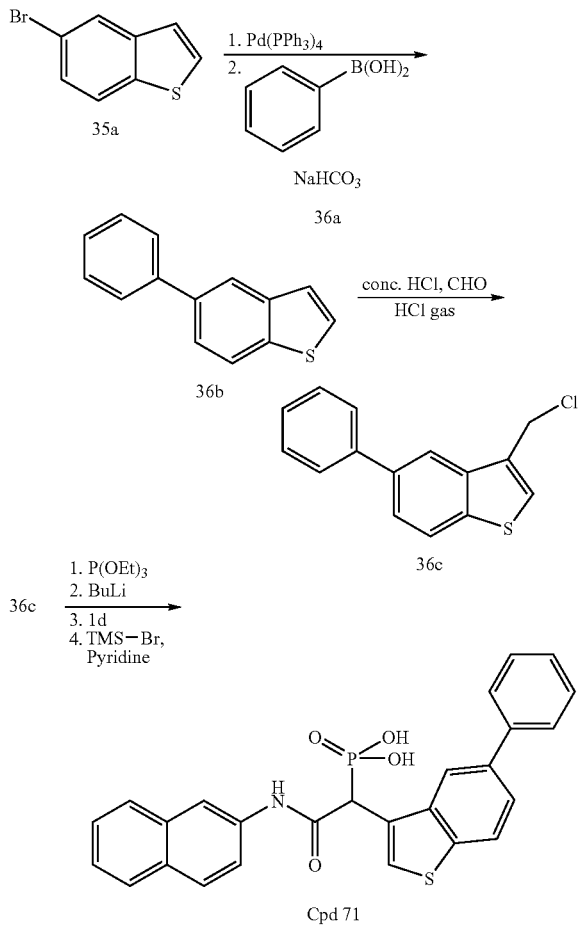

Other compounds of the present invention may be prepared by those skilled in the art by varying the starting materials, reagent(s) and conditions used. Using the procedure of Example 36, the following compounds were prepared without further purification:

| Cpd | MS (MH⁺) |
|-----|----------|
| 143 | 623 (M + pyr)H⁺ |

Example 37

[(Naphthalen-2-ylcarbamoyl)-(1-phenyl-1H-indol-3-yl)-methyl]-phosphonic acid, Cpd 82

N-phenyl indole Compound 37a was prepared by the procedure described in *JOC* 2001, 66(23), 7729-7737.

Using the procedure described in Example 18, substituting Compound 37a for Compound 18b, Compound 82 was prepared: HPLC: 4.04 min; MS (ES) m/z 457 (MH⁺).

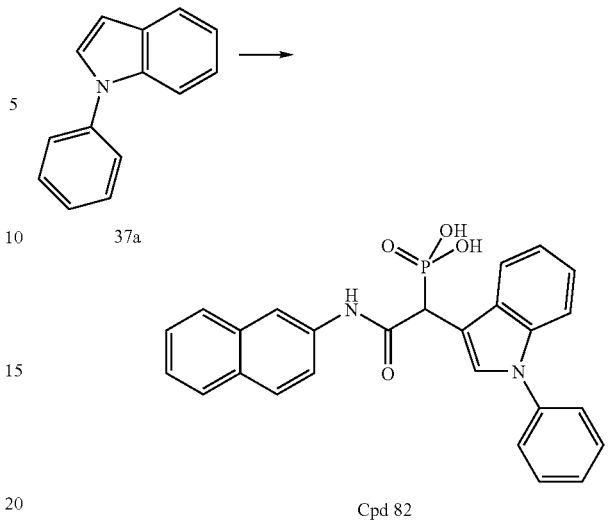

Example 38

[(3-Benzyloxy-naphthalen-2-ylcarbamoyl)-naphthalen-1-yl-methyl]-phosphonic acid, Cpd 122

Using the procedure described in Example 17, substituting Compound 38a (0.30 g, 1.89 mmol) for Compound 17i, Compound 38b (0.38 g) was prepared: HPLC: 3.85 min, 95%; MS (ES) m/z 464 (MH⁺).

Using the method described in *JACS* 1998, 110(14), 4789, Compound 38b (0.22 g, 0.48 mmol) was converted to Compound 38c (0.16 g): HPLC: 4.43 min, 98%.

Compound 38c (0.14 g, 0.25 mmol) was deethylated by Procedure A to give Compound 122 (0.114 g): HPLC: 4.08 min; MS (ES) m/z 498 (MH⁺).

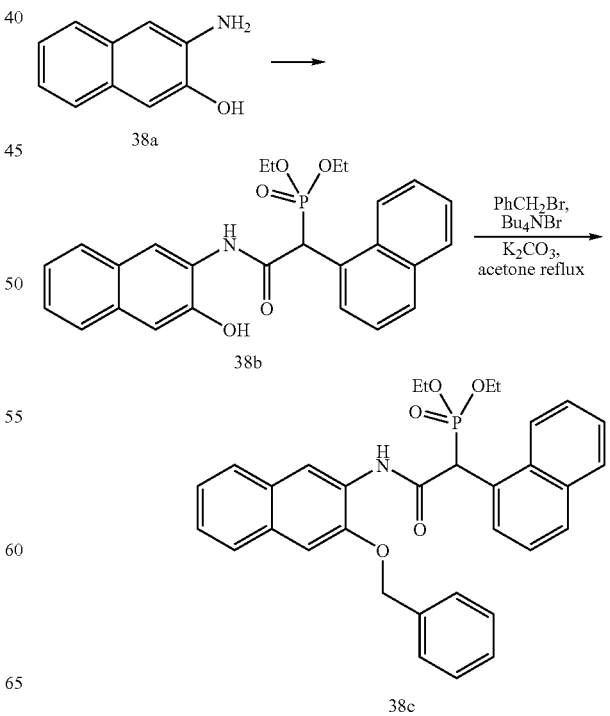

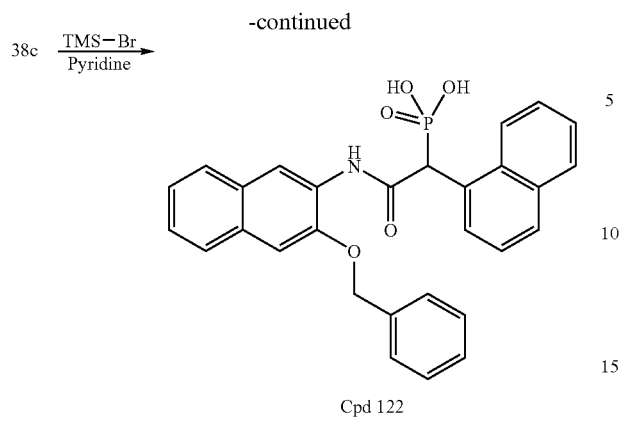

Cpd 122

Other compounds of the present invention may be prepared by those skilled in the art by varying the starting materials, reagent(s) and conditions used. Using the procedure of Example 38, the following compounds were prepared without further purification:

| Cpd | MS (MH⁺) |
| --- | --- |
| 108 | 408 |
| 121 | 524 |
| 123 | 480 |

Example 39

[Naphthalen-1-yl-(3-phenylcarbamoyloxy-naphthalen-2-yl-carbamoyl)-methyl]-phosphonic acid, Cpd 95

Using the procedure described in Example 27, substituting Compound 38b (0.19 g, 0.41 mmol) for Compound 27a and phenylisocyanate for benzylisocyanate, Compound 39a (0.18 g) was prepared: HPLC: 4.30 min, 95%; MS (ES) m/z 583 (MH⁺).

Compound 39a (0.18 g, 0.31 mmol) was deethylated by Procedure A to give Compound 95 (0.12 g): HPLC: 4.16 min; MS (ES) m/z 527 (MH⁺).

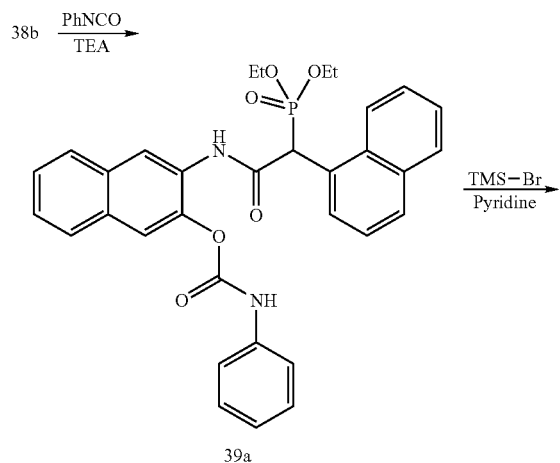

39a

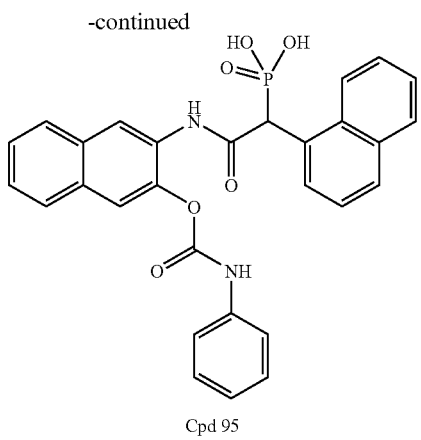

Cpd 95

Example 40

[(3-{[1-(Naphthalene-2-carbonyl)-piperidine-4-carbonyl]-amino}-naphthalen-2-ylcarbamoyl)-naphthalen-1-yl-methyl]-phosphonic acid, Cpd 141

Compound 40a was synthesized by the method described in *JACS* 1993, 115(4), 1321-1329.

Using the procedure described in Example 17, substituting Compound 40a (0.80 g, 3.11 mmol) for Compound 17c, Compound 40b (0.53 g) was prepared: HPLC: 4.20 min.

Compound 40b (0.28 g, 0.50 mmol) was dissolved in TFA (1 mL) and allowed to stand for 30 min. The solution was concentrated under reduced pressure at rt to yield 0.47 g of Compound 40c as a 4.2 TFA solvate: HPLC: 3.40 min; MS (ES) m/z 463 (MH⁺).

To a solution of Compound 40c (0.47 g), diisopropylamine (0.37 mL, 2.1 mm 1), HOBt (0.068 g, 0.50 mmol), and Boc-isonipecotic acid (0.115 g, 0.50 mmol) in CH₂Cl₂ (5 mL) was added DCC (0.103 g, 0.50 mmol). After stirring for 72 h, the mixture was diluted with CH₂Cl₂ and filtered. The filtrate was washed sequentially with 1N KHSO₄, saturated NaHCO₃ (aq), and brine, then dried (Na₂SO₄), filtered and concentrated under reduced pressure at rt. The residue was crystallized from CH₃CN to yield 0.14 g of Compound 40d as a white solid: HPLC: 4.08 min; MS (ES) m/z 674 (MH⁺).

Compound 40d (0.14 g, 0.21 mmol) was stirred with TFA (1 mL) for 45 min, then concentrated. The residue was dissolved in CH₂Cl₂ (5 mL) containing DIPEA (0.21 mL, 1.2 mmol). To the mixture was added 2-naphthoyl chloride (0.04 g, 0.21 mmol) and the reaction stirred for 20 min. The mixture was washed sequentially with 1N KHSO₄ (aq), saturated NaHCO₃ (aq), and brine, then dried (Na₂SO₄), filtered and concentrated under reduced pressure at rt to yield 0.15 g of Compound 40e as a white solid: HPLC: 4.01 min.

Compound 40e was deethylated by Procedure A to yield Compound 141: HPLC: 3.75 min; MS (ES) m/z 672 (MH⁺).

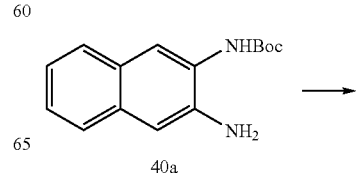

40a

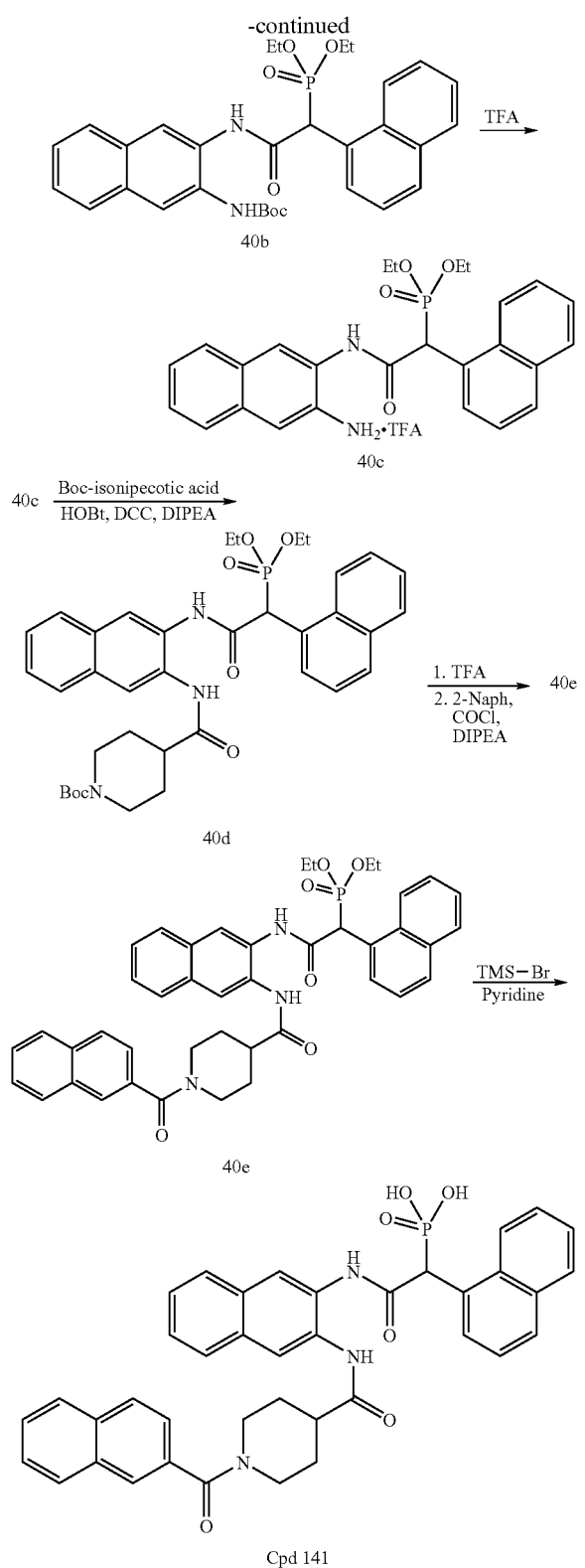

| Cpd | MS (MH+) |
| --- | --- |
| 132 | 407 |

Example 41

[2-(2-Naphthalen-1-yl-2-phosphono-acetylamino)-naphthalen-1-yloxy]-acetic acid methyl ester, Cpd 134

Using the procedure described in Example 38 for the conversion of Compound 38a to 38c, substituting methyl bromoacetate for benzyl bromide, Compound 41a was reacted to give Compound 41 b.

Compound 41 b was deethylated by Procedure A to yield Compound 134: HPLC: 4.23 min; MS (ES) m/z 498 (MH+).

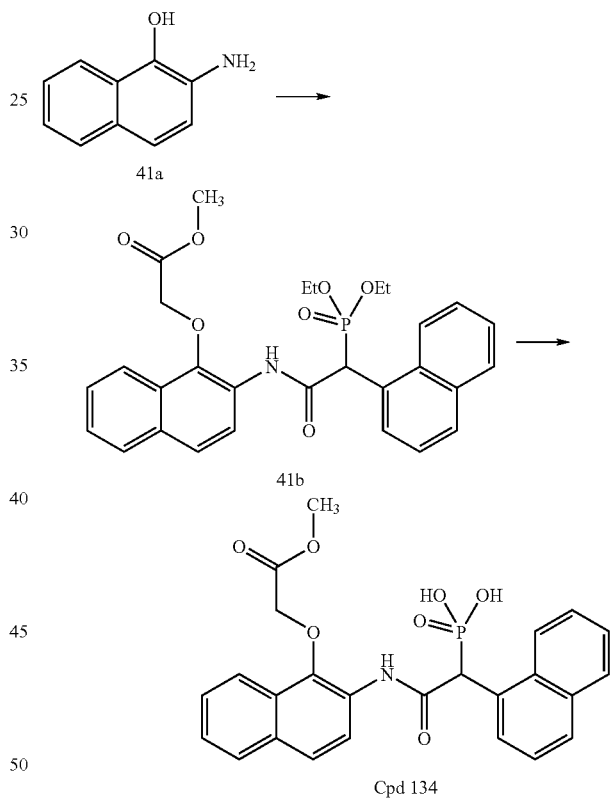

Example 42

(Naphthalen-1-yl-{1-[2-oxo-2-(4-phenyl-piperidin-1-yl)-ethoxy]-naphthalen-2-ylcarbamoyl}-5 methyl)-phosphonic acid, Cpd 114

Using the procedure of Example 32 for the saponification of Compound 32a to 32b, Compound 41b (1.01 g, 1.89 mmol) was converted to Compound 42a (1.12 g): HPLC: 3.78 min; MS (ES) m/z 522 (MH+).

Using the procedure described in Example 24, substituting Compound 42a (0.25 g, 0.48 mmol) for Compound 24e, Compound 42b (0.27 g) was prepared: HPLC: 4.54 min, 97%; MS (ES) m/z 665 (MH+).

Other compounds of the present invention may be prepared by those skilled in the art by varying the starting materials, reagent(s) and conditions used. Using the procedure of Example 40, the following compounds were prepared without further purification:

Compound 42b (0.15 g, 0.23 mmol) was deethylated by Procedure A to give of Compound 114 (0.096 g): HPLC: 4.19 min; MS (ES) m/z 609 (MH+).

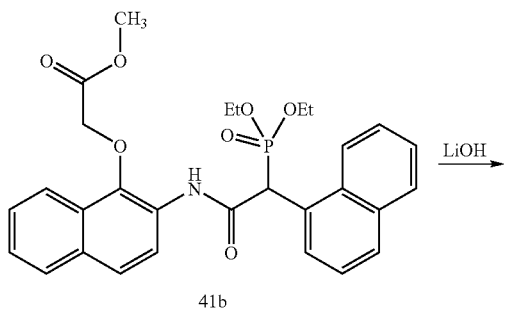

41b

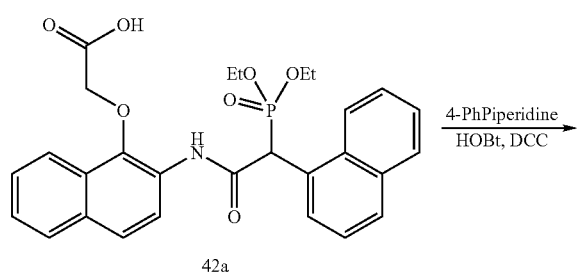

42a

42b

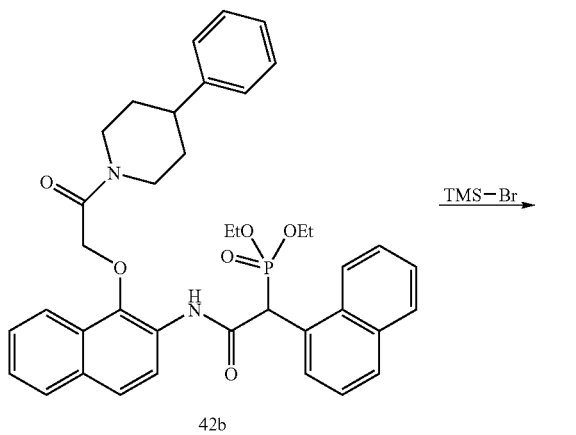

42b

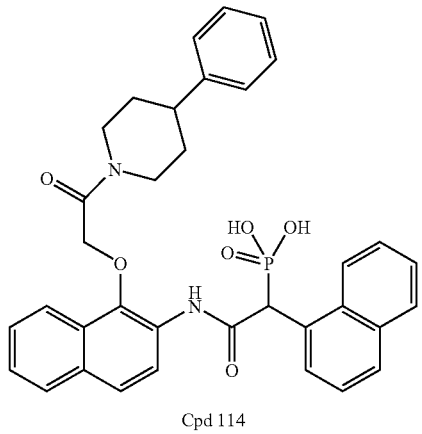

Cpd 114

Other compounds of the present invention may be prepared by those skilled in the art by varying the starting materials, reagent(s) and conditions used. Using the procedure of Example 40, the following compounds were prepared without further purification:

| Cpd | MS (MH+) |
| --- | --- |
| 130 | 583 |

Example 43

{[(5-Chloro-benzo[b]thiophen-3-yl)-[2-(4-hydroxyl-phenyl)-vinylcarbamoyl]-methyl}-methyl-phosphonic acid, Cpd 66

Compound 43a (0.100 g, 0.192 mmol), prepared as in Example 11, was deethylated by Procedure A and the crude product was dissolved in 5 mL of methanol and treated with 0.210 g of KOH. The mixture was stirred for 7.5 h, then acidified with 1N HCl (aq), concentrated under reduced pressure at rt and purified by reverse phase HPLC (12-90% MeCN/H$_2$O) to yield 0.014 g of Compound 66 as a grey powder: HPLC: 3.04 min; 77%; MS (ES) m/z 422 (MH−).

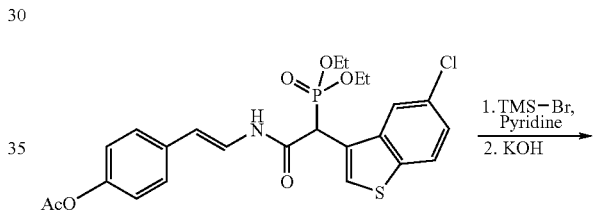

43a

Cpd 66

Example 44

{(5-Chloro-benzo[b]thiophen-3-yl)-[2-(2-hydroxy-phenyl)-vinylcarbamoyl]-methyl}-methyl-phosphinic acid, Cpd 149

A solution of Compound 44a (0.29 g, 0.63 mmol; prepared according to Example 6) in 15 mL of methanol containing 5 mL of 1N NaOH (aq) was stirred for 25 min. The solution was concentrated under reduced pressure, and the residue was suspended in 1N HCl (aq) and stirred for 1 h. The solid was collected, rinsed sequentially with 1N HCl and water, then dried under a stream of N$_2$ to yield 0.23 g of Compound 149 as a pale yellow powder: HPLC: 3.71 min; MS (ES) m/z 422 (MH+).

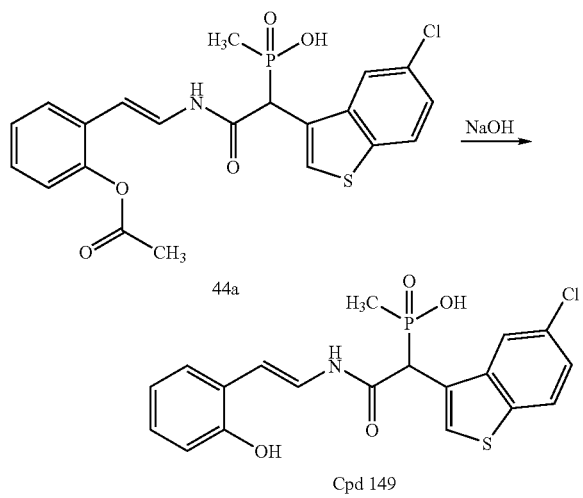

44a

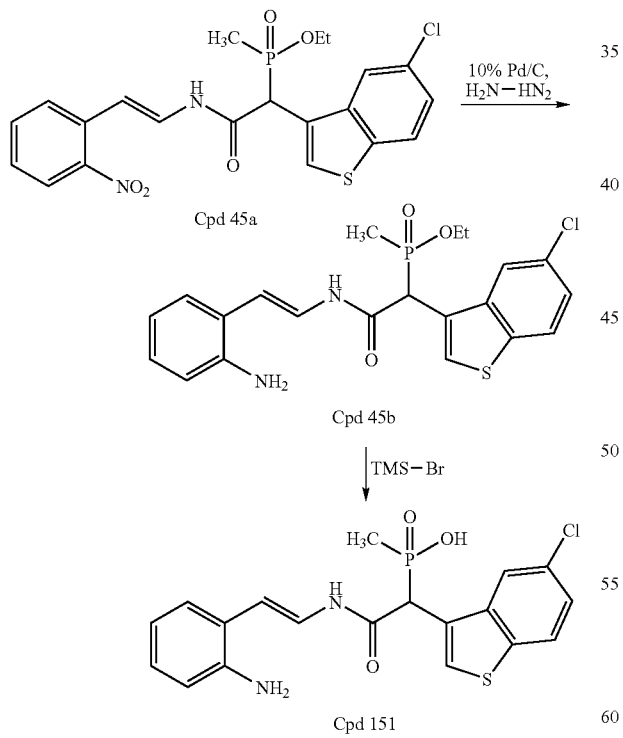

| Cpd | MS (MH⁺) |
|---|---|
| 172 | 421 |

Example 46

{(5-Chloro-benzo[b]thiophen-3-yl)-[2-(2-ureido-phenyl)-vinylcarbamoyl]-methyl}-methyl-phosphinic acid, Cpd 158

To a suspension of Compound 45b (0.14 g, 0.31 mmol), acetic acid (0.4 mL) and water (1.6 mL) was added a five-fold excess of sodium cyanate. The reaction was stirred at 60° C. for 1 h, and the crude product was collected, washed with water, dried under a stream of $N_2$ and deethylated by Procedure A. The product was subjected to reverse phase HPLC (25-90% MeCN/$H_2O$) to yield 0.026 g of Compound 158 as a white powder: HPLC: 3.22 min; MS (ES) m/z 464 (MH⁺), and 0.037 g of Compound 159 as a white powder: HPLC: 3.46 min; MS (ES) m/z 507 (MH⁺).

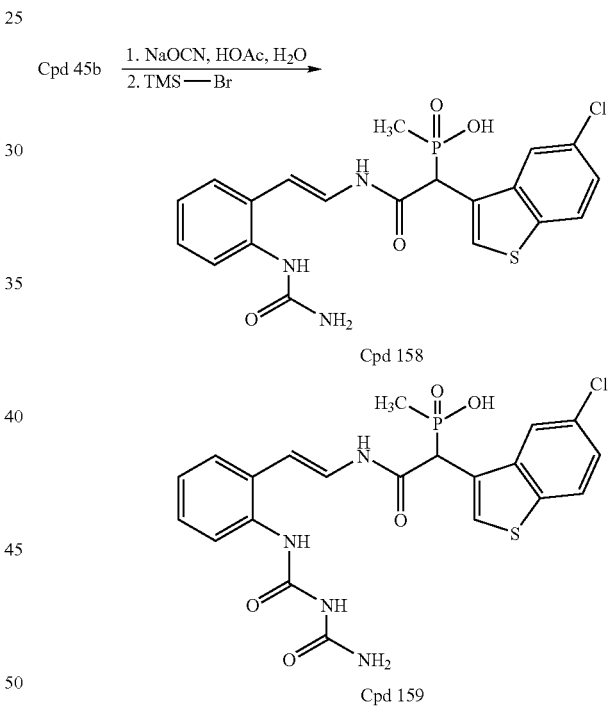

Example 45

[[2-(2-Amino-phenyl)-vinylcarbamoyl]-(5-chloro-benzo[b]thiophen-3-yl)-methyl]-methyl-phosphinic acid, Cpd 151

Compound 45a (prepared according to Example 6) was converted to compound 45b by the method of Example 10. Compound 45b was deethylated according to Procedure A and purified by trituration with 1N HCl (aq) to yield Compound 151: HPLC: 2.78 min; MS (ES) m/z 421 (MH⁺).

Other compounds of the present invention may be prepared by those skilled in the art by varying the starting materials, reagent(s) and conditions used. Using the procedure of Example 45, the following compounds were prepared without further purification:

Example 47

(Naphthalen-1-yl-styrylcarbamoyl-methyl)-phosphonic acid didiethylcarbamoylmethyl ester, Cpd 180

To a solution of Compound 37 (0.21 g, 0.53 mmol) and N,N-diethyl-2-hydroxyacetamide (0.15 g, 1.17 mmol) in pyridine (5 mL) was added 1-(mesitylene-2-sulfonyl)-3-nitro-1,2,4-triazole (MSNT; 0.47 g, 1.59 mmol) and the mixture was stirred at rt for 3.5 h. The reaction was concentrated under reduced pressure, and the residue taken up in EtOAc. The solution was washed sequentially with 1N $KHSO_4$ (aq), saturated $NaHCO_3$ (aq), and brine, then dried ($Na_2SO_4$), and concentrated under reduced pressure. The crude product was purified by flash column chromatography (silica, 0-30% acetone/heptane) to yield 0.07 g of Compound 180 as a yellow solid: HPLC: 3.88 min; MS (ES) m/z 594 (MH$^+$).

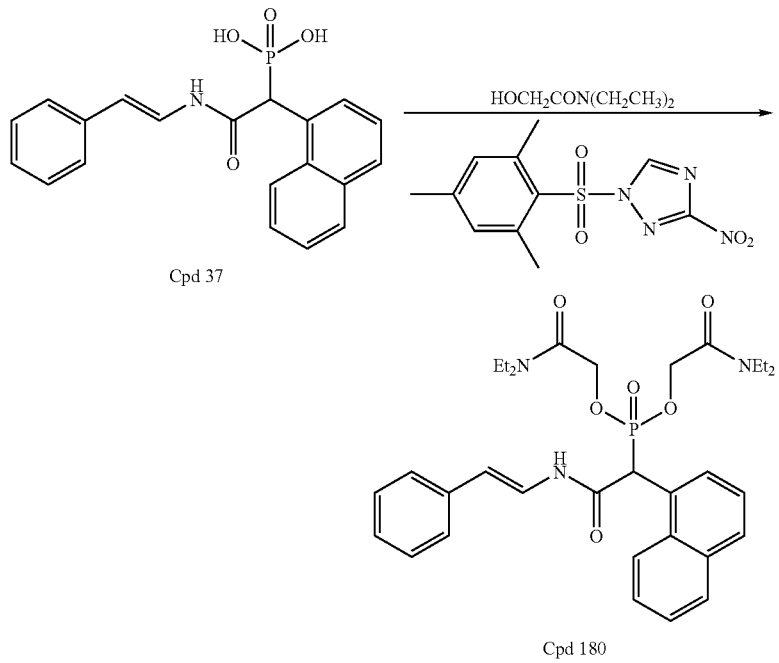

Cpd 37

Cpd 180

Other compounds of the present invention may be prepared by those skilled in the art by varying the starting materials, reagent(s) and conditions used. Using the procedure of Example 47, the following compounds were prepared:

| Cpd | MS (MH$^+$) |
|---|---|
| 179 | 510 |
| 181 | 656 |

Example 48

2-Naphthalen-1-yl-2-(2-oxo-2l5-[1,3,2]dioxaphosphinan-2-yl)-N-styryl-acetamide, Cpd 178

Using the procedure described in Example 47, Compound 37 (0.10 g, 0.27 mmol), 1,3-propanediol (0.02 g, 0.27 mmol), and MSNT (0.48 g, 1.62 mmol) in pyridine (5 ml) afforded 0.01 g of Compound-178, as a white powder: HPLC: 3.52 min; MS (ES) m/z 408 (MH$^+$).

Other compounds of the present invention may be prepared by those skilled in the art by varying the starting materials, reagent(s) and conditions used. Using the procedure of Example 48, the following compound was prepared:

| Cpd | MS (MH$^+$) |
|---|---|
| 173 | 436 |

Example 49

{(5-Chloro-benzo[b]thiophen-3-yl)-[2-(3,4-difluoro-phenyl)-vinylcarbamoyl]-methyl}-methyl-phosphinic acid diethylcarbamoylmethyl ester, Cpd 185

Using the procedure described in Example 47, Compound 17 (0.25 g, 0.57 mmol), N,N-diethyl-2-hydroxyacetamide (0.37 g, 2.86 mmol), and MSNT (0.25 g, 0.86 mmol) in pyridine (5 ml) yielded 0.14 g of Compound 185, as a white powder (~3:1 mixture of diastereomers). HPLC: 4.03 min (24%), 4.11 min (76%); MS (ES) m/z 555 (MH$^+$).

Other compounds of the present invention may be prepared by those skilled in the art by varying the starting materials, reagent(s) and conditions used. Using the procedure of Example 49, the following compound was prepared:

| Cpd | MS (MH$^+$) | Diastereomer ratio |
|---|---|---|
| 183 | 513 | 1:1 |

Example 50

{(5-Chloro-benzo[b]thiophen-3-yl)-[2-(3,4-difluoro-phenyl)-vinylcarbamoyl]-methyl}-methyl-phosphinic acid 2-amino-ethyl ester, Cpd 184

Using the procedure described in Example 47, Compound 17 (0.27 g, 0.61 mmol), N-Boc-ethanolamine (0.11 g, 0.67 mmol), and MSNT (0.54 g, 1.83 mmol) in pyridine (5 mL) yielded 0.27 g of Compound 50a, as a white powder: (~2:1 mixture of diastereomers). HPLC: 4.17 min (22%), 4.20 min (46%); MS (ES) m/z 585 (MH⁺).

A solution of Compound 50a (0.27 g, 0.46 mmol) in 3 mL of TFA was stirred for 30 min, then concentrated under reduced pressure. The residue was purified by reverse phase HPLC (30-90% MeCN/H$_2$O) to afford 0.12 g of Compound 184 as a white powder (TFA salt; ~1:1 mixture of diastereomers by $^1$H NMR); HPLC: 3.17 min; MS (ES) m/z 485 (MH⁺).

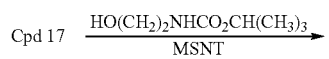

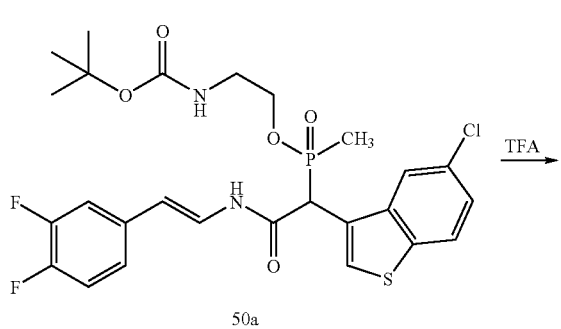

50a

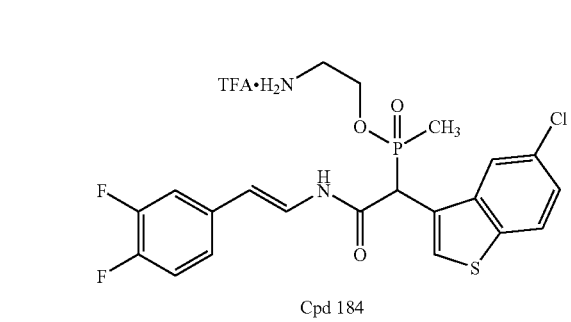

Cpd 184

Example 51

2,2-Dimethyl-propionic acid {(5-chloro-benzo[b]thiophen-3-yl)-[2-(3,4-difluoro-phenyl)-vinylcarbamoyl]-methyl}-(2,2-dimethyl-propionyloxymethoxy)-phosphinoyloxymethyl ester, Cpd 186 and 2,2-Dimethyl-propionic acid {(5-chloro-benzo[b]thiophen-3-yl)-[2-(3,4-difluoro-phenyl)-vinylcarbamoyl]-methyl}-hydroxy-phosphinoyloxymethyl ester, Cpd 187

A solution of Compound 2 (0.25 g, 0.56 mmol), triethylamine (0.31 mL, 2.24 mmol), and chloromethylpivaloate (0.32 ml, 2.24 g) in DMF (2 ml) was heated at 60° C. for 2.5 h. The mixture was cooled to rt and concentrated under reduced pressure. The crude product mixture was subjected to reverse phase HPLC (37.5-90% MeCN/H$_2$O) to yield 0.035 g of Compound 186 as a white powder; HPLC: 4.77 min; MS (ES) m/z 672 (MH⁺), and 0.16 g of Compound 187 which was converted to its tromethamine salt by treatment of a methanol solution of Compound 186 with 1 eq of tris-(hydroxymethyl)methylamine. The mixture was concentrated under reduced pressure to afford the tromethamine salt of Compound 187 as a white powder: HPLC: 5.13 min; MS (ES) m/z 558 (MH⁺).

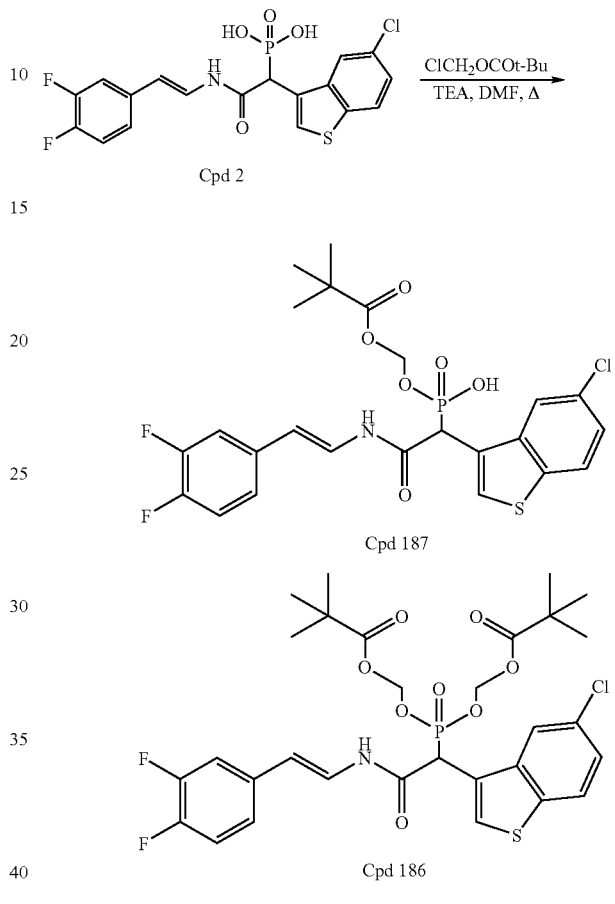

Other compounds of the present invention may be prepared by those skilled in the art by varying the starting materials, reagent(s) and conditions used. Using the procedure of Example 51, the following compounds were prepared:

| Cpd | MS (MH⁺) |
|---|---|
| 188 | 670 |
| 190 | 514 (MH⁻) |
| 191 | 670 |

Using the procedure of Example 51, and substituting Compound 37 for Compound 2, the following compounds were prepared:

| Cpd | MS (MH⁺) |
|---|---|
| 174 | 438 (MH⁻) |
| 175 | 512 |
| 176 | 466 (MH⁻) |
| 177 | 482 |

Using the procedure of Example 51, and substituting Compound 17 for Compound 2, the following compounds were prepared:

| Cpd | MS (MH⁺) | Diastereomer ratio |
|---|---|---|
| 182 | 556 | 3:2 |

The following compounds can be made by those skilled in the art by using Example 6 followed by Example 51, and varying the starting materials, reagent(s) and conditions used: compounds 210, 211, 212, 213, 214, 215, 216, 217, 218, 219, 220, 221, 222, 223, 224, 225, 226, 227, 316, 317, 318, 319, 320, 321, 322, and 323.

The following compounds can be made by those skilled in the art by using Example 11 followed by Example 51, and varying the starting materials, reagent(s) and conditions used: compounds 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 282, 283, 284, 285, 286, 287, 288, 289, 290, 291, 292, 293, 294, 295, 296, 297, 298, 299, 324, 325, 326, 327, 328, 329, 330, 331, 332, 333, 334, 335, 336, 337, 338, 339, 348, 349, 350, 351, 352, 353, 354, and 355.

Example 52

2-(5-Chloro-benzo[b]thiophen-3-yl)-N-[2-(3,4-difluoro-phenyl)-vinyl]-2-(2-oxo-2,5-[1,3,2]dioxaphosphinan-2-yl)-acetamide, Cpd 189

A solution of Compound 1a (1.75 g, 6.69 mmol) and Compound 52a (prepared according to JACS 1969, 91(24), 6838-6841; 1.36 g, 10.04 mmol) in toluene (15 mL) was refluxed for 24 h. After cooling to rt, the mixture was concentrated under reduced pressure and the residue was purified by flash column chromatography (silica; 0-30% acetone/heptane) to afford 1.0 g of Compound 52b as a viscous oil: HPLC: 3.03 min; MS (ES) m/z 303 (MH⁺).

From Compound 52b (0.51 g, 1.69 mmol) was prepared 0.28 g of Compound 189 by the procedure of Example 1: HPLC: 3.96 min; MS (ES) m/z 484 (MH⁺).

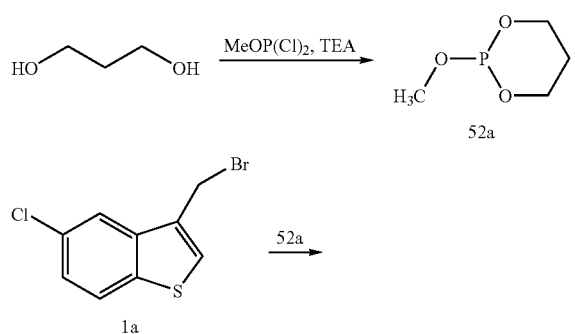

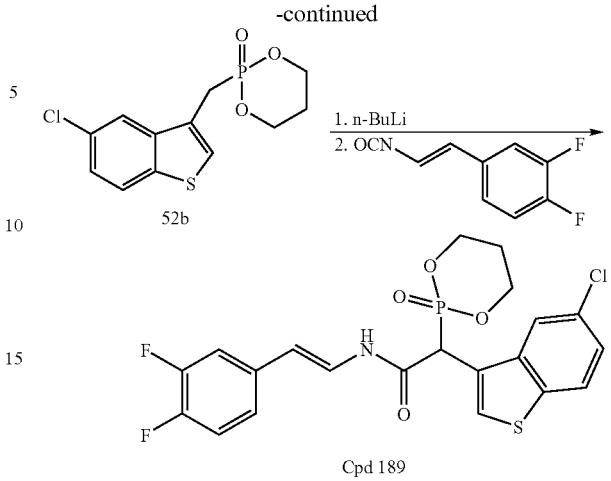

Cpd 189

The following compounds can be made by those skilled in the art by using Example 52 and varying the starting materials, reagent(s) and conditions used: compounds 264, 265, 266, 267, 268, 269, 270, 271, 272, 273, 274, 275, 276, 277, 278, 279, 280, 281, 340, 341, 342, 343, 344, 345, 346, and 347.

BIOLOGICAL EXPERIMENTAL EXAMPLES

The utility of the compounds of the present invention as a serine protease inhibitor and, particularly, as a chymase inhibitor useful for the treatment of inflammatory or serine protease mediated disorders can be determined according to the procedures described herein.

Example 1

Enzyme-Catalyzed Hydrolysis Assays

Enzyme-catalyzed hydrolysis rates were measured spectro-photometrically using human skin chymase (Cortex Biochem), a chromogenic substrate (Suc-Ala-Ala-Pro-Phe-pNa) (Bachem) in aqueous buffer (450 mM Tris, 1800 mM NaCl, pH 8.0), and a microplate reader (Molecular Devices). $IC_{50}$ experiments were conducted by fixing the enzyme and substrate concentrations (10 nM enzyme, 0.7 mM substrate) and varying the inhibitor concentration. Changes in absorbance at 405 nM were monitored using the software program Softmax (Molecular Devices), upon addition of enzyme, with and without inhibitor present at 37° C. for 30 minutes. Percent inhibition was calculated by comparing the initial reaction slopes of the samples without inhibitor to those with inhibitor. $IC_{50}$ values were determined using a four parameter fit logistics model. The term "NT" indicates a compound that was not tested.

Table VI summarizes the assay results for chymase inhibition for compounds of the present invention:

TABLE VI

| Cpd | $IC_{50}$ (µM) Chymase | N |
|---|---|---|
| 1 | 0.010 ± 0 | 2 |
| 2 | 0.011 ± 0 | 2 |
| 3 | 0.013 ± 0.007 | 2 |
| 4 | 0.016 ± 0.005 | 2 |

TABLE VI-continued

| Cpd | IC$_{50}$ (μM) Chymase | N |
|---|---|---|
| 5 | 0.019 ± 0.005 | 2 |
| 6 | 0.020 ± 0 | 2 |
| 7 | 0.021 ± 0.004 | 2 |
| 8 | 0.021 ± 0.010 | 4 |
| 9 | 0.029 ± 0.009 | 2 |
| 10 | 0.029 ± 0.010 | 3 |
| 11 | 0.037 ± 0.010 | 2 |
| 12 | 0.038 ± 0.013 | 6 |
| 13 | 0.040 ± 0.020 | 3 |
| 14 | 0.050 ± 0.010 | 2 |
| 15 | 0.052 ± 0.015 | 3 |
| 16 | 0.055 ± 0.005 | 2 |
| 17 | 0.058 ± 0.012 | 7 |
| 18 | 0.060 ± 0.020 | 3 |
| 19 | 0.066 ± 0.010 | 6 |
| 20 | 0.080 ± 0.004 | 2 |
| 21 | 0.080 ± 0.020 | 2 |
| 22 | 0.090 ± 0.028 | 4 |
| 23 | 0.100 ± 0.030 | 3 |
| 24 | 0.100 ± 0.033 | 3 |
| 25 | 0.109 ± 0.030 | 3 |
| 26 | 0.120 ± 0.030 | 4 |
| 27 | 0.130 ± 0.020 | 2 |
| 28 | 0.160 ± 0.004 | 2 |
| 29 | 0.166 ± 0.012 | 2 |
| 30 | 0.170 ± 0.010 | 2 |
| 31 | 0.190 | 1 |
| 32 | 0.210 ± 0.010 | 2 |
| 33 | 0.210 ± 0.690 | 2 |
| 34 | 0.220 ± 0.010 | 2 |
| 35 | 0.235 ± 0.045 | 2 |
| 36 | 0.240 ± 0.010 | 2 |
| 37 | 0.250 ± 0.120 | 7 |
| 38 | 0.284 ± 0.108 | 2 |
| 39 | 0.310 ± 0.040 | 2 |
| 40 | 0.320 ± 0.140 | 2 |
| 41 | 0.330 ± 0.020 | 2 |
| 42 | 0.340 ± 0.130 | 4 |
| 43 | 0.350 ± 0.070 | 2 |
| 44 | 0.350 ± 0.220 | 2 |
| 45 | 0.371 ± 0.110 | 2 |
| 46 | 0.388 ± 0.116 | 2 |
| 47 | 0.410 ± 0.100 | 2 |
| 48 | 0.421 ± 0.151 | 2 |
| 49 | 0.430 ± 0.090 | 2 |
| 50 | 0.430 ± 0.150 | 4 |
| 51 | 0.460 ± 0.060 | 2 |
| 52 | 0.480 ± 0.180 | 2 |
| 53 | 0.490 ± 0.160 | 2 |
| 54 | 0.510 ± 0.124 | 3 |
| 55 | 0.520 ± 0.510 | 2 |
| 56 | 0.606 ± 0.130 | 2 |
| 57 | 0.609 | 1 |
| 58 | 0.630 ± 0.130 | 4 |
| 59 | 0.635 | 1 |
| 60 | 0.663 | 1 |
| 61 | 0.710 | 1 |
| 62 | 0.820 ± 0.500 | 3 |
| 63 | 0.830 ± 0.180 | 4 |
| 64 | 0.830 ± 0.080 | 2 |
| 65 | 0.840 ± 0.190 | 3 |
| 66 | 0.868 ± 0.130 | 6 |
| 67 | 0.920 ± 0.250 | 4 |
| 68 | 0.920 ± 0.530 | 2 |
| 69 | 0.930 ± 0.950 | 2 |
| 70 | 0.930 ± 0.070 | 2 |
| 71 | 1.000 ± 0.300 | 5 |
| 72 | 1.300 ± 0.610 | 2 |
| 73 | 1.352 ± 0.168 | 3 |
| 74 | 1.390 ± 0.554 | 2 |
| 75 | 1.400 ± 0.600 | 3 |
| 76 | 1.430 ± 0.451 | 2 |
| 77 | 1.480 ± 0.450 | 2 |
| 78 | 1.500 ± 0.430 | 2 |
| 79 | 1.600 | 1 |
| 80 | 1.650 ± 0.680 | 2 |
| 81 | 1.700 ± 0.210 | 6 |
| 82 | 1.700 ± 0.410 | 2 |
| 83 | 1.723 | 1 |
| 84 | 1.750 ± 0.285 | 2 |
| 85 | 1.800 ± 1.200 | 2 |
| 86 | 1.900 ± 0.400 | 2 |
| 87 | 2.036 | 1 |
| 88 | 2.040 ± 0.190 | 3 |
| 89 | 2.100 ± 0.200 | 2 |
| 90 | 2.153 | 1 |
| 91 | 2.320 | 1 |
| 92 | 2.400 | 1 |
| 93 | 2.703 | 1 |
| 94 | 2.755 | 1 |
| 95 | 2.800 | 1 |
| 96 | 2.800 | 1 |
| 97 | 2.882 ± 0.899 | 2 |
| 98 | 2.900 | 1 |
| 99 | 2.963 ± 1.180 | 2 |
| 100 | 3.001 ± 1.431 | 3 |
| 101 | 3.115 | 1 |
| 102 | 3.450 | 1 |
| 103 | 3.627 | 1 |
| 104 | 3.879 ± 2.414 | 3 |
| 105 | 4.100 | 1 |
| 106 | 4.300 | 1 |
| 107 | 4.300 ± 0.030 | 2 |
| 108 | 4.338 | 1 |
| 109 | 4.400 | 1 |
| 110 | 4.451 | 1 |
| 111 | 4.617 | 1 |
| 112 | 4.735 ± 1.655 | 5 |
| 113 | 4.803 ± 1.688 | 2 |
| 114 | 4.899 ± 1.339 | 2 |
| 115 | 5.362 | 1 |
| 116 | 5.400 | 1 |
| 117 | 5.624 ± 1.074 | 2 |
| 118 | 5.720 ± 0.013 | 2 |
| 119 | 5.800 | 1 |
| 120 | 5.860 ± 1.080 | 5 |
| 121 | 5.900 | 1 |
| 122 | 5.944 ± 1.688 | 2 |
| 123 | 6.600 | 1 |
| 124 | 6.700 | 1 |
| 125 | 6.700 | 1 |
| 126 | 7.000 | 1 |
| 127 | 7.000 ± 1.100 | 2 |
| 128 | 7.300 | 1 |
| 129 | 7.400 | 1 |
| 130 | 7.436 ± 3.734 | 2 |
| 131 | 7.681 | 1 |
| 132 | 7.900 | 1 |
| 133 | 8.083 ± 3.153 | 4 |
| 134 | 8.110 ± 4.753 | 2 |
| 135 | 8.300 | 1 |
| 136 | 8.630 ± 0.810 | 2 |
| 137 | 8.665 | 1 |
| 138 | 8.700 | 1 |
| 139 | 8.800 | 1 |
| 140 | 9.200 ± 0.730 | 6 |
| 141 | 9.500 | 1 |
| 142 | 9.538 ± 4.204 | 2 |
| 143 | 9.800 | 1 |
| 144 | 1.26 ± 0.29 | 2 |
| 145 | 0.035 ± 0.02 | 2 |
| 146 | 0.11 ± 0 | 2 |
| 147 | 1.44 ± 0.48 | 2 |
| 148 | 0.23 ± 0.04 | 2 |
| 149 | 0.043 ± 0 | 2 |
| 150 | 0.091 ± 0.02 | 2 |
| 151 | 0.40 ± 0.12 | 2 |
| 152 | 0.13 ± 0.03 | 2 |
| 153 | 0.06 ± 0.01 | 2 |
| 154 | 0.036 ± 0.05 | 2 |
| 155 | 0.34 ± 0.04 | 2 |
| 156 | 0.036 ± 0.01 | 2 |

TABLE VI-continued

| Cpd | IC$_{50}$ (µM) Chymase | N |
|---|---|---|
| 157 | 11.0 ± 1.2 | 2 |
| 158 | 6.0 ± 1.9 | 2 |
| 159 | 3.0 ± 0.19 | 2 |
| 160 | 0.065 ± 0.02 | 2 |
| 161 | 0.0035 ± 0 | 2 |
| 162 | 0.0090 ± 0 | 2 |
| 163 | 0.017 ± 0 | 2 |
| 164 | 0.10 ± 0.02 | 2 |
| 165 | 0.078 ± 0.03 | 2 |
| 166 | 0.0387 ± 0.02 | 2 |
| 167 | 0.017 ± 0.04 | 2 |
| 168 | 0.0059 ± 0.01 | 2 |
| 169 | 0.042 ± 0 | 2 |
| 170 | 0.0031 ± 0 | 2 |
| 171 | 0.025 ± 0.01 | 2 |
| 172 | 0.041 ± 0.02 | 2 |
| 199 | 0.0018 ± 0 | 2 |

Example 2

Anti-Asthmatic Effects in a Sheep Model of Asthma

The efficacy of Compound 17 for the treatment of asthma was evaluated in a validated model of *Ascaris suum* antigen-induced asthmatic response in conscious sheep (Abraham, W. M., Pharmacology of allergen-induced early and late airway responses and antigen-induced airway hyperresponsiveness in allergic sheep, *Pulmonary Pharmacology*, 1989, 2, 33-40).

Experimental Protocol

Baseline (BSL) dose response curves to aerosol carbachol were obtained from historical control responses prior to antigen challenge. Baseline values of specific lung resistance (SR$_L$) were obtained and the sheep were then given a specified amount (mg) of the test compound as an inhaled aerosol or as a oral dose at a specified time before antigen challenge. Post-drug measurements of SR$_L$ were obtained and the sheep were then challenged with *Ascaris suum* antigen. Measurements of SR$_L$ were obtained immediately after challenge, hourly from 1-6 h after challenge and on the half-hour from 6½-8 h after challenge. Measurements of SR$_L$ were obtained 24 h after challenge followed by a 24 h post-challenge with carbachol to measure airway hyperreactivity.

Compound 17 was administered as an aerosol at 4.5 mg/dose (ca. 0.1 mg/Kg/dose, based on a 45 Kg sheep), twice-a-day (BID) for three consecutive days, followed by a dose on day 4, 0.5 h prior to antigen challenge. *Ascaris suum* antigen challenge was given at the zero time point.

Compound 17 was administered as an oral solution at 15 mg/Kg/dose, twice-a-day (BID) for three consecutive days, followed by a dose on day 4, 2 h prior to antigen challenge. *Ascaris suum* antigen challenge was given at the zero time point.

FIG. 1 shows that after aerosol administration the early airway response (0-2 h after antigen challenge) was unchanged and that the late airway response (6-8 h after antigen challenge) was completely blocked (n=2 sheep/group).

Figure 2:
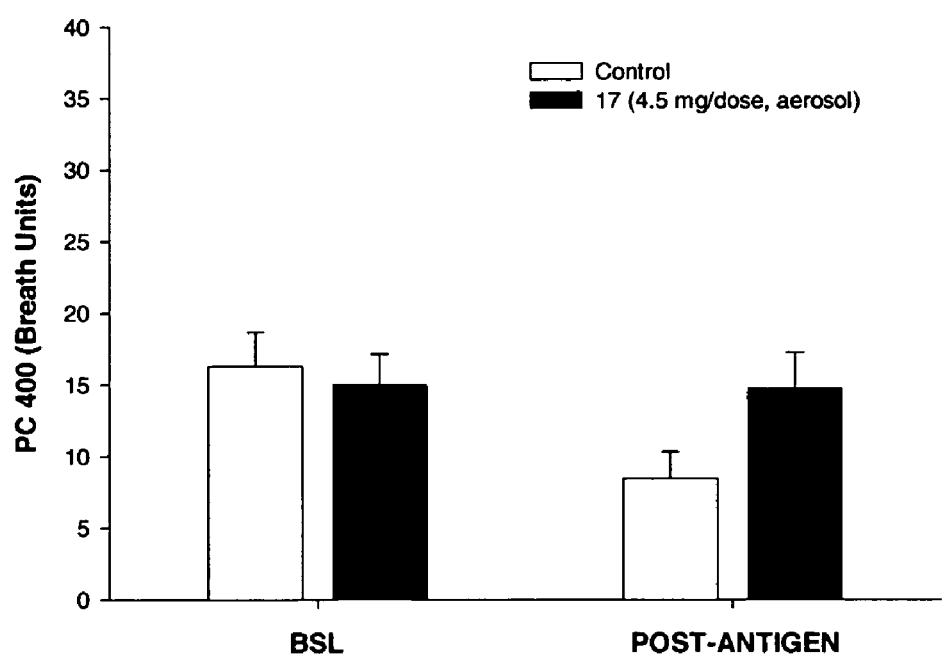

FIG. 2 shows that the delayed airway hyperreactivity measured at 24 h post antigen challenge as measured using carbachol challenge was also completely blocked by compound following aerosol administration.

Figure 3:
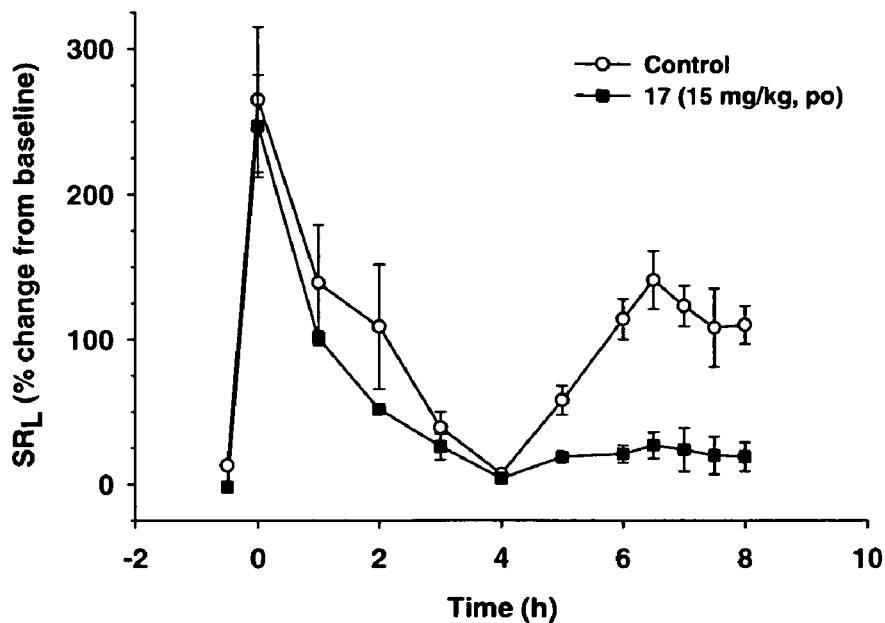

FIG. 3 shows that after oral administration the early airway response (0-2 h after antigen challenge) was unchanged and that the late airway response (6-8 h after antigen challenge) was completely blocked (n=2 sheep/group).

Figure 4:
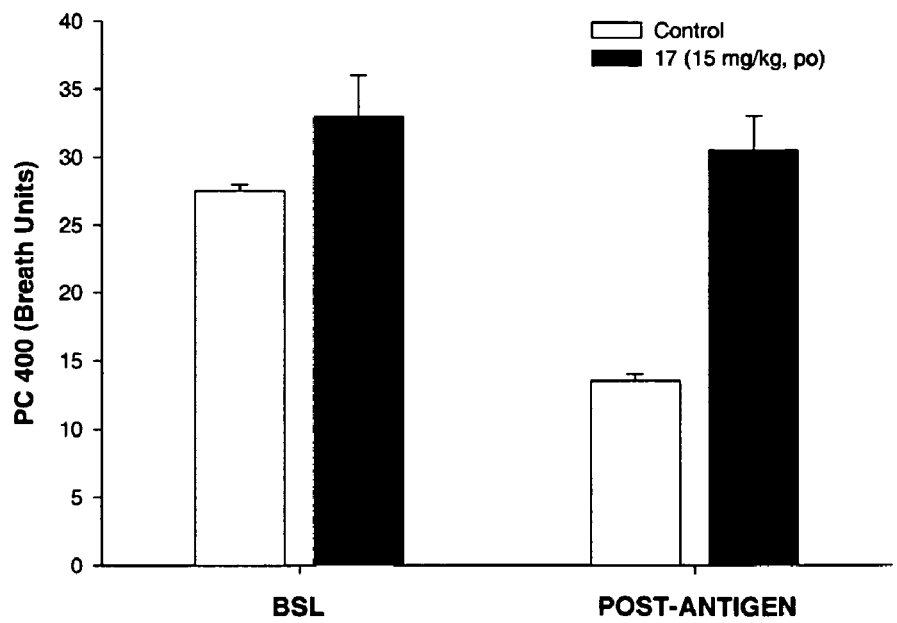

FIG. 4 shows that the delayed airway hyperreactivity measured at 24 h post antigen challenge as measured using carbachol challenge was also completely blocked by compound following oral administration.

Example 3

Pharmacokinetic Assay for Evaluation of Oral Absorption Potential Procedural Overview Male Sprague Dawley rats, weighing 250-300 g, were fasted overnight then dosed by oral gavage at a level of 15 mg/kg with a compound. Compounds were formulated in 20% hydroxy-beta-cyclo dextran.

Blood samples (0.5 mL) were collected into lithium heparinized tubes at 0.5, 1.0 and 2.0 h post dose via orbital sinus puncture. Blood samples were centrifuged at 2000 rpm for ~3 min for cell removal, approximately 200 µL of plasma supernatant was then transferred to a clean vial, frozen then placed on dry ice and delivered to SFBC Analytical Labs, Inc. for analysis.

Plasma samples were prepared as follows. Two hundred microliters of acetonitrile containing 1 µM internal standard was added to 100 µL of plasma to precipitate proteins. Samples were centrifuged at 5000 g for 5 min and supernatant removed for analysis by LC-MS. Two hundred microliters of water was added to adjust sample solvent strength and prevent peak splitting. Calibration standards were prepared by adding appropriate volumes of stock solution directly into plasma and treated identically to collected plasma samples. Calibration standards were prepared in the range of 0.1 to 10 µM for quantitation. LC-MS analysis was performed using MRM (Multiple Reaction Monitoring) detection of characteristic ions for each drug candidate and internal standard.

| Cpd | PK Data (N = 2) C$_{Max}$ (µM) @ 2 h |
|---|---|
| 173 | 0.1 ± 0.02 |
| 174 | 0.56 ± 0.36 |
| 175 | 0.2 ± 0.03 |
| 176 | 0.3 ± 0.04 |
| 177 | 2.0 ± 1.1 |
| 178 | 4.1 ± 0.28 |
| 179 | <0.1 ± 0.0 |
| 180 | <0.1 ± 0.0 |
| 181 | 0.2 ± 0.05 (C$_{max}$ at 30 min) |
| 182 | 11.8 ± 3.26 |
| 183 | 0.1 ± 0.01 |
| 184 | 0.1 ± 0.05 |
| 185 | 2.1 ± 0.23 |
| 186 | 20.1 ± 3.5 |
| 187 | 21.4 ± 11 |
| 188 | 0.1 ± 0.05 |
| 189 | 21.1 ± 2.3 |
| 190 | 2.3 ± 0.55 |
| 191 | 19 (N = 1) |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I)

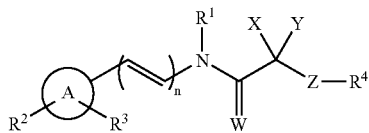

Formula (I)

wherein $R^1$ is selected from the group consisting of hydrogen and $C_{1-4}$alkyl;

is selected from the group consisting of aryl, heteroaryl, benzo fused heterocyclyl, cyclopropyl when n is 0 and one of $R^2$ or $R^3$ is phenyl, and benzo fused cycloalkyl, and ring A is optionally substituted with $R^2$ and $R^3$;

$R^2$ is one to two substituents independently selected from the group consisting of $C_{1-6}$alkyl, $C_{2-6}$alkenyl, $C_{2-6}$alkynyl, methoxy, $C_{2-6}$alkoxy, $C_{1-6}$alkylthio, —$OCF_3$, —$NH_2$, —$NH(C_{1-6})$alkyl, —$N(C_{1-6})$dialkyl, aryl, heteroaryl, aryloxy, heteroaryloxy, halogen, hydroxy, and nitro; furthermore, $R^2$ is optionally oxo when ring A is heteroaryl or benzo fused heterocyclyl; and, wherein any aryl-containing substituent of $R^2$ is optionally substituted with a substituent independently selected from the group consisting of $C_{1-6}$alkyl, $C_{1-6}$alkoxy, $C_{2-6}$ alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, halogen, hydroxy, and nitro;

and, wherein any of the foregoing $C_{1-6}$alkyl or $C_{2-6}$alkoxy containing substituents of $R^2$ are optionally substituted with a substituent independently selected from the group consisting of —$NR^{11}R^{12}$, aryl, heteroaryl, one to three halogens and hydroxy; wherein $R^{11}$ and $R^{12}$ are independently hydrogen; $C_{1-6}$ alkyl optionally substituted with hydroxy, aryl, —$C(=O)C_{1-4}$alkoxy, or —$NR^{15}R^{16}$; or aryl;

$R^{15}$ and $R^{16}$ are substituents independently selected from the group consisting of hydrogen, $C_{1-6}$ alkyl, and aryl, and said $R^{15}$ and $R^{16}$ are optionally taken together with the atoms to which they are attached to form a ring of five to seven members;

$R^3$ is one to three substituents independently selected from the group consisting of $C_{1-6}$alkyl, $C_{2-6}$alkenyl, $C_{2-6}$alkynyl, $C_{1-6}$alkoxy, $C_{1-6}$alkylthio, —$OCF_3$, —$OCH_2(C_{2-6})$alkenyl, —$NH_2$, —$NH(C_{1-6})$alkyl, —$N(C_{1-6})$dialkyl, —$NHC(=O)Cy$, —$N(C_{1-6}$alkyl$)C(=O)Cy$, —$(NC(=O))_2NH_2$, —$C(=O)C_{1-4}$alkoxy, —$C(=O)NR^{17}R^{18}$, —$C(=O)NH$cycloalkyl, —$C(=O)N(C_{1-6}$alkyl)cycloalkyl, —$C(=O)NHCy$, —$C(=O)N(C_{1-6}$alkyl)Cy, —$C(=O)Cy$, —$OC(=O)C_{1-6}$alkyl, —$OC(=O)NR^{19}R^{20}$, —$C(=O)O$aryl, —$C(=O)O$heteroaryl, —$CO_2H$, ureido, halogen, hydroxy, nitro, cyano, aryl, heteroaryl, heteroaryloxy, and aryloxy;

wherein any of the foregoing $C_{1-6}$alkyl or $C_{1-6}$ alkoxy containing substituents of $R^3$ are optionally substituted with one to three substituents independently selected from the group consisting of —$NR^{21}R^{22}$, —$NH$(cycloalkyl), —$N(C_{1-6}$alkyl)(cycloalkyl), —$NHCy$, —$N(C_{1-6}$alkyl$)Cy$, aryl, heteroaryl, hydroxy, halogen, —$C(=O)NR^{23}R^{24}$, —$OC(=O)NR^{25}R^{26}$, —$C(=O)C_{1-4}$alkoxy, and —$C(=O)Cy$;

wherein said $R^{17}$, $R^{18}$, $R^{19}$, $R^{20}$, $R^{21}$, $R^{22}$, $R^{23}$, $R^{24}$, $R^{25}$, $R^{26}$ are substituents independently selected from the group consisting of hydrogen, $C_{1-6}$ alkyl, and aryl, wherein $C_{1-6}$ alkyl is optionally substituted with hydroxy, aryl, —$C(=O)C_{1-4}$alkoxy, $NH_2$, $NH(C_{1-6}$alkyl), or —$N(C_{1-6})$dialkyl; and $R^{17}$ and $R^{18}$, $R^{19}$ and $R^{20}$, $R^{21}$ and $R^{22}$, $R^{23}$ and $R^{24}$, and $R^{25}$ and $R^{26}$ are optionally taken together with the atoms to which they are attached to form a ring of five to seven members;

Cy is a heterocyclyl optionally substituted with a substituent selected from the group consisting of $C_{1-6}$alkyl, $C_{1-6}$alkyl$C(=O)C_{1-6}$alkyl, —$C_{1-6}$alkyl$C(=O)C_{1-6}$alkoxy, $C_{1-6}$alkyl$C(=O)$aryl, —$C(=O)(C_{1-6})$alkyl, —$C(=O)(C_{1-6})$alkoxy, —$C(=O)$aryl, —$SO_2$aryl, aryl, heteroaryl, and heterocyclyl; wherein the aryl portion of any aryl-containing substituent of Cy is optionally substituted with one to three substituents independently selected from the group consisting of $C_{1-6}$alkyl, $C_{1-6}$alkoxy, $C_{1-6}$alkylthio, halogen, hydroxy, $NH_2$, $NH(C_{1-6}$alkyl), and —$N(C_{1-6})$dialkyl; and wherein heterocyclyl is optionally substituted with aryl, one to three halogen atoms, or one to three oxo substituents; and heterocyclyl is optionally spiro-fused to said Cy;

and wherein the $C_{1-6}$alkenyl and $C_{1-6}$alkynyl substituents of $R^3$ are optionally substituted with aryl or —$C(=O)NR^{27}R^{28}$; wherein said $R^{27}$ and $R^{28}$ are independently hydrogen; $C_{1-6}$ alkyl optionally substituted with hydroxy, aryl, —$C(=O)C_{1-4}$alkoxy, $NH_2$, $NH(C_{1-6}$alkyl), or —$N(C_{1-6})$dialkyl; or aryl; and $R^{27}$ and $R^{28}$ are optionally taken together with the atoms to which they are attached to form a ring of five to seven members;

wherein the aryl, heteroaryl, and cycloalkyl substituents of $R^3$ are optionally substituted with one to three substituents independently selected from $R^{14}$;

wherein $R^{14}$ is independently hydrogen, $C_{1-6}$alkyl, $C_{1-6}$alkoxy, $C_{2-6}$alkenyl, $C_{1-6}$alkylthio, —$NH_2$, —$NH(C_{1-6})$alkyl, —$N(C_{1-6})$dialkyl, aryl, heteroaryl, aryloxy, heteroaryloxy, halogen, hydroxy, or nitro;

and any one of the foregoing $C_{1-6}$alkyl- or $C_{1-6}$alkoxy-containing substituents of $R^{14}$ is optionally substituted on a terminal carbon atom with a substituent selected from —$NR^{29}R^{30}$, aryl, heteroaryl, one to three halogen atoms, or hydroxy; wherein $R^{29}$ and $R^{30}$ are independently hydrogen; $C_{1-6}$ alkyl optionally substituted with hydroxy, aryl, —$C(=O)C_{1-4}$alkoxy, $NH_2$, $NH(C_{1-6}$alkyl), or —$N(C_{1-6})$dialkyl; or aryl; and $R^{29}$ and $R^{30}$ are optionally taken together with the atoms to which they are attached to form a ring of five to seven members;

n is 0 or 1;

W is O or S;

X is hydrogen or $C_{1-3}$alkyl;

Y is independently selected from $SO_3H$ and $P(=O)OR^5R^6$;

$R^5$ is selected from the group consisting of hydrogen; $C_{1-6}$alkyl optionally substituted with $NH_2$, —$NH(C_{1-6})$alkyl, —$N(C_{1-6})$dialkyl, 1,3-dioxolan-2-yl, $C_{1-6}$alkylcarbonyloxy, $C_{1-6}$alkoxycarbonyloxy, $C_{1-6}$alkylcarbonylthio, $(C_{1-6})$alkylaminocarbonyl, di$(C_{1-6})$alkylaminocarbonyl, one to three halogens, or hydroxy; and aryl optionally substituted with $C_{1-6}$alkyl, $C_{1-6}$alkoxy, $C_{1-6}$alkylthio, $C_{2-6}$alkenyl, —$NH_2$, —$NH$ $(C_{1-6})$alkyl, $-N(C_{1-6})$dialkyl, aryl, heteroaryl, aryloxy, heteroaryloxy, halogen, hydroxy, or nitro; alternatively, when $R^6$ is $C_{1-8}$alkoxy, $R^5$ and $R^6$ are taken together with the atoms to which they are attached to form a 5-8 membered monocyclic ring; provided that $R^5$ is other than $C_{1-6}$alkyl substituted with di($C_{1-6}$)alkylamino-carbonyl when ring system A is 3,4-difluoro-phenyl, n is 1, $R^6$ is OH, and Z-$R^4$ is 5-chloro-benzothiophen-3-yl; and provided that $R^5$ is other than $C_{1-6}$alkyl substituted with $C_{1-6}$alkylcarbonylthio when ring system A is 3,4-difluoro-phenyl, n is 1, $R^6$ is $CH_3$, and Z-$R^4$ is 5-chloro-benzothiophen-3-yl;

$R^6$ is selected from the group consisting of $C_{1-8}$alkyl, $C_{1-8}$alkoxy, $C_{2-8}$alkenyl, heteroaryl, aryl, and hydroxy; wherein $C_{1-8}$alkyl, $C_{1-8}$alkoxy, and $C_{2-8}$alkenyl are optionally substituted with a substituent selected from the group consisting of $C_{1-6}$alkoxy, aryl, heterocyclyl, heteroaryl, $NH_2$, $-NH(C_{1-6})$alkyl, $-N(C_{1-6})$dialkyl, $C_{1-6}$alkyl-carbonyloxy, $C_{1-6}$alkylcarbonylthio, $C_{1-6}$alkoxycarbonyloxy, $(C_{1-6})$alkylamino-carbonyl, di($C_{1-6}$)alkylaminocarbonyl, one to three halogen atoms, and hydroxy; and when $R^6$ is $C_{1-8}$alkyl, said $C_{1-8}$alkyl is optionally substituted with one to four additional halogen atoms such that one to three halogen atoms are optionally chlorine and one to seven of the halogen atoms are optionally fluorine;

wherein the heteroaryl and aryl substituents of $R^6$ are optionally substituted with a substituent independently selected from the group consisting of $C_{1-6}$alkyl, $C_{1-6}$alkoxy, $C_{2-6}$alkenyl, $C_{1-6}$alkylthio, $-NH_2$, $-NH(C_{1-6})$alkyl, $-N(C_{1-6})$dialkyl, aryl, heteroaryl, aryloxy, heteroaryloxy, halogen, hydroxy, and nitro;

Z is a seven to fifteen membered monocyclic or polycyclic ring system selected from the group consisting aryl, heteroaryl, benzo fused heterocyclyl, or benzo fused cycloalkyl;

$R^4$ is one to three substituents selected from the group consisting of: H, $C_{1-6}$alkyl, $C_{1-6}$alkenyl, $C_{1-6}$alkoxy, $C_{1-6}$alkylthio, aryl($C_{1-6}$)alkyl, aryl($C_{2-6}$)alkenyl, halogen, $-C(=O)Cy$, $-C(=O)NR^{31}R^{32}$, aryl, $-CO_2H$, oxo, and cyano; wherein $C_{1-6}$alkyl, $C_{1-6}$alkenyl and $C_{1-6}$alkoxy are optionally substituted with $-NR^{33}R^{34}$, aryl, heteroaryl, cycloalkyl, one to three halogen atoms, or hydroxy; and aryl and heteroaryl are each optionally substituted with a substituent independently selected from the group consisting of $C_{1-6}$alkyl, $C_{1-6}$alkoxy, $C_{2-6}$ alkenyl, $C_{1-6}$alkylthio, $-NH_2$, $-NH(C_{1-6})$alkyl, $-N(C_{1-6})$dialkyl, aryl, heteroaryl, aryloxy, heteroaryloxy, one to three halogen atoms, hydroxy, and nitro;

wherein said $R^{31}$, $R^{32}$, $R^{33}$, and $R^{34}$ are substituents independently selected from the group consisting of hydrogen, $C_{1-6}$ alkyl, and aryl, wherein alkyl is optionally substituted with hydroxy, aryl, $-C(=O)C_{1-4}$alkoxy, $NH_2$, $NH(C_{1-6}$alkyl), or $-N(C_{1-6})$dialkyl; and $R^{31}$ with $R^{32}$, and $R^{33}$ with $R^{34}$ are optionally taken together with the atoms to which they are attached to form a ring of five to seven members;

and pharmaceutically acceptable salts thereof.

2. The compound of claim 1 wherein $R^1$ is hydrogen.

3. The compound of claim 1 wherein

is independently selected from the group consisting of aryl, heteroaryl, and benzo fused heterocyclyl, optionally substituted with $R^2$ and $R^3$.

4. The compound of claim 1 wherein

is a bicyclic ring system of the formula:

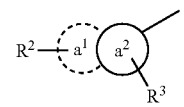

wherein the $a^1$ portion of said $a^1a^2$ is optionally substituted with $R^2$; and the $a^2$ portion is optionally substituted with $R^3$.

5. The compound of claim 4 wherein $a^2$ is aromatic.

6. The compound of claim 1 wherein

is selected from group consisting of naphthyl, benzothiazolyl, benzothiophenyl, quinolinyl, isoquinolinyl, dihydronaphthyl, indanyl, tetralinyl, and benzodioxolyl when n is equal to zero; and A is selected from phenyl, pyridin-2-yl, and pyridin-3-yl when n is equal to one.

7. The compound of claim 1 wherein

is selected from naphthyl and benzothiazolyl when n is equal to zero; and A is selected from phenyl, pyridin-2-yl, and pyridin-3-yl when n is equal to one.

8. The compound of claim 1 wherein $R^2$ is one to three substituents independently selected from the group consisting of $C_{1-6}$alkyl, methoxy, $C_{2-6}$alkoxy, $-NH_2$, $-NH(C_{1-6}$ alkyl), $-N(C_{1-6})$dialkyl, aryl, heteroaryl, halogen, hydroxy, and nitro; wherein $C_{1-6}$alkyl and $C_{2-6}$alkoxy are optionally substituted with a substituent selected from the group consisting of $-NR^{11}R^{12}$, aryl, heteroaryl, one to three halogens, and hydroxy.

9. The compound of claim 1 wherein $R^2$ is a substituent independently selected from the group consisting of $C_{1-4}$alkyl, methoxy, $C_{2-4}$alkoxy, hydroxy, halogen, and $-NH_2$.

10. The compound of claim 1 wherein $R^2$ is $C_{1-4}$alkyl, halogen, or $-NH_2$.

11. The compound of claim 1 wherein $R^3$ is one to three substituents independently selected from the group consisting of $C_{1-6}$alkyl, $C_{2-6}$alkenyl, $C_{1-6}$alkoxy, —OCH$_2$($C_{2-6}$)alkenyl, NH$_2$, —NH($C_{1-6}$alkyl), —N($C_{1-6}$)dialkyl, —NHC(=O)Cy, —N($C_{1-6}$alkyl)C(=O)Cy, —C(=O)$C_{1-4}$alkoxy, —C(=O)NR$^{17}$R$^{18}$, —C(=O)NHcycloalkyl, —C(=O)N($C_{1-6}$alkyl)cycloalkyl, —C(=O)NHCy, —C(=O)N($C_{1-6}$alkyl)Cy, —C(=O)Cy, —OC(=O)NR$^{19}$R$^{20}$, halogen, hydroxy, nitro, cyano, aryl, and aryloxy; wherein alkyl and alkoxy are optionally substituted with one to three substituents independently selected from the group consisting of —NR$^{21}$R$^{22}$, —NHcycloalkyl, —N($C_{1-6}$alkyl)cycloalkyl, —NHCy, —N($C_{1-6}$alkyl)Cy, aryl, heteroaryl, halogen, —C(=O)NR$^{23}$R$^{24}$, —OC(=O)NR$^{25}$R$^{26}$, —C(=O)($C_{1-4}$)alkoxy, and —C(=O)Cy; wherein alkenyl is optionally substituted on a terminal carbon with aryl and —C(=)NR$^{27}$R$^{28}$; and, wherein aryl and cycloalkyl are optionally substituted with one to three substituents independently selected from R$^{14}$.

12. The compound of claim 1 wherein R$^3$ is one to three substituents independently selected from the group consisting of $C_{1-6}$alkyl, $C_{1-6}$alkoxy, —NR$^{19}$R$^{20}$, —NHC(=O)Cy, —C(=O)NR$^{17}$R$^{18}$, —C(=O)NHcycloalkyl, —C(=O)N($C_{1-6}$alkyl)cycloalkyl, halogen, and aryl; wherein alkyl and alkoxy are optionally substituted on a terminal carbon atom with one to three fluorine atoms, —NH$_2$, —NHCy, or —N($C_{1-4}$alkyl)Cy; and wherein aryl and cycloalkyl are optionally substituted with a group independently selected from R$^{14}$.

13. The compound of claim 1 wherein R$^3$ is one to two substituents independently selected from trifluoromethyl; $C_{1-4}$alkoxy optionally substituted with one to three fluorine atoms; —NH$_2$; —NHC(=O)Cy; or halogen.

14. The compound of claim 1 wherein R$^3$ is NHC(=O)Cy, and Cy is piperadinyl; wherein said piperadinyl is substituted with a substituent selected from the group consisting of $C_{1-4}$alkyl, $C_{1-4}$alkylC(=O)$C_{1-4}$alkyl, —$C_{1-4}$alkylC(=O)$C_{1-4}$alkoxy, $C_{1-4}$alkylC(=O)aryl, —C(=O)($C_{1-4}$)alkyl, —C(=O)($C_{1-4}$)alkoxy, —C(=O)aryl, —SO$_2$aryl, aryl, heteroaryl, and heterocyclyl; wherein aryl and the aryl portion of the $C_{1-4}$alkylC(=O)aryl, —C(=O)aryl and —SO$_2$aryl is optionally substituted with one to three substituents independently selected from the group consisting of $C_{1-4}$alkyl, $C_{1-4}$alkoxy, halogen, hydroxy, NH$_2$, NH($C_{1-6}$alkyl), or —N($C_{1-4}$dialkyl; and wherein heterocyclyl is optionally substituted with aryl, one to three halogen atoms, or one oxo substituents.

15. The compound of claim 1 wherein R$^3$ is trifluoromethyl, one to two fluorine atoms, chloro, methoxy, trifluoromethoxy, or NH$_2$; furthermore, when A is naphthyl and n is equal to zero, R$^3$ is (4-{[1-(naphthalen-2-yl-carbonyl)-piperadin-4-yl-carbonyl]-amino}naphthalen-2-yl.

16. The compound of claim 1 wherein X is $C_{1-3}$alkyl.

17. The compound of claim 1 wherein X is hydrogen.

18. The compound of claim 1 wherein Y is P(=O)OR$^5$R$^6$.

19. The compound of claim 1 wherein R$^5$ is selected from the group consisting of hydrogen; $C_{1-3}$alkyl optionally substituted with NH$_2$, —NH($C_{1-6}$)alkyl, —N($C_{1-6}$)dialkyl, $C_{1-6}$alkylcarbonyloxy, $C_{1-6}$alkoxycarbonyloxy, $C_{1-6}$alkylcarbonylthio, ($C_{1-6}$)alkylaminocarbonyl, di($C_{1-6}$)alkylaminocarbonyl, one to three halogens, or hydroxy; and aryl optionally substituted with $C_{1-6}$alkyl, $C_{1-6}$alkoxy, $C_{1-6}$alkylthio, $C_{2-6}$ alkenyl, —NH$_2$, —NH($C_{1-6}$)alkyl, —N($C_{1-6}$)dialkyl, aryl, heteroaryl, aryloxy, heteroaryloxy, halogen, hydroxy, or nitro; alternatively, when R$^6$ is $C_{1-8}$alkoxy, R$^5$ and R$^6$ are taken together with the atoms to which they are attached to form a 5-8 membered monocyclic ring; and provided that R$^5$ is other than $C_{1-3}$alkyl substituted with di($C_{1-6}$)alkylaminocarbonyl when ring system A is 3,4-difluoro-phenyl, n is 1, R$^6$ is OH, and Z-R$^4$ is 5-chloro-benzothiophen-3-yl; and provided that R$^5$ is other than $C_{1-3}$alkyl substituted with $C_{1-6}$alkylcarbonylthio when ring system A is 3,4-difluoro-phenyl, n is 1, R$^6$ is CH$_3$, and Z-R$^4$ is 5-chloro-benzothiophen-3-yl.

20. The compound of claim 1 wherein R$^5$ is selected from the group consisting of hydrogen, $C_{1-3}$alkyl optionally substituted with $C_{1-6}$alkylcarbonyloxy, $C_{1-6}$alkoxycarbonyloxy, $C_{1-6}$alkylcarbonylthio, ($C_{1-6}$)alkylaminocarbonyl, di($C_{1-6}$)alkylaminocarbonyl, one to three halogens, or hydroxyl; and aryl; alternatively, when R$^6$ is $C_{1-8}$alkoxy, R$^5$ and R$^6$ are taken together with the atoms to which they are attached to form a 6-7 membered monocyclic ring; and provided that when R$^5$ is $C_{1-3}$alkyl substituted with either di($C_{1-6}$)alkylaminocarbonyl or $C_{1-6}$alkylcarbonylthio, ring system A is other than 3,4-difluoro-phenyl when n is 1 and Z-R$^4$5-chloro-benzothiophen-3-yl.

21. The compound of claim 1 wherein R$^5$ is hydrogen or $C_{1-3}$alkyl optionally substituted with $C_{1-6}$alkylcarbonyloxy, $C_{1-6}$alkoxycarbonyloxy, $C_{1-6}$alkylcarbonylthio, ($C_{1-6}$)alkylaminocarbonyl, or di($C_{1-6}$alkylaminocarbonyl; and alternatively, when R$^6$ is $C_{1-8}$alkoxy, R$^5$ and R$^6$ are taken together with the atoms to which they are attached to form a 6-membered monocyclic ring; and provided that R$^5$ is other than $C_{1-3}$alkyl substituted with di($C_{1-6}$)alkylaminocarbonyl when ring system A is 3,4-difluoro-phenyl, n is 1, R$^6$ is OH, and Z-R$^4$ is 5-chloro-benzothiophen-3-yl; and provided that R$^5$ is other than $C_{1-3}$alkyl substituted with $C_{1-6}$alkylcarbonylthio when ring system A is 3,4-difluoro-phenyl, n is 1, R$^6$ is CH$_3$, and Z-R$^4$ is 5-chloro-benzothiophen-3-yl.

22. The compound of claim 1 wherein R$^6$ is selected from the group consisting of $C_{1-8}$alkyl, $C_{1-8}$alkoxy, $C_{2-8}$alkenyl, heteroaryl, aryl, and hydroxy; wherein alkyl, alkoxy, and alkenyl are optionally substituted on a terminal carbon atom with a substituent independently selected from the group consisting of $C_{1-4}$alkoxy, aryl, heteroaryl, heterocyclyl, $C_{1-6}$alkylcarbonyloxy, $C_{1-6}$alkylcarbonylthio, $C_{1-6}$alkoxycarbonyloxy, ($C_{1-6}$)alkylaminocarbonyl, di($C_{1-6}$)alkylaminocarbonyl, and hydroxy; and wherein heteroaryl and aryl are optionally substituted with one to three substituents independently selected from the group consisting of aryl, hydroxy, $C_{1-6}$alkoxy, and halogen.

23. The compound of claim 1 wherein R$^6$ is selected from the group consisting of $C_{1-6}$alkyl, $C_{1-8}$alkoxy, heteroaryl, aryl, and hydroxy; wherein alkyl and is optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen.

24. The compound of claim 1 wherein R$^6$ is selected from the group consisting of methyl, ethyl, methoxypropyl, phenethyl, benzo[1,3]dioxol-5-yl-propyl, hydroxy, and $C_{1-3}$alkoxy optionally substituted with $C_{1-6}$alkylcarbonyloxy, and di($C_{1-6}$)alkylaminocarbonyl.

25. The compound of claim 1 wherein Z is a bicyclic aryl or bicyclic heteroaryl; wherein aryl and heteroaryl are optionally substituted with the group R$^4$; provided that when Y is CO$_2$H, A and Z must both be a bicycle.

26. The compound of claim 1 wherein Z is independently selected from the group consisting of indolyl, benzothiophenyl, naphthalenyl, quinolinyl, isoquinolinyl and benzothiazolone.

27. The compound of claim 1 wherein Z is indolyl, benzothiophenyl, or naphthalenyl.

28. The compound of claim 1 wherein $R^4$ is one to three substituents selected from the group consisting of $C_{1-6}$alkyl, $C_{1-6}$alkenyl, $C_{1-6}$alkoxy, aryl($C_{2-6}$)alkenyl, halogen, —C(=O)Cy, —C(=O)NR$^{31}$R$^{32}$, aryl, —CO$_2$H, oxo, and cyano; wherein the alkyl and alkoxy are optionally substituted with a substituent independently selected from the group consisting of —NR$^{33}$R$^{34}$, aryl, one to three halogen atoms, and hydroxy; wherein the aryl is optionally substituted with a substituent independently selected from the group consisting of hydrogen, $C_{1-6}$alkyl, $C_{1-6}$alkoxy, aryl, halogen, hydroxy, and nitro.

29. The compound of claim 1 wherein $R^4$ is one to two substituents selected from the group consisting of fluorine, chlorine, bromine, methyl, phenyl($C_{2-6}$)alkenyl, and —C(=O)(2-(4-phenyl-piperidin-1-carbonyl)).

30. A compound of Formula (Ia)

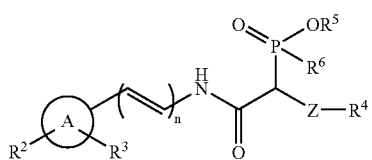

(Ia)

wherein n is 0 or 1;

is independently selected from the group consisting of aryl, heteroaryl, and benzo fused heterocyclyl, optionally substituted with $R^2$ and $R^3$;

$R^2$ is one to three substituents independently selected from the group consisting of $C_{1-4}$alkyl, methoxy, $C_{2-6}$alkoxy, NH$_2$, NH($C_{1-6}$alkyl), —N($C_{1-6}$)dialkyl, aryl, heteroaryl, halogen, hydroxy, and nitro; wherein $C_{1-6}$alkyl and $C_{2-6}$alkoxy are optionally substituted with a substituent selected from the group consisting of —NR$^{11}$R$^{12}$, aryl, heteroaryl, one to three halogens and hydroxyl;

wherein $C_{1-4}$alkyl and $C_{2-6}$ alkoxy substituents of $R^2$ are optionally substituted with a substituent independently selected from the group consisting of —NR$^{11}$R$^{12}$, aryl, heteroaryl, one to three halogens and hydroxy; wherein $R^{11}$ and $R^{12}$ are substituents independently selected from the group consisting of hydrogen, $C_{1-6}$ alkyl, and aryl;

wherein $C_{1-6}$alkyl substituent of $R^{11}$ or $R^{12}$ is optionally substituted with substituent selected from the group consisting of hydroxy, aryl, —C(=O)$C_{1-4}$alkoxy, and —NR$^{15}$R$^{16}$;

wherein said $R^{15}$ and $R^{16}$ are substituents independently selected from the group consisting of hydrogen, $C_{1-6}$ alkyl, and aryl, and said $R^{15}$ and $R^{16}$ are optionally taken together with the atoms to which they are attached to form a ring of five to seven members;

$R^3$ is one to three substituents independently selected from the group consisting of $C_{1-6}$alkyl, $C_{2-6}$alkenyl, $C_{1-6}$alkoxy, —OCH$_2$($C_{2-6}$)alkenyl, NH$_2$, —NH($C_{1-6}$ alkyl), —N($C_{1-6}$) dialkyl, —NHC(=O)Cy, —N($C_{1-6}$ alkyl)C(=O)Cy, —C(=O)$C_{1-4}$alkoxy, —C(=O) NR$^{17}$R$^{18}$, —C(=O)NHcycloalkyl, —C(=O)N($C_{1-6}$ alkyl)cycloalkyl, —C(=O)NHCy, —C(=O)N ($C_{1-6}$alkyl)Cy, —C(=O)Cy, —OC(=O)NR$^{19}$R$^{20}$, halogen, hydroxy, nitro, cyano, aryl, and aryloxy; wherein alkyl and alkoxy are optionally substituted with one to three substituents independently selected from the group consisting of —NR$^{21}$R$^{22}$, —NHcycloalkyl, —N($C_{1-6}$alkyl)cycloalkyl, —NHCy, —N($C_{1-6}$alkyl)Cy, aryl, heteroaryl, halogen, —C(=O)NR$^{23}$R$^{24}$, —OC (=O)NR$^{25}$R$^{26}$, —C(=O)($C_{1-4}$)alkoxy, and —C(=O) Cy; wherein alkenyl is optionally substituted on a terminal carbon with aryl and —C(=O)NR$^{27}$R$^{28}$; and, wherein aryl and cycloalkyl are optionally substituted with one to three substituents independently selected from R$^{14}$;

Cy is a heterocyclyl optionally substituted with a substituent selected from the group consisting of $C_{1-6}$ alkyl, $C_{1-6}$alkylC(=O)$C_{1-6}$alkyl, —$C_{1-6}$alkylC(=O) $C_{1-6}$alkoxy, $C_{1-6}$alkylC(=O)aryl, —C(=O)($C_{1-6}$) alkyl, —C(=O)($C_{1-6}$)alkoxy, —C(=O)aryl, -SO$_2$aryl, aryl, heteroaryl, and heterocyclyl; wherein aryl and the aryl portion of the $C_{1-6}$alkylC(=O)aryl, —C(=O)aryl and —SO$_2$aryl are optionally substituted with one to three substituents independently selected from the group consisting of $C_{1-6}$alkyl, $C_{1-6}$alkoxy, halogen, hydroxy, NH$_2$, NH($C_{1-6}$alkyl), or —N($C_{1-6}$)dialkyl; and wherein heterocyclyl is optionally substituted with aryl, one to three halogen atoms, or one to three oxo substituents; and, wherein heterocyclyl is optionally spiro-fused to said Cy;

$R^5$ is selected from the group consisting of hydrogen; $C_{1-3}$alkyl optionally substituted with NH$_2$, —NH($C_{1-6}$) alkyl, —N($C_{1-6}$)dialkyl, $C_{1-6}$alkylcarbonyloxy, $C_{1-6}$alkoxycarbonyloxy, $C_{1-6}$alkylcarbonylthio, ($C_{1-6}$) alkylaminocarbonyl, di($C_{1-6}$)alkylaminocarbonyl, one to three halogens, or hydroxy; and aryl optionally substituted with $C_{1-6}$alkyl, $C_{1-6}$alkoxy, $C_{1-6}$alkylthio, $C_{2-6}$ alkenyl, —NH$_2$, —NH($C_{1-6}$)alkyl, —N($C_{1-6}$)dialkyl, aryl, heteroaryl, aryloxy, heteroaryloxy, halogen, hydroxy, or nitro; alternatively, when $R^6$ $C_{1-8}$alkoxy are $C_{1-8}$alkoxy, $R^5$ and $R^6$ are taken together with the atoms to which they are attached to form a 5-8 membered monocyclic ring; and provided that $R^5$ is other than $C_{1-3}$alkyl substituted with di($C_{1-6}$)alkylamino-carbonyl when ring system A is 3,4-difluoro-phenyl, n is 1, $R^6$ is OH, and Z-$R^4$ is 5-chloro-benzothiophen-3-yl; and provided that $R^5$ is other than $C_{1-3}$alkyl substituted with $C_{1-6}$alkylcarbonylthio when ring system A is 3,4-difluoro-phenyl, n is 1, $R^6$ is CH$_3$, and Z-$R^4$ is 5-chloro-benzothiophen-3-yl;

$R^6$ is selected from the group consisting of $C_{1-6}$alkyl, $C_{1-8}$alkoxy, heteroaryl, aryl, and hydroxy; wherein alkyl and $C_{1-8}$alkoxy are optionally substituted on a terminal carbon atom with a substituent selected from $C_{1-3}$alkoxy, aryl, or hydroxy; and alkoxy is optionally substituted on a terminal carbon with a substituent independently selected from the group consisting of $C_{1-6}$alkylcarbonyloxy, and di($C_{1-6}$)alkylaminocarbonyl; and wherein heteroaryl and aryl are optionally substituted with one to three substituents independently selected from the group consisting of aryl, hydroxy, $C_{1-6}$alkoxy, and halogen;

Z is a bicyclic aryl or bicyclic heteroaryl;

$R^4$ is one to three substituents selected from the group consisting of H, $C_{1-6}$alkyl, $C_{1-6}$alkenyl, $C_{1-6}$alkoxy, aryl($C_{2-6}$)alkenyl, halogen, —C(=O)Cy, —C(=O) NR$^{31}$R$^{32}$, aryl, —CO$_2$H, oxo, and cyano; wherein the alkyl and alkoxy are optionally substituted with a substituent independently selected from the group consisting of —NR$^{33}$R$^{34}$, aryl, one to three halogen atoms, and hydroxy; wherein the aryl is optionally substitututed with a substituent independently selected from the group consisting of hydrogen, C$_{1-6}$alkyl, C$_{1-6}$alkoxy, aryl, halogen, hydroxy, and nitro;

wherein said R$^{31}$, R$^{32}$, R$^{33}$, and R$^{34}$ are substituents independently selected from the group consisting of hydrogen, C$_{1-6}$ alkyl, and aryl, wherein alkyl is optionally substituted with hydroxy, aryl, —C(=O)C$_{1-4}$alkoxy, NH$_2$, NH(C$_{1-6}$alkyl), or —N(C$_{1-6}$) dialkyl; and R$^{31}$ with R$^{32}$, and R$^{33}$ with R$^{34}$ are optionally taken together with the atoms to which they are attached to form a ring of five to seven members;

and pharmaceutically acceptable salts thereof.

31. The compound of claim 30 wherein

is selected from group consisting of naphthyl, benzothiazolyl, benzothiophenyl, quinolinyl, isoquinolinyl, dihydronaphthyl, indanyl, tetralinyl and benzodioxolyl when n is equal to zero; and A is selected from phenyl, pyridin-2-yl, or pyridin-3-yl when n is equal to one.

32. The compound of claim 30 wherein

is selected from phenyl, pyridin-2-yl, or pyridin-3-yl when n is equal to one.

33. The compound of claim 32 wherein R$^2$ is a substituent independently selected from the group consisting of C$_{1-4}$alkyl, methoxy, C$_{2-4}$alkoxy, hydroxy, halogen, and —NH$_2$.

34. The compound of claim 33 wherein R$^3$ is one to three substituents independently selected from the group consisting of C$_{1-6}$alkyl, C$_{1-6}$alkoxy, —NR$^{19}$R$^{20}$, —NHC(=O)Cy, —C(=O)NR$^{17}$R$^{18}$, —C(=O)NHcycloalkyl, —C(=O)N(C$_{1-6}$alkyl)cycloalkyl, halogen, and aryl; wherein alkyl and alkoxy are optionally substituted on a terminal carbon atom with one to three fluorine atoms, —NH$_2$, —NHCy, or —N(C$_{1-4}$alkyl)Cy; and wherein aryl and cycloalkyl are optionally substituted with a group independently selected from R$^{14}$.

35. The compound of claim 34 wherein R$^5$ is hydrogen or C$_{1-3}$alkyl optionally substituted with C$_{1-6}$alkylcarbonyloxy, C$_{1-6}$alkoxycarbonyloxy, C$_{1-6}$alkylcarbonylthio, (C$_{1-6}$) alkylaminocarbonyl, or di(C$_{1-6}$)alkylaminocarbonyl; and alternatively, when R$^6$ is C$_{1-8}$alkoxy, R$^5$ and R$^6$ are taken together with the atoms to which they are attached to form a 6-membered monocyclic ring; and provided that R$^5$ is other than C$_{1-3}$alkyl substituted with di(C$_{1-6}$)alkylamino-carbonyl when ring system A is 3,4-difluoro-phenyl, n is 1, R$^6$ is OH, and Z-R$^4$ is 5-chloro-benzothiophen-3-yl; and provided that R$^5$ is other than C$_{1-3}$alkyl substituted with C$_{1-6}$alkylcarbonylthio when ring system A is 3,4-difluoro-phenyl, n is 1, R$^6$ is CH$_3$, and Z-R$^4$ is 5-chloro-benzothiophen-3-yl.

36. The compound of claim 35 wherein R$^6$ is selected from the group consisting of methyl, ethyl, methoxypropyl, phenethyl, benzo[1,3]dioxol-5-yl-propyl, hydroxy, and C$_{1-3}$alkoxy optionally substituted with C$_{1-6}$alkylcarbonyloxy, and di(C$_{1-6}$)alkylamino-carbonyl.

37. The compound of claim 36 wherein Z is independently selected from the group consisting of indolyl, benzothiophenyl, naphthalenyl, quinolinyl, isoquinolinyl and benzothiazolonyl.

38. The compound of claim 37 wherein R$^4$ is one to three substituents selected from the group consisting of C$_{1-6}$alkyl, C$_{1-6}$alkenyl, aryl(C$_{2-6}$)alkenyl, halogen, and —C(=O)Cy; wherein aryl is optionally substituted with a substituent selected from halogen or C$_{1-4}$alkoxy.

39. The compound of claim 30 wherein

is a ring system of the formula:

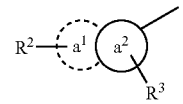

wherein the a$^1$ portion of said a$^1$a$^2$ is optionally substituted with R$^2$; and the a$^2$ portion is optionally substituted with R$^3$ and n is 0.

40. The compound of claim 39 wherein a$^2$ portion is aromatic and

is selected from group consisting of naphthyl, benzothiazolyl, benzothiophenyl, quinolinyl, isoquinolinyl, dihydronaphthyl, indanyl, tetralinyl and benzodioxolyl.

41. The compound of claim 40 wherein R$^2$ is a substituent independently selected from the group consisting of C$_{1-4}$alkyl, methoxy, C$_{2-4}$alkoxy, hydroxy, halogen, and —NH$_2$.

42. The compound of claim 41 wherein R$^3$ is one to three substituents independently selected from the group consisting of C$_{1-6}$alkyl, C$_{1-6}$alkoxy, —NR$^{19}$R$^{20}$, —NHC(=O)Cy, —C(=O)NR$^{17}$R$^{18}$, —C(=O)NHcycloalkyl, —C(=O)N(C$_{1-6}$alkyl)cycloalkyl, halogen, and aryl; wherein alkyl and alkoxy are optionally substituted on a terminal carbon atom with one to three fluorine atoms, —NH$_2$, —NHCy, or —N(C$_{1-4}$alkyl)Cy; and wherein aryl and cycloalkyl are optionally substituted with a group independently selected from R$^{14}$.

43. The compound of claim 42 wherein R$^5$ is hydrogen or C$_{1-3}$alkyl optionally substituted with C$_{1-6}$alkylcarbonyloxy, C$_{1-6}$alkoxycarbonyloxy, C$_{1-6}$alkylcarbonylthio, (C$_{1-6}$) alkylaminocarbonyl, or di(C$_{1-6}$)alkylaminocarbonyl; and alternatively, when R$^6$ is C$_{1-8}$alkoxy, R$^5$ and R$^6$ are taken together with the atoms to which they are attached to form a 6-membered monocyclic ring; provided that $R^5$ is other than $C_{1-3}$alkyl substituted with di($C_{1-6}$)alkylaminocarbonyl when ring system A is 3,4-difluoro-phenyl, n is 1, $R^6$ is OH, and Z-$R^4$ is 5-chloro-benzothiophen-3-yl; and provided that $R^5$ is other than $C_{1-3}$alkyl substituted with $C_{1-6}$alkylcarbonylthio when ring system A is 3,4-difluoro-phenyl, n is 1, $R^6$ is $CH_3$, and Z-$R^4$ is 5-chloro-benzothiophen-3-yl.

44. The compound of claim 43 wherein $R^6$ is selected from the group consisting of methyl, ethyl, methoxypropyl, phenethyl, benzo[1,3]dioxol-5-yl-propyl, hydroxy, and $C_{1-3}$alkoxy optionally substituted with $C_{1-6}$alkylcarbonyloxy, and di($C_{1-6}$)alkylamino-carbonyl.

45. The compound of claim 44 wherein Z is independently selected from the group consisting of indolyl, benzothiophenyl, naphthalenyl, quinolinyl, isoquinolinyl, and benzothiazolone.

46. The compound of claim 45 wherein $R^4$ is one to three substituents selected from the group consisting of $C_{1-6}$alkyl, $C_{1-6}$alkenyl, aryl($C_{2-6}$)alkenyl, halogen, and —C(=O)Cy; wherein aryl is optionally substituted with a substituent selected from halogen or $C_{1-4}$alkoxy.

47. The compound of claim 30 wherein $R^1$, ring A, $R^2R^3$, $R^5$, $R^6$, Z, and $R^4$ are dependently selected from the group consisting of

| $R^2 \quad R^3$ | $R^5$ | $R^6$ | n | W | Z—$R^4$ |
|---|---|---|---|---|---|
| naphthalen-2-yl | H | $CH_3$ | 0 | O | 5-Cl—N-methyl-indol-3-yl |
| 3,4-difluoro-phenyl | H | OH | 1 | O | 5-Cl-benzothiophen-3-yl |
| naphthalen-2-yl | H | OH | 0 | O | 5-Cl—N-methyl-indol-3-yl |
| 4-fluoro-phenyl | H | OH | 1 | O | 5-Cl—N-methyl-indol-3-yl |
| naphthalen-2-yl | H | OH | 0 | O | 5-Me-benzothiophen-2-yl |
| 3-fluoro-phenyl | H | $CH_3$ | 1 | O | 5-Cl—N-methyl-indol-3-yl |
| 3,4-difluoro-phenyl | H | $CH_3$ | 1 | O | 5-Cl—N-methyl-indol-3-yl |
| 4-{[1-(naphthalen-2-ylcarbonyl)-piperadin-4-ylcarbonyl]-amino}naphthalen-2-yl | H | OH | 0 | O | naphthalen-1-yl |
| naphthalen-2-yl | H | OH | 0 | O | 5-Cl-benzothiophen-3-yl |
| naphthalen-2-yl | H | OH | 0 | O | 5-F-benzothiophen-3-yl |
| naphthalen-2-yl | H | OH | 0 | O | 5-F—N-methyl-indol-3-yl |
| 4-amino-phenyl | H | OH | 1 | O | 5-Cl-benzothiophen-3-yl |
| naphthalen-2-yl | H | OH | 0 | O | 5-Br—N-methyl-indol-3-yl |
| Phenyl | H | $CH_3$ | 1 | O | 5-Cl-benzothiophen-3-yl |
| 3-fluoro-phenyl | H | $CH_3$ | 1 | O | 5-Cl-benzothiophen-3-yl |
| 3,4-trifluoro-phenyl | H | $CH_3$ | 1 | O | 5-Cl-benzothiophen-3-yl |
| 3,4-difluoro-phenyl | H | $CH_3$ | 1 | O | 5-Cl-benzothiophen-3-yl |
| phenyl | H | OH | 1 | O | 5-Cl-benzothiophen-2-yl |
| 4-fluoro-phenyl | H | OH | 1 | O | 5-Cl-benzothiophen-3-yl |
| naphthalen-2-yl | H | $CH_3$ | 0 | O | 5-Cl-benzothiophen-3-yl |
| 2-fluoro-phenyl | H | $CH_3$ | 1 | O | 5-Cl-benzothiophen-3-yl |
| naphthalen-2-yl | H | OH | 0 | O | N-methyl-indol-3-yl |
| naphthalen-2-yl | H | OH | 0 | O | 5-Br-benzothiophen-3-yl |
| 4-fluoro-phenyl | H | $CH_3$ | 1 | O | 5-Cl-benzothiophen-3-yl |
| pyridin-3-yl | H | OH | 1 | O | 5-Cl-benzothiophen-3-yl |
| naphthalen-2-yl | H | OH | 0 | O | benzothiophen-3-yl |
| naphthalen-2-yl | H | OH | 0 | O | N-(3-phenyl-allyl)-indol-3-yl |
| naphthalen-2-yl | H | $CH_2CH_3$ | 0 | O | 5-Cl-benzothiophen-3-yl |
| 3,4-difluoro-phenyl | H | $CH_2CH_3$ | 1 | O | 5-Cl-benzothiophen-3-yl |
| benzothiazol-6-yl | H | OH | 0 | O | 5-Cl-benzothiophen-3-yl |
| naphthalen-2-yl | H | OH | 0 | O | naphthalen-1-yl |
| naphthalen-2-yl | H | $CH_3$ | 0 | O | 2-(4-phenyl-piperidin-1-ylcarbonyl)-benzothiophen-3-yl |
| naphthalen-2-yl | H | $CH_3$ | 0 | O | naphthalen-1-yl |
| naphthalen-2-yl | H | 3-methoxy-propyl | 0 | O | 5-Cl-benzothiophen-3-yl |
| naphthalen-2-yl | H | $CH_3$ | 0 | O | 2-(4-(4-methoxyphenyl)-pipendin-1-ylcarbonyl) benzothiophen-3-yl |
| naphthalen-2-yl | H | Phenethyl | 0 | O | 5-Cl-benzothiophen-3-yl |
| phenyl | H | OH | 1 | O | naphthalen-1-yl |
| 4-methoxy-phenyl | H | OH | 1 | O | 5-Cl-benzothiophen-3-yl |
| naphthalen-2-yl | H | 3-(Benzo[1,3]dioxol-5-yl)-propyl | 0 | O | 5-Cl-benzothiophen-3-yl |
| naphthalen-2-yl | H | 3-(naphthylen-1yl)propyl | 0 | O | 5-Cl-benzothiophen-3-yl |

-continued

| $R^2$ $R^3$ | $R^5$ | $R^6$ | n | W | Z—$R^4$ |
|---|---|---|---|---|---|
| naphthalen-2-yl | H | CH₃ | 0 | O | 2-(4-Benzyloxycarbonyl)-piperazin-1-ylcarbonyl))-benzothiophen-3-yl |
| 4-methyl-phenyl | H | OH | 1 | O | 5-Cl-benzothiophen-2-yl |
| naphthalen-2-yl | H | 3-(4-hydroxy phenyl) propyl | 0 | O | 5-Cl-benzothiophen-3-yl |
| 3-((N-Benzoyl-piperidin-4-ylamino)-methyl)-naphthalen-2-yl | H | OH | 0 | O | naphthalen-1-yl |
| naphthalen-2-yl | H | OH | 0 | S | 5-Cl-benzothiophen-3-yl |
| 3-[(1-phenyl)-cyclohex-1-enyl-N-methyl aminocarbonyl]-naphthalen-2-yl | H | OH | 0 | O | naphthalen-1-yl |
| naphthalen-2-yl | H | CH₃ | 0 | O | 2-((4-F-phenyl)-piperidin-1-ylcarbonyl)-benzothiophen-3-yl |
| naphthalen-2-yl | H | (3-phenyl) propyl | 0 | O | 5-Cl-benzothiophen-3-yl |
| 3,4-dimethoxy-phenyl | H | OH | 1 | O | 5-Cl-benzothiophen-3-yl |
| naphthalen-2-yl | H | (4-phenyl) butyl | 0 | O | 5-Cl-benzothiophen-3-yl |
| naphthalen-2-yl | H | OH | 0 | O | 6-Cl—N-methyl-indol-3-yl |
| naphthalen-2-yl | H | 3-(4-methoxy phenyl) propyl | 0 | O | 5-Cl-benzothiophen-3-yl |
| 3-[4-((3-Phenethyl)-pyrrolidin-1-ylcarbonyl)]-naphthalen-2-yl | H | OH | 0 | O | naphthalen-1-yl |
| benzothiophen-5-yl | H | OH | 0 | O | 5-Cl-benzothiophen-3-yl |
| naphthalen-2-yl | H | OH | 0 | O | 5-carboxy-N—Me-indol-3-yl- |
| quinolin-3-yl | H | OH | 0 | O | naphthalen-1-yl |
| naphthalen-2-yl | H | OH | 0 | O | 7-Cl—N-methyl-indol-3-yl |
| benzo[b]thiophen-6-yl | H | OH | 0 | O | naphthalen-1-yl |
| 3-[4-(6-Chloro-2-oxo-2,3-dihydro-benzoimidazol-1-yl)-piperidin-1-ylcarbonyl]-naphthalen-2-yl | H | OH | 0 | O | naphthalen-1-yl |
| 4-biphenyl | H | OH | 0 | O | naphthalen-1-yl |
| naphthalen-2-yl | H | OH | 0 | O | N-cyclopropyl methyl-indol-3-yl |
| naphthalen-2-yl | H | OH | 0 | O | 4-Cl—N-methyl-indol-3-yl |
| benzothiophen-2-yl | H | OH | 0 | O | naphthalen-1-yl |
| naphthalen-2-yl | H | OH | 0 | O | 5-cyano-N-methyl-indol-3-yl |
| 4-hydroxy-phenyl | H | OH | 1 | O | 5-Cl-benzothiophen-3-yl |
| (6-Br)-naphthalen-2-yl | H | OH | 0 | O | 5-Cl-benzothiophen-3-yl |
| naphthalen-2-yl | H | OH | 0 | O | Indol-3-yl |
| 2-Amino-benzothiazol-6-yl | H | OH | 0 | O | 5-Cl-benzothiophen-3-yl |
| 3-(Cyclohexylamino) methyl-naphthalen-2-yl | H | OH | 0 | O | naphthalen-1-yl |
| naphthalen-2-yl | H | OH | 0 | O | 5-Ph-benzothiophen-3-yl |
| 3-(N-benzyl-aminocarbonyloxy methyl) naphthalen-2-yl | H | OH | 0 | O | naphthalen-1-yl |
| 3-(pyridin-4-yl-pyrrolidin-1-ylcarbonyl)-naphthalen-2-yl | H | OH | 0 | O | naphthalen-1-yl |
| naphthalen-2-yl | H | OH | 0 | O | 5-methoxy-N-methyl-indol-3-yl |
| 3-(methoxycarbonyl)-naphthalen-2-yl | H | OH | 0 | O | naphthalen-1-yl |
| naphthalen-2-yl | H | OH | 0 | O | 6-Br-benzothiophen-3-yl |
| naphthalen-2-yl | H | OH | 0 | O | N-isopropyl-indol-3-yl |
| 4-chloro-phenyl | H | CH₃ | 1 | O | 5-Cl-benzothiophen-3-yl |
| quinolin-6-yl | H | OH | 0 | O | naphthalen-1-yl |
| 4-trifluoromethyl-phenyl | H | OH | 1 | O | 5-Cl-benzothiophen-3-yl |
| naphthalen-2-yl | H | OH | 0 | O | N-phenyl-indol-3-yl |
| (4-(1H-indol-3-yl)-piperidin-1-ylcarbonyl)-naphthalen-2-yl | H | OH | 0 | O | naphthalen-1-yl |
| Indanyl | H | OH | 0 | O | naphthalen-1-yl |
| naphthalen-2-yl | H | OH | 0 | O | 5-Cl-1,1-dioxo-benzothiophen-3-yl |

-continued

| R², R³ | R⁵ | R⁶ | n | W | Z—R⁴ |
|---|---|---|---|---|---|
| ((3-phenyl)pyrrolidin-1-ylcarbonyl)-naphthalen-2-yl | H | OH | 0 | O | naphthalen-1-yl |
| naphthalen-2-yl | H | Ph | 0 | O | 5-Cl-benzothiophen-3-yl |
| ((3-Methyl)-cyclohexylamino)methyl-naphthalen-2-yl | H | OH | 0 | O | naphthalen-1-yl |
| 3-(cyclopentyl-N-methylamino-carbonyl)-naphthalen-2-yl | H | OH | 0 | O | naphthalen-1-yl |
| 3-((5-methoxy carbonyl)aminomethyl)-naphthalen-2-yl | H | OH | 0 | O | naphthalen-1-yl |
| 3-(4-(2-oxo-2,3-dihydro-benzoimidazol-1-yl) piperidin-1-ylcarbonyl)-naphthalen-2-yl | H | OH | 0 | O | naphthalen-1-yl |
| 3-(phenyl-aminocarbonyloxy)-methyl)-naphthalen-2-yl | H | OH | 0 | O | naphthalen-1-yl |
| 3-(phenyl-aminocarbonyl)-methyl)-naphthalen-2-yl | H | OH | 0 | O | naphthalen-1-yl |
| quinolin-2-yl | H | OH | 0 | O | naphthalen-1-yl |
| 3-((4-Phenoxy-phenyl)-aminocarbonyloxy methyl)-naphthalen-2-yl | H | OH | 0 | O | naphthalen-1-yl |
| naphthalen-2-yl | H | OH | 0 | O | 5-(4-F-phenyl)-N-methyl-indol-3-yl |
| naphthalen-2-yl | H | OH | 0 | O | 4-Br-benzo thiophen-3-yl |
| 3-[(4-Benzotriazol-1-yl piperidin-1-ylcarbonyl)]-naphthalen-2-yl | H | OH | 0 | O | naphthalen-1-yl |
| 3-(4-phenyl)-piperidin-1-ylcarbonyl)-naphthalen-2-yl | H | OH | 0 | O | naphthalen-1-yl |
| 3-((naphthalen-2-ylcarbonyl)-piperidin-4-ylmethylamino-methyl) naphthalen-2-yl | H | OH | 0 | O | naphthalen-1-yl |
| 3-((3-Benzenesulfonyl)-pyrrolidin-1-ylcarbonyl)-naphthalen-2-yl | H | OH | 0 | O | naphthalen-1-yl |
| 3-(N-[3-(4-Oxo-1-phenyl 1,3,8-triaza-spiro[4.5] decane-8-carbonyl)-naphthalen-2-yl | H | OH | 0 | O | naphthalen-1-yl |
| 3-(naphthalen-2-ylaminocarbonyloxy-methyl)-naphthalen-2-yl | H | OH | 0 | O | naphthalen-1-yl |
| 2-fluorenyl | H | OH | 0 | O | naphthalen-1-yl |
| 3-(Benzylaminomethyl)-naphthalen-2-yl | H | OH | 0 | O | naphthalen-1-yl |
| (3-OH)naphthalen-2-yl | H | OH | 0 | O | naphthalen-1-yl |
| 3-(N-Benzyl-3-acrylamide)naphthalen-2-yl | H | OH | 0 | O | naphthalen-1-yl |
| 3-((5-Phenyl)-pentylamino)-naphthalen-2-yl | H | OH | 0 | O | naphthalen-1-yl |
| 3-(N-Benzyl-N-methyl-aminocarbonyl)-naphthalen-2-yl | H | OH | 0 | O | naphthalen-1-yl |
| 3-[(5H-Dibenzo[a,d]cyclohepten-5-yl)-propyl]-methyl-amino-methyl-naphthalen-2-yl | H | OH | 0 | O | naphthalen-1-yl |
| 3-(4-(Benzothiazol-2-yl-piperidin-1-ylcarbonyl))-naphthalen-2-yl | H | OH | 0 | O | naphthalen-1-yl |
| 1-(2-Oxo-2-(4-phenyl-piperidin-1-yl)-ethoxy)-naphthalen-2-yl | H | OH | 0 | O | naphthalen-1-yl |
| 3-([2-(3,4-dimethoxy-phenyl)-ethyl]-N-methyl-aminocarbonyl)-naphthalen-2-yl | H | OH | 0 | O | naphthalen-1-yl |

-continued

| R2 R3 | R5 | R6 | n | W | Z—R4 |
|---|---|---|---|---|---|
| naphthalen-2-yl | H | OH | 0 | O | 1-Me-1H-pyrrolo[2,3-b]pyridine |
| 3-((4-OH-cyclohexylamino)-methyl)-naphthalen-2-yl | H | OH | 0 | O | naphthalen-1-yl |
| naphthalen-2-yl | H | CH3 | 0 | O | 2-carboxy-benzothiophen-3-yl |
| 3-(Benzyl aminocarbonyl)-naphthalen-2-yl | H | OH | 0 | O | naphthalen-1-yl |
| 3-(3-Phenyl-allyloxy)-naphthalen-2-yl | H | OH | 0 | O | naphthalen-1-yl |
| 3-(Benzyloxy)-naphthalen-2-yl | H | OH | 0 | O | naphthalen-1-yl |
| 3-(methoxycarbonyl-methoxy)-naphthalen-2-yl | H | OH | 0 | O | naphthalen-1-yl |
| 3-(Cyclopentylamino-methyl)-naphthalen-2-yl | H | OH | 0 | O | naphthalen-1-yl |
| naphthalen-2-yl | H | OH | 0 | O | 5-Cl-benzothiophen-2-yl |
| 3-(Phenethyl-methylaminomethyl) naphthalen-2-yl | H | OH | 0 | O | naphthalen-1-yl |
| naphthalen-2-yl | H | CH3 | 0 | O | 2-(benzylaminocarbonyl)-benzothiophen-3-yl |
| naphthalen-2-yl | H | OH | 0 | O | N-phenyl-indol-4-yl |
| Indol-5-yl | H | OH | 0 | O | naphthalen-1-yl |
| 3-(3-Phenyl-propylcarbamoyl)-methoxy)-naphthalen-2-yl | H | OH | 0 | O | naphthalen-1-yl |
| 3-(2-phenyl-pyrrolidin-1-ylcarbonyl)-naphthalen-2-yl | H | OH | 0 | O | naphthalen-1-yl |
| 3-amino-naphthalen-2-yl | H | OH | 0 | O | naphthalen-1-yl |
| 3-((5-hydroxypentylamino)-methyl)-naphthalen-2-yl | H | OH | 0 | O | naphthalen-1-yl |
| 1-(methoxycarbonyl methoxy)-naphthalen-2-yl | H | OH | 0 | O | naphthalen-1-yl |
| benzo[1,3]dioxolyl | H | OH | 0 | O | naphthalen-1-yl |
| isoquinolin-3-yl | H | OH | 0 | O | naphthalen-1-yl |
| 3-phenoxy-phenyl | H | OH | 0 | O | naphthalen-1-yl |
| 3-(isopropyloxycarbonyl)-naphthalen-2-yl | H | OH | 0 | O | naphthalen-1-yl |
| naphthalen-2-yl | H | OH | 0 | O | benzothiophen-2-yl |
| 3-{[1-(naphthalen-2-ylcarbonyl)-piperidin-4-ylcarbonyl]-amino) naphthalen-2-yl | H | OH | 0 | O | naphthalen-1-yl |
| 3-(benzylmethyl aminomethyl)-naphthalen-2-yl | H | OH | 0 | O | naphthalen-1-yl |
| naphthalen-2-yl | H | OH | 0 | O | 6-(4-butylphenyl)-benzothiophen-3-yl |
| trans 2-phenylcycloprop-1-yl | H | CH3 | 0 | O | 5-Cl-benzothiophen-3-yl |
| 2-methoxy-phenyl | H | CH3 | 1 | O | 5-Cl-benzothiophen-3-yl |
| benzofuran-2-yl | H | CH3 | 0 | O | 5-Cl-benzothiophen-3-yl |
| 2-nitro-phenyl | H | CH3 | 1 | O | 5-Cl-benzothiophen-3-yl |
| 2-methylcarbonyloxy-phenyl | H | CH3 | 1 | O | 5-Cl-benzothiophen-3-yl |
| 2-hydroxy-phenyl | H | CH3 | 1 | O | 5-Cl-benzothiophen-3-yl |
| pyridin-2-yl | H | CH3 | 1 | O | 5-Cl-benzothiophen-3-yl |
| 2-amino-phenyl | H | CH3 | 1 | O | 5-Cl-benzothiophen-3-yl |
| 3-trifluoromethyl-phenyl | H | CH3 | 1 | O | 5-Cl-benzothiophen-3-yl |
| 3-trifluoromethoxy-phenyl | H | CH3 | 1 | O | 5-Cl-benzothipphen-3-yl |
| 3-methoxy-phenyl | H | CH3 | 1 | O | 5-Cl-benzothiophen-3-yl |
| 2-methyl-phenyl | H | CH3 | 1 | O | 5-Cl-benzothiophen-3-yl |
| 2,6-difluoro-phenyl | H | CH3 | 1 | O | 5-Cl-benzothiophen-3-yl |
| 4-cyano-phenyl | H | CH3 | 1 | O | 5-Cl-benzothiophen-3-yl |
| 2-ureido-phenyl | H | CH3 | 1 | O | 5-Cl-benzothiophen-3-yl |
| 2-(NHO(=O))2NH2-phenyl | H | CH3 | 1 | O | 5-Cl-benzothiophen-3-yl |
| 2-chloro-phenyl | H | CH3 | 1 | O | 5-Cl-benzothiophen-3-yl |
| 3-chloro-phenyl | H | CH3 | 1 | O | 5-Cl-benzothiophen-3-yl |
| 3,5-difluoro-phenyl | H | CH3 | 1 | O | 5-Cl-benzothiophen-3-yl |
| 2,3-difluoro-phenyl | H | CH3 | 1 | O | 5-Cl-benzothiophen-3-yl |
| 2-bromo-phenyl | H | CH3 | 1 | O | 5-Cl-benzothiophen-3-yl |
| 2,3-dimethoxy-phenyl | H | CH3 | 1 | O | 5-Cl-benzothiophen-3-yl |
| 3-nitro-phenyl | H | CH3 | 1 | O | 5-Cl-benzothiophen-3-yl |
| 3-bromo-phenyl | H | CH3 | 1 | O | 5-Cl-benzothiophen-3-yl |

-continued

| R² R³ | R⁵ | R⁶ | n | W | Z—R⁴ |
|---|---|---|---|---|---|
| 3,5-dimethoxy-phenyl | H | CH₃ | 1 | O | 5-Cl-benzothiophen-3-yl |
| 2,5-difluoro-phenyl | H | CH₃ | 1 | O | 5-Cl-benzothiophen-3-yl |
| 3,5-dichloro-phenyl | H | CH₃ | 1 | O | 5-Cl-benzothiophen-3-yl |
| 2,4-difluoro-phenyl | H | CH₃ | 1 | O | 5-Cl-benzothiophen-3-yl |
| 3-amino-phenyl | H | CH₃ | 1 | O | 5-Cl-benzothiophen-3-yl |
| phenyl | —CH₂C(Me)₂CH₂O— | | 1 | O | naphthalen-1-yl |
| phenyl | 3-methoxy-prop-1-yl | OH | 1 | O | naphthalen-1-yl |
| phenyl | 3-methoxy-prop-1-yl | 3-methoxy-prop-1-yl-oxy | 1 | O | naphthalen-1-yl |
| phenyl | 2-(1,3-dioxolan-2-yl)-eth-1-yl | OH | 1 | O | naphthalen-1-yl |
| phenyl | —CH₂OC(=O)t-butyl | OH | 1 | O | naphthalen-1-yl |
| phenyl | —CH₂CH₂CH₂O— | | 1 | O | naphthalen-1-yl |
| phenyl | (2-dimethyl amino)-eth-1-yl | 2-dimethyl amino-ethoxy | 1 | O | naphthalen-1-yl |
| phenyl | —CH₂C(=O)NEt₂ | —OCH₂C(=O)NEt₂ | 1 | O | naphthalen-1-yl |
| phenyl | —(CH₂)₂SC(=O)t-butyl | —O(CH₂)₂SC(=O)1-butyl | 1 | O | naphthalen-1-yl |
| 3,4-difluoro-phenyl | —CH₂OC(=O)t-butyl | CH₃ | 1 | O | 5-Cl-benzothiophen-3-yl |
| 3,4-difluoro-phenyl | (2-dimethyl-amino)-eth-1-yl | CH₃ | 1 | O | 5-Cl-benzothiophen-3-yl |
| 3,4-difluoro-phenyl | (2-amino)-eth-1-yl | CH₃ | 1 | O | 5-Cl-benzothiophen-3-yl |
| 3,4-difluoro-phenyl | —CH₂C(=O)NEt₂ | CH₃ | 1 | O | 5-Cl-benzothiophen-3-yl |
| 3,4-difluoro-phenyl | —CH₂OC(=O)t-butyl | —OCH₂OC(=O)t-butyl | 1 | O | 5-Cl-benzothiophen-3-yl |
| 3,4-difluoro-phenyl | —CH₂OC(=O)t-butyl | OH | 1 | O | 5-Cl-benzothiophen-3-yl |
| 3,4-difluoro-phenyl | —CH₂OC(=O)NEt₂ | —OCH₂C(=O)NEt₂ | 1 | O | 5-Cl-benzothiophen-3-yl |
| 3,4-difluoro-phenyl | —CH₂CH₂CH₂O— | | 1 | O | 5-Cl-benzothiophen-3-yl |
| 3,4-difluoro-phenyl | —CH₂OC(=O)methyl | OH | 1 | O | 5-Cl-benzothiophen-3-yl |
| 3,4-difluoro-phenyl | —CH₂OC(=O)isopropyloxy | OH | 1 | O | 5-Cl-benzothiophen-3-yl |
| 2-methoxy-phenyl | H | OH | 1 | O | 5-Cl-benzothiophen-3-yl |
| pyridin-2-yl | H | OH | 1 | O | 5-Cl-benzothiophen-3-yl |
| 3-trifluoromethoxy-phenyl | H | OH | 1 | O | 5-Cl-benzothiophen-3-yl |
| 3-methoxy-phenyl | H | OH | 1 | O | 5-Cl-benzothiophen-3-yl |
| 2,6-difluoro-phenyl | H | OH | 1 | O | 5-Cl-benzothiophen-3-yl |
| 2-chloro-phenyl | H | OH | 1 | O | 5-Cl-benzothiophen-3-yl |
| 3-chloro-phenyl | H | OH | 1 | O | 5-Cl-benzothiophen-3-yl |
| 3,5-difluoro-phenyl | H | OH | 1 | O | 5-Cl-benzothiophen-3-yl |
| 2,3-difluoro-phenyl | H | OH | 1 | O | 5-Cl-benzothiophen-3-yl |
| 2-bromo-phenyl | H | OH | 1 | O | 5-Cl-benzothiophen-3-yl |
| 2,3-dimethoxy-phenyl | H | OH | 1 | O | 5-Cl-benzothiophen-3-yl |
| 3-nitro-phenyl | H | OH | 1 | O | 5-Cl-benzothiophen-3-yl |
| 3-bromo-phenyl | H | OH | 1 | O | 5-Cl-benzothiophen-3-yl |
| 3,5-dimethoxy-phenyl | H | OH | 1 | O | 5-Cl-benzothiophen-3-yl |
| 2,5-difluoro-phenyl | H | OH | 1 | O | 5-Cl-benzothiophen-3-yl |
| 3,5-dichloro-phenyl | H | OH | 1 | O | 5-Cl-benzothiophen-3-yl |
| 2,4-difluoro-phenyl | H | OH | 1 | O | 5-Cl-benzothiophen-3-yl |
| 3-amino-phenyl | H | OH | 1 | O | 5-Cl-benzothiophen-3-yl |
| 2-methoxy-phenyl | —CH₂OC(=O)t-butyl | CH₃ | 1 | O | 5-Cl-benzothiophen-3-yl |
| pyridin-2-yl t-butyl | —CH₂OC(=O)t-butyl | CH₃ | 1 | O | 5-Cl-benzothiophen-3-yl |
| 3-trifluoromethoxy-phenyl | —CH₂OC(=O)t-butyl | CH₃ | 1 | O | 5-Cl-benzothiophen-3-yl |
| 3-methoxy-phenyl | —CH₂OC(=O)t-butyl | CH₃ | 1 | 0 | 5-Cl-benzothiophen-3-yl |

-continued

| R² R³ | R⁵ | R⁶ | n | W | Z—R⁴ |
|---|---|---|---|---|---|
| 2,6-difluoro-phenyl | —CH₂OC(=O)t-butyl | CH₃ | 1 | O | 5-Cl-benzothiophen-3-yl |
| 2-chloro-phenyl | —CH₂OC(=O)t-butyl | CH₃ | 1 | O | 5-Cl-benzothiophen-3-yl |
| 3-chloro-phenyl | —CH₂OC(=O)t-butyl | CH₃ | 1 | O | 5-Cl-benzothiophen-3-yl |
| 3,5-difluoro-phenyl | —CH₂OC(=O)t-butyl | CH₃ | 1 | O | 5-Cl-benzothiophen-3-yl |
| 2,3-difluoro-phenyl | —CH₂OC(=O)t-butyl | CH₃ | 1 | O | 5-Cl-benzothiophen-3-yl |
| 2-bromo-phenyl | —CH₂OC(=O)t-butyl | CH₃ | 1 | O | 5-Cl-benzothiophen-3-yl |
| 2,3-dimethoxy-phenyl | —CH₂OC(=O)t-butyl | CH₃ | 1 | O | 5-Cl-benzothiophen-3-yl |
| 3-nitro-phenyl | —CH₂OC(=O)t-butyl | CH₃ | 1 | O | 5-Cl-benzothipphen-3-yl |
| 3-bromo-phenyl | —CH₂OC(=O)t-butyl | CH₃ | 1 | O | 5-Cl-benzothiophen-3-yl |
| 3,5-dimethoxy-phenyl | —CH₂OC(=O)t-butyl | CH₃ | 1 | O | 5-Cl-benzothiophen-3-yl |
| 2,5-difluoro-phenyl | —CH₂OC(=O)t-butyl | CH₃ | 1 | O | 5-Cl-benzothiophen-3-yl |
| 3,5-dichloro-phenyl | —CH₂OC(=O)t-butyl | CH₃ | 1 | O | 5-Cl-benzothiophen-3-yl |
| 2,4-difluoro-phenyl | —CH₂OC(=O)t-butyl | CH₃ | 1 | O | 5-Cl-benzothiophen-3-yl |
| 3-amino-phenyl | —CH₂OC(=O)t-butyl | CH₃ | 1 | O | 5-Cl-benzothiophen-3-yl |
| 2-methoxy-phenyl | —CH₂OC(=O)t-butyl | —CH₂OC(=O)t-butyl | 1 | O | 5-Cl-benzothiophen-3-yl |
| pyridin-2-yl | —CH₂OC(=O)t-butyl | —OCH₂OC(=O)t-butyl | 1 | O | 5-Cl-benzothiophen-3-yl |
| 3-trifluoromethoxy-phenyl | —CH₂OC(=O)t-butyl | —OCH₂OC(=O)t-butyl | 1 | O | 5-Cl-benzothiophen-3-yl |
| 3-methoxy-phenyl | —CH₂OC(=O)1-butyl | —OCH₂OC(=O)t-butyl | 1 | O | 5-Cl-benzothiophen-3-yl |
| 2,6-difluoro-phenyl | —CH₂OC(=O)t-butyl | —OCH₂OC(=O)t-butyl | 1 | O | 5-Cl-benzothiophen-3-yl |
| 2-chloro-phenyl | —CH₂OC(=O)t-butyl | —OCH₂OC(=O)t-butyl | 1 | O | 5-Cl-benzothiophen-3-yl |
| 3-chloro-phenyl | —CH₂OC(=O)t-butyl | —OCH₂OC(=O)t-butyl | 1 | O | 5-Cl-benzothiophen-3-yl |
| 3,5-difluoro-phenyl | —CH₂OC(=O)t-butyl | —OCH₂OC(=O)t-butyl | 1 | O | 5-Cl-benzothiophen-3-yl |
| 2,3-difluoro-phenyl | —CH₂OC(=O)t-butyl | —OCH₂OC(=O)t-butyl | 1 | O | 5-Cl-benzothiophen-3-yl |
| 2-bromo-phenyl | —CH₂OC(=O)t-butyl | —OCH₂OC(=O)t-butyl | 1 | O | 5-Cl-benzothiophen-3-yl |
| 2,3-dimethoxy-phenyl | —CH₂OC(=O)t-butyl | —OCH₂OC(=O)t-butyl | 1 | O | 5-Cl-benzothiophen-3-yl |
| 3-nitro-phenyl | —CH₂OC(=O)t-butyl | —OCH₂OC(=O)t-butyl | 1 | O | 5-Cl-benzothiophen-3-yl |
| 3-bromo-phenyl | —CH₂OC(=O)t-butyl | —OCH₂OC(=O)t-butyl | 1 | O | 5-Cl-benzothiophen-3-yl |
| 3,5-dimethoxy-phenyl | —CH₂OC(=O)t-butyl | —OCH₂OC(=O)t-butyl | 1 | O | 5-Cl-benzothiophen-3-yl |
| 2,5-difluoro-phenyl | —CH₂OC(=O)t-butyl | —OCH₂OC(=O)t-butyl | 1 | O | 5-Cl-benzothiophen-3-yl |
| 3,5-dichloro-phenyl | —CH₂OC(=O)t-butyl | —OCH₂ | 1 | O | 5-Cl-benzothiophen-3-yl |

-continued

| R² R³ | R⁵ | R⁶ | n | W | Z—R⁴ |
|---|---|---|---|---|---|
|  | t-butyl | OC(=O)<br>t-butyl |  |  |  |
| 2,4-difluoro-phenyl | —CH₂OC(=O)<br>t-butyl | —OCH₂<br>OC(=O)<br>1-butyl | 1 | O | 5-Cl-benzothiophen-3-yl |
| 3-amino-phenyl | —CH₂OC(=O)<br>t-butyl | —OCH₂<br>OC(=O)<br>t-butyl | 1 | O | 5-Cl-benzothiophen-3-yl |
| 2-methoxy-phenyl | —CH₂OC(=O)<br>t-butyl | —OCH₂ | 1 | O | 5-Cl-benzothiophen-3-yl |
| pyridin-2-yl | —CH₂OC(=O)<br>t-butyl | —OCH₂ | 1 | O | 5-Cl-benzothiophen-3-yl |
| 3-trifluoromethoxy-phenyl | —CH₂OC(=O)<br>t-butyl | OH | 1 | O | 5-Cl-benzothiophen-3-yl |
| 3-methoxy-phenyl | —CH₂OC(=O)<br>t-butyl | OH | 1 | O | 5-Cl-benzothiophen-3-yl |
| 2,6-difluoro-phenyl | —CH₂OC(=O)<br>t-butyl | OH | 1 | O | 5-Cl-benzothiophen-3-yl |
| 2-chloro-phenyl | —CH₂OC(=O)<br>t-butyl | OH | 1 | O | 5-Cl-benzothiophen-3-yl |
| 3-chloro-phenyl | —CH₂OC(=O)<br>t-butyl | OH | 1 | O | 5-Cl-benzothiophen-3-yl |
| 3,5-difluoro-phenyl | —CH₂OC(=O)<br>t-butyl | OH | 1 | O | 5-Cl-benzothiophen-3-yl |
| 2,3-difluoro-phenyl | —CH₂OC(=O)<br>t-butyl | OH | 1 | O | 5-Cl-benzothiophen-3-yl |
| 2-bromo-phenyl | —CH₂OC(=O)<br>t-butyl | OH | 1 | O | 5-Cl-benzothipphen-3-yl |
| 2,3-dimethoxy-phenyl | —CH₂OC(=O)<br>t-butyl | OH | 1 | O | 5-Cl-benzothiophen-3-yl |
| 3-nitro-phenyl | —CH₂OC(=O)<br>t-butyl | OH | 1 | O | 5-Cl-benzothiophen-3-yl |
| 3-bromo-phenyl | —CH₂OC(=O)<br>t-butyl | OH | 1 | O | 5-Cl-benzothiophen-3-yl |
| 3,5-dimethoxy-phenyl | —CH₂OC(=O)<br>t-butyl | OH | 1 | O | 5-Cl-benzothiophen-3-yl |
| 2,5-difluoro-phenyl | —CH₂OC(=O)<br>t-butyl | OH | 1 | O | 5-Cl-benzothiophen-3-yl |
| 3,5-dichloro-phenyl | —CH₂OC(=O)<br>t-butyl | OH | 1 | O | 5-Cl-benzothiophen-3-yl |
| 2,4-difluoro-phenyl | —CH₂OC(=O)<br>t-butyl | OH | 1 | O | 5-Cl-benzothiophen-3-yl |
| 3-amino-phenyl | —CH₂OC(=O)<br>t-butyl | OH | 1 | O | 5-Cl-benzothiophen-3-yl |
| 2-methoxy-phenyl | —CH₂CH₂CH₂O— |  | 1 | O | 5-Cl-benzothiophen-3-yl |
| pyridin-2-yl | —CH₂CH₂CH₂O— |  | 1 | O | 5-Cl-benzothiophen-3-yl |
| 3-trifluoromethoxy-phenyl | —CH₂CH₂CH₂O— |  | 1 | O | 5-Cl-benzothiophen-3-yl |
| 3-methoxy-phenyl | —CH₂CH₂CH₂O— |  | 1 | O | 5-Cl-benzothiophen-3-yl |
| 2,6-difluoro-phenyl | —CH₂CH₂CH₂O— |  | 1 | O | 5-Cl-benzothiophen-3-yl |
| 2-chloro-phenyl | —CH₂CH₂CH₂O— |  | 1 | O | 5-Cl-benzothiophen-3-yl |
| 3-chloro-phenyl | —CH₂CH₂CH₂O— |  | 1 | O | 5-Cl-benzothiophen-3-yl |
| 3,5-difluoro-phenyl | —CH₂CH₂CH₂O— |  | 1 | O | 5-Cl-benzothiophen-3-yl |
| 2,3-difluoro-phenyl | —CH₂CH₂CH₂O— |  | 1 | O | 5-Cl-benzothiophen-3-yl |
| 2-bromo-phenyl | —CH₂CH₂CH₂O— |  | 1 | O | 5-Cl-benzothiophen-3-yl |
| 2,3-dimethoxy-phenyl | —CH₂CH₂CH₂O— |  | 1 | O | 5-Cl-benzothiophen-3-yl |
| 3-nitro-phenyl | —CH₂CH₂CH₂O— |  | 1 | O | 5-Cl-benzothiophen-3-yl |
| 3-bromo-phenyl | —CH₂CH₂CH₂O— |  | 1 | O | 5-Cl-benzothiophen-3-yl |
| 3,5-dimethoxy-phenyl | —CH₂CH₂CH₂O— |  | 1 | O | 5-Cl-benzothiophen-3-yl |
| 2,5-difluoro-phenyl | —CH₂CH₂CH₂O— |  | 1 | O | 5-Cl-benzothiophen-3-yl |
| 3,5-dichloro-phenyl | —CH₂CH₂CH₂O— |  | 1 | O | 5-Cl-benzothiophen-3-yl |
| 2,4-difluoro-phenyl | —CH₂CH₂CH₂O— |  | 1 | O | 5-Cl-benzothiophen-3-yl |
| 3-amino-phenyl | —CH₂CH₂CH₂O— |  | 1 | O | 5-Cl-benzothiophen-3-yl |
| 2-methoxy-phenyl | —CH₂OC(=O)<br>isopropyloxy | OH | 1 | O | 5-Cl-benzothiophen-3-yl |
| pyridin-2-yl | —CH₂OC(=O)<br>isopropyloxy | OH | 1 | O | 5-Cl-benzothiophen-3-yl |
| 3-trifluoromethoxy-phenyl | —CH₂OC(=O)<br>isopropyloxy | OH | 1 | O | 5-Cl-benzothiophen-3-yl |
| 3-methoxy-phenyl | —CH₂OC(=O)<br>isopropyloxy | OH | 1 | O | 5-Cl-benzothiophen-3-yl |
| 2,6-difluoro-phenyl | —CH₂OC(=O)<br>isopropyloxy | OH | 1 | O | 5-Cl-benzothiophen-3-yl |
| 2-chloro-phenyl | —CH₂OC(=O)<br>isopropyloxy | OH | 1 | O | 5-Cl-benzothiophen-3-yl |

-continued

| R² R³ | R⁵ | R⁶ | n | W | Z—R⁴ |
|---|---|---|---|---|---|
| 3-chloro-phenyl | —CH₂OC(=O)isopropyloxy | OH | 1 | O | 5-Cl-benzothiophen-3-yl |
| 3,5-difluoro-phenyl | —CH₂OC(=O)isopropyloxy | OH | 1 | O | 5-Cl-benzothiophen-3-yl |
| 2,3-difluoro-phenyl | —CH₂OC(=O)isopropyloxy | OH | 1 | O | 5-Cl-benzothiophen-3-yl |
| 2-bromo-phenyl | —CH₂OC(=O)isopropyloxy | OH | 1 | O | 5-Cl-benzothiophen-3-yl |
| 2,3-dimethoxy-phenyl | —CH₂OC(=O)isopropyloxy | OH | 1 | O | 5-Cl-benzothiophen-3-yl |
| 3-nitro-phenyl | —CH₂OC(=O)isopropyloxy | OH | 1 | O | 5-Cl-benzothiophen-3-yl |
| 3-bromo-phenyl | —CH₂OC(=O)isopropyloxy | OH | 1 | O | 5-Cl-benzothiophen-3-yl |
| 3,5-dimethoxy-phenyl | —CH₂OC(=O)isopropyloxy | OH | 1 | O | 5-Cl-benzothiophen-3-yl |
| 2,5-difluoro-phenyl | —CH₂OC(=O)isopropyloxy | OH | 1 | O | 5-Cl-benzothiophen-3-yl |
| 3,5-dichloro-phenyl | —CH₂OC(=O)isopropyloxy | OH | 1 | O | 5-Cl-benzothiophen-3-yl |
| 2,4-difluoro-phenyl | —CH₂OC(=O)isopropyloxy | OH | 1 | O | 5-Cl-benzothiophen-3-yl |
| 3-amino-phenyl | —CH₂OC(=O)isopropyloxy | OH | 1 | O | 5-Cl-benzothiophen-3-yl |
| 3-fluoro-5-chloro-phenyl | H | CH₃ | 1 | O | 5-Cl-benzothiophen-3-yl |
| 2-fluoro-3-chloro-phenyl | H | CH₃ | 1 | O | 5-Cl-benzothiophen-3-yl |
| 4-fluoro-3-chloro-phenyl | H | CH₃ | 1 | O | 5-Cl-benzothiophen-3-yl |
| 2-fluoro-5-chloro-phenyl | H | CH₃ | 1 | O | 5-Cl-benzothiophen-3-yl |
| 3,5-dibromo-phenyl | H | CH₃ | 1 | O | 5-Cl-benzothiophen-3-yl |
| 3-cyano-phenyl | H | CH₃ | 1 | O | 5-Cl-benzothiophen-3-yl |
| 2-cyano-phenyl | H | CH₃ | 1 | O | 5-Cl-benzothiophen-3-yl |
| 3-fluoro-5-trifluoromethyl-phenyl | H | CH₃ | 1 | O | 5-Cl-benzothiophen-3-yl |
| 3-fluoro-5-chloro-phenyl | H | OH | 1 | O | 5-Cl-benzothiophen-3-yl |
| 2-fluoro-3-chloro-phenyl | H | OH | 1 | O | 5-Cl-benzothiophen-3-yl |
| 4-fluoro-3-chloro-phenyl | H | OH | 1 | O | 5-Cl-benzothiophen-3-yl |
| 2-fluoro-5-chloro-phenyl | H | OH | 1 | O | 5-Cl-benzothiophen-3-yl |
| 3,5-dibromo-phenyl | H | OH | 1 | O | 5-Cl-benzothiophen-3-yl |
| 3-cyano-phenyl | H | OH | 1 | O | 5-Cl-benzothiophen-3-yl |
| 2-cyano-phenyl | H | OH | 1 | O | 5-Cl-benzothiophen-3-yl |
| 3-fluoro-5-trifluoromethyl-phenyl | H | OH | 1 | O | 5-Cl-benzothiophen-3-yl |
| 3-fluoro-5-chloro-phenyl | —CH₂OC(=O)t-butyl | CH₃ | 1 | O | 5-Cl-benzothiophen-3-yl |
| 2-fluoro-3-chloro-phenyl | —CH₂OC(=O)t-butyl | CH₃ | 1 | O | 5-Cl-benzothiophen-3-yl |
| 4-fluoro-3-chloro-phenyl | —CH₂OC(=O)t-butyl | CH₃ | 1 | O | 5-Cl-benzothiophen-3-yl |
| 2-fluoro-5-chloro-phenyl | —CH₂OC(=O)t-butyl | CH₃ | 1 | O | 5-Cl-benzothiophen-3-yl |
| 3,5-dibromo-phenyl | —CH₂OC(=O)t-butyl | CH₃ | 1 | O | 5-Cl-benzothiophen-3-yl |
| 3-cyano-phenyl | —CH₂OC(=O)t-butyl | CH₃ | 1 | O | 5-Cl-benzothiophen-3-yl |
| 2-cyano-phenyl | —CH₂OC(=O)t-butyl | CH₃ | 1 | O | 5-Cl-benzothiophen-3-yl |
| 3-fluoro-5-trifluoromethyl-phenyl | —CH₂OC(=O)t-butyl | CH₃ | 1 | O | 5-Cl-benzothiophen-3-yl |
| 3-fluoro-5-chloro-phenyl | —CH₂OC(=O)t-butyl | —OCH₂OC(=O)t-butyl | 1 | O | 5-Cl-benzothiophen-3-yl. |
| 2-fluoro-3-chloro-phenyl | —CH₂OC(=O)t-butyl | —OCH₂OC(=O)t-butyl | 1 | O | 5-Cl-benzothiophen-3-yl |
| 4-fluoro-3-chloro-phenyl | —CH₂OC(=O)t-butyl | —OCH₂OC(=O)t-butyl | 1 | O | 5-Cl-benzothiophen-3-yl |
| 2-fluoro-5-chloro-phenyl | —CH₂OC(=O)t-butyl | —OCH₂OC(=O)t-butyl | 1 | O | 5-Cl-benzothiophen-3-yl |
| 3,5-dibromo-phenyl | —CH₂OC(=O)t-butyl | —OCH₂OC(=O)t-butyl | 1 | O | 5-Cl-benzothiophen-3-yl |
| 3-cyano-phenyl | —CH₂OC(=O) | —OCH₂ | 1 | O | 5-Cl-benzothiophen-3-yl |

-continued

| R² R³ (A) | R⁵ | R⁶ | n | W | Z—R⁴ |
|---|---|---|---|---|---|
|  | t-butyl | OC(=O) t-butyl |  |  |  |
| 2-cyano-phenyl | —CH₂OC(=O) t-butyl | —OCH₂ OC(=O) t-butyl | 1 | O | 5-Cl-benzothiophen-3-yl |
| 3-fluoro-5-trifluoromethyl phenyl | —CH₂OC(=O) t-butyl | —OCH₂ OC(=O) t-butyl | 1 | O | 5-Cl-benzothiophen-3-yl |
| 3-fluoro-5-chloro-phenyl | —CH₂OC(=O) t-butyl | OH | 1 | O | 5-Cl-benzothiophen-3-yl |
| 2-fluoro-3-chloro-phenyl | —CH₂OC(=O) t-butyl | OH | 1 | O | 5-Cl-benzothiophen-3-yl |
| 4-fluoro-3-chloro-phenyl | —CH₂OC(=O) t-butyl | OH | 1 | O | 5-Cl-benzothiophen-3-yl |
| 2-fluoro-5-chloro-phenyl | —CH₂OC(=O) t-butyl | OH | 1 | O | 5-Cl-benzothiophen-3-yl |
| 3,5-dibromo-phenyl | —CH₂OC(=O) t-butyl | OH | 1 | O | 5-Cl-benzothiophen-3-yl |
| 3-cyano-phenyl | —CH₂OC(=O) t-butyl | OH | 1 | O | 5-Cl-benzothiophen-3-yl |
| 2-cyano-phenyl | —CH₂OC(=O) t-butyl | OH | 1 | O | 5-Cl-benzothiophen-3-yl |
| 3-fluoro-5-trifluoromethyl-phenyl | —CH₂OC(=O) t-butyl | OH | 1 | O | 5-Cl-benzothiophen-3-yl |
| 3-fluoro-5-chloro-phenyl | —CH₂CH₂CH₂O— |  | 1 | O | 5-Cl-benzothiophen-3-yl |
| 2-fluoro-3-chloro-phenyl | —CH₂CH₂CH₂O— |  | 1 | O | 5-Cl-benzothiophen-3-yl |
| 4-fluoro-3-chloro-phenyl | —CH₂CH₂CH₂O— |  | 1 | O | 5-Cl-benzothiophen-3-yl |
| 2-fluoro-5-chloro-phenyl | —CH₂CH₂CH₂O— |  | 1 | O | 5-Cl-benzothiophen-3-yl |
| 3,5-dibromo-phenyl | —CH₂CH₂CH₂O— |  | 1 | O | 5-Cl-benzothiophen-3-yl |
| 3-cyano-phenyl | —CH₂CH₂CH₂O— |  | 1 | O | 5-Cl-benzothiophen-3-yl |
| 2-cyano-phenyl | —CH₂CH₂CH₂O— |  | 1 | O | 5-Cl-benzothiophen-3-yl |
| 3-fluoro-5-trifluoromethyl-phenyl | —CH₂CH₂CH₂O— |  | 1 | O | 5-Cl-benzothiophen-3-yl |
| 3-fluoro-5-chloro-phenyl | —CH₂OC(=O) isopropyloxy | OH | 1 | O | 5-Cl-benzothiophen-3-yl |
| 2-fluoro-3-chloro-phenyl | —CH₂OC(=O) isopropyloxy | OH | 1 | O | 5-Cl-benzothiophen-3-yl |
| 4-fluoro-3-chloro-phenyl | —CH₂OC(=O) isopropyloxy | OH | 1 | O | 5-Cl-benzothiophen-3-yl |
| 2-fluoro-5-chloro-phenyl | —CH₂OC(=O) isopropyloxy | OH | 1 | O | 5-Cl-benzothiophen-3-yl |
| 3,5-dibromo-phenyl | —CH₂OC(=O) isopropyloxy | OH | 1 | O | 5-Cl-benzothiophen-3-yl |
| 3-cyano-phenyl | —CH₂OC(=O) isopropyloxy | OH | 1 | O | 5-Cl-benzothiophen-3-yl |
| 2-cyano-phenyl | —CH₂OC(=O) isopropyloxy | OH and | 1 | O | 5-Cl-benzothiophen-3-yl |
| 3-fluoro-5-trifluoromethyl phenyl | —CH₂OC(=O) isopropyloxy | OH | 1 | O | 5-Cl-benzothiophen-3-yl. |

48. The compounds of claim 30 wherein the compounds have a formula selected from the group consisting of:

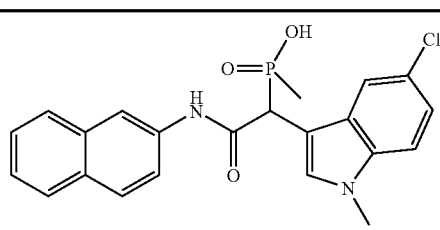

-continued

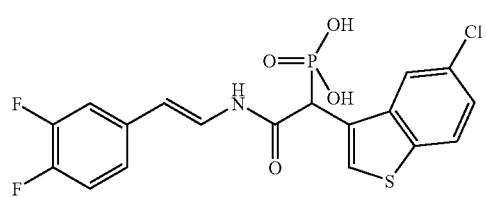

-continued
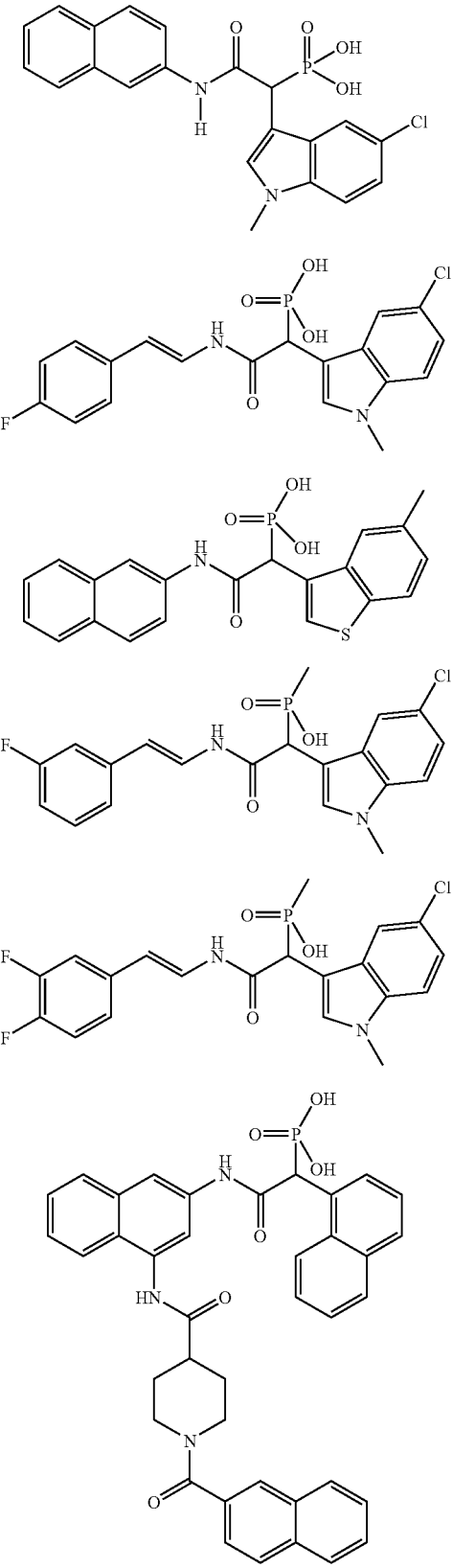
-continued
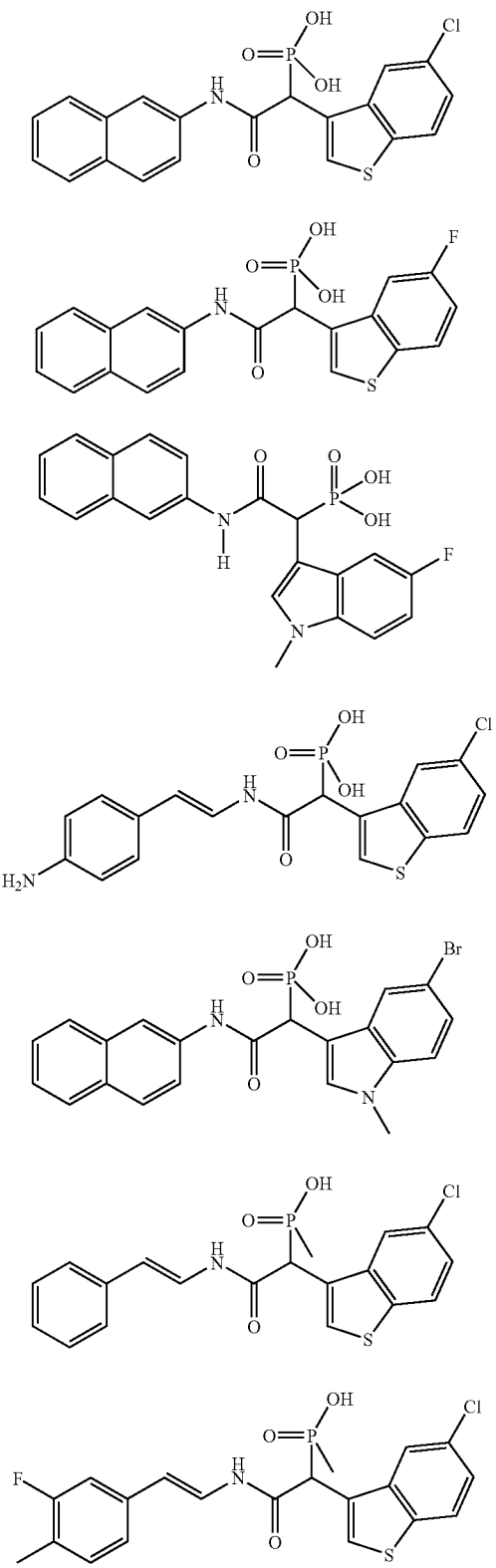

-continued
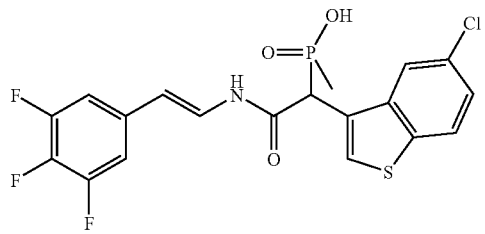
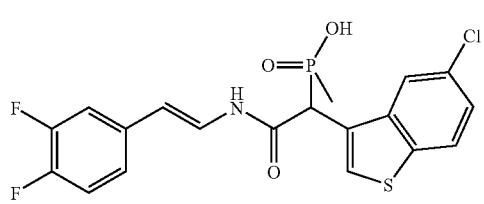
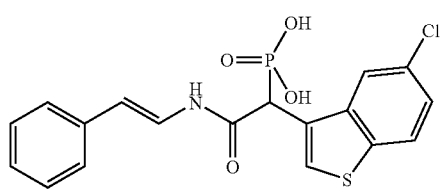
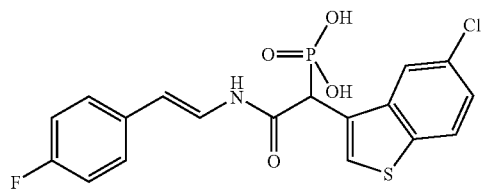
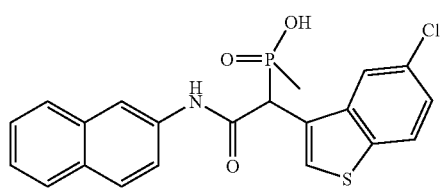
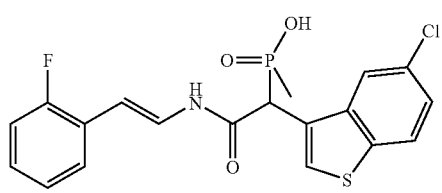
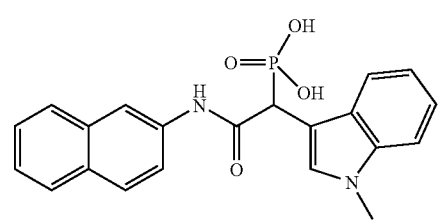
-continued
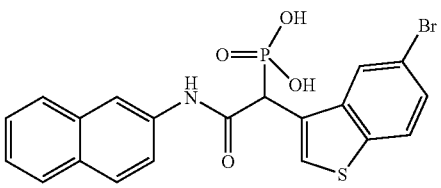
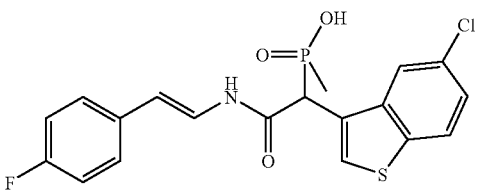
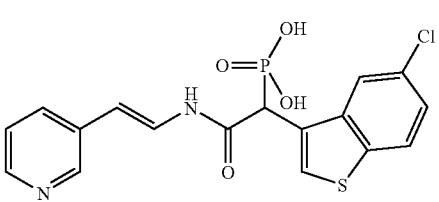
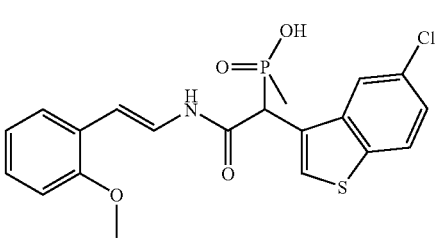
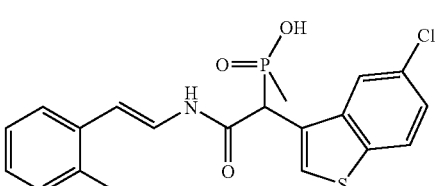
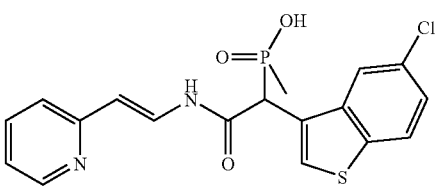
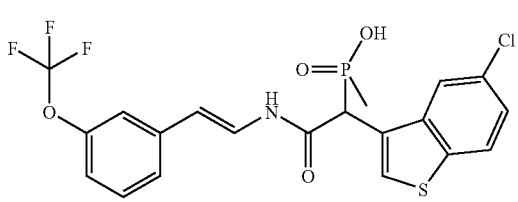

-continued
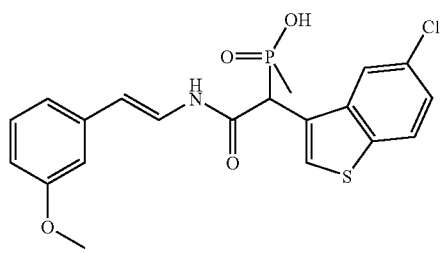
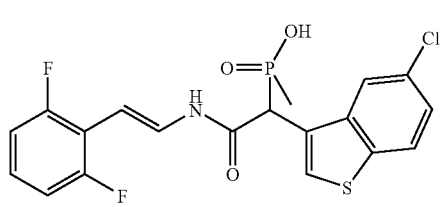
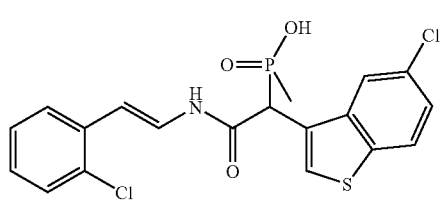
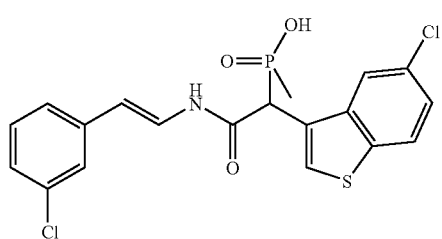
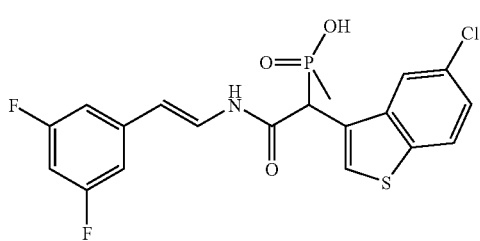
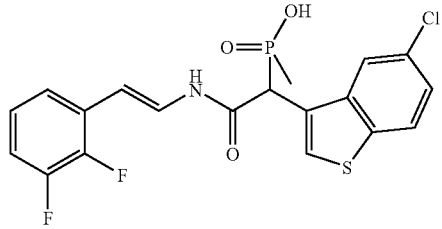
-continued
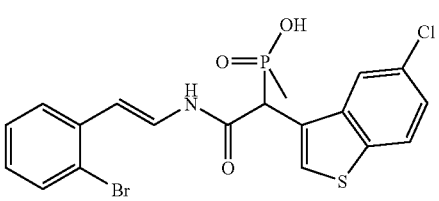
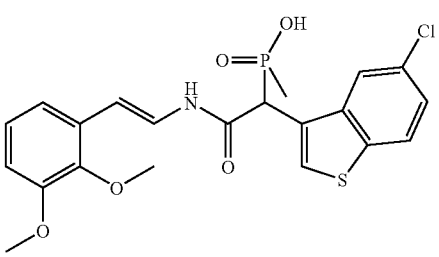
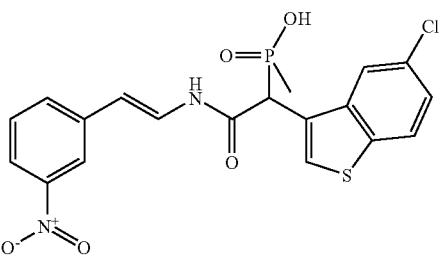
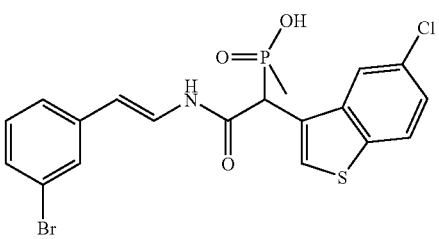
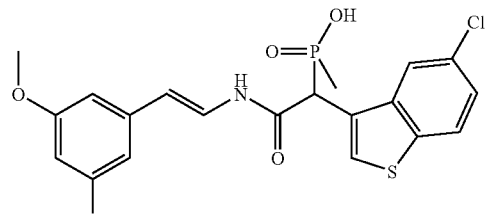
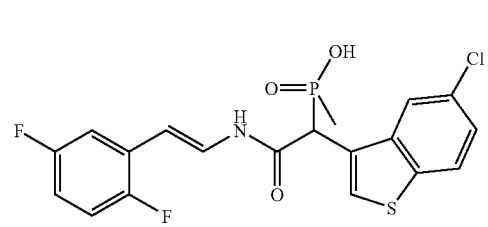

-continued
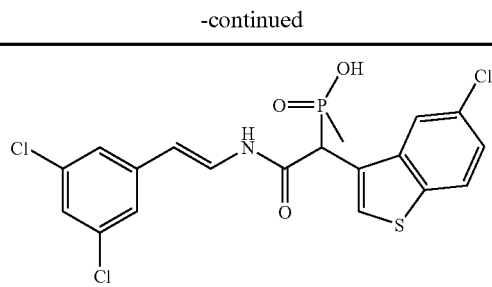
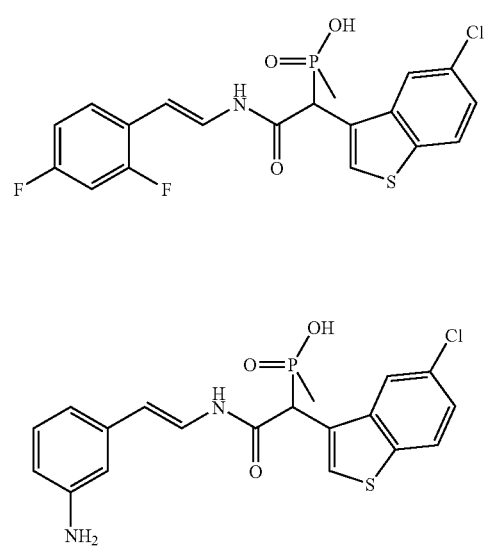
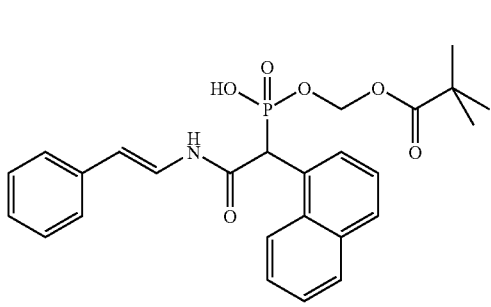
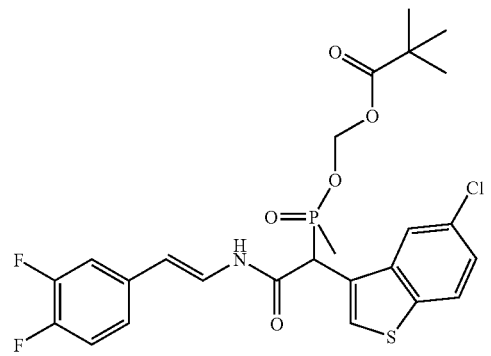
-continued
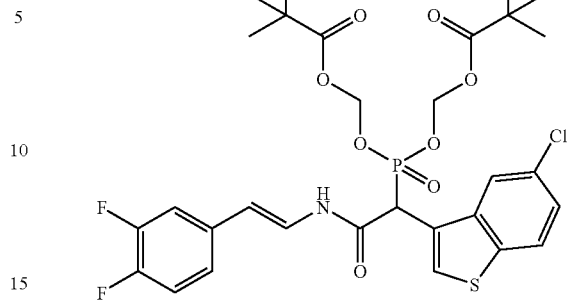
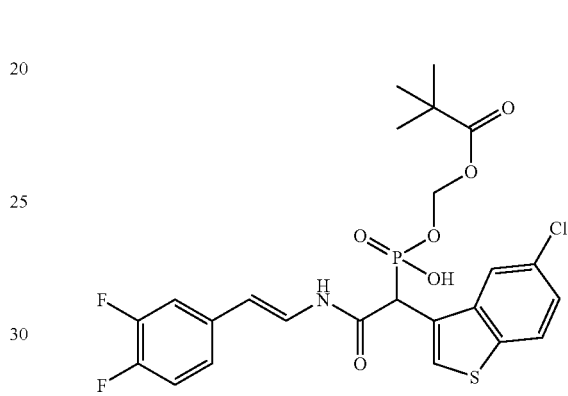
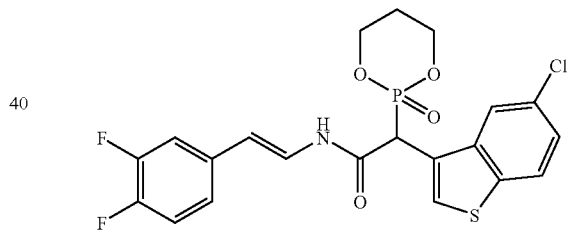
and

49. The compounds of claim 30 wherein the compounds have a formula of:
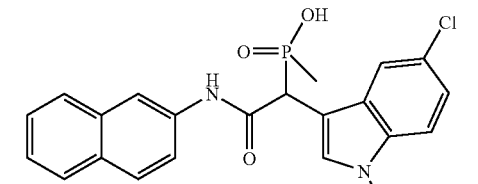
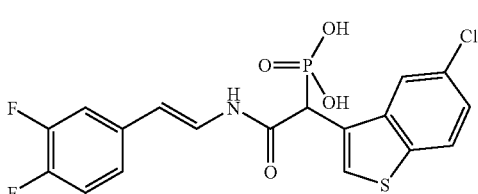
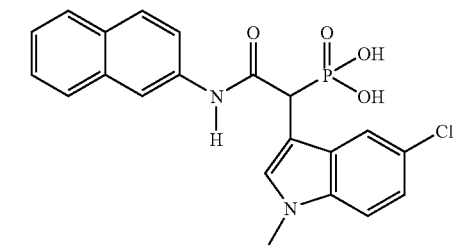
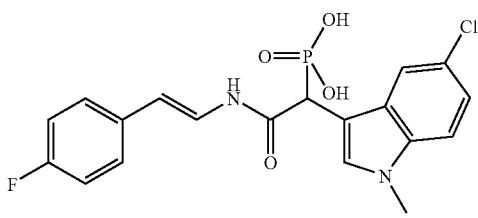
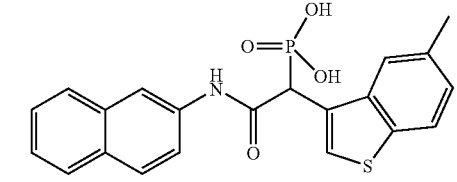
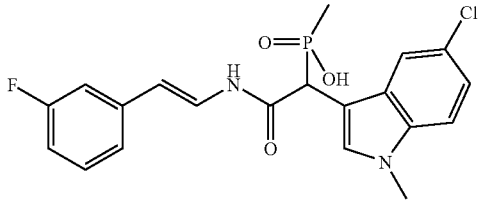
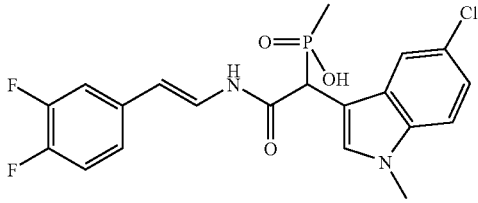
-continued
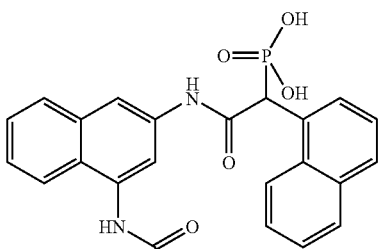
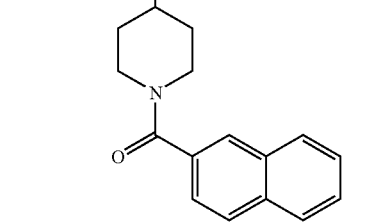
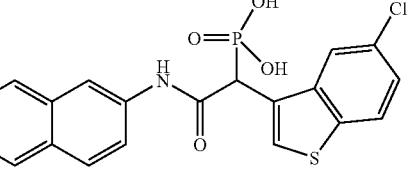
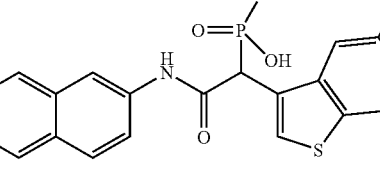
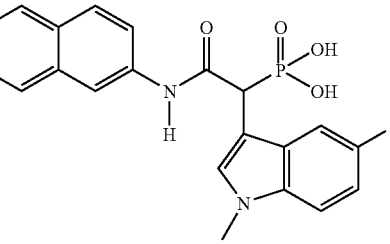
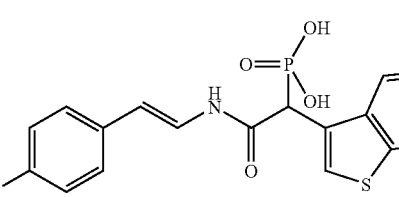
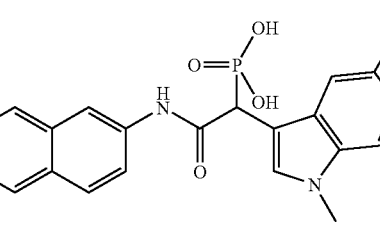

| 187 | 188 |
|---|---|
| -continued | -continued |
| 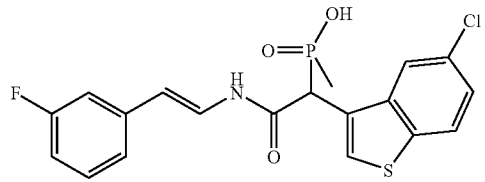 | 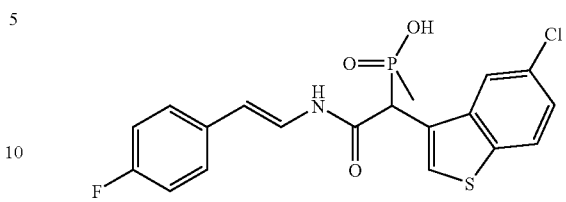 |
| 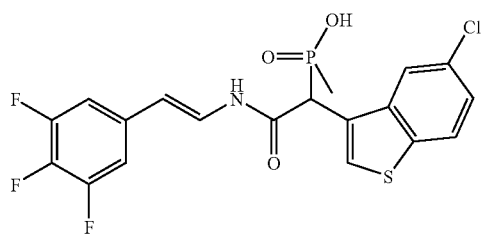 | 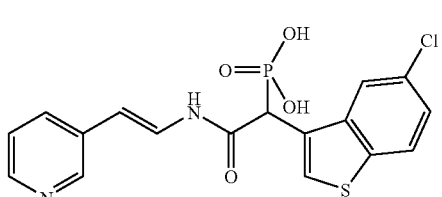 |
| 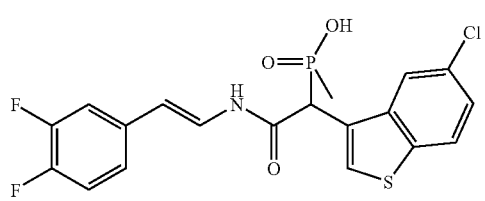 | 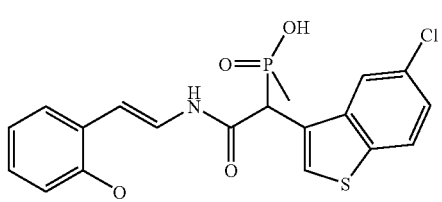 |
| 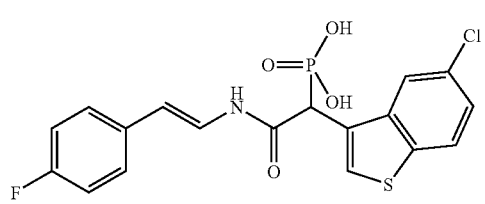 | 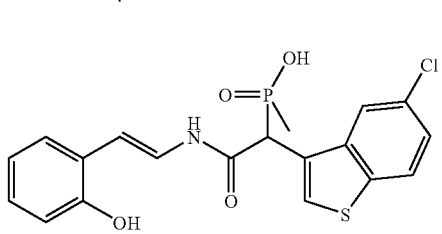 |
| 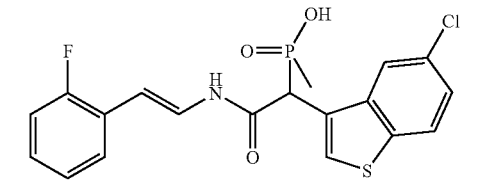 | 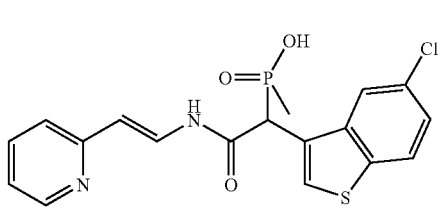 |
| 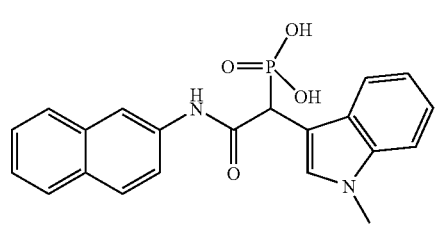 | 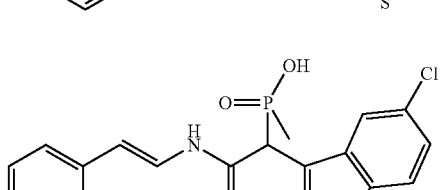 |
| 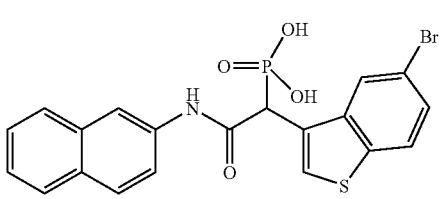 | 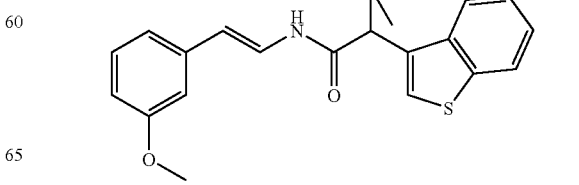 |

-continued
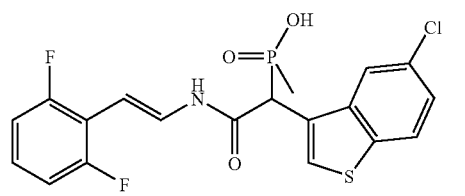
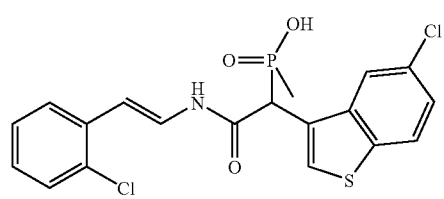
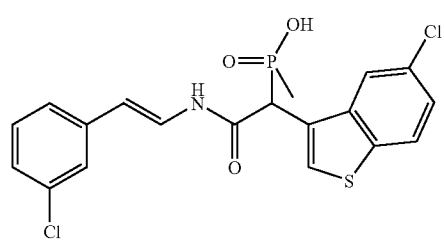
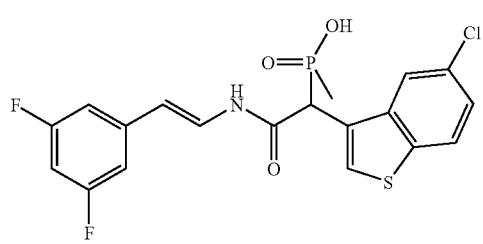
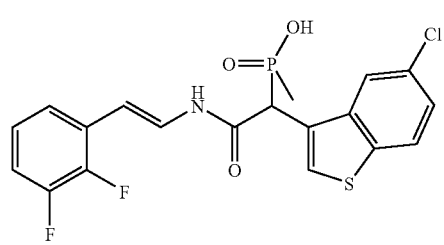
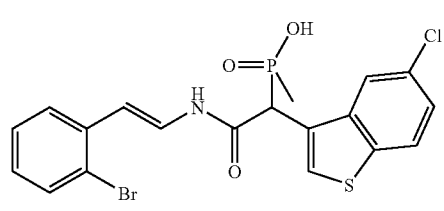
-continued
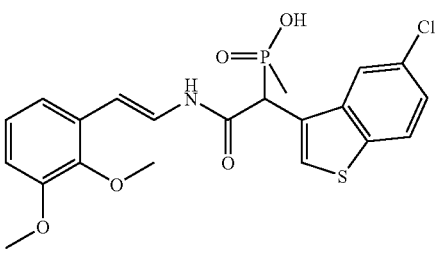
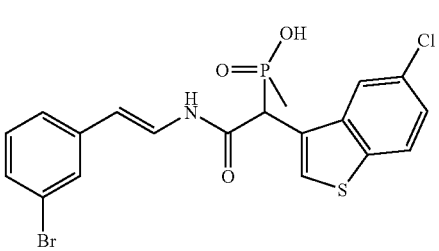
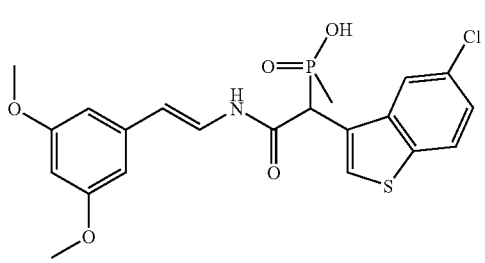
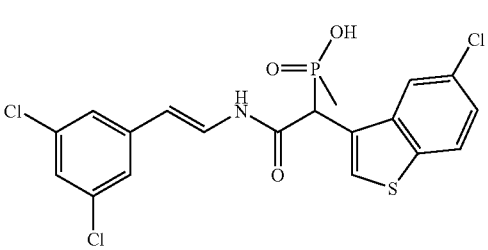
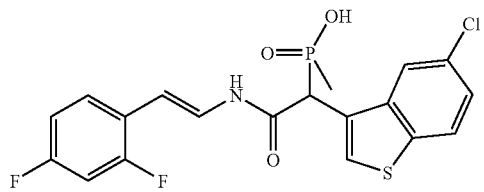
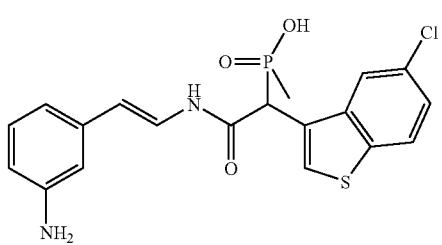

-continued

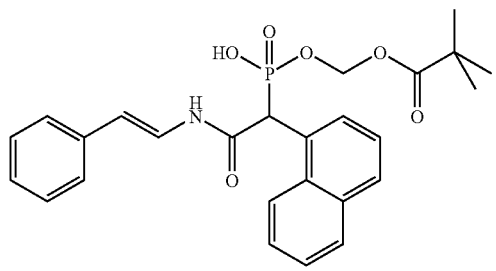

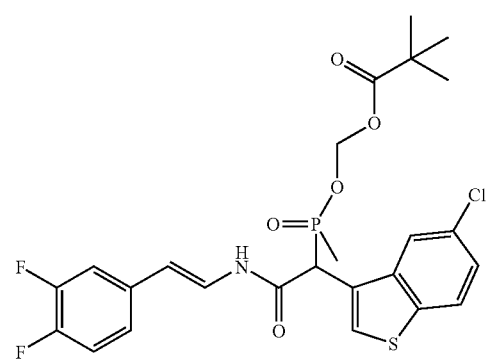

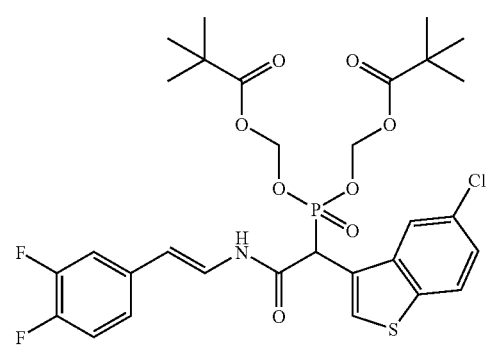

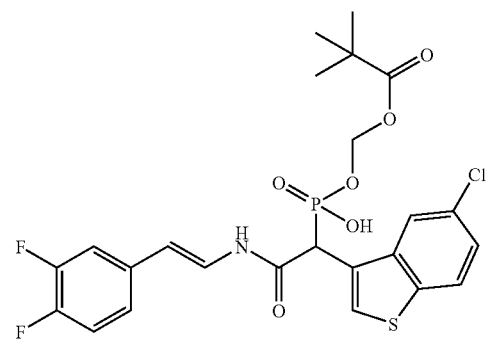

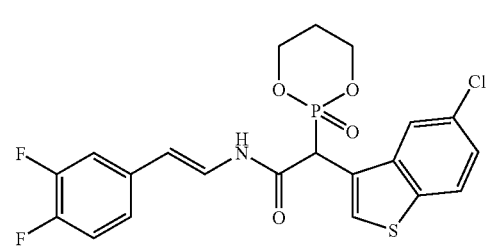

and

-continued

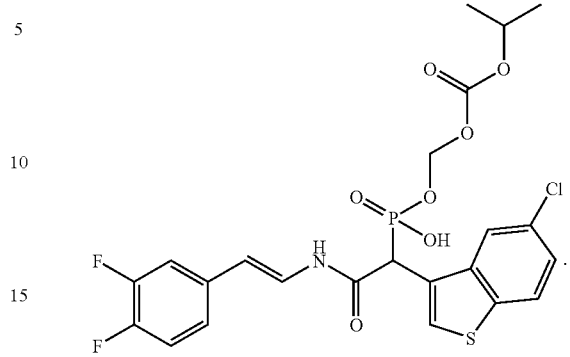

50. A composition comprising the compound of claim 1 and a pharmaceutically acceptable carrier.

51. A composition made by mixing the compound of claim 30 and a pharmaceutically acceptable carrier.

52. A composition comprising the compound of claim 30 and a pharmaceutically acceptable carrier.

53. A composition made by mixing the compound of claim 30 and a pharmaceutically acceptable carrier.

54. A compound of Formula Ia selected from the group consisting of:

(Ia)

| CPD | $R^2$ | $R^3$ | $R^5$ | $R^6$ | n | W | $Z-R^4$ |
|---|---|---|---|---|---|---|---|
| 2 | 3,4-difluorophenyl | | H | OH | 1 | O | 5-Cl-benzothiophen-3-yl |
| 17 | 3,4-difluorophenyl | | H | $CH_3$ | 1 | O | 5-Cl-benzothiophen-3-yl |
| 170 | 3,5-dichlorophenyl | | H | $CH_3$ | 1 | O | 5-Cl-benzothiophen-3-yl |
| 187 | 3,4-difluorophenyl | | —$CH_2$OC(=O) t-butyl | OH | 1 | O | 5-Cl-benzothiophen-3-yl |
| 191 | 3,4-difluorophenyl | | —$CH_2$OC(=O) isopropyloxy | OH | 1 | O | 5-Cl-benzothiophen-3-yl |
| 207 | 3,5-dichlorophenyl | | H | OH | 1 | O | 5-Cl-benzothiophen-3-yl |
| 261 | 3,5-dichlorophenyl | | —$CH_2$OC(=O) t-butyl | OH | 1 | O | 5-Cl-benzothiophen-3-yl |
| 297 | 3,5-dichlorophenyl | | —$CH_2$OC(=O) isopropyloxy | OH | 1 | O | 5-Cl-benzothiophen-3-yl. |

55. A compound of claim 54 that is
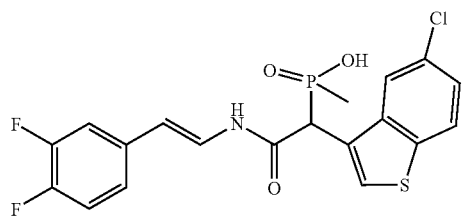
56. A compound of claim 54 that is:
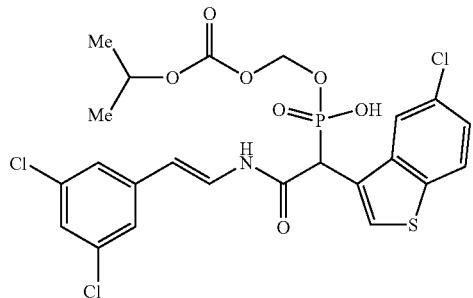
57. A compound of claim 1 of Formula II
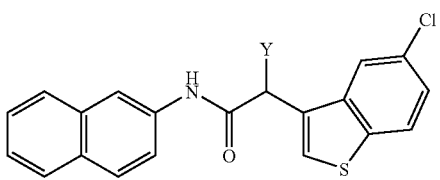
wherein Y is —SO₃H.
58. A compound of claim 54 that is:
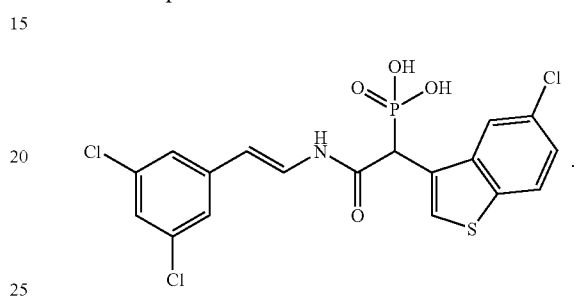
\* \* \* \* \*